(12) United States Patent
Kawano et al.

(10) Patent No.: US 9,051,333 B2
(45) Date of Patent: Jun. 9, 2015

(54) 6,7-DIHYDROIMIDAZO [2,1-B] [1,3]OXAZINE BACTERICIDES

(75) Inventors: Yoshikazu Kawano, Osaka (JP);
Yoshikazu Haraguchi, Osaka (JP);
Hirofumi Sasaki, Osaka (JP); Yukitaka Uematsu, Osaka (JP); Hidetsugu Tsubouchi, Osaka (JP); Hiromi Yata, Osaka (JP); Hiroshi Shimizu, Osaka (JP); Kazuho Kohashi, Osaka (JP);
Motohiro Itotani, Osaka (JP); Kuninori Tai, Osaka (JP); Isao Takemura, Osaka (JP); Mikayo Hayashi, Osaka (JP);
Hiroyuki Hashizume, Osaka (JP); Miki Matsuba, Osaka (JP); Izuru Nakamura, Osaka (JP); Xiuhao Chen, Osaka (JP);
Makoto Matsumoto, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/111,262

(22) PCT Filed: Apr. 13, 2012

(86) PCT No.: PCT/JP2012/060645
§ 371 (c)(1),
(2), (4) Date: Oct. 11, 2013

(87) PCT Pub. No.: WO2012/141338
PCT Pub. Date: Oct. 18, 2012

(65) Prior Publication Data
US 2014/0031342 A1    Jan. 30, 2014

Related U.S. Application Data

(60) Provisional application No. 61/476,003, filed on Apr. 15, 2011.

(51) Int. Cl.
*C07D 498/04* (2006.01)
*A61K 31/5383* (2006.01)

(52) U.S. Cl.
CPC .................................. *C07D 498/04* (2013.01)

(58) Field of Classification Search
USPC .................. 544/91; 514/230.5, 375
See application file for complete search history.

(56) References Cited

U.S. PATENT DOCUMENTS

2006/0094767 A1    5/2006    Tsubouchi et al.
2008/0119478 A1    5/2008    Tsubouchi et al.

FOREIGN PATENT DOCUMENTS

| JP | 2004-149527 A | 5/2004 |
|---|---|---|
| JP | 2005-320316 A | 11/2005 |
| WO | 97/01562 A1 | 1/1997 |
| WO | 2009/120789 A1 | 10/2009 |
| WO | 2011/014774 A1 | 2/2011 |
| WO | 2011/014776 A1 | 2/2011 |

OTHER PUBLICATIONS

International Search Report of PCT/JP2012/060645, dated Jul. 3, 2012.
Michael D. Iseman, "A Clinician's Guide to Tuberculosis", Lippincott Williams & Wilkins, 2000, pp. 274-295.
"Kekkaku", 1992, pp. 48-54, Second Edition.
"Kekkaku", Kyoto University, 1999, pp. 43-82, vol. 74.
"Multidrug and extensively drug-resistant TB (M/XDR/TB)", 2010 Global Report on Surveillance and Response, World Health Organization, pp. 1-71.
S.K. Verma, et al., "HIV-Tuberculosis Co-Infection", The Internet Journal of Pulmonary Medicine, ISSN: 1531-2984, 2008, pp. 1-3, vol. 10.
"The Global Plan to Stop TB 2011-2015", Transforming the Fight Towards Elimination of Tuberculosis, World Health Organization, pp. 1-101.

*Primary Examiner* — Kahsay Habte
(74) *Attorney, Agent, or Firm* — Sughrue Mion, PLLC

(57) ABSTRACT

The present invention provides a novel 6,7-dihydroimidazo [2,1-b][1,3]oxazine compound that has excellent bactericidal action against tubercle bacilli, multidrug-resistant tubercle bacilli, and atypical acid-fast bacilli. Specifically, the present invention provides a compound represented by Formula (1):

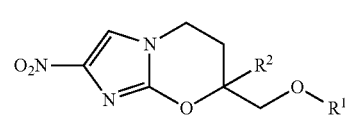

(1)

or a salt thereof,
wherein $R^1$ represents tetrahydroisoquinolyl, tetrahydroquinolyl, tetrahydrobenzoazepinyl, benzoxazolyl, benzothiazolyl, indolyl, isoindolinyl, naphthyl, quinolyl, phenyl, biphenylyl, or pyridyl, these groups being optionally substituted, the phenyl, biphenylyl, and pyridyl represented by $R^1$ each being substituted directly or via a linker with at least one group selected from the group consisting of tetrahydropyridyl, diazepanyl, diazabicycloheptanyl, tetrahydrotriazolopyrazinyl, tetrahydroimidazopyrazinyl, azabicyclooctanyl, oxazolyl, piperazinyl, piperidyl, thiazolyl, and the like, each of these groups being optionally substituted; and $R^2$ represents hydrogen or lower alkyl. The present invention further provides a pharmaceutical composition containing the above.

9 Claims, No Drawings

6,7-DIHYDROIMIDAZO [2,1-B] [1,3]OXAZINE BACTERICIDES

TECHNICAL FIELD

The present invention relates to a 6,7-dihydroimidazo[2,1-b][1,3]oxazine compound.

BACKGROUND ART

Among acid-fast bacilli, *Mycobacterium tuberculosis* is widely known, and one-third of the human population are said to be infected therewith. In addition to *Mycobacterium tuberculosis*, *Mycobacterium africanum* and *Mycobacterium bovis* are also known to be grouped in the *Mycobacterium tuberculosis* complex, and are known as mycobacteria, which are highly pathogenic to humans.

The treatment of these tuberculosis uses three agents, i.e., rifampicin, isoniazid, and ethambutol (or streptomycin), or four agents, i.e., the above three agents and pyrazinamide, which serve as first-line drugs.

However, the treatment of tuberculosis requires a distinctly long-term drug administration, which causes poor compliance, often resulting in treatment failure.

Further, the aforementioned agents have been reported to cause side effects as exemplified below: rifampicin causes hepatopathy, flu syndrome, and drug allergy, and is contraindicated for use in combination with other agents due to P450 related enzyme induction; isoniazid causes peripheral neuropathy and induces serious hepatopathy when used in combination with rifampicin; ethambutol causes failing vision due to optic neuropathy; streptomycin causes hearing deterioration due to eighth cranial nerve neuropathy; and pyrazinamide causes hepatopathy, gout attacks accompanied by an increase in the uric acid level, as well as vomiting, and the like (Non-patent Literature 1 and 2).

As a practical matter, cases have been reported where standard chemotherapy could not be performed due to the aforementioned side effects, which account for 70% of the cases where drug administration was discontinued (approximately 23%, 52 cases) of the total number of cases (228 hospital patients surveyed in all) (Non-patent Literature 3).

In particular, out of the above-mentioned five agents, which are used in combination as first-line drugs, rifampicin, isoniazid, and pyrazinamide commonly cause hepatotoxicity, which is known as the most frequently occurring side effect. Meanwhile, tubercle bacilli that are resistant to antituberculosis agents, tubercle bacilli that are resistant to multiple drugs, etc., have been increasing, making treatment more difficult.

A WHO survey (2008) reported that there are 390,000 to 510,000 patients with multidrug-resistant tuberculosis in the world, which account for 3.6% of the total number of tuberculosis patients, and that 5.4% of multidrug-resistant tuberculosis are equal to extensively drug-resistant tuberculosis (Non-patent Literature 4).

Further, one-third of HIV positive patients are suspected of being co-infected with tuberculosis; the number of such patients is said to be 14 million (Non-patent Literature 5). It is also reported that co-infection of HIV and tuberculosis poses a 20 to 37 times greater risk of developing tuberculosis than usual (Non-patent Literature 6).

In view of the above-described current status, examples of the profiles of a desired antituberculosis agent include (1) an agent that is also effective against multidrug-resistant tubercle bacilli; (2) an agent that enables short-term chemotherapy; (3) an agent with few side effects; (4) an agent that shows efficacy against latent infection with tubercle bacilli (latent tuberculosis); (5) an agent that can be administered orally; and the like.

Examples of bacteria known to be pathogenic to humans include pathogens of recently increasing MAC infections (*Mycobacterium avium-intracellulare* complex infections), such as *Mycobacterium avium* and *Mycobacterium intracellulare*; and other atypical acid-fast bacilli, such as *Mycobacterium kansasii*, *Mycobacterium marinum*, *Mycobacterium simiae*, *Mycobacterium scrofulaceum*, *Mycobacterium szulgai*, *Mycobacterium xenopi*, *Mycobacterium malmoense*, *Mycobacterium haemophilum*, *Mycobacterium ulcerans*, *Mycobacterium shimoidei*, *Mycobacterium fortuitum*, *Mycobacterium chelonae*, *Mycobacterium smegmatis*, and *Mycobacterium aurum*.

At present, there are few promising therapeutic agents against atypical mycobacteriosis, and the current status is that an antituberculosis agent, such as rifampicin, isoniazid, ethambutol, streptomycin, and kanamycin, is used in combination with a therapeutic agent against general bacterial infections, such as a new quinolone agent, a macrolide antimicrobial agent, an aminoglycoside antimicrobial agent, and a tetracycline antimicrobial agent.

However, compared with the treatment of infections with common bacteria, the treatment of atypical mycobacteriosis requires long-term drug administration, and in some cases, according to reports, atypical mycobacteriosis become intractable, possibly causing death. In order to overcome the current status, the development of a drug with a higher efficacy is in demand.

For example, Patent Literature 1 discloses that a 6-nitro-1,2,3,4-tetrahydro[2,1-b]imidazopyran compound is useful as an antituberculosis agent, because the compound has bactericidal action in vitro against tubercle bacilli (H37Rv strain) and multidrug-resistant tubercle bacilli, as well as because the compound shows, when orally administered, a therapeutic effect on an animal model infected with tuberculosis.

Patent Literature 2 and 3 disclose that a 2,3-dihydroimidazo[2,1-b]oxazole compound has bactericidal action against tubercle bacilli, multidrug-resistant tubercle bacilli, and atypical acid-fast bacilli.

Patent Literature 4 discloses that nitroimidazooxazine and nitroimidazooxazole compounds can be used as a drug against *Mycobacterium tuberculosis*.

However, the compounds disclosed in the above-mentioned literature have a structure different from that of the compounds of the present invention, and thus are dissimilar compounds.

CITATION LIST

Patent Literature

PTL 1: WO 97/01562 (Japanese Unexamined Patent Publication No. H11-508270)
PTL 2: Japanese Unexamined Patent Publication No. 2004-149527
PTL 3: Japanese Unexamined Patent Publication No. 2005-320316
PTL 4: WO 2011/014776

Non Patent Literature

NPL 1: A Clinician's Guide To Tuberculosis, Michael D. Iseman 2000 by Lippincott Williams & Wilkins, printed in the USA, ISBN 0-7817-1749-3

NPL 2: Kekkaku, Second edition, Fumiyuki KUZE, Takateru IZUMI, Igaku-Shoin, 1992
NPL 3: Kekkaku Vol. 74: 77-82, 1999
NPL 4: Multidrug and extensively drug-resistant TB (M/XDR-TB): 2010 Global Report on Surveillance and Response
NPL 5: The Internet Journal of Pulmonary Medicine 2008: Volume 10, Number 1
NPL 6: The Global Plan To Stop TB 2011-2015

SUMMARY OF INVENTION

Technical Problem

An object of the present invention is to provide a compound having excellent bactericidal action against tubercle bacilli and multidrug-resistant tubercle bacilli. It is a further object of the present invention to provide a compound having excellent bactericidal action against atypical acid-fast bacilli.

Solution to Problem

In order to achieve the aforementioned objects, the present inventors conducted extensive research and, as a result, accomplished the synthesis of a novel 6,7-dihydroimidazo[2,1-b][1,3]oxazine compound that has excellent bactericidal action against tubercle bacilli, multidrug-resistant tubercle bacilli, and atypical acid-fast bacilli. The present invention was completed based on such findings.

The present invention provides a compound represented by Formula (1):

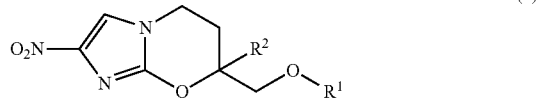

(1)

or a salt thereof,
wherein $R^1$ represents tetrahydroisoquinolyl, tetrahydroquinolyl, tetrahydrobenzoazepinyl, benzoxazolyl, benzothiazolyl, indolyl, isoindolinyl, naphthyl, quinolyl, phenyl, biphenylyl, or pyridyl, these groups being optionally substituted,
the phenyl and pyridyl represented by $R^1$ each being substituted directly or via a linker with at least one group selected from the group consisting of tetrahydropyridyl, diazepanyl, diazabicycloheptanyl, tetrahydrotriazolopyrazinyl, tetrahydroimidazopyrazinyl, azabicyclooctanyl, oxazolyl, piperazinyl, piperidyl, and thiazolyl, each of these groups being optionally substituted,
the biphenylyl represented by $R^1$ being substituted directly or via a linker with at least one group selected from the group consisting of tetrahydropyridyl, diazepanyl, diazabicycloheptanyl, tetrahydrotriazolopyrazinyl, tetrahydroimidazopyrazinyl, azabicyclooctanyl, oxazolyl, piperazinyl, piperidyl, thiazolyl, and phenyl, each of these groups being optionally substituted; and
$R^2$ represents hydrogen or lower alkyl.

The present invention further provides a compound represented by Formula (1) above, or a salt thereof, wherein $R^1$ is a group represented by Formula (2):

(2)

wherein A represents a divalent group selected from (A1) to (A12):

(A1) tetrahydroisoquinolinediyl,
(A2) tetrahydroquinolinediyl,
(A3) tetrahydrobenzoazepinediyl,
(A4) benzoxazolediyl,
(A5) benzothiazolediyl,
(A6) indolediyl,
(A7) isoindolinediyl,
(A8) naphthalenediyl,
(A9) quinolinediyl,
(A10) phenylene,
(A11) biphenyldiyl, and
(A12) pyridinediyl,
these groups (A1) to (A12) being optionally substituted on the ring(s) with at least one group selected from the group consisting of halogen and lower alkyl;
L1 represents a single bond, lower alkylene, —N(lower alkyl)-, —O—, —O-lower alkylene, —O-lower alkylene-O—, lower alkylene-O—, lower alkylene-O-lower alkylene, or lower alkenylene;
B represents a divalent group selected from (B1) to (B11):
(B1) tetrahydropyridinediyl,
(B2) diazepinediyl,
(B3) diazabicycloheptanediyl,
(B4) tetrahydrotriazolopyrazinediyl,
(B5) tetrahydroimidazopyrazinediyl,
(B6) azabicyclooctanediyl,
(B7) oxazolediyl,
(B8) piperazinediyl,
(B9) piperidinediyl,
(B10) thiazolediyl, and
(B11) phenylene,
these groups (B1) to (B11) being optionally substituted on the ring(s) with at least one group selected from the group consisting of lower alkyl, halo-lower alkyl, alkenyl, lower alkoxy, halo-lower alkoxy, lower alkoxycarbonyl, lower alkenyloxycarbonyl, hydroxy, lower alkylsulfonyl, and halo-lower alkylsulfonyl;
L2 represents a single bond, —CO—, —COO—, —COO-lower alkynylene, —COO-lower alkylene (this lower alkylene is optionally substituted with phenyl), —COO-lower alkenylene, —N(lower alkyl)-, —N(lower alkyl)-lower alkylene, —NH—, —NH-lower alkylene, —O—, —O-lower alkylene, —S—, lower alkylene (this lower alkylene is optionally substituted with optionally protected hydroxy), lower alkylene (this lower alkylene is optionally substituted with optionally protected hydroxy)-O—, lower alkylene-N-(lower alkyl)-, lower alkylene-N(lower alkyl)-lower alkylene, lower alkylene-O-lower alkylene, lower alkylene-S—, or lower alkenylene (this lower alkenylene is optionally substituted with lower alkyl or phenyl);
C represents a divalent group or a single bond selected from (C1) to (C28):
(C1) tetrahydroquinolinediyl,
(C2) dihydrobenzodioxindiyl,
(C3) dihydrobenzoxazolediyl,
(C4) dihydrobenzofurandiyl,
(C5) dihydrobenzoxazinediyl,
(C6) adamantanediyl,
(C7) benzothiophenediyl,
(C8) benzodioxolediyl,
(C9) benzimidazolediyl,
(C10) benzofurandiyl,
(C11) carbazolediyl,
(C12) chromandiyl,
(C13) cyclohexanediyl,
(C14) fluorenediyl,
(C15) furandiyl, (C16) imidazopyridinediyl,
(C17) imidazolediyl,
(C18) indolediyl,
(C19) naphthalenediyl,
(C20) piperidinediyl,
(C21) pyrazolediyl,
(C22) pyridinediyl,
(C23) pyrrolediyl,
(C24) quinolinediyl,
(C25) thiazolediyl,
(C26) thiophenediyl,
(C27) phenylene, and
(C28) single bond, these groups (C1) to (C27) being optionally substituted on the ring(s) with at least one group selected from the group consisting of alkoxy, halo-lower alkoxy, alkyl, haloalkyl, halogen, hydroxy, lower alkoxycarbonyl, oxo, lower alkanoylamino, lower alkanoyloxy, nitro, lower alkylthio, halo-lower alkylthio, cyclo-lower-alkyl, cyclo-lower alkoxy, cyano, lower alkoxycarbonylamino, nitro, amino, (mono- or di-lower alkyl)amino, lower alkylsulfonyl, lower alkylsulfonylamino, alkenyloxy, and (mono- or di-lower alkyl)amino lower alkoxy;

D represents a group or an atom selected from (D1) to (D35):
(D1) oxadiazolyl-lower alkoxy,
(D2) triazolyl,
(D3) isoxazolyl-lower alkoxy,
(D4) imidazolyl,
(D5) imidazolyl-lower alkyl,
(D6) thiazolyl-lower alkoxy,
(D7) thienyl,
(D8) thienyl-lower alkoxy,
(D9) furyl-lower alkoxy,
(D10) tetrahydropyranyl,
(D11) pyrazinyl-lower alkoxy,
(D12) piperazinylphenyl,
(D13) pyrazolyl,
(D14) pyridyl,
(D15) pyridyloxy,
(D16) pyridyl-lower alkoxy,
(D17) pyrrolidinyl,
(D18) pyrrolyl,
(D19) phenyl,
(D20) (mono- or di-phenyl)amino,
(D21) phenyl-lower alkyl,
(D22) phenyl-lower alkenyl,
(D23) (phenyl-lower alkyl)(lower alkyl)amino,
(D24) (phenyl-lower alkyl)amino,
(D25) phenyl-lower alkylsulfonyl,
(D26) phenyl-lower alkylsulfinyl,
(D27) phenyl-lower alkylthio,
(D28) phenyl-lower alkenyloxy,
(D29) phenyl-lower alkoxy,
(D30) phenyl-lower alkoxyphenyl,
(D31) phenoxy,
(D32) phenoxy-lower alkyl,
(D33) phenoxypiperidyl,
(D34) morpholinyl-lower alkyl, and
(D35) hydrogen, these groups (D1) to (D34) being optionally substituted on the ring(s) with at least one group selected from the group consisting of lower alkyl, halo-lower alkyl, lower alkylthio, lower alkoxy, halo-lower alkoxy, and halogen, with the proviso that when A is group (A10) or (A12), and B is group (B11), C is selected from groups (C1) to (C27).

The present invention provides a pharmaceutical composition comprising a compound represented by Formula (1) (including all subclasses of the compounds of Formula (1) stated in this specification; the same applies hereinafter) or a salt thereof, and a pharmaceutically acceptable carrier.

The present invention provides a prophylactic and/or therapeutic agent for tuberculosis, comprising a compound of Formula (1), or a salt thereof, and a pharmaceutically acceptable carrier.

The present invention provides a compound represented by Formula (1), or a salt thereof, for use in the prevention and/or treatment of tuberculosis.

The present invention provides the use of a compound represented by Formula (1), or a salt thereof, for the production of a pharmaceutical composition.

The present invention provides the use of a compound of Formula (1), or a salt thereof, as a pharmaceutical composition.

The present invention provides a method for preventing and/or treating tuberculosis, comprising administering an effective amount of a compound of Formula (1), or a salt thereof, to a patient.

Advantageous Effects of Invention

The compounds of the present invention have specific efficacy against, in particular, acid-fast bacilli (mycobacterium tuberclosis complex and nontuberculosis mycobacterium complex).

The compounds of the present invention have an excellent effect on multidrug-resistant tubercle bacilli. The compounds of the present invention have an antibacterial action against anaerobic bacteria.

The compounds of the present invention exert the above-described activities not only in vitro but also in oral administration.

The compounds of the present invention do not cause diarrhea, which can be caused by a known antimicrobial agent that has a broad spectrum against general bacteria, such as gram positive and gram negative bacteria. In addition, the compounds of the present invention have fewer side effects than existing drugs. Therefore, the compounds of the present invention can serve as pharmaceutical preparations that can be administered for a long period of time.

The compounds of the present invention can be satisfactorily distributed throughout the lung tissue, which is a main organ infected with mycobacteriosis. In addition, the compounds of the present invention have properties such as sustained drug efficacy and excellent safety. For this reason, the compounds of the present invention are expected to have high therapeutic effects.

Additionally, compared with existing antituberculosis agents, the compounds of the present invention exhibit stronger bactericidal activity against intracellular parasites, such as parasitic tubercle *bacillus* in human-derived macrophages. Therefore, the compounds of the present invention enable a reduction in the tuberculosis relapse rate and also enable short-term chemotherapy. Further, the compounds of the present invention are also expected to be used as a principal drug for preventive administration that is performed against a mixed infection with HIV and tuberculosis, which has become a serious problem.

The compounds of the present invention exhibit excellent metabolic stability in plasma, and thus have a feature of providing satisfactorily sustained bactericidal action in vivo.

DESCRIPTION OF EMBODIMENTS

The groups represented by $R^1$, $R^2$, A, B, C, D, L1, and L2, and the substituents of these groups, as used herein, are described below.

The term "at least one" means usually one to ten, preferably one to six, and more preferably one to three.

Examples of "alkyl" include straight- or branched-chain alkyl groups having 1 to 12 carbon atoms, such as the "lower alkyl" mentioned below, heptyl, octyl, nonyl, decyl, and dodecyl.

Examples of "lower alkyl" include straight- or branched-chain alkyl groups having 1 to 6 carbon atoms, such as methyl, ethyl, n-propyl, isopropyl, n-butyl, isobutyl, tert-butyl, sec-butyl, n-pentyl, neopentyl, n-hexyl, isohexyl, and 3-methylpentyl.

Examples of "alkenyl" include straight- or branched-chain alkenyl groups having 2 to 12 carbon atoms, such as the "lower alkenyl" mentioned below, heptenyl, octenyl, nonenyl, decenyl, dodecenyl, and —CH$_2$CH=C(CH$_3$)CH$_2$CH$_2$CH=C(CH$_3$)$_2$.

Examples of "lower alkenyl" include straight- or branched-chain alkenyl groups having 2 to 6 carbon atoms, such as methyl, vinyl, 1-propenyl, allyl, 1-, 2- or 3-butenyl, 1,3-butanedienyl, and 1,2-, 3-, or 4-pentenyl.

Examples of "lower alkylene" include straight- or branched-chain alkylene groups having 1 to 6 carbon atoms, such as methylene, ethylene, trimethylene, 2-methyltrimethylene, 2,2-dimethyltrimethylene, 1-methyltrimethylene, methylmethylene, ethylmethylene, dimethylmethylene, tetramethylene, pentamethylene, and hexamethylene.

Examples of "lower alkenylene" include straight- or branched-chain alkenylene groups having 2 to 6 carbon atoms, such as ethenylene, propenylene, butenylene, pentenylene, and hexenylene.

Examples of "lower alkynylene" include straight- or branched-chain alkynylene groups having 2 to 6 carbon atoms, such as ethynylene, propynylene, butynylene, pentynylene, and hexynylene.

Examples of "cyclo-lower alkyl" include cycloalkyl having 3 to 8, preferably 3 to 7 carbon atoms, such as cyclopropyl, cyclobutyl, cyclopentyl, cyclohexyl, cyclopropylmethyl, and cyclohexylmethyl.

Examples of "alkoxy" include straight- or branched-chain alkoxy groups having 1 to 12 carbon atoms, such as the "lower alkoxy" mentioned below, n-heptyloxy, n-octyloxy, n-nonyloxy, n-decyloxy, and n-dodecyloxy.

Examples of "lower alkoxy" include straight- or branched-chain alkoxy groups having 1 to 6 carbon atoms, such as methoxy, ethoxy, n-propoxy, isopropoxy, n-butoxy, isobutoxy, tert-butoxy, sec-butoxy, n-pentyloxy, neopentyloxy, n-hexyloxy, isohexyloxy, and 3-methylpentyloxy.

Examples of "cyclo-lower alkoxy" include cycloalkoxy having 3 to 8, preferably 3 to 7 carbon atoms, such as cyclopropyloxy, cyclobutyloxy, cyclopenthyloxy, cyclohexyloxy, cyclopropylmethyloxy, and cyclohexylmethyloxy.

Examples of "lower alkanoyl" include straight- or branched-chain alkanoyl groups having 1 to 6 carbon atoms, such as formyl, acetyl, propionyl, butyryl, isobutyryl, pentanoyl, tert-butylcarbonyl, and hexanoyl.

Examples of "lower alkoxycarbonyl" include (straight- or branched-chain alkoxy having 1 to 6 carbon atoms) carbonyl, such as methoxycarbonyl, ethoxycarbonyl, propoxycarbonyl, butoxycarbonyl, isobutoxycarbonyl, and tert-butoxycarbonyl.

Examples of "lower alkenyloxycarbonyl" include (straight- or branched chain alkenyloxy having 2 to 6 carbon atoms) carbonyl, such as vinyloxycarbonyl, allyloxycarbonyl, butenyloxycarbonyl, and isobutenyloxycarbonyl.

"Halogen" represents fluorine, chlorine, bromine, and iodine.

Examples of "haloalkyl" include groups in which at least one hydrogen (for example, 1 to whole, 1 to 10, further 1 to 6, in particular 1 to 3 hydrogen atoms) of the above-mentioned "alkyl" is substituted with halogen(s).

Examples of "halo-lower alkyl" include groups in which at least one hydrogen (for example, 1 to 10, further 1 to 6, in particular 1 to 3 hydrogen atoms) of the above-mentioned "lower alkyl" is substituted with halogen(s), such as trihalomethyl (e.g., —CF$_3$), trihaloethyl (e.g., —CH$_2$CF$_3$), pentahaloethyl (e.g., —CF$_2$CF$_3$), or nonahalobutyl (e.g., —CF$_2$CF$_2$CF$_2$CF$_3$).

Examples of "halo-lower alkoxy" include groups in which at least one hydrogen (e.g., 1 to 10, further 1 to 6, in particular 1 to 3 hydrogen atoms) of the above-mentioned "lower alkoxy" is substituted with halogen(s), such as trihalomethoxy (e.g., —OCF$_3$), pentahaloethoxy (e.g., —OCF$_2$CF$_3$), or nonahalobutoxy (e.g., —OCF$_2$CF$_2$CF$_2$CF$_3$).

Examples of protecting groups of "optionally protected hydroxy" include tetrahydropyranyl, acetyl, trialkylsilyl, (e.g., trimethylsilyl, triethylsilyl, tert-butyldimethylsilyl), alkyldiphenylsilyl, (e.g., tert-butyldimethylsilyl), and the like.

The present invention provides a 6,7-dihydroimidazo[2,1-b][1,3]oxazine compound represented by Formula (1):

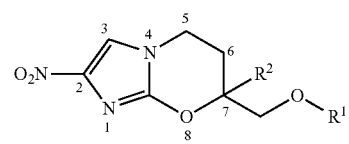

or a salt thereof, wherein $R^1$ represents tetrahydroisoquinolyl, tetrahydroquinolyl, tetrahydrobenzoazepinyl, benzoxazolyl, benzothiazolyl, indolyl, isoindolinyl, naphthyl, quinolyl, phenyl, biphenylyl, or pyridyl, these groups being optionally substituted, the phenyl and pyridyl represented by $R^1$ each being substituted directly or via a linker with at least one group selected from the group consisting of tetrahydropyridyl, diazepanyl, diazabicycloheptanyl, tetrahydrotriazolopyrazinyl, tetrahydroimidazopyrazinyl, azabicyclooctanyl, oxazolyl, piperazinyl, piperidyl, and thiazolyl, each of these groups being optionally substituted, the biphenylyl represented by $R^1$ being substituted directly or via a linker with at least one group selected from the group consisting of tetrahydropyridyl, diazepanyl, diazabicycloheptanyl, tetrahydrotriazolopyrazinyl, tetrahydroimidazopyrazinyl, azabicyclooctanyl, oxazolyl, piperazinyl, piperidyl, thiazolyl, and phenyl, each of these groups being optionally substituted; and $R^2$ represents hydrogen or lower alkyl.

The pyridyl represented by $R^1$ is preferably substituted directly or via a linker with at least one group selected from the group consisting of piperazinyl and piperidyl, these groups (piperazinyl and piperidyl) being optionally substituted.

In Formula (1), the carbon atom at position 7 is an asymmetric carbon, and the compounds represented by Formula (1) include R—, S—, and racemic forms based on the asymmetric carbon atom, and the mixtures thereof.

In Formula (1), $R^1$ is preferably a group represented by Formula (2):

-A-L1-B-L2-C-D     (2)

In this formula, A represents a divalent group selected from (A1) to (A12):
(A1) tetrahydroisoquinolinediyl,
(A2) tetrahydroquinolinediyl,
(A3) tetrahydrobenzoazepinediyl,
(A4) benzoxazolediyl,
(A5) benzothiazolediyl,
(A6) indolediyl,
(A7) isoindolinediyl,
(A8) naphthalenediyl,
(A9) quinolinediyl,
(A10) phenylene,
(A11) biphenyldiyl, and
(A12) pyridinediyl.

These groups (A1) to (A12) are optionally substituted on the ring(s) with at least one group (further 1 to 3, in particular 1 or 2 groups) selected from the group consisting of halogen and lower alkyl.

The "(A1) tetrahydroisoquinolinediyl" represented by A is a divalent group obtained by removing two hydrogen atoms from tetrahydroisoquinoline. Examples of tetrahydroisoquinoline include 1,2,3,4-tetrahydroisoquinoline. Specific examples of tetrahydroisoquinolinediyl include a group represented by:

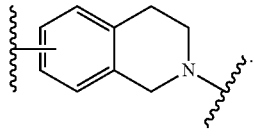

Preferable examples thereof include 1,2,3,4-tetrahydroisoquinoline-2,6-diyl and 1,2,3,4-tetrahydroisoquinoline-2,7-diyl.

The "(A2) tetrahydroquinolinediyl" represented by A is a divalent group obtained by removing two hydrogen atoms from tetrahydroquinoline. Examples of tetrahydroquinoline include 1,2,3,4-tetrahydroquinoline. Specific examples of tetrahydroquinolinediyl include a group represented by:

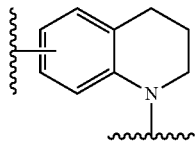

Preferable examples thereof include 1,2,3,4-tetrahydroquinoline-1,6-diyl.

The "(A3) tetrahydrobenzoazepinediyl" represented by A is a divalent group obtained by removing two hydrogen atoms from tetrahydrobenzoazepine. Examples of tetrahydrobenzoazepine include 2,3,4,5-tetrahydro-1H-benzo[b]azepine and 2,3,4,5-tetrahydro-1H-benzo[c]azepine. Specific examples of tetrahydrobenzoazepinediyl include a group represented by:

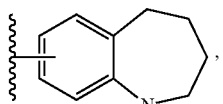

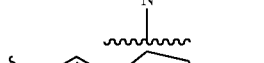

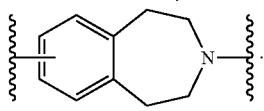

Preferable examples thereof include 2,3,4,5-tetrahydro-1H-benzo[b]azepine-1,7-diyl and 2,3,4,5-tetrahydro-1H-benzo[c]azepine-2,7-diyl.

The "(A4) benzoxazolediyl" represented by A is a divalent group obtained by removing two hydrogen atoms from benzoxazole. Examples of benzoxazole include benzo[d]oxazole. Specific examples of benzoxazolediyl include a group represented by:

2-methylbenzo[d]thiazole

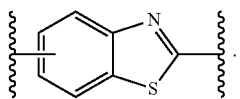

Preferable examples thereof include 2,5-benzo[d]oxazolediyl and 2,6-benzo[d]oxazolediyl.

The "(A5) benzothiazolediyl" represented by A is a divalent group obtained by removing two hydrogen atoms from benzothiazole. Examples of benzothiazole include benzo[d]thiazol. Specific examples of benzothiazolediyl include a group represented by:

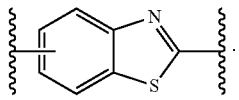

Preferable examples thereof include 2,6-benzo[d]thiazolediyl.

The "(A6) indolediyl" represented by A is a divalent group obtained by removing two hydrogen atoms from indole. Specific examples of indolediyl include a group represented by:

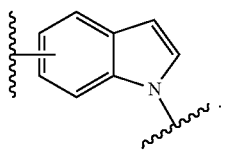

Preferable examples thereof include 1,5-indolediyl.

The "(A7) isoindolinediyl" represented by A is a divalent group obtained by removing two hydrogen atoms from isoindoline. Specific examples of isoindolinediyl include a group represented by:

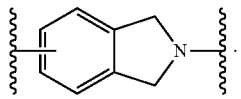

Preferable examples thereof include 2,5-isoindolinediyl.

The "(A8) naphthalenediyl" represented by A is a divalent group obtained by removing two hydrogen atoms from naphthalene. Specific examples of naphthalenediyl include a group represented by:

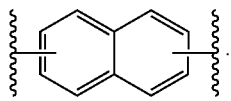

Preferable examples thereof include 2,6-naphthalenediyl.

The "(A9) quinolinediyl" represented by A is a divalent group obtained by removing two hydrogen atoms from quinoline. Specific examples of quinolinediyl include a group represented by:

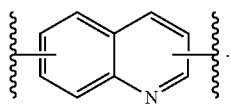

Preferable examples thereof include 2,6-quinolinediyl.

The "(A10) phenylene" represented by A is a divalent group obtained by removing two hydrogen atoms from benzene. Specific examples of phenylene include 1,2-phenylene, 1,3-phenylene, and 1,4-phenylene, with 1,4-phenylene being preferable.

The "(A11) biphenyldiyl" represented by A is a divalent group obtained by removing two hydrogen atoms from biphenyl. Specific examples of biphenyldiyl include a group represented by:

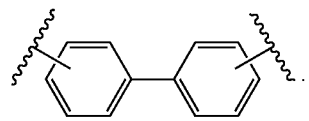

Preferable examples thereof include 4,4'-biphenyldiyl.

The "(A12) pyridinediyl" represented by A is a divalent group obtained by removing two hydrogen atoms from pyridine. Specific examples of pyridinediyl include 2,3-pyridinediyl, 2,4-pyridinediyl, 2,5-pyridinediyl, 2,6-pyridinediyl, 3,4-pyridinediyl, and 3,5-pyridinediyl, with 2,5-pyridinediyl being preferable.

L1 represents a single bond or a linker. Specifically, L1 represents a single bond, lower alkylene, —N(lower alkyl)-, —O—, —O-lower alkylene, —O-lower alkylene-O—, lower alkylene-O—, lower alkylene-O-lower alkylene, or lower alkenylene.

B represents a divalent group selected from (B1) to (B11):
(B1) tetrahydropyridinediyl,
(B2) diazepinediyl,
(B3) diazabicycloheptanediyl,
(B4) tetrahydrotriazolopyrazinediyl,
(B5) tetrahydroimidazopyrazinediyl,
(B6) azabicyclooctanediyl,
(B7) oxazolediyl,
(B8) piperazinediyl,
(B9) piperidinediyl,
(B10) thiazolediyl, and
(B11) phenylene.

These groups (B1) to (B11) are optionally substituted on the ring(s) with at least one group (further 1 to 3, in particular 1 or 2 groups) selected from the group consisting of lower alkyl, halo-lower alkyl, alkenyl, lower alkoxy, halo-lower alkoxy, lower alkoxycarbonyl, lower alkenyloxycarbonyl, hydroxy, lower alkylsulfonyl, and halo-lower alkylsulfonyl.

The "(B1) tetrahydropyridinediyl" represented by B is a divalent group obtained by removing two hydrogen atoms from tetrahydropyridine. Examples of tetrahydropyridine include 1,2,3,4-tetrahydropyridine and 1,2,3,6-tetrahydropyridine. Specific examples of tetrahydropyridinediyl include a group represented by:

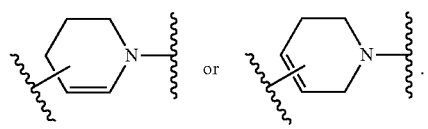

Preferable examples thereof include 1,2,3,6-tetrahydropyridine-1,4-diyl.

The "(B2) diazepinediyl" represented by B is a divalent group obtained by removing two hydrogen atoms from diazepine. Specific examples of diazepinediyl include a group represented by:

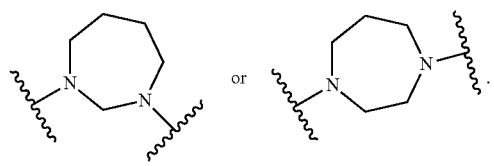 [SMILES: *N1CCCCN(*)C1 ; *N1CCCN(*)CC1]

Preferable examples thereof include 1,4-diazepinediyl.

The "(B3) diazabicycloheptanediyl" represented by B is a divalent group obtained by removing hydrogen atoms from diazabicycloheptane. Examples of diazabicycloheptane include 2,5-diazabicyclo[2,2,1]heptane. Specific examples of diazabicycloheptanediyl include a group represented by:

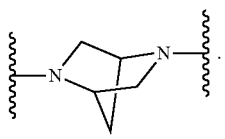 [SMILES: *N1CC2CC1CN2*]

The "(B4) tetrahydrotriazolopyrazinediyl" represented by B is a divalent group obtained by removing two hydrogen atoms from tetrahydrotriazolopyrazine. Examples of tetrahydrotriazolopyrazine include 5,6,7,8-tetrahydro[1,2,4]triazolo[4,3-a]pyrazine. Specific examples of tetrahydrotriazolopyrazinediyl include a group represented by:

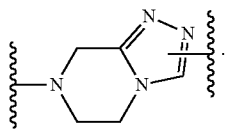

Preferable examples thereof include 5,6,7,8-tetrahydro[1,2,4]triazolo[4,3-a]pyrazine-3,7-diyl.

The "(B5) tetrahydroimidazopyrazinediyl" represented by B is a divalent group obtained by removing two hydrogen atoms from tetrahydroimidazopyrazine. Examples of tetrahydrotriazolopyrazine include 5,6,7,8-tetrahydroimidazo[1,2-a]pyrazine. Specific examples of tetrahydroimidazopyrazinediyl include a group represented by:

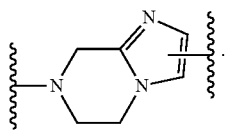

Preferable examples thereof include 5,6,7,8-tetrahydroimidazo[1,2-a]pyrazine-3,7-diyl.

The "(B6) azabicyclooctanediyl" represented by B is a divalent group obtained by removing two hydrogen atoms from azabicyclooctane. Examples of azabicyclooctane include 8-azabicyclo[3,2,1]octane. Specific examples of azabicyclooctanediyl include a group represented by:

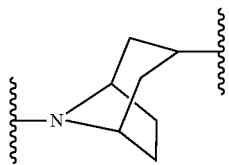

The "(B7) oxazolediyl" represented by B is a divalent group obtained by removing two hydrogen atoms from oxazoline. Specific examples of oxazolediyl include a group represented by:

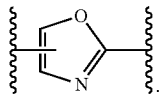

Preferable examples thereof include 2,4-oxazolediyl.

The "(B8) piperazinediyl" represented by B is a divalent group obtained by removing two hydrogen atoms from piperazine. Specific examples of piperazinediyl include a group represented by:

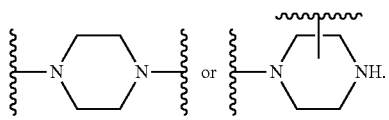

Preferable examples thereof include 1,4-piperazinediyl.

The "(B9) piperidinediyl" represented by B is a divalent group obtained by removing two hydrogen atoms from piperidine. Specific examples of piperidinediyl include a group represented by:

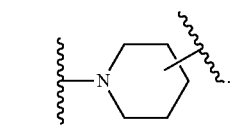

Preferable examples thereof include 1,4-piperidinediyl.

The "(B10) thiazolediyl" represented by B is a divalent group obtained by removing two hydrogen atoms from thiazoline. Specific examples of thiazolediyl include a group represented by:

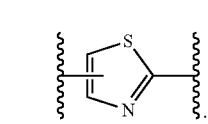

Preferable examples thereof include 2,4-thiazolediyl.

The "(B11) phenylene" represented by B is a divalent group obtained by removing two hydrogen atoms from benzene. Examples of phenylene include 1,2-phenylene, 1,3-phenylene, and 1,4-phenylene, with 1,4-phenylene being preferable.

L2 represents a single bond or a linker. Specifically, L2 represents a single bond, —CO—, —COO—, —COO-lower alkynylene, —COO-lower alkylene (this lower alkylene is optionally substituted with phenyl), —COO-lower alkenylene, —N(lower alkyl)-, —N(lower alkyl)-lower alkylene, —NH—, —NH-lower alkylene, —O—, —O-lower alkylene, —S—, lower alkylene (this lower alkylene is optionally substituted with optionally protected hydroxy), lower alkylene (this lower alkylene is optionally substituted with optionally protected hydroxy)-O—, lower alkylene-N-(lower alkyl)-, lower alkylene-N(lower alkyl)-lower alkylene, lower alkylene-O-lower alkylene, lower alkylene-S—, or lower alkenylene (this lower alkenylene is optionally substituted with lower alkyl or phenyl).

C represents a divalent group or a single bond selected from (C1) to (C28):
(C1) tetrahydroquinolinediyl,
(C2) dihydrobenzodioxindiyl,
(C3) dihydrobenzoxazolediyl,
(C4) dihydrobenzofurandiyl,
(C5) dihydrobenzoxazinediyl,
(C6) adamantanediyl,
(C7) benzothiophenediyl,
(C8) benzodioxolediyl,
(C9) benzimidazolediyl,
(C10) benzofurandiyl,
(C11) carbazolediyl,
(C12) chromandiyl,
(C13) cyclohexanediyl,
(C14) fluorenediyl,
(C15) furandiyl,
(C16) imidazopyridinediyl,
(C17) imidazolediyl,
(C18) indolediyl,
(C19) naphthalenediyl,
(C20) piperidinediyl, (C21) pyrazolediyl,
(C22) pyridinediyl,
(C23) pyrrolediyl,
(C24) quinolinediyl,
(C25) thiazolediyl,
(C26) thiophenediyl,
(C27) phenylene, and
(C28) single bond.

These groups (C1) to (C27) are optionally substituted on the ring(s) with at least one group (further 1 to 3, in particular 1 or 2 groups) selected from the group consisting of alkoxy, halo-lower alkoxy, alkyl, haloalkyl, halogen, hydroxy, lower alkoxycarbonyl, oxo, lower alkanoylamino, lower alkanoyloxy, nitro, lower alkylthio, halo-lower alkylthio, cyclo-lower alkyl, cyclo-lower alkoxy, cyano, lower alkoxycarbonylamino, nitro, amino, (mono- or di-lower alkyl)amino, lower alkylsulfonyl, lower alkylsulfonylamino, alkenyloxy, and (mono- or di-lower alkyl)amino-lower alkoxy.

D represents a group or an atom selected from (D1) to (D35):
(D1) oxadiazolyl-lower alkoxy,
(D2) triazolyl,
(D3) isoxazolyl-lower alkoxy,
(D4) imidazolyl,
(D5) imidazolyl-lower alkyl,
(D6) thiazolyl-lower alkoxy,
(D7) thienyl,
(D8) thienyl-lower alkoxy,
(D9) furyl-lower alkoxy,
(D10) tetrahydropyranyl,
(D11) pyrazinyl-lower alkoxy,
(D12) piperazinylphenyl,
(D13) pyrazolyl,
(D14) pyridyl,
(D15) pyridyloxy,
(D16) pyridyl-lower alkoxy,
(D17) pyrrolidinyl,
(D18) pyrrolyl,
(D19) phenyl,
(D20) (mono- or di-phenyl)amino,
(D21) phenyl-lower alkyl,
(D22) phenyl-lower alkenyl,
(D23) (phenyl-lower alkyl)(lower alkyl)amino,
(D24) (phenyl-lower alkyl)amino,
(D25) phenyl-lower alkylsulfonyl,
(D26) phenyl-lower alkylsulfinyl,
(D27) phenyl-lower alkylthio,
(D28) phenyl-lower alkenyloxy,
(D29) phenyl-lower alkoxy,
(D30) phenyl-lower alkoxyphenyl,
(D31) phenoxy,
(D32) phenoxy-lower alkyl,
(D33) phenoxypiperidyl,
(D34) morpholinyl-lower alkyl, and
(D35) hydrogen.

These groups (D1) to (D34) are optionally substituted on the ring(s) with at least one group (further 1 to 3, in particular 1 or 2 groups) selected from the group consisting of lower alkyl, halo-lower alkyl, lower alkylthio, lower alkoxy, halo-lower alkoxy, and halogen.

In Formula (2), when A is group (A10) or (A12), and B is group (B11), C is preferably selected from groups (C1) to (C27).

In Formula (2), A is preferably
(A1) tetrahydroisoquinolinediyl,
(A2) tetrahydroquinolinediyl,
(A9) quinolinediyl,
(A10) phenylene,
(A11) biphenyldiyl, or
(A12) pyridinediyl, these groups (A1), (A2), and (A9) to (A12) being optionally substituted on the ring(s) with at least one group (preferably 1, 2, or 3 groups) selected from the group consisting of halogen and lower alkyl.

Among the compounds represented by Formula (1), preferable compounds are those in which $R^1$ is a group represented by Formula (2),
wherein A is
(A1) tetrahydroisoquinolinediyl (preferably 1,2,3,4-tetrahydroisoquinoline-2,6-diyl),
(A2) tetrahydroquinolinediyl (preferably 1,2,3,4-tetrahydroquinoline-1,6-diyl),
(A9) quinolinediyl (preferably 2,6-quinolinediyl),
(A10) phenylene (preferably 1,4-phenylene),
(A11) biphenyldiyl (preferably 4,4'-biphenyldiyl), or
(A12) pyridinediyl (preferably 2,5-pyridinediyl), these groups (A1), (A2), (A9) to (A12) being optionally substituted on the ring(s) with one or two halogen atoms (preferably fluorine);

L1 is a single bond, lower alkylene, —O—, —O-lower alkylene, or lower alkylene-O—;

B is
(B7) oxazolediyl (preferably 2,4-oxazolediyl),
(B8) piperazinediyl (preferably 1,4-piperazinediyl),
(B9) piperidinediyl (preferably 1,4-piperidinediyl),
(B10) thiazolediyl (preferably 2,4-thiazolediyl), or
(B11) phenylene (preferably 1,4-phenylene), these groups (B7) to (B11) being optionally substituted on the ring with at least one or two groups selected from the group consisting of lower alkyl, lower alkoxy, halo-lower alkyl, halo-lower alkoxy, hydroxy, and halo-lower alkylsulfonyl;

L2 is a single bond, —N(lower alkyl)-, —O—, —O-lower alkylene, lower alkylene, lower alkylene-O—, or lower alkenylene;

C is
(C13) cyclohexanediyl,
(C20) piperidinediyl,
(C27) phenylene, or
(C28) single bond,
(with the proviso that when A is (A10) or (A12), and B is (B11), C is (C13), (C20), or (C27)), these groups (C13), (C20), and (C27) being optionally substituted on the ring with one or two groups selected from the group consisting of halo-lower alkoxy, halo-lower alkyl, hydroxy, and halo-lower alkylthio;

D is
(D21) phenyl-lower alkyl,
(D24) (phenyl-lower alkyl)amino,
(D29) phenyl-lower alkoxy,
(D31) phenoxy, or
(D35) hydrogen, these groups (D21), (D24), (D29), and (D31) being optionally substituted on the ring with one or two groups selected from the group consisting of halo-lower alkyl and halo-lower alkoxy.

Among the compounds represented by Formula (1), preferable compounds are those represented by Formula (1-1):

(1-1)

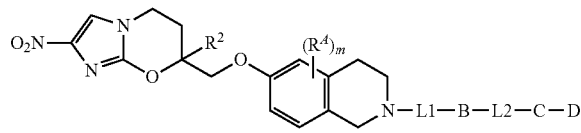

wherein $R^A$ is halogen or lower alkyl; m is 0, 1, or 2, wherein when m is 2, each $R^A$ may be the same or different; and $R^2$, L1, B, L2, C, and D are the same as defined above.

Among these, $R^A$ is preferably F.

m is preferably zero.

L1 is preferably lower alkylene (in particular —CH$_2$—).

B is preferably 1,4-phenylene.

L2 is preferably —O-lower alkylene (in particular —O—CH$_2$—).

C is preferably phenylene optionally substituted on the ring with one halo-lower alkyl (in particular trifluoromethyl).

D is preferably hydrogen.

Among the compounds represented by Formula (1), preferable compounds are those represented by Formula (1-2):

(1-2)

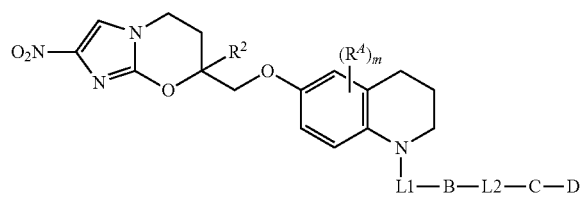

wherein $R^A$, m, $R^2$, L1, B, L2, C, and D are the same as defined above.

Among these, m is preferably zero.

L1 is preferably lower alkylene-O— (in particular trimethylene-O—).

B is preferably phenylene optionally substituted on the ring with one halo-lower alkoxy (in particular trifluoromethoxy).

L2 and C each represent a single bond.

D is preferably hydrogen.

Among the compounds represented by Formula (1), preferable compounds are those represented by Formula (1-3):

(1-3)

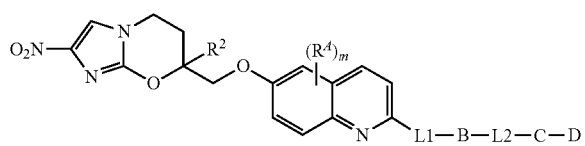

wherein $R^A$, m, $R^2$, L1, B, L2, C, and D are the same as defined above.

Among these, m is preferably zero.

L1 is preferably —O-lower alkylene (in particular —O—CH$_2$—).

B is preferably phenylene optionally substituted on the ring with one halo-lower alkoxy (in particular trifluoromethoxy).

L2 and C each represent a single bond.

D is preferably hydrogen.

Among the compounds represented by Formula (1), preferable compounds are those represented by Formula (1-4):

(1-4)

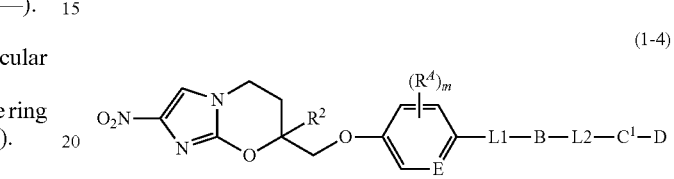

wherein E is N or CH; $C^1$ is a divalent group selected from groups (C1) to (C27) above (the substituents on the ring(s) of these groups are the same as defined above); and $R^A$, m, $R^2$, L1, B, L2, and D are the same as defined above.

Among these, $R^A$ is preferably F.

m is preferably 0 or 1, more preferably 0.

E is preferably CH.

L1 is preferably a single bond.

B is preferably 1,4-piperidinediyl or 1,4-piperazinediyl, each of which is optionally substituted on the ring with one or two substituents selected from the group consisting of lower alkyl (in particular methyl), halo-lower alkylsulfonyl (in particular perfluorobutylsulfonyl), and lower alkoxy (in particular methoxy).

L2 is preferably a single bond, lower alkylene, —O—, lower alkylene-O—, —N(lower alkyl)-, or lower alkenylene.

C is preferably phenylene, cyclohexanediyl, or piperidinediyl, each of which is optionally substituted on the ring with one or two groups selected from the group consisting of halo-lower alkoxy (in particular trifluoromethoxy), halo-lower alkyl (in particular trifluoromethyl), and halo-lower alkylthio (in particular trifluoromethylthio).

D is preferably phenyl-lower alkyl (in particular benzyl), (phenyl-lower alkyl)amino (in particular benzylamino), phenyl-lower alkoxy (in particular benzyloxy), phenoxy, or hydrogen, each of which is optionally substituted on the ring with one or two groups selected from the group consisting of halo-lower alkyl (in particular trifluoromethyl) and halo-lower alkoxy (in particular trifluoromethoxy).

Among the compounds represented by Formula (1), preferable compounds are those represented by Formula (1-5):

(1-5)

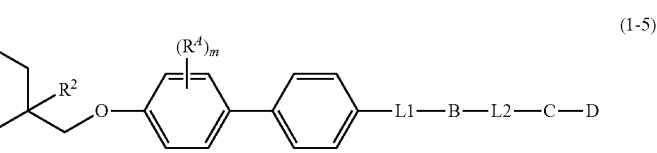

wherein $R^A$, m, $R^2$, L1, B, L2, C, and D are the same as defined above.

Among these, m is preferably zero.

L1 is preferably a single bond.

B is preferably piperidinediyl optionally substituted on the ring with one or two groups selected from the group consisting of halo-lower alkyl (in particular trifluoromethyl) and hydroxy.

L2 is preferably a single bond or —O—.

C is preferably a single bond or phenylene optionally substituted on the ring with one halo-lower alkoxy (in particular trifluoromethoxy).

D is preferably hydrogen or phenoxy optionally substituted on the ring with one halo-lower alkoxy (in particular trifluoromethoxy).

Among the compounds represented by Formula (1), preferable compounds are those represented by Formula (1a) to (1n) shown in Reaction Schemes 1 to 11 below.

Among the compounds represented by Formula (1), those described in Examples 1 to 772, and the salts thereof are furthermore preferable. The compounds described in the Examples 1, 3, 53, 56, 64, 79, 90, 143, 147, 153, 182, 198, 206, 228, 254, 282, 290, 299, 304, 335, 364, 372, 379, 380, 382, 383, 395, 400, 411, 414, 415, 446, 471, and 490, and salts thereof are still furthermore preferable.

In this specification, each of the divalent groups indicated by the letters A, L1, B, L2, and C, or by the structural formulae, in relation to the groups represented by Formula (2) above, can be attached in an arbitrary direction to the two groups on both sides of the divalent group. For example, when L1 is "lower alkylene-O—," its binding mode with groups A and B represents both "A-(lower alkylene-O)—B" and "A-(O-lower alkylene)-B." Of these, a preferable binding mode is such that the divalent group is attached as is as stated on the paper to a group represented by Formula (2) (-A-L1-B-L2-C-D) as stated on the paper. For example, when L1 is "lower alkylene-O—," a binding mode with groups A and B is preferably "A-(lower alkylene-O)—B."

The 6,7-dihydroimidazo[2,1-b][1,3]oxazine compound represented by Formula (1), or a salt thereof, can be produced, for example, in the following manner.

Reaction Scheme 1

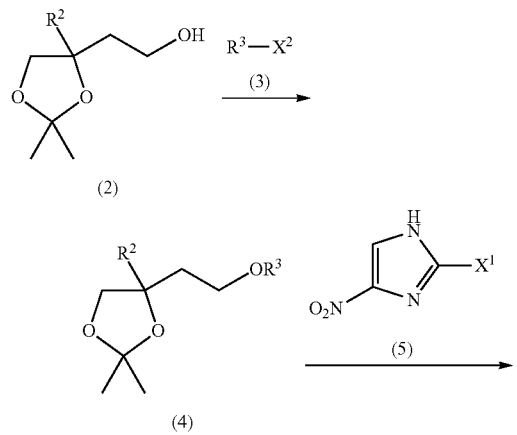

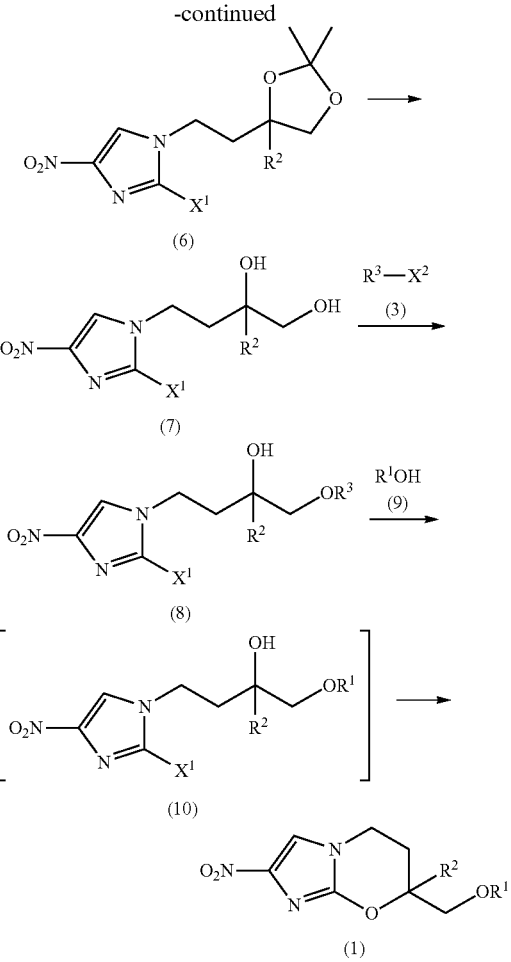

wherein $R^1$ and $R^2$ are the same as defined above; $R^3$ represents lower alkylsulfonyl optionally substituted with halogen, or benzenesulfonyl optionally substituted with lower alkyl or nitro; and $X^2$ and $X^2$ are the same or different and each represent halogen.

Examples of the lower alkylsulfonyl optionally substituted with halogen represented by $R^3$ include $C_{1-6}$ alkylsulfonyl optionally substituted with 1 to 3 halogen atoms, such as methanesulfonyl, ethanesulfonyl, and trifluoromethanesulfonyl.

Examples of the benzenesulfonyl optionally substituted with lower alkyl represented by $R^3$ include benzenesulfonyl optionally substituted with 1 to 3 $C_{1-6}$ alkyl groups, such as benzenesulfonyl and p-toluenesulfonyl.

Examples of the benzenesulfonyl optionally substituted with nitro represented by $R^3$ include benzenesulfonyl optionally substituted with 1 to 3 nitro groups, such as o-nitrobenzenesulfonyl and p-nitrobenzenesulfonyl.

The halogen represented by $X^2$ and $X^2$ is fluorine, chlorine, bromine, or iodine, with chlorine and bromine being preferable.

(2)+(3)→(4):

In the reaction of Compound (2) and Compound (3), the reaction conditions of a general sulfonylation reaction of alcohol can be widely applied. For example, Compound (4) can be produced by using Compound (2) and Compound (3) without a solvent or by dissolving them in an appropriate solvent (e.g., methylene chloride, acetonitrile, dimethylformamide (DMF), dimethylsulfoxide (DMSO), or toluene), and allowing a reaction to occur in the presence of a basic compound (e.g., potassium carbonate, potassium hydrogen carbonate, sodium carbonate, sodium hydrogen carbonate, pyridine, triethylamine, diisopropylethylamine, tetramethylethylenediamine (TMEDA), or tetramethylpropylenediamine (TMPDA)).

The basic compound is used in an amount of usually equimolar to excess mole, preferably 1- to 5-fold mol, and more preferably 1- to 2-fold mol, of Compound (2).

Compound (3) is used in an amount of usually equimolar to excess mole, preferably 0.9- to 2-fold mol, and more preferably 0.9- to 1.5-fold mol, of Compound (2).

The reaction temperature is usually −50 to 150° C., preferably −20 to 100° C., and more preferably −10 to 50° C. The reaction time is usually 10 minutes to 24 hours, preferably 10 minutes to 12 hours.

(4)+(5)→(6):

Compound (4) and Compound (5) can be reacted in an appropriate solvent (e.g., methylene chloride, acetonitrile, DMF, or dimethylacetamide (DMAc)) in the presence of a basic compound (e.g., potassium carbonate, potassium hydrogen carbonate, sodium carbonate, sodium hydrogen carbonate, pyridine, triethylamine, diisopropylethylamine, tetramethylethylenediamine (TMEDA), or tetramethylpropylenediamine (TMPDA)). As an activator, an alkali metal iodide, such as sodium iodide or potassium iodide, may also be added to the reaction system, if necessary.

The basic compound is used in an amount of usually equimolar to excess mole, preferably 1- to 5-fold mol, and more preferably 1- to 2-fold mol, of Compound (5).

When an activator is used, the amount of the activator is usually equimolar to excess mole, preferably 1- to 5-fold mol, and more preferably 1- to 2-fold mol, of Compound (5).

Compound (4) is used in an amount of usually 0.5-fold mol to excess mole, further equimolar to excess mole, preferably 0.9- to 2-fold mol, and more preferably 0.9- to 1.5-fold mol, of Compound (5).

The reaction temperature is usually −50 to 150° C., preferably −30 to 100° C., and more preferably −10 to 100° C. The reaction time is usually 10 minutes to 48 hours, preferably 10 minutes to 24 hours.

(6)→(7):

Compound (7) can be produced by subjecting Compound (6) to a hydrolysis reaction. In the hydrolysis reaction, known reaction conditions generally employed are applicable. For example, the reaction can be performed in an appropriate solvent (e.g., water or a mixed solvent of water with, for example, ethanol or tetrahydrofuran (THF)) in the presence of an acid (e.g., hydrochloric acid or sulfuric acid).

An acid is used in an amount of a catalytic amount to excess mole of Compound (6). The reaction temperature is usually 0 to 50° C. The reaction time is usually 10 minutes to 24 hours.

(7)+(3)→(8):

In the reaction of Compound (7) and Compound (3), the reaction conditions of a general sulfonylation reaction of alcohol can be widely applied. For example, the reaction can be performed under the same reaction conditions for producing Compound (4) from Compound (2) and Compound (3).

(8)+(9)→(10):

Compound (8) and Compound (9) can be reacted in an appropriate solvent in the presence of a basic compound.

Any known solvent can be used as long as it does not hinder the reaction. Examples of such solvents include water; DMF, DMSO, acetonitrile, and like aprotic polar solvents; benzene, toluene, xylene, tetralin, liquid paraffin, cyclohexane, and like hydrocarbon solvents; ethanol, isopropanol, n-butanol, tert-butanol, and like alcohol solvents; THF, dioxane, dipropyl ether, diethyl ether, diglyme, and like ether solvents; ethyl acetate, and like ester solvents; acetone, methylethylketone, and like ketone solvents; mixtures of such solvents; and the like.

Examples of basic compounds include sodium hydride and like alkali metal hydrides; sodium methoxide, sodium ethoxide, sodium tert-butoxide, potassium tert-butoxide, and like metal alcoholates; sodium hydroxide, potassium hydroxide, and like alkali metal hydroxides; sodium carbonate, potassium carbonate, cesium carbonate, and like alkali metal carbonates; sodium hydrogen carbonate, potassium hydrogen carbonate, and like alkali metal hydrogen carbonates; tripotassium phosphate and like alkali metal phosphates; sodium amide; sodium acetate, potassium acetate, and like acetates; triethylamine, trimethylamine, diisopropylethylamine, pyridine, dimethylaniline, 1-methylpyrrolidine, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO), and like nitrogen-containing organic bases. These bases can be used singly, or in a combination of two or more in an appropriate ratio.

As a catalyst (or a reaction promoter), for example, an alkali metal halide, such as cesium fluoride, or an alkali metal iodide, such as sodium iodide or potassium iodide, may be added, if necessary.

The basic compound is used in an amount of usually equimolar to excess mole, preferably 1- to 5-fold mol, and more preferably 1- to 2-fold mol, of Compound (8).

Compound (9) is used in an amount of usually 0.5- to 5-fold mol, preferably 0.8- to 2-fold mol, and more preferably 0.9- to 1.5-fold mol, of Compound (8).

When a catalyst is used, the amount of the catalyst is usually a catalytic amount to excess mole, preferably 0.01- to 5-fold mole, and more preferably 0.1- to 2-fold mol, of Compound (8).

The reaction temperature is usually −30 to 150° C., preferably −10 to 100° C., and more preferably −10 to 80° C. The reaction time is usually 10 minutes to 24 hours, preferably 10 minutes to 12 hours, and more preferably 20 minutes to 7 hours.

(10)→(1):

Compound (1) can be produced by subjecting Compound (10) to a ring-closure reaction.

The ring-closure reaction can be performed in an appropriate solvent (e.g., N-methylpyrrolidone (NMP), DMF, or DMAc) in the presence of a basic compound (e.g., sodium hydride or sodium tert-butoxide).

The basic compound is used in an amount of usually equimolar to excess mole, preferably 1- to 5-fold mol, and more preferably 1- to 2-fold mol, of Compound (10).

The reaction temperature is usually −50 to 150° C., preferably −20 to 100° C., and more preferably −10 to 50° C. The reaction time is usually 10 minutes to 100 hours, and preferably 10 minutes to 72 hours.

In the present invention, the reaction mixture obtained by the reaction of Compound (8) and Compound (9) can be subjected to the subsequent ring-closure reaction as is, without isolating Compound (10), to produce target Compound (1). Further, when the reaction is performed at usually −10 to 200° C., and preferably 0 to 100° C., using a basic compound in an amount of equimolar to excess mole of Compound (8), Compound (1) can be produced at once without isolation of the intermediate, i.e., Compound (10).

23

Reaction Scheme 2

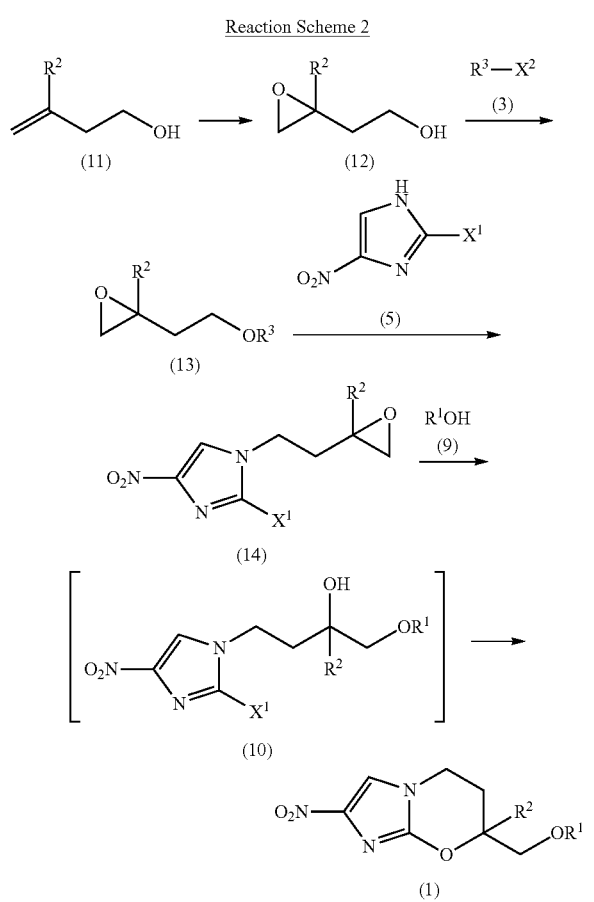

wherein $R^1$, $R^2$, $R^3$, $X^1$, and $X^2$ are the same as defined above.

(11)→(12):

Compound (12) can be produced by subjecting Compound (11) to an oxidation reaction. In the oxidation reaction, known reaction conditions generally employed can be widely applied. For example, the reaction can be carried out by reacting Compound (12) with an oxidizing agent (e.g., m-chloroperbenzoic acid (mCPBA) or hydrogen peroxide) in an appropriate solvent.

(12)+(3)→(13):

In the reaction of Compound (12) and Compound (3), the reaction conditions of a general sulfonylation reaction of alcohol can be widely applied. For example, the reaction can be performed under the same reaction conditions as employed in Reaction Scheme 1 for producing Compound (4) from Compound (2) and Compound (3).

(13)+(5)→(14):

The reaction of Compound (13) and Compound (5) can be performed under the same reaction conditions as employed in Reaction Scheme 1 for producing Compound (6) from Compound (4) and Compound (5).

(14)+(9)→(10):

The reaction of Compound (14) and Compound (9) can be performed under the same reaction conditions as employed in Reaction Scheme 1 for producing Compound (10) from Compound (8) and Compound (9).

(10)→(1):

The reaction for producing Compound (1) from Compound (10) can be performed under the same reaction conditions as employed in Reaction Scheme 1 for producing Compound (1) from Compound (10).

24

In the present invention, the reaction mixture obtained by the reaction of Compound (14) and Compound (9) can be subjected to the subsequent ring-closure reaction as is, without isolating Compound (10), to produce target Compound (1). Further, when the reaction is performed at usually −10 to 200° C., and preferably 0 to 100° C., using a basic compound in an amount of equimolar to excess mole of Compound (14), Compound (1) can be produced at once without isolation of the intermediate, i.e., Compound (10)

Reaction Scheme 3

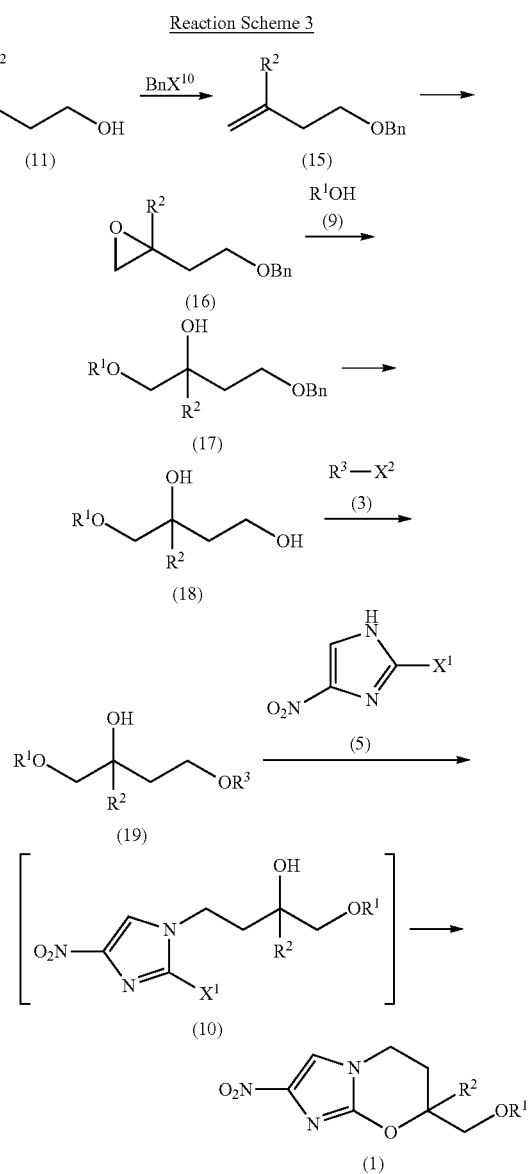

wherein $R^1$, $R^2$, $R^3$, $X^1$, and $X^2$ are the same as defined above, and $X^{10}$ represents halogen.

Examples of the halogen represented by $X^{10}$ include chlorine, bromine, and iodine.

(11)→(15):

Compound (15) can be produced by reacting Compound (11) with a benzyl halide (e.g., benzyl chloride or benzyl bromide) in an appropriate solvent in the presence of a basic compound (an O-benzylation reaction). In the O-benzylation reaction, known reaction conditions generally employed can be widely applied.

(15)→(16):

The reaction for producing Compound (16) from Compound (15) can be performed under the same reaction conditions as employed in Reaction Scheme 2 for producing Compound (12) from Compound (11).

(16)+(9)→(17):

The reaction for producing Compound (17) from Compound (16) and Compound (9) can be performed under the same reaction conditions as employed in Reaction Scheme 2 for producing Compound (10) from Compound (14) and Compound (9).

(17)→(18):

Compound (17) can be produced by subjecting Compound (18) to debenzylation. In the debenzylation reaction, known reaction conditions generally employed can widely be applied. For example, the reaction can be performed by subjecting Compound (17) to catalytic hydrogenation.

(18)+(3)→(19):

In the reaction of Compound (18) and Compound (3), the reaction conditions of a general sulfonylation reaction of alcohol can be widely applied. For example, the reaction can be performed under the same reaction conditions as employed in Reaction Scheme 1 for producing Compound (4) from Compound (2) and Compound (3).

(19)+(5)→(10):

The reaction of Compound (19) and Compound (5) can be performed under the same reaction conditions as employed in Reaction Scheme 1 for producing Compound (6) from Compound (4) and Compound (5).

(10)→(1):

The reaction for producing Compound (1) from Compound (10) can be performed under the same reaction conditions as employed in Reaction Scheme 1 for producing Compound (1) from Compound (10).

In the present invention, the reaction mixture obtained by the reaction of Compound (19) and Compound (5) can be subjected to the subsequent ring-closure reaction as is, without isolating Compound (10), to produce target Compound (1). Further, when the reaction is performed at usually −10 to 200° C., and preferably 0 to 100° C., using a basic compound in an amount of equimolar to excess mole of Compound (19), Compound (1) can be produced at once without isolation of the intermediate, i.e., Compound (10)

Reaction Scheme 4

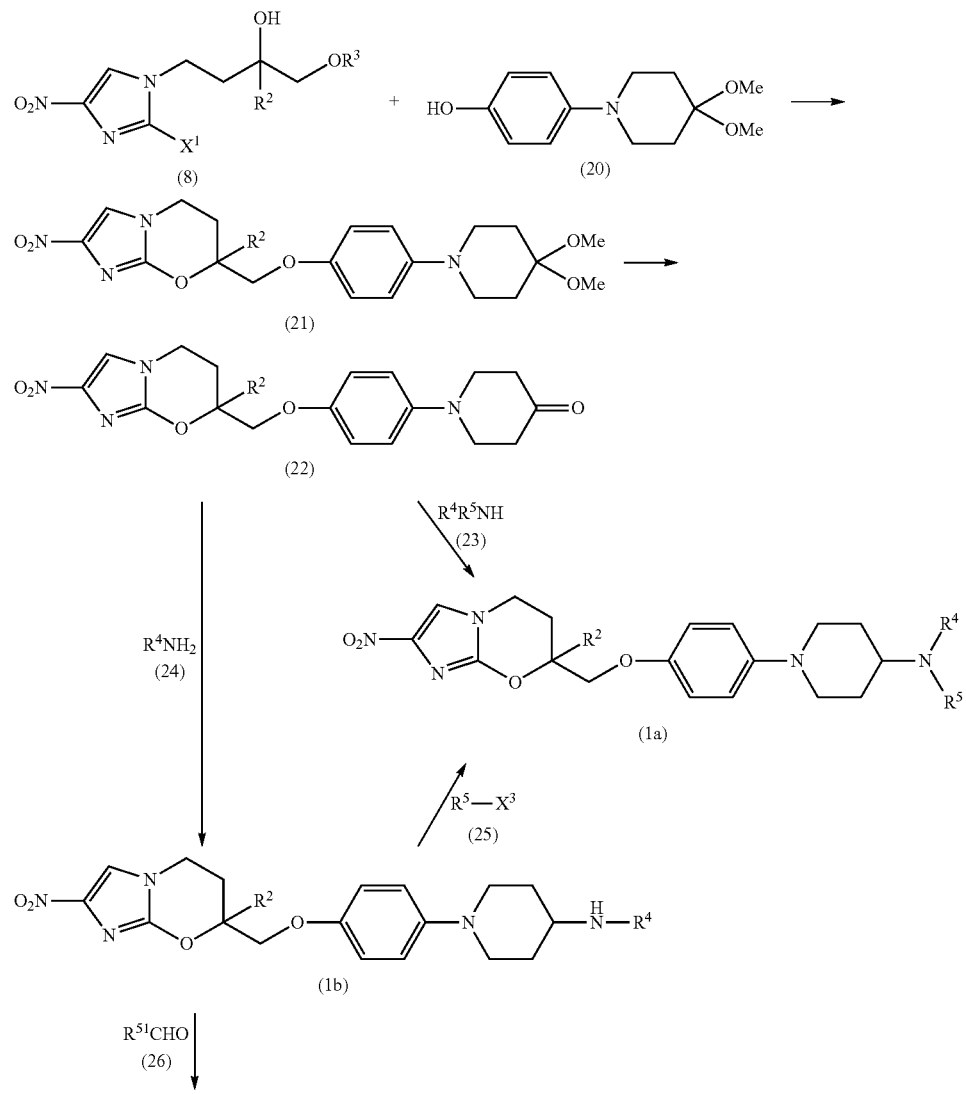

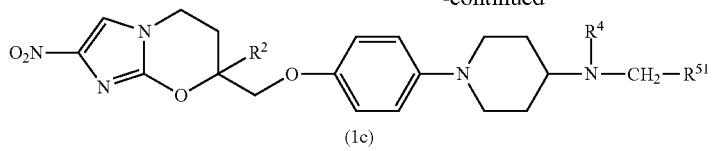

(1c)

wherein $R^2$, $R^3$, and $X^1$ are the same as defined above; $R^4$ represents a group represented by the above-mentioned —C-D; $R^5$ represents lower alkyl; $R^{51}$ represents lower alkyl; and $X^3$ represents a leaving group.

Examples of the lower alkyl represented by $R^5$ include straight- or branched-chain alkyl groups having 1 to 6 carbon atoms, such as methyl, ethyl, n-propyl, isopropyl, n-butyl, isobutyl, tert-butyl, sec-butyl, n-pentyl, neopentyl, n-hexyl, isohexyl, and 3-methylpentyl.

Examples of the lower alkyl represented by $R^{51}$ include straight- or branched-chain alkyl groups having 1 to 5 carbon atoms, such as methyl, ethyl, n-propyl, isopropyl, n-butyl, isobutyl, tert-butyl, sec-butyl, n-pentyl, and neopentyl.

Examples of the leaving group represented by $X^3$ include halogen (e.g., chlorine, bromine, and iodine), sulfonyloxy (e.g., p-toluenesulfonyloxy, o- or p-nitrobenzenesulfonyloxy, and methanesulfonyloxy), and the like.

(8)+(20)→(21):

The reaction for producing Compound (21) from Compound (8) and Compound (20) can be performed under the same reaction conditions as employed in Reaction Scheme 1 for producing Compound (1) through Compound (10) obtained from Compound (8) and Compound (9).

(21)→(22):

The reaction for producing Compound (22) from Compound (21) can be performed under the same reaction conditions as employed in Reaction Scheme 1 for producing Compound (7) from Compound (6).

(22)+(23)→(1a):

The reaction of Compound (22) and Compound (23) can be performed without a solvent or in an appropriate solvent in the presence of a reducing agent (a reductive amination reaction).

Compound (23) is used in an amount of usually 0.5- to 10-fold mol, preferably 0.6- to 5-fold mol, and more preferably 0.7- to 2-fold mol, of Compound (22).

Examples of solvents include water; methanol, ethanol, isopropanol, butanol, tert-butanol, ethylene glycol, and like lower alcohols; acetonitrile; formic acid, acetic acid, trifluoroacetic acid, and like fatty acids; diethyl ether, THF, dioxane, monoglyme, diglyme, and like ethers; benzene, toluene, xylene, and like aromatic hydrocarbons; dichloromethane, dichloroethane, chloroform, carbon tetrachloride, and like halogenated hydrocarbons; mixtures of such solvents; and the like.

Examples of reducing agents include formic acid, sodium formate, and like alkali metal formates; sodium borohydride, sodium cyanoborohydride, sodium triacetoxyborohydride, lithium aluminium hydride, and like hydride reducing agents or mixtures of these hydride reducing agents; palladium black, palladium carbon, platinum oxide, platinum black, Raney nickel, and like catalytic hydrogenation reducing agents.

When formic acid and/or an alkali metal formate is used as a reducing agent, a suitable reaction temperature is usually from about room temperature to 200° C., and preferably about 50 to 150° C. The reaction completes in about 10 minutes to 10 hours. The formic acid and/or alkali metal formate is preferably used in a large excess relative to Compound (22).

When a hydride reducing agent is used, a suitable reaction temperature is usually about −80 to 100° C., and preferably about −80 to 70° C., and the reaction completes in about 30 minutes to 100 hours. A hydride reducing agent may be used in an amount of usually about equimolar to 20-fold mol, and preferably about equimolar to 6-fold mol, of Compound (22). To the reaction system of the reaction may be added an acid, such as acetic acid, formic acid, or tetraisopropoxy titanium; an amine, such as trimethylamine, triethylamine, and N-ethyldiisopropylamine; molecular sieves, such as molecular sieves 3A (MS-3A) and molecular sieves 4A (MS-4A), and the like.

When a catalytic hydrogenation reducing agent is used, the reaction is performed at a temperature of usually about −30 to 100° C., and preferably about 0 to 60° C., in a hydrogen atmosphere at a pressure of usually about atmospheric pressure to 20 atm, and preferably about atmospheric pressure to 10 atm, or in the presence of a hydrogen donor, such as formic acid, ammonium formate, cyclohexene, or hydrazine hydrate. The reaction usually completes in about 1 to 12 hours. The catalytic hydrogenation reducing agent is usually used in an amount of about 0.1 to 40 wt %, and preferably about 1 to 20 wt %, of compound (22).

(22)+(24)→(1b):

The reaction of Compound (22) and Compound (24) can be performed under the same reaction conditions as employed in the reaction for producing Compound (1a) from Compound (22) and Compound (23).

(1b)+(25)→(1a):

In the reaction of Compound (1b) and Compound (25), the reaction conditions employed in a general N-alkylation reaction can be widely applied. For example, the reaction can be carried out by reacting Compound (1b) with Compound (25) in an appropriate solvent in the presence of a basic compound.

(1b)+(26)→(1c):

The reaction of Compound (1b) and Compound (26) can be performed under the same reaction conditions as employed in the reaction for producing Compound (1a) from Compound (22) and Compound (23).

Reaction Scheme 5

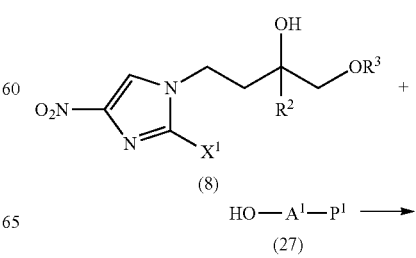

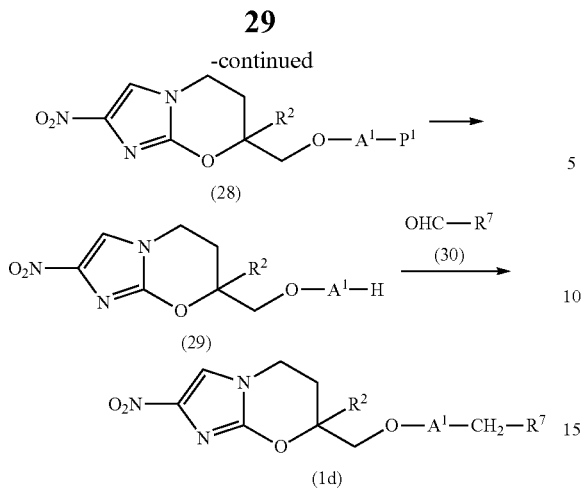

(28)

(29)

(1d)

wherein $R^2$, $R^3$, and $X^1$ are the same as defined above; $A^1$ is tetrahydroisoquinolinediyl, tetrahydroquinolinediyl, tetrahydrobenzoazepinediyl, or isoindolinediyl (these groups are optionally substituted on the ring(s) with at least one group selected from the group consisting of halogen and lower alkyl) and represents a group in which the atom attached to $P^1$ is nitrogen; $R^7$ is a group represented by the above-mentioned —C-D; and $P^1$ represents a protecting group of nitrogen.

The protecting group of nitrogen represented by $P^1$ is not particularly limited as long as it does not have an adverse effect on the reaction. Examples thereof include formyl, lower alkyl carbonyl (e.g., acetyl and ethylcarbonyl), phenylcarbonyl, lower alkoxycarbonyl (e.g., methoxycarbonyl, ethoxycarbonyl, and tert-butoxycarbonyl (Boc)), benzyloxycarbonyl (Cbz), allyloxycarbonyl (Alloc), and the like. These protecting groups are further optionally substituted with 1 to 5, (e.g., 1 to 3) substituents, such as halogen (fluorine, chlorine, bromine, or iodine) or nitro. Boc is a preferable protecting group of nitrogen.

(8)+(27)→(28):

The reaction for producing Compound (28) from Compound (8) and Compound (27) can be performed under the same reaction conditions as employed in Reaction Scheme 1 for producing Compound (1) through Compound (10) obtained from Compound (8) and Compound (9).

(28)→(29):

Compound (29) can be obtained by performing deprotection of $P^1$ from Compound (28). A deprotection reaction may be performed in accordance with a general method for deprotection of a nitrogen protecting group, for example, a method disclosed in Green's Protective Groups in Organic Synthesis, -4-th ed. John Wiley & Sons, Inc. For example, when $P^1$ is Boc, Compound (28) can be subjected to a deprotection reaction without a solvent or in an appropriate solvent in the presence of an acid (e.g., hydrochloric acid or trifluoroacetic acid). When $P^1$ is Cbz, the reaction can be performed without a solvent or in an appropriate solvent in the presence of a reducing agent (e.g., an alkali metal formate, a hydride reducing agent, or a catalytic hydrogenation reducing agent). When $P^1$ is Alloc, the deprotection reaction can be performed in the presence of a palladium catalyst.

(29)+(30)→(1d):

The reaction of Compound (29) and Compound (30) can be performed under the same reaction conditions as employed in Reaction Scheme 4 for producing Compound (1a) from Compound (22) and Compound (23).

Reaction Scheme 6

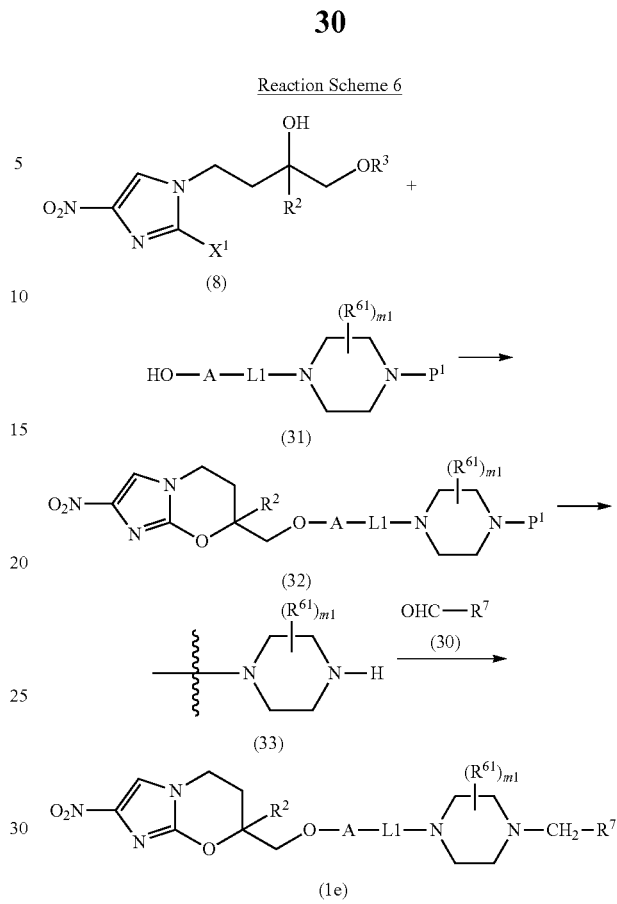

(8)

(31)

(32)

(33)

(1e)

wherein A, L1, $R^2$, $R^3$, $R^7$, $X^1$ and $P^1$ are the same as defined above; $R^{61}$ represents lower alkyl, halo-lower alkyl, or alkenyl; and m1 represents 0, 1, or 2.

Examples of the lower alkyl represented by $R^{61}$ include straight- or branched-chain alkyl groups having 1 to 6 carbon atoms, such as methyl, ethyl, n-propyl, isopropyl, n-butyl, isobutyl, tert-butyl, sec-butyl, n-pentyl, neopentyl, n-hexyl, isohexyl, and 3-methylpentyl.

The halo-lower alkyl represented by $R^{61}$ is a group in which at least one hydrogen atom (e.g., 1 to 10, further 1 to 6, in particular 1 to 3 hydrogen atoms) of the above-mentioned "lower alkyl" is substituted with halogen(s). Examples thereof include trihalomethyl (e.g., —$CF_3$), trihaloethyl (e.g., —$CH_2CF_3$), pentahaloethyl (e.g., —$CF_2CF_3$), and nonahalobutyl (e.g., —$CF_2CF_2CF_2CF_3$).

Examples of the alkenyl represented by $R^{61}$ include straight- or branched-chain alkenyl groups having 2 to 6 carbon atoms, such as methyl, vinyl, 1-propenyl, allyl, 1-, 2-, or 3-butenyl, 1,3-butanedienyl, 1-, 2-, 3-, or 4-pentenyl, heptenyl, octenyl, nonenyl, decenyl, dodecenyl, and —$CH_2CH=C(CH_3)CH_2CH_2CH=C(CH_3)_2$.

A is preferably phenylene, and more preferably para-phenylene.

L1 is preferably a single bond.

(8)+(31)→(32):

The reaction for producing Compound (32) from Compound (8) and Compound (31) can be performed under the same reaction conditions as employed in Reaction Scheme 1 for producing Compound (1) through Compound (10) obtained from Compound (8) and Compound (9).

(32)→(33):

Compound (33) can be obtained by performing deprotection of $P^1$ from Compound (32). The deprotection reaction can be performed under the same reaction conditions as employed in Reaction Scheme 5 for producing Compound (29) from Compound (28).

(33)+(30)→(1e):

The reaction of Compound (33) and Compound (30) can be performed under the same reaction conditions as employed in Reaction Scheme 4 for producing Compound (1a) from Compound (22) and Compound (23).

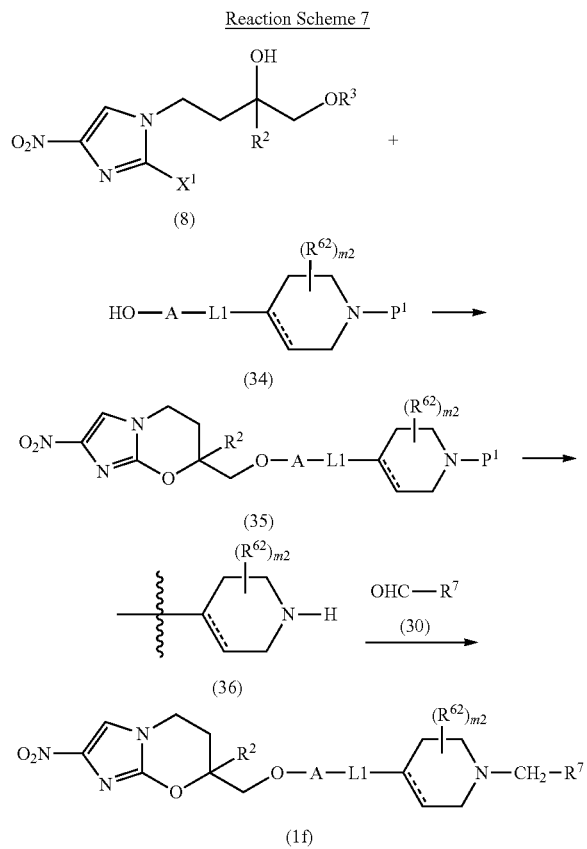

wherein A, L1, $R^2$, $R^3$, $R^7$, $X^1$, and $P^1$ are the same as defined above; $R^{62}$ represents lower alkyl, halo-lower alkyl, alkenyl, lower alkoxy, halo-lower alkoxy, or hydroxy; m2 represents 0, 1, or 2; and the dashed lines indicate that the bond may be a double bond.

The lower alkyl, halo-lower alkyl, and alkenyl represented by $R^{62}$ are the same as defined above for $R^{61}$.

Examples of the lower alkoxy represented by $R^{62}$ include straight- or branched-chain alkoxy groups having 1 to 6 carbon atoms, such as methoxy, ethoxy, n-propoxy, isopropoxy, n-butoxy, isobutoxy, tert-butoxy, sec-butoxy, n-pentyloxy, neopentyloxy, n-hexyloxy, isohexyloxy, and 3-methylpentyloxy.

Examples of the halo-lower alkoxy represented by $R^{62}$ include a group in which at least one hydrogen atom (e.g., 1 to 10, further 1 to 6, in particular 1 to 3 hydrogen atoms) of the above-mentioned "lower alkoxy" is substituted with halogen (s). Examples thereof include trihalomethoxy (e.g., —$OCF_3$), pentahaloethyl (e.g., —$CF_2CF_3$), and nonahalobutyl (e.g., —$CF_2CF_2CF_2CF_3$).

A is preferably phenylene, and more preferably para-phenylene.

L1 is preferably a single bond.

(8)+(34)→(35):

The reaction for producing Compound (35) from Compound (8) and Compound (34) can be performed under the same reaction conditions as employed in Reaction Scheme 1 for producing Compound (1) through Compound (10) obtained from Compound (8) and Compound (9).

(35)→(36):

Compound (36) can be obtained by performing deprotection of $P^1$ from Compound (35). The deprotection reaction can be performed under the same reaction conditions as employed in Reaction Scheme 5 for producing Compound (29) from Compound (28).

(36)+(30)→(1f):

The reaction of Compound (36) and Compound (30) can be performed under the same reaction conditions as employed in Reaction Scheme 4 for producing Compound (1a) from Compound (22) and Compound (23).

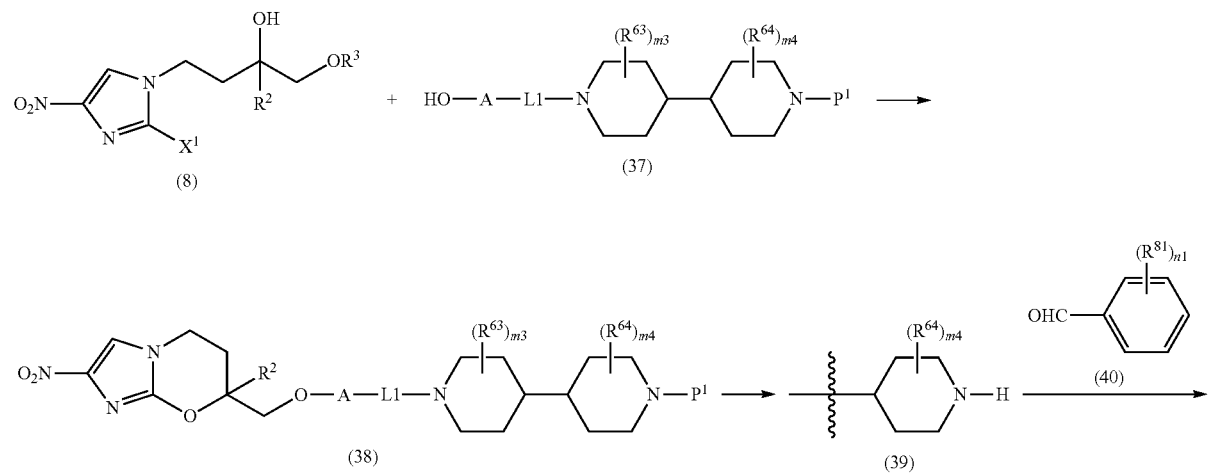

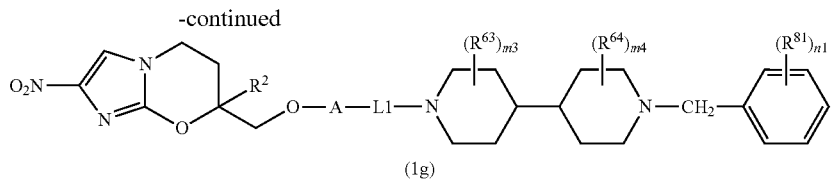

(1g)

wherein A, L1, $R^2$, $R^3$, $X^1$, and $P^2$ are the same as defined above; $R^{63}$ and $R^{64}$ are the same or different and each represent lower alkyl, halo-lower alkyl, alkenyl, lower alkoxy, halo-lower alkoxy, or hydroxy; m3 and m4 are the same or different and each represent 0, 1, or 2; $R^{81}$ represents lower alkyl, halo-lower alkyl, lower alkoxy, halo-lower alkoxy, or hydroxy; and n1 represents an integer of 1 to 5.

The lower alkyl, halo-lower alkyl, alkenyl, lower alkoxy, halo-lower alkoxy, and hydroxy represented by $R^{63}$, $R^{64}$, or $R^{81}$ are the same as those defined above for $R^{62}$.

A is preferably phenylene, and more preferably para-phenylene.

L1 is preferably a single bond.

(8)+(37)→(38):

The reaction for producing Compound (38) from Compound (8) and Compound (37) can be performed under the same reaction conditions as employed in Reaction Scheme 1 for producing Compound (1) through Compound (10) obtained from Compound (8) and Compound (9).

(38)→(39):

Compound (39) can be obtained by performing deprotection of $P^1$ from Compound (38). The deprotection reaction can be performed under the same reaction conditions as employed in Reaction Scheme 5 for producing Compound (29) from Compound (28).

(39)+(40)→(1g):

The reaction of Compound (39) and Compound (40) can be performed under the same reaction conditions as employed in Reaction Scheme 4 for producing Compound (1a) from Compound (22) and Compound (23).

Reaction Scheme 9

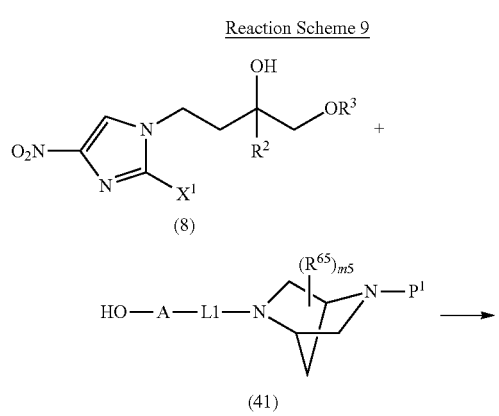

(8)

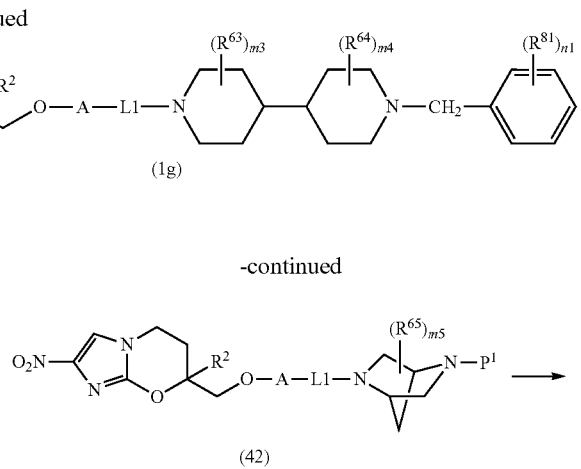

(42)

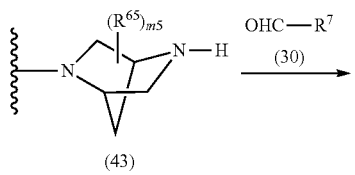

(43)

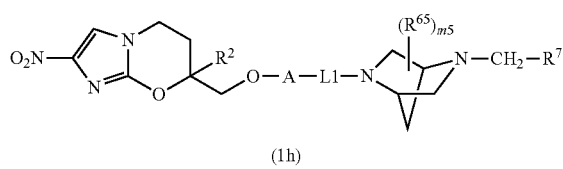

(1h)

wherein A, L1, $R^2$, $R^3$, $R^7$, $X^1$, and $P^1$ are the same as defined above; $R^{65}$ represents lower alkyl or halo-lower alkyl; and m5 represents 0 or 1.

(8)+(41)→(42):

The reaction for producing Compound (42) from Compound (8) and Compound (41) can be performed under the same reaction conditions as employed in Reaction Scheme 1 for producing Compound (1) through Compound (10) obtained from Compound (8) and Compound (9).

(42)→(43):

Compound (43) can be produced by performing deprotection of $P^1$ from Compound (42). The deprotection reaction can be performed under the same reaction conditions as employed in Reaction Scheme 5 for producing Compound (29) from Compound (28).

(43)+(30)→(1h):

The reaction of Compound (43) and Compound (30) can be performed under the same reaction conditions as employed in Reaction Scheme 4 for producing Compound (1a) from Compound (22) and Compound (23).

Reaction Scheme 10

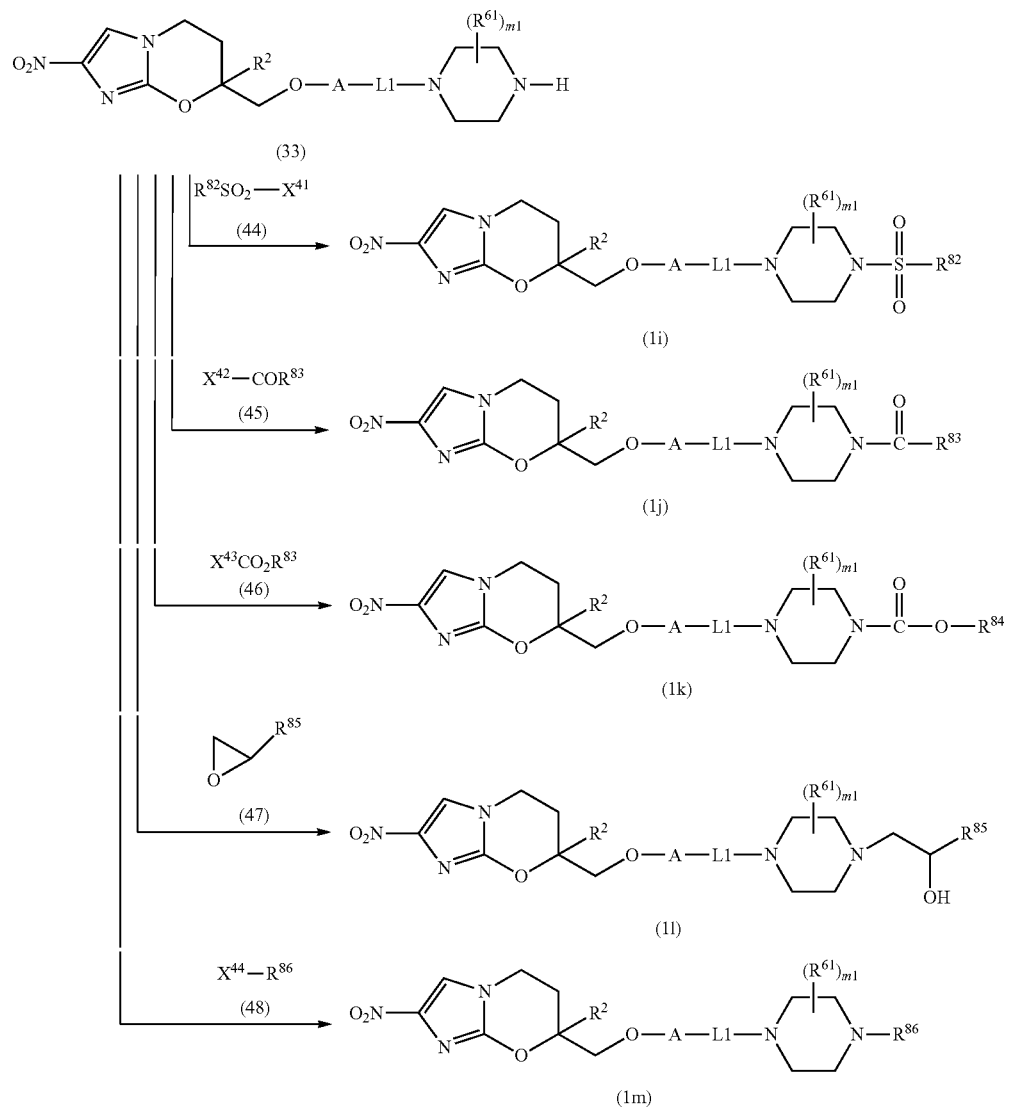

wherein A, L1, R², R⁶¹, and m1 are the same as defined above; R⁸² represents lower alkyl or halo-lower alkyl; R⁸³ represents a group represented by —C-D; R⁸⁴ represents a group represented by -L2¹-C-D, wherein L2¹ represents lower alkynylene, lower alkylene (this lower alkylene is optionally substituted with phenyl), or lower alkenylene; R⁸⁵ is a group represented by -L2²-C-D, wherein L2² represents a single bond or lower alkylene-O—; R⁸⁶ represents a group represented by -L2-C-D; and X⁴¹, X⁴², X⁴³, and X⁴⁴ each represent a leaving group.

Examples of the leaving group represented by X⁴¹ include halogen (e.g., chlorine and bromine) and a group represented by O—SO₂R⁸².

Examples of the leaving group represented by X⁴² include halogen (e.g., chlorine and bromine), hydroxy, and the like.

Examples of the leaving group represented by X⁴³ include halogen (e.g., chlorine and bromine).

Examples of the leaving group represented by X⁴⁴ include halogen (e.g., chlorine and bromine), sulfonyloxy (e.g., p-toluenesulfonyloxy, o- or p-nitrobenzenesulfonyloxy, methanesulfonyloxy, and trifluoromethanesulfonyloxy), and the like.

(33)+(44)→(1i):

In the reaction of Compound (33) and Compound (44), the reaction conditions of a general sulfonylation reaction of amine can be widely applied. For example, Compound (1i) can be produced by using Compound (33) and Compound (44) without a solvent or by dissolving them in an appropriate solvent (e.g., methylene chloride, acetonitrile, DMF, DMSO, or toluene) and allowing a reaction to occur in the presence of a basic compound (e.g., triethylamine or diisopropylethylamine).

The basic compound is used in an amount of usually equimolar to excess mole, preferably 1- to 5-fold mol, and more preferably 1- to 4-fold mol, of Compound (33).

Compound (44) is used in an amount of usually equimolar to excess mole, preferably 1- to 2-fold mol, and more preferably 1- to 1.5-fold mol, of Compound (33).

The reaction temperature is usually −50 to 150° C., preferably −20 to 100° C., and more preferably −10 to 50° C. The reaction time is usually 10 minutes to 24 hours, and preferably 10 minutes to 12 hours.

(33)+(45)→(1j):

In the reaction of Compound (33) and Compound (45), the reaction conditions of a general acylation reaction of amine can be widely applied.

For example, when $X^{42}$ of Compound (45) is halogen, Compound (1j) can be produced by using Compound (33) and Compound (45) without a solvent or by dissolving them in an appropriate solvent (e.g., methylene chloride, acetonitrile, DMF, DMSO, or toluene) and allowing a reaction to occur in the presence of a basic compound (e.g., potassium carbonate, potassium hydrogen carbonate, sodium carbonate, sodium hydrogen carbonate, pyridine, triethylamine, or diisopropylethylamine).

When $X^{42}$ of Compound (45) is hydroxy, Compound (1j) can be produced by using Compound (33) and Compound (45) without a solvent or by dissolving them in an appropriate solvent (e.g., methylene chloride, acetonitrile, DMF, DMSO, or toluene) and allowing a reaction to occur in the presence of a reaction to occur in the presence of a basic compound (e.g., potassium carbonate, potassium hydrogen carbonate, sodium carbonate, sodium hydrogen carbonate, pyridine, triethylamine, or diisopropylethylamine).

(33)+(47)→(1l):

In the reaction of Compound (33) and Compound (47), the reaction conditions of a ring-opening reaction of epoxy with amine can be widely applied.

For example, Compound (1l) can be produced by using Compound (33) and Compound (47) without a solvent or by dissolving them in an appropriate solvent (e.g., methylene chloride, acetonitrile, DMF, DMSO, NMP, or toluene) and allowing a reaction to occur.

(33)+(48)→(1m):

In the reaction for producing Compound (1m) from Compound (33) and Compound (48), the reaction conditions of a general alkylation reaction of amine can be widely applied. For example, the reaction can be performed under the same reaction conditions as employed in Reaction Scheme 4 for producing Compound (1a) from Compound (1b) and Compound (25).

Reaction Scheme 11

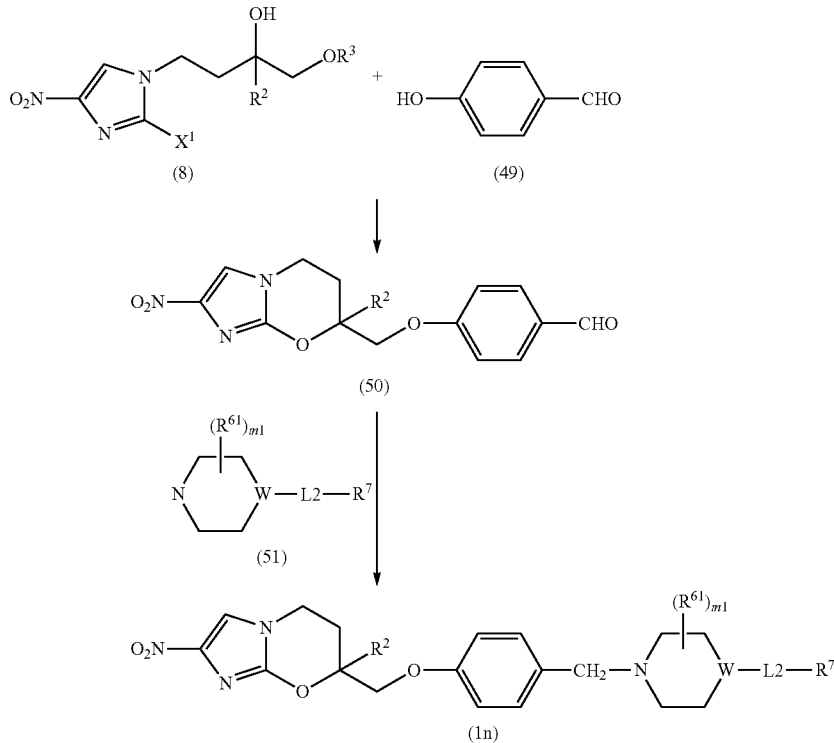

wherein $R^2$, $R^3$, $R^7$, $X^1$, $R^{61}$, m1, and L2 are the same as defined above; and W represents N or CH.

(8)+(49)→(50):

The reaction for producing Compound (50) from Compound (8) and Compound (49) can be performed under the same reaction conditions as employed in Reaction Scheme 1 for producing Compound (1) through Compound (10) obtained from Compound (8) and Compound (9).

(50)+(51)→(1n):

The reaction for producing Compound (1n) from Compound (50) and Compound (51) can be performed under the a suitable condensing agent (e.g., 1-ethyl-3-(3-dimethylaminopropyl)carbodiimide hydrochloride/1-hydroxybenzotriazole).

(33)+(46)→(1k):

In the reaction of Compound (33) and Compound (46), the reaction conditions of a general urethanation reaction of amine can be widely applied.

For example, Compound (1k) can be produced by using Compound (33) and Compound (46) without a solvent or by dissolving them in an appropriate solvent (e.g., methylene chloride, acetonitrile, DMF, DMSO, or toluene) and allowing same reaction conditions as employed in Reaction Scheme 4 for producing Compound (1a) from Compound (22) and Compound (23).

The compounds of Formula (1) according to the present invention, the intermediate compounds thereof, and the starting material compounds thereof can be produced by the above-described synthesis processes. They can also be produced based on the synthesis processes described in the Reference Examples and Examples of this specification in light of a technique that is well known or known at the time of the filing of this application.

Before subjecting the starting material compounds and intermediate compounds shown in each of the schemes above to each reaction, the functional groups thereof can be protected with suitable protecting groups using a well known method, if necessary, and, after completion of the reaction, deprotection of the protecting groups can be carried out by a well known method.

Each of the target compounds obtained in accordance with the above schemes can be isolated and purified. For example, after cooling the reaction mixture, an isolation procedure, such as filtration, concentration, or extraction, is performed to separate a crude reaction product, and thereafter, the crude reaction product is subjected to a general purifying procedure, such as column chromatography or recrystallization, thereby enabling isolation and purification from the reaction mixture.

The starting material compounds and the target compounds shown in each scheme above include those in the form of a solvate with a solvent (e.g., hydrate and ethanol solvate).

The compounds of Formula (1) according to the present invention (the final compound), the intermediate compounds obtained in each scheme above, and the starting material compounds thereof include geometrical isomers, stereoisomers, and optical isomers.

Various isomers can be isolated by well known separation methods. For example, a racemic compound can be led to a stereochemically pure isomer by a general optical resolution method (e.g., optical resolution by crystallization, or direct optical resolution by chromatography). Further, an optically active compound can also be produced by the use of a suitable optically active starting material.

The starting material compounds and the target compounds shown in each of the schemes above can be used in the form of an appropriate salt.

The compounds of the present invention include pharmaceutically acceptable salts. Among the compounds of the present invention, those containing a basic group or basic groups can form salts with general pharmaceutically acceptable acids. Examples of such acids include hydrochloric acid, hydrobromic acid, nitric acid, sulfuric acid, phosphoric acid, and like inorganic acids, and methanesulfonic acid, p-toluenesulfonic acid, acetic acid, citrate, tartaric acid, maleic acid, fumaric acid, malic acid, lactic acid, and like organic acids.

Among the compounds of the present invention, those containing an acidic group or acidic groups can form salts with pharmaceutically acceptable basic compounds. Examples of such basic compounds include sodium hydroxide, potassium hydroxide, calcium hydroxide, sodium carbonate, potassium carbonate, sodium hydrogen carbonate, potassium hydrogen carbonate, and the like.

In the compounds of the present invention, one or more atoms can be substituted with one or more isotope atoms. Examples of isotope atoms include deuterium ($^2$H), tritium ($^3$H), $^{13}$C, $^{14}$N, $^{18}$O, and the like.

The following describes pharmaceutical preparations (pharmaceutical compositions) comprising a compound of the present invention as an active ingredient.

Such pharmaceutical preparations are obtained by formulating a compound of the present invention into usual pharmaceutical preparations, using a compound of the present invention and a pharmaceutically acceptable carrier. Examples of such carriers include usually employed diluents and excipients, such as fillers, extenders, binders, wetting agents, disintegrants, surfactants, and lubricants.

The form of such pharmaceutical preparations can be selected from various forms, depending on the therapeutic purpose. Typical examples thereof include tablets, pills, powders, solutions, suspensions, emulsions, granules, capsules, suppositories, injections (solutions, suspensions, etc.), and the like.

To form tablets, any of various known carriers can be used, including, for example, lactose, sucrose, sodium chloride, glucose, urea, starch, calcium carbonate, kaolin, crystalline cellulose, and like excipients; water, ethanol, propanol, simple syrup, glucose solutions, starch solutions, gelatin solutions, carboxymethylcellulose, shellac, methylcellulose, potassium phosphate, polyvinylpyrrolidone, and like binders; dry starch, sodium alginate, agar powder, laminaran powder, sodium hydrogen carbonate, calcium carbonate, polyoxyethylene sorbitan fatty acid esters, sodium lauryl sulfate, stearic acid monoglyceride, starch, lactose, and like disintegrants; sucrose, stearin, cacao butter, hydrogenated oils, and like disintegration inhibitors; quaternary ammonium base, sodium lauryl sulfate, and like absorption promoters; glycerin, starch, and other wetting agents; starch, lactose, kaolin, bentonite, colloidal silica, and like adsorbents; purified talc, stearates, boric acid powder, polyethylene glycol, and like lubricants; and the like.

Such tablets may be coated with usual coating materials as required, to prepare, for example, sugar-coated tablets, gelatin-coated tablets, enteric-coated tablets, film-coated tablets, or double- or multi-layered tablets.

To form pills, any of various known carriers can be used, including, for example, glucose, lactose, starch, cacao butter, hydrogenated vegetable oils, kaolin, talc, and other excipients; gum arabic powder, tragacanth powder, gelatin, ethanol, and other binders; laminaran, agar, and other disintegrants; etc.

To form suppositories, any of various known carriers can be used, including, for example, polyethylene glycol, cacao butter, higher alcohols, esters of higher alcohols, gelatin, semi-synthetic glycerides, etc.

To form an injection, a solution, emulsion, or suspension is sterilized and preferably made isotonic with blood. Any of various known widely used diluents can be employed to prepare the solution, emulsion, or suspension. Examples of such diluents include water, ethanol, propylene glycol, ethoxylated isostearyl alcohol, polyoxylated isostearyl alcohol, fatty acid esters of polyoxyethylene sorbitan, and the like. In this case, the pharmaceutical preparation may contain sodium chloride, glucose, or glycerin in an amount sufficient to prepare an isotonic solution, and may contain usual solubilizers, buffers, analgesic agents, etc., and may further contain, if necessary, coloring agents, preservatives, flavors, sweetening agents, etc., and/or other medicines.

The proportion of the compound of the present invention in the pharmaceutical preparation is not limited and can be suitably selected from a wide range. It is preferable that the pharmaceutical preparation usually contain the compound of the present invention in a proportion of 1 to 70 wt %.

The route of administration of the pharmaceutical preparation according to the present invention is not limited, and the preparation is administered by a route suitable for the form of the preparation, the patient's age and sex, conditions of the disease, and other conditions. For example, tablets, pills, solutions, suspensions, emulsions, granules, and capsules are administered orally. Injections are intravenously administered singly or as mixed with usual injection transfusions, such as glucose solutions or amino acid solutions, or singly administered intramuscularly, intracutaneously, subcutaneously or intraperitoneally, as required. Suppositories are administered intrarectally.

The dosage of the pharmaceutical preparation is suitably selected according to the method of use, the patient's age and sex, severity of the disease, and other conditions, and is usually about 0.01 to 100 mg/kg body weight/day, and preferably 0.1 to 50 mg/kg body weight/day, in single or divided doses.

According to variations of various conditions, there may be cases where a dosage smaller than the above range is sufficient or where a dosage larger than the above range is required.

The compounds of the present invention have specific efficacy against tubercle bacilli, such as acid-fast bacilli (the genera of tubercle bacilli and atypical acid-fast bacilli). The compounds of the present invention have an excellent effect on multidrug-resistant tubercle bacilli. The compounds of the present invention have an antibacterial action against anaerobic bacteria. Accordingly, the compounds of the present invention are useful as a prophylactic and/or therapeutic agent for tuberculosis.

The compounds of the present invention do not cause diarrhea, which can be caused by a known antimicrobial agent that has a broad spectrum against general bacteria, such as gram positive and gram negative bacteria. In addition, the compounds of the present invention have fewer side effects than existing drugs. Therefore, the compounds of the present invention can serve as pharmaceutical preparations that can be administered for a long period of time.

The compounds of the present invention can be satisfactorily distributed throughout the lung tissue, which is a main organ infected with mycobacteriosis. In addition, the compounds of the present invention have properties such as sustained drug efficacy and excellent safety. For this reason, the compounds of the present invention are expected to have high therapeutic effects.

Additionally, compared with existing antituberculosis agents, the compounds of the present invention exhibit stronger bactericidal activity against intracellular parasites, such as parasitic tubercle *bacillus* in human-derived macrophages. Therefore, the compounds of the present invention enable a reduction in the tuberculosis relapse rate and also enable short-term chemotherapy. Further, the compounds of the present invention are also expected to be used as a principal drug for preventive administration that is performed against a mixed infection with HIV and tuberculosis, which has become an acute problem.

The compounds of the present invention exhibit excellent metabolic stability in plasma, and thus have a feature of providing satisfactorily sustained bactericidal action in vivo.

The compounds of the present invention can be used in combination with other therapeutic agents. Examples of drugs that can be used in combination with the compounds of the present invention include first-line antituberculosis drugs, second-line antituberculosis drugs, quinolone antibacterial drugs, macrolide antibacterial drugs, sulfa drugs, anti-HIV drugs, delamanid, PA-824, which is a drug currently being developed, and the like.

DESCRIPTION OF EMBODIMENTS

The present invention is described in more detail below with reference to Examples. However, the scope of the invention is not limited thereto.

The compounds whose physical property data are not shown in the Reference Examples were used in the subsequent reaction without further purification.

Reference Example 1

Preparation of 2-chloro-1-[2-(2-methyloxiranyl) ethyl]-4-nitro-1H-imidazol

Potassium carbonate (1.16 g) and cesium fluoride (196 mg) were added to a DMF solution (20 ml) of 2-chloro-4-nitro-1H-imidazole (953 mg) and 4-nitrobenzene sulfonic acid 2-(2-methyloxiranyl)ethyl ester (1.856 g), and the mixture was stirred at 60° C. overnight. Thereafter the reaction mixture was cooled to room temperature. Water was added to the reaction solution, and the reaction mixture was then extracted repeatedly with ethyl acetate. The combined organic layer was washed with water and a saturated sodium chloride aqueous solution, and then dried over sodium sulfate. The sodium sulfate was filtered off and the filtrate was concentrated under reduced pressure. The residue was purified by silica gel column chromatography (dichloromethane:methanol=20:1) to afford the title compound as a yellow oil (1.1 g).

Reference Example 2

Preparation of 2-chloro-4-nitro-1-(2-oxiranylethyl)-1H-imidazole

The title compound was prepared in the same manner as in Reference Example 1 using suitable starting materials.

Yellow Oil

Reference Example 3

Preparation of 2-chloro-1-[2-((R)-2,2-dimethyl[1,3] dioxolan-4-yl)-ethyl]-4-nitro-1H-imidazole A solution of (4R)-2'-(2,2-dimethyl-[1,3]-dioxolan-4-yl) ethanol (100 g) in acetonitrile (400 ml) at −20° C. was treated with N,N,N',N'-tetramethyl-1,3-propanediamine (172 ml). A solution of p-toluenesulfonyl chloride (156.5 g) in acetonitrile (350 ml) was added dropwise at 0° C. or less and then the reaction mixture was stirred at 0 to 10° C. for 1 hour. Water was added to the reaction solution, and the reaction mixture was then extracted with ethyl acetate. The organic layer was washed with water and a saturated sodium chloride aqueous solution, and then dried over sodium sulfate. The sodium sulfate was filtered off and the filtrate was concentrated under reduced pressure. Acetonitrile (1,000 ml) was added to the resulting residue. 2-Chloro-4-nitro-1H-imidazole (100.90 g), potassium carbonate (132.35 g) and sodium iodide (122.3 g) were further added, and then the mixture was heated at reflux overnight. Thereafter the reaction mixture was concentrated under reduced pressure, and water was added to the resulting residue, followed by extraction with ethyl acetate. The organic layer was washed with water and a saturated sodium chloride aqueous solution, dried over sodium sulfate, and then subjected to filtration. The filtrate was concentrated under reduced pressure. The residue was purified by silica gel column chromatography (ethyl acetate:n-hexane=2:1→1:2)

and washed with isopropyl ether to afford the title compound as a pale yellow powder (101.35 g).

1H NMR (CDCl3) δ: 1.35 (3H, s), 1.43 (3H, s), 1.95-2.00 (1H, m), 2.00-2.05 (1H, m), 3.63-3.68 (1H, m), 4.00-4.15 (2H, m), 4.18-4.30 (2H, m), 7.83 (1H, m).

Reference Example 4

Preparation of 2-chloro-1-[2-((S)-2,2-dimethyl-[1,3]dioxolan-4-yl)ethyl]-4-nitro-1H-imidazole The title compound was prepared in the same manner as in Reference Example 3 using suitable starting materials.

Colorless Columnar

Reference Example 5

Preparation of 2-chloro-1-[2-(2,2-dimethyl-[1,3]dioxolan-4-yl)ethyl]-4-nitro-1H-imidazole The title compound was prepared in the same manner as in Reference Example 3 using suitable starting materials.

Colorless Columnar

Reference Example 6

Preparation of (R)-4-(2-chloro-4-nitroimidazol-1-yl)-butane-1,2-diol

While stirring a tetrahydrofuran solution (700 ml) of 2-chloro-1-[2-((R)-2,2-dimethyl-[1,3]dioxolan-4-yl)ethyl]-4-nitro-1H-imidazole (196.2 g) at room temperature, 1.0 M hydrochloric acid ethanol solution (1,100 ml) was added thereto and stirred at room temperature for 6 hours. The reaction mixture was concentrated under reduced pressure, hexane was added to the residue obtained and concentrated under reduced pressure. Thereafter, ethyl acetate was added thereto and concentrated under reduced pressure. Isopropyl ether was added to the resulting solid and stirred for a while. The precipitated crystal was collected by filtration to afford the title compound as a colorless solid (166.5 g).

1H NMR (DMSO-d6) δ: 1.63-1.74 (1H, m), 1.91-2.01 (1H, m), 3.22-3.28 (1H, m), 3.30-3.36 (1H, m), 3.40-3.49 (1H, m), 4.08-4.23 (2H, m), 4.62 (1H, t, J=5.6 Hz), 4.81 (1H, d, J=5.1 Hz), 8.56 (1H, s).

Reference Example 7

Preparation of (S)-4-(2-chloro-4-nitroimidazol-1-yl)butane-1,2-diol

The title compound was prepared in the same manner as in Reference Example 6 using suitable starting materials.

Pale Yellow Solid

Reference Example 8

Preparation of 4-(2-chloro-4-nitroimidazol-1-yl)butane-1,2-diol

The title compound was prepared in the same manner as in Reference Example 6 using suitable starting materials.

White Powder

Reference Example 9

Preparation of toluene-4-sulfonic acid (R)-4-(2-chloro-4-nitroimidazol-1-yl)-2-hydroxybutyl ester 2-Chloro-1-[4-((R)-1,2-dihydroxy)butyl]-4-nitro-1H-imidazole (166.5 g) was dissolved in pyridine (333 ml) and cooled to −30° C., p-toluenesulfonyl chloride (148.19 g) was gradually added thereto at −10° C. or less, and the mixture was stirred at −10° C. for 2 hours. The reaction mixture was added to a mixture of concentrated hydrochloric acid (430 ml) and water (1,500 ml), followed by extraction with ethyl acetate. The organic layer was washed with water and a saturated sodium chloride aqueous solution, dried over sodium sulfate, and subjected to filtration. The filtrate was concentrated under reduced pressure. The residue was purified by silica gel column chromatography (methylene chloride:ethyl acetate=96:4→ethyl acetate) and recrystallized from ethyl acetate-isopropyl ether to afford the title compound as a colorless solid (212.12 g).

1H NMR (CDCl3) δ: 1.83-2.00 (2H, m), 2.47 (3H, s), 2.53-2.73 (1H, m), 3.80-3.90 (1H, m), 3.93-3.98 (1H, m), 4.03-4.08 (1H, m), 4.23-4.28 (2H, m), 7.37 (2H, d, J=8.0 Hz), 7.73-7.80 (3H, m).

Reference Example 10

Preparation of toluene-4-sulfonic acid (S)-4-(2-chloro-4-nitroimidazol-1-yl)-2-hydroxybutyl ester The title compound was prepared in the same manner as in Reference Example 9 using suitable starting materials.

White Powder

Reference Example 11

Preparation of toluene-4-sulfonic acid 4-(2-chloro-4-nitroimidazol-1-yl)-2-hydroxy-butyl ester The title compound was prepared in the same manner as in Reference Example 9 using suitable starting materials.

White Solid

Reference Example 12

Preparation of 4-(2-chloro-4-nitroimidazol-1-yl)-1-{4-[4-(4-trifluoromethoxyphenoxy)piperidin-1-yl]phenoxy}butan-2-ol Toluene-4-sulfonic acid 4-(2-chloro-4-nitroimidazol-1-yl)-2-hydroxy-butyl ester (0.78 g) was suspended in ethanol (12 ml), an ethanol solution (0.68 ml) of 20% sodium ethoxide was added thereto, followed by stirring at room temperature for 1 hour. 4-[4-(4-Trifluoromethoxyphenoxy)piperidin-1-yl]phenol (0.707 g) and tripotassium phosphate (0.509 g) were added thereto and stirred at 80° C. for 2 hours. The mixture was cooled to room temperature and filtered through Celite to remove insoluble matter and, then the residue was washed with ethyl acetate. The filtrate and liquid were combined and concentrated under reduced pressure. The residue was purified by silica gel column chromatography (ethyl acetate:hexane=1:1→9:1) to afford the title compound as a pale yellow powder (0.314 g).

Reference Example 13

Preparation of 4-(2-chloro-4-nitroimidazol-1-yl)-1-(4-{4-[N-(4-chlorophenyl)-N-methylamino]piperidin-1-yl}phenoxy)butan-2-ol 2-Chloro-4-nitro-1-(2-oxiranylethyl)-1H-imidazole (810 mg) was suspended in ethanol (20 ml) and 4-{4-[N-(4-chlorophenyl)-N-methylamino]piperidin-1-yl}phenol (982 mg) and tripotassium phosphate (200 mg) were added thereto, followed by stirring at 70° C. overnight. Thereafter the reaction solution was cooled to room temperature, and filtered through Celite to remove insoluble matter and, then the residue was washed with ethyl acetate. The filtrate and liquid were combined and concentrated under reduced pressure. The residue was purified by silica gel column chromatography (ethyl acetate:hexane=10:1) and recrystallized from methylene chloride-ethyl acetate to afford the title compound as a yellow solid (486 mg).

Reference Example 14

Preparation of 4-{4-[4-(2-chloro-4-nitroimidazol-1-yl)-2-hydroxybutoxy]phenyl}piperazine-1-carboxylic acid tert-butyl ester The title compound was prepared in the same manner as in Reference Example 13 using suitable starting materials.

Yellow Amorphous

Reference Example 15

Preparation of 4-(2-chloro-4-nitroimidazol-1-yl)-1-{4-[4-(4-trifluoromethylbenzyloxymethyl)piperidin-1-yl]phenoxy}butan-2-ol The title compound was prepared in the same manner as in Reference Example 13 using suitable starting materials.

Brown Oil

Reference Example 16

Preparation of 4-(2-chloro-4-nitroimidazol-1-yl)-1-{4-[4-(4-trifluoromethylphenoxymethyl)piperidin-1-yl]phenoxy}butan-2-ol The title compound was prepared in the same manner as in Reference Example 13 using suitable starting materials.

Brown Solid

Reference Example 17

Preparation of 4-(2-chloro-4-nitroimidazol-1-yl)-1-{4-[4-(4-trifluoromethoxybenzyloxy)piperidin-1-yl]phenoxy}butan-2-ol The title compound was prepared in the same manner as in Reference Example 12 using suitable starting materials.

White Powder

Reference Example 18

Preparation of 4-(2-chloro-4-nitroimidazol-1-yl)-1-{4-[4-(4-trifluoromethoxybenzyl)piperidin-1-yl]phenoxy}butan-2-ol The title compound was prepared in the same manner as in Reference Example 12 using suitable starting materials.

White Powder

Reference Example 19

Preparation of 4-(2-chloro-4-nitroimidazol-1-yl)-1-(4-{4-[N-methyl-N-(4-trifluoromethoxyphenyl)amino]piperidin-1-yl}phenoxy)butan-2-ol The title compound was prepared in the same manner as in Reference Example 12 using suitable starting materials.

White Powder

Reference Example 20

Preparation of 4-(2-chloro-4-nitroimidazol-1-yl)-1-(4-{4-[2-(4-trifluoromethoxyphenyl)ethyl]piperidin-1-yl}phenoxy)butan-2-ol The title compound was prepared in the same manner as in Reference Example 12 using suitable starting materials.

White Powder

Reference Example 21

Preparation of (S)-4-(2-chloro-4-nitroimidazol-1-yl)-1-{4-[4-(4-trifluoromethoxyphenoxy)piperidin-1-yl]phenoxy}butan-2-ol The title compound was prepared in the same manner as in Reference Example 12 using suitable starting materials.

White Powder

Reference Example 22

Preparation of 4-(2-chloro-4-nitroimidazol-1-yl)-1-{4-[4-(4-trifluoromethoxybenzyloxymethyl)piperidin-1-yl]phenoxy}butan-2-ol The title compound was prepared in the same manner as in Reference Example 12 using suitable starting materials.

Pale Brown Powder

Reference Example 23

Preparation of 4-(2-chloro-4-nitroimidazol-1-yl)-1-{4-[4-(4-trifluoromethoxyphenoxymethyl)piperidin-1-yl]phenoxy}butan-2-ol The title compound was prepared in the same manner as in Reference Example 12 using suitable starting materials.

White Powder

Reference Example 24

Preparation of 1-{4-[4-(4-chlorobenzyloxymethyl)piperidin-1-yl]phenoxy}-4-(2-chloro-4-nitroimidazol-1-yl)butan-2-ol The title compound was prepared in the same manner as in Reference Example 12 using suitable starting materials.

White Powder

Reference Example 25

Preparation of 1-{4-[4-(4-chlorobenzyloxy)piperidin-1-yl]phenoxy}-4-(2-chloro-4-nitroimidazol-1-yl)butan-2-ol The title compound was prepared in the same manner as in Reference Example 12 using suitable starting materials.

White Powder

Reference Example 26

Preparation of (R)-4-(2-chloro-4-nitroimidazol-1-yl)-1-{4-[4-(4-trifluoromethoxyphenoxy)piperidin-1-yl]phenoxy}butan-2-ol The title compound was prepared in the same manner as in Reference Example 12 using suitable starting materials.

Pale Yellow Amorphous

Reference Example 27

Preparation of 4-(2-chloro-4-nitroimidazol-1-yl)-1-{4-[4-(4-trifluoromethylphenoxy)piperidin-1-yl]phenoxy}butan-2-ol The title compound was prepared in the same manner as in Reference Example 12 using suitable starting materials.

White Powder

Reference Example 28

Preparation of 4-(2-chloro-4-nitroimidazol-1-yl)-1-{4-[4-(4-chlorophenoxy)piperidin-1-yl]phenoxy}butan-2-ol The title compound was prepared in the same manner as in Reference Example 12 using suitable starting materials.

White Powder

Reference Example 29

Preparation of 4-(2-chloro-4-nitroimidazol-1-yl)-1-{4-[4-(4-trifluoromethoxyphenyl)piperidin-1-yl]phenoxy}butan-2-ol The title compound was prepared in the same manner as in Reference Example 12 using suitable starting materials.

White Powder

Reference Example 30

Preparation of 4-(2-chloro-4-nitroimidazol-1-yl)-1-(4-{4-[N-methyl-N-(4-trifluoromethylphenyl)amino]piperidin-1-yl}phenoxy)butan-2-ol The title compound was prepared in the same manner as in Reference Example 12 using suitable starting materials.

Pale Yellow Powder

Reference Example 31

Preparation of 4-(2-chloro-4-nitroimidazol-1-yl)-1-{4-[4-(3-trifluoromethylphenoxy)piperidin-1-yl]phenoxy}butan-2-ol The title compound was prepared in the same manner as in Reference Example 12 using suitable starting materials.

White Powder

Reference Example 32

Preparation of 1-{4-[4-(3,5-bis-trifluoromethylphenoxy)piperidin-1-yl]phenoxy}-4-(2-chloro-4-nitroimidazol-1-yl)butan-2-ol The title compound was prepared in the same manner as in Reference Example 12 using suitable starting materials.

White Powder

Reference Example 33

Preparation of 4-(2-chloro-4-nitroimidazol-1-yl)-1-{4-[1-(4-trifluoromethoxyphenyl)piperidin-4-yl]phenoxy}butan-2-ol The title compound was prepared in the same manner as in Reference Example 12 using suitable starting materials.

Pale Yellow Powder

Reference Example 34

Preparation of 4-(2-chloro-4-nitroimidazol-1-yl)-1-{4-[1-(4-trifluoromethylphenyl)piperidin-4-yl]phenoxy}butan-2-ol The title compound was prepared in the same manner as in Reference Example 12 using suitable starting materials.

White Powder

Reference Example 35

Preparation of 4-{4-[4-(2-chloro-4-nitroimidazol-1-yl)-2-hydroxybutoxy]phenyl}piperidine-1-carboxylic acid tert-butyl ester The title compound was prepared in the same manner as in Reference Example 12 using suitable starting materials.

White Powder

Reference Example 36

Preparation of 4-(2-chloro-4-nitroimidazol-1-yl)-1-
{4-[4-(4-trifluoromethylbenzyl)piperidin-1-yl]
phenoxy}butan-2-ol The title compound was prepared in the same manner as in
Reference Example 12 using suitable starting materials.

White Powder

Reference Example 37

Preparation of 1-{4-[4-(4-chlorobenzyl)piperidin-1-
yl]phenoxy}-4-(2-chloro-4-nitroimidazol-1-yl)butan-
2-ol The title compound was prepared in the same manner as in
Reference Example 12 using suitable starting materials.

Pale Yellow Powder

Reference Example 38

Preparation of 4-(2-chloro-4-nitroimidazol-1-yl)-1-
(4-{4-[N-(4-chlorophenyl)-N-ethylamino]piperidin-
1-yl}phenoxy)butan-2-ol The title compound was prepared in the same manner as in
Reference Example 12 using suitable starting materials.
Brown Oil
MS (m/z): 547[M+H]$^+$

Reference Example 39

Preparation of 4-(2-chloro-4-nitroimidazol-1-yl)-1-
(4-{4-[N-ethyl-N-(4-trifluoromethylphenyl)amino]
piperidin-1-yl}phenoxy)butan-2-ol The title compound was prepared in the same manner as in
Reference Example 12 using suitable starting materials.
Brown Oil
MS (m/z): 582[M+H]$^+$

Reference Example 40

Preparation of 4-(2-chloro-4-nitroimidazol-1-yl)-1-
(4-{4-[N-ethyl-N-(4-trifluoromethoxyphenyl)amino]
piperidin-1-yl}phenoxy)butan-2-ol The title compound was prepared in the same manner as in
Reference Example 12 using suitable starting materials.
Brown Oil
MS (m/z): 598[M+H]$^+$

Reference Example 41

Preparation of 4-{4-[4-(2-chloro-4-nitroimidazol-1-
yl)-2-hydroxybutoxy]phenyl}-[1,4]diazepane-1-car-
boxylic acid tert-butyl ester The title compound was prepared in the same manner as in
Reference Example 12 using suitable starting materials.
Brown Amorphous
MS (m/z): 510[M+H]$^+$

Reference Example 42

Preparation of 4-(2-chloro-4-nitroimidazol-1-yl)-1-
{4-[4-(4-trifluoromethoxyphenyl)-oxazol-2-ylm-
ethyl]phenoxy}butan-2-ol The title compound was prepared in the same manner as in
Reference Example 12 using suitable starting materials.

Powder

Reference Example 43

Preparation of 4-(2-chloro-4-nitroimidazol-1-yl)-1-
{4-[2-(4-trifluoromethoxyphenyl)-oxazol-4-yl]
phenoxy}butan-2-ol The title compound was prepared in the same manner as in
Reference Example 12 using suitable starting materials.

White Powder

Reference Example 44

Preparation of 4-(2-chloro-4-nitroimidazol-1-yl)-1-
{4-[2-(4-trifluoromethoxyphenoxymethyl)-oxazol-4-
yl]phenoxy}butan-2-ol The title compound was prepared in the same manner as in
Reference Example 12 using suitable starting materials.

Powder

Reference Example 45

Preparation of 4-(2-chloro-4-nitroimidazol-1-yl)-1-
{4-[2-(4-trifluoromethoxyphenoxymethyl)thiazol-4-
yl]phenoxy}butan-2-ol The title compound was prepared in the same manner as in
Reference Example 12 using suitable starting materials.

White Powder

Reference Example 46

Preparation of 4-(2-chloro-4-nitroimidazol-1-yl)-1-
{4-[2-(4-trifluoromethoxyphenyl)thiazol-4-yl]
phenoxy}butan-2-ol The title compound was prepared in the same manner as in
Reference Example 12 using suitable starting materials.

Yellow Powder

Reference Example 47

Preparation of 4-(2-chloro-4-nitroimidazol-1-yl)-1-
(4-{4-[2-(4-trifluoromethoxyphenoxy)ethyl]piperi-
din-1-yl}phenoxy)butan-2-ol The title compound was prepared in the same manner as in
Reference Example 12 using suitable starting materials.

White Powder

Reference Example 48

Preparation of 4-(2-chloro-4-nitroimidazol-1-yl)-1-(4-{4-[3-(4-trifluoromethoxyphenoxy)propyl]piperidin-1-yl}phenoxy)butan-2-ol The title compound was prepared in the same manner as in Reference Example 12 using suitable starting materials.

White Powder

Reference Example 49

Preparation of 4-(2-chloro-4-nitroimidazol-1-yl)-1-(4-{4-[3-(4-trifluoromethoxyphenyl)propyl]piperidin-1-yl}phenoxy)butan-2-ol The title compound was prepared in the same manner as in Reference Example 12 using suitable starting materials.

White Powder

Reference Example 50

Preparation of 1-{4-[4-(2-chloro-4-nitroimidazol-1-yl)-2-hydroxybutoxy]phenyl}-4-trifluoromethylpiperidin-4-ol The title compound was prepared in the same manner as in Reference Example 12 using suitable starting materials.

White Powder

Reference Example 51

Preparation of 4-{5-[4-(2-chloro-4-nitroimidazol-1-yl)-2-hydroxybutoxy]pyridin-2-yl}piperazine-1-carboxylic acid tert-butyl ester The title compound was prepared in the same manner as in Reference Example 12 using suitable starting materials.
Pale Red Powder
MS (m/z): 496[M]$^+$

Reference Example 52

Preparation of 4-(2-chloro-4-nitroimidazol-1-yl)-1-{4-[2-(4-trifluoromethoxybenzyl)thiazol-4-yl]phenoxy}butan-2-ol The title compound was prepared in the same manner as in Reference Example 12 using suitable starting materials.

Pale Yellow Powder

Reference Example 53

Preparation of 4-(2-chloro-4-nitroimidazol-1-yl)-1-(4-{4-[2-(5-trifluoromethylpyridin-2-yloxy)ethyl]piperidin-1-yl}phenoxy)butan-2-ol The title compound was prepared in the same manner as in Reference Example 12 using suitable starting materials.

White Powder

Reference Example 54

Preparation of 4-(2-chloro-4-nitroimidazol-1-yl)-1-{4-[4-(5-trifluoromethylpyridin-2-yloxymethyl)piperidin-1-yl]phenoxy}butan-2-ol The title compound was prepared in the same manner as in Reference Example 12 using suitable starting materials.

White Powder

Reference Example 55

Preparation of 4-(2-chloro-4-nitroimidazol-1-yl)-1-[4-(4-methoxy-4-trifluoromethylpiperidin-1-yl)phenoxy]butan-2-ol The title compound was prepared in the same manner as in Reference Example 12 using suitable starting materials.

White Powder

Reference Example 56

Preparation of 4-(2-chloro-4-nitroimidazol-1-yl)-1-{4-[4-(5-trifluoromethylpyridin-2-yloxy)piperidin-1-yl]phenoxy}butan-2-ol The title compound was prepared in the same manner as in Reference Example 12 using suitable starting materials.

Pale Yellow Powder

Reference Example 57

Preparation of 4-(2-chloro-4-nitroimidazol-1-yl)-1-{6-[4-(4-trifluoromethoxyphenoxy)piperidin-1-yl]pyridin-3-yloxy}butan-2-ol The title compound was prepared in the same manner as in Reference Example 12 using suitable starting materials.

Orange Amorphous

Reference Example 58

Preparation of 4-(2-chloro-4-nitroimidazol-1-yl)-1-{6-[4-(4-trifluoromethoxybenzyl)piperidin-1-yl]pyridin-3-yloxy}butan-2-ol The title compound was prepared in the same manner as in Reference Example 12 using suitable starting materials.

Brown Amorphous

Reference Example 59

Preparation of 4-(2-chloro-4-nitroimidazol-1-yl)-1-{6-[4-(4-trifluoromethoxyphenoxymethyl)piperidin-1-yl]pyridin-3-yloxy}butan-2-ol The title compound was prepared in the same manner as in Reference Example 12 using suitable starting materials.

Pale Yellow Powder

Reference Example 60

Preparation of 4-(2-chloro-4-nitroimidazol-1-yl)-1-(6-{4-[2-(4-trifluoromethoxyphenoxy)ethyl]piperidin-1-yl}pyridin-3-yloxy)butan-2-ol The title compound was prepared in the same manner as in Reference Example 12 using suitable starting materials.

Pale Brown Powder

Reference Example 61

Preparation of (S)-4-(2-chloro-4-nitroimidazol-1-yl)-1-(4-{4-[2-(4-trifluoromethoxyphenyl)ethyl]piperidin-1-yl}phenoxy)butan-2-ol The title compound was prepared in the same manner as in Reference Example 12 using suitable starting materials.

Pale Yellow Powder

Reference Example 62

Preparation of 4-(2-chloro-4-nitroimidazol-1-yl)-1-[4-(4-propoxy-4-trifluoromethylpiperidin-1-yl)phenoxy]butan-2-ol The title compound was prepared in the same manner as in Reference Example 12 using suitable starting materials.

White Powder

Reference Example 63

Preparation of 4-{4-[(S)-4-(2-chloro-4-nitroimidazol-1-yl)-2-hydroxybutoxy]phenyl}piperazine-1-carboxylic acid tert-butyl ester The title compound was prepared in the same manner as in Reference Example 12 using suitable starting materials.
Brown Oil
MS (m/z): 495[M]$^+$ Reference Example 64

Preparation of (S)-4-(2-chloro-4-nitroimidazol-1-yl)-1-(4-{4-[N-methyl-N-(4-trifluoromethoxyphenyl)amino]piperidin-1-yl}phenoxy)butan-2-ol The title compound was prepared in the same manner as in Reference Example 12 using suitable starting materials.

Dark Red Amorphous

Reference Example 65

Preparation of (R)-4-(2-chloro-4-nitroimidazol-1-yl)-1-(4-{4-[2-(4-trifluoromethoxyphenyl)ethyl]piperidin-1-yl}phenoxy)butan-2-ol The title compound was prepared in the same manner as in Reference Example 12 using suitable starting materials.

Pale Yellow Powder

Reference Example 66

Preparation of 4-(2-chloro-4-nitroimidazol-1-yl)-1-{4-[4-(3-chloro-5-trifluoromethylpyridin-2-yloxy)piperidin-1-yl]phenoxy}butan-2-ol The title compound was prepared in the same manner as in Reference Example 12 using suitable starting materials.

Yellow Amorphous

Reference Example 68

Preparation of (R)-4-(2-chloro-4-nitroimidazol-1-yl)-1-(4-{4-[N-methyl-N-(4-trifluoromethoxyphenyl)amino]piperidin-1-yl}phenoxy)butan-2-ol The title compound was prepared in the same manner as in Reference Example 12 using suitable starting materials.

Red Amorphous

Reference Example 69

Preparation of 4-(2-chloro-4-nitroimidazol-1-yl)-1-{6-[4-(4-chlorophenoxy)piperidin-1-yl]pyridin-3-yloxy}butan-2-ol The title compound was prepared in the same manner as in Reference Example 12 using suitable starting materials.

Brown Amorphous

Reference Example 70

Preparation of 4-(2-chloro-4-nitroimidazol-1-yl)-1-{6-[4-(4-trifluoromethoxybenzyloxy)piperidin-1-yl]pyridin-3-yloxy]butan-2-ol The title compound was prepared in the same manner as in Reference Example 12 using suitable starting materials.

Pale Yellow Powder

Reference Example 71

Preparation of 4-(2-chloro-4-nitroimidazol-1-yl)-1-{6-[4-(4-trifluoromethylphenoxy)piperidin-1-yl]pyridin-3-yloxy]butan-2-ol The title compound was prepared in the same manner as in Reference Example 12 using suitable starting materials.

Yellow Amorphous

Reference Example 73

Preparation of 4-(2-chloro-4-nitroimidazol-1-yl)-1-{4-[1-(4-trifluoromethoxyphenyl)piperidin-4-ylmethyl]phenoxy}butan-2-ol The title compound was prepared in the same manner as in Reference Example 12 using suitable starting materials.

Pale Yellow Amorphous

Reference Example 74

Preparation of 4-(2-chloro-4-nitroimidazol-1-yl)-1-{4-[1-(4-trifluoromethylphenyl)piperidin-4-ylmethyl]phenoxy}butan-2-ol The title compound was prepared in the same manner as in Reference Example 12 using suitable starting materials.

Yellow Amorphous

Reference Example 75

Preparation of 4-{4-[4-(2-chloro-4-nitroimidazol-1-yl)-2-hydroxybutoxy]benzyl}piperidine-1-carboxylic acid tert-butyl ester The title compound was prepared in the same manner as in Reference Example 12 using suitable starting materials.

Pale Yellow Oil

Reference Example 76

Preparation of 4-(2-chloro-4-nitroimidazol-1-yl)-1-(6-{4-[3-(4-trifluoromethoxyphenyl)propyl]piperidin-1-yl}pyridin-3-yloxy)butan-2-ol The title compound was prepared in the same manner as in Reference Example 12 using suitable starting materials.

Yellow Oil

Reference Example 77

Preparation of 4-(2-chloro-4-nitroimidazol-1-yl)-1-[6-(4-trifluoromethoxybenzyloxymethyl)pyridin-3-yloxy]butan-2-ol The title compound was prepared in the same manner as in Reference Example 12 using suitable starting materials.

Pale Yellow Solid

Reference Example 78

Preparation of 4-(2-chloro-4-nitroimidazol-1-yl)-1-(4-{4-[2-(4-trifluoromethylphenoxy)ethyl]piperidin-1-yl}phenoxy)butan-2-ol The title compound was prepared in the same manner as in Reference Example 12 using suitable starting materials.

White Powder

Reference Example 79

Preparation of 4-(2-chloro-4-nitroimidazol-1-yl)-1-(4-{4-[2-(4-chlorophenoxy)ethyl]piperidin-1-yl}phenoxy)butan-2-ol The title compound was prepared in the same manner as in Reference Example 12 using suitable starting materials.

White Powder

Reference Example 80

Preparation of 4-(2-chloro-4-nitroimidazol-1-yl)-1-(4-{4-[2-(4-trifluoromethylphenyl)ethyl]piperidin-1-yl}phenoxy)butan-2-ol The title compound was prepared in the same manner as in Reference Example 12 using suitable starting materials.

Pale Yellow Powder

Reference Example 81

Preparation of 4-(2-{4-[4-(2-chloro-4-nitroimidazol-1-yl)-2-hydroxybutoxy]phenyl}-ethyl)piperidine-1-carboxylic acid tert-butyl ester The title compound was prepared in the same manner as in Reference Example 12 using suitable starting materials.

White Powder

Reference Example 82

Preparation of 4-(2-chloro-4-nitroimidazol-1-yl)-1-{2-chloro-4-[4-(4-trifluoromethoxyphenoxy)piperidin-1-yl]phenoxy}butan-2-ol The title compound was prepared in the same manner as in Reference Example 12 using suitable starting materials.

Pale Yellow Amorphous

Reference Example 83

Preparation of 4-(2-chloro-4-nitroimidazol-1-yl)-1-(4-{4-[2-(4-chlorophenyl)ethyl]piperidin-1-yl}phenoxy)butan-2-ol The title compound was prepared in the same manner as in Reference Example 12 using suitable starting materials.

Pale Yellow Powder

Reference Example 84

Preparation of 4-(2-chloro-4-nitroimidazol-1-yl)-1-(4-{4-[3-(4-trifluoromethylphenyl)propyl]piperidin-1-yl}phenoxy)butan-2-ol The title compound was prepared in the same manner as in Reference Example 12 using suitable starting materials.

Pale Yellow Powder

Reference Example 85

Preparation of 4-(2-chloro-4-nitroimidazol-1-yl)-1-(4-{4-[3-(4-trifluoromethylphenoxy)propyl]piperidin-1-yl}phenoxy)butan-2-ol The title compound was prepared in the same manner as in Reference Example 12 using suitable starting materials.

Pale Yellow Powder

Reference Example 86

Preparation of 1-{4-[4-(5-chlorobenzofuran-2-ylmethyl)piperidin-1-yl]phenoxy}-4-(2-chloro-4-nitroimidazol-1-yl)butan-2-ol The title compound was prepared in the same manner as in Reference Example 12 using suitable starting materials.

White Powder

Reference Example 87

Preparation of 1-{4-[4-(5-chlorobenzofuran-2-ylmethoxy)piperidin-1-yl]phenoxy}-4-(2-chloro-4-nitroimidazol-1-yl)butan-2-ol The title compound was prepared in the same manner as in Reference Example 12 using suitable starting materials.

White Powder

Reference Example 88

Preparation of 4-{4-[4-(2-chloro-4-nitroimidazol-1-yl)-2-hydroxy-2-methylbutoxy]phenyl}piperazine-1-carboxylic acid tert-butyl ester 4-{4-[2-Hydroxy-2-methyl-4-(toluene-4-sulfonyloxy)butoxy]phenyl}piperazine-1-carboxylic acid tert-butyl ester (4.69 g, 8.77 mmol), 2-chloro-4-nitro-1H-imidazole (1.55 g, 10.52 mmol), sodium hydrogen carbonate (0.88 g) and dimethylformamide (47 ml) were mixed, and the mixture was stirred at 90 to 100° C. overnight. Water was added to the reaction mixture, followed by extraction with ethyl acetate. The organic layer was washed with a saturated sodium chloride aqueous solution, and dried over magnesium sulfate. After filtering under reduced pressure, the filtrate was concentrated, and the residue was purified by silica gel column chromatography (hexane:ethyl acetate=1:0→3:7) to afford the title compound as a yellow amorphous solid (2.12 g).
MS (m/z): 509[M]⁺

Reference Example 89

Preparation of 4-(2-chloro-4-nitroimidazol-1-yl)-1-(4-{4-[3-(4-chlorophenoxy)propyl]piperidin-1-yl}phenoxy)butan-2-ol The title compound was prepared in the same manner as in Reference Example 12 using suitable starting materials.

White Powder

Reference Example 90

Preparation of 4-(2-chloro-4-nitroimidazol-1-yl)-1-{4-[4-(5-trifluoromethylbenzofuran-2-ylmethyl)piperidin-1-yl]phenoxy}butan-2-ol The title compound was prepared in the same manner as in Reference Example 12 using suitable starting materials.

White Powder

Reference Example 91

Preparation of 4-(2-chloro-4-nitroimidazol-1-yl)-1-(4-{4-[3-(4-chlorophenyl)propyl]piperidin-1-yl}phenoxy)butan-2-ol The title compound was prepared in the same manner as in Reference Example 12 using suitable starting materials.

White Powder

Reference Example 92

Preparation of 4-(2-chloro-4-nitroimidazol-1-yl)-1-{4-[4-(5-trifluoromethoxybenzofuran-2-ylmethyl)piperidin-1-yl]phenoxy}butan-2-ol The title compound was prepared in the same manner as in Reference Example 12 using suitable starting materials.

White Powder

Reference Example 93

Preparation of 1-{4-[4-(5-chlorobenzofuran-2-ylmethoxymethyl)piperidin-1-yl]phenoxy}-4-(2-chloro-4-nitroimidazol-1-yl)butan-2-ol The title compound was prepared in the same manner as in Reference Example 12 using suitable starting materials.

Powder

Reference Example 94

Preparation of 4-(2-chloro-4-nitroimidazol-1-yl)-1-{1-[3-(4-trifluoromethoxyphenoxy)propyl]-1,2,3,4-tetrahydroquinolin-6-yloxy}butan-2-ol The title compound was prepared in the same manner as in Reference Example 12 using suitable starting materials.

Orange Amorphous

Reference Example 95

Preparation of (R)-4-(2-chloro-4-nitroimidazol-1-yl)-1-{1-[3-(4-trifluoromethoxyphenoxy)propyl]-1,2,3,4-tetrahydroquinolin-6-yloxy}butan-2-ol The title compound was prepared in the same manner as in Reference Example 12 using suitable starting materials.

Red Amorphous

Reference Example 96

Preparation of (R)-4-(2-chloro-4-nitroimidazol-1-yl)-1-{1-[3-(4-trifluoromethoxyphenoxy)propyl]-1H-indole-5-yloxy}butan-2-ol The title compound was prepared in the same manner as in Reference Example 12 using suitable starting materials.

Red Amorphous

Reference Example 97

Preparation of (R)-4-(2-chloro-4-nitroimidazol-1-yl)-1-{1-[3-(4-trifluoromethoxyphenoxy)propyl]-1,2,3,4-tetrahydroquinolin-5-yloxy}butan-2-ol The title compound was prepared in the same manner as in Reference Example 12 using suitable starting materials.

Yellow Amorphous

Reference Example 98

Preparation of (R)-4-(2-chloro-4-nitroimidazol-1-yl)-1-{1-[3-(4-trifluoromethoxyphenoxy)propyl]-2,3,4,5-tetrahydro-1H-benzo[b]azepin-7-yloxy}butan-2-ol The title compound was prepared in the same manner as in Reference Example 12 using suitable starting materials.

Red Amorphous

Reference Example 99

Preparation of (R)-4-(2-chloro-4-nitroimidazol-1-yl)-1-{1-[4-(4-trifluoromethoxyphenoxy)benzyl]-1,2,3,4-tetrahydroquinolin-6-yloxy}butan-2-ol The title compound was prepared in the same manner as in Reference Example 12 using suitable starting materials.

Red Amorphous

Reference Example 100

Preparation of (R)-4-(2-chloro-4-nitroimidazol-1-yl)-1-{1-[4-(4-trifluoromethoxyphenoxy)benzyl]-2,3,4,5-tetrahydro-1H-benzo[b]azepin-7-yloxy}butan-2-ol The title compound was prepared in the same manner as in Reference Example 12 using suitable starting materials.

Yellow Amorphous

Reference Example 101

Preparation of (R)-4-(2-chloro-4-nitroimidazol-1-yl)-1-{2-[4-(4-trifluoromethoxyphenoxy)piperidin-1-yl]-quinolin-6-yloxy}butan-2-ol The title compound was prepared in the same manner as in Reference Example 12 using suitable starting materials.

Brown Amorphous

Reference Example 102

Preparation of 4-{6-[(R)-4-(2-chloro-4-nitroimidazol-1-yl)-2-hydroxybutoxy]-quinolin-2-yl}piperazine-1-carboxylic acid tert-butyl ester The title compound was prepared in the same manner as in Reference Example 12 using suitable starting materials.

Yellow Amorphous

Reference Example 103

Preparation of (R)-4-(2-chloro-4-nitroimidazol-1-yl)-1-{2-[4-(4-trifluoromethoxyphenoxy)piperidin-1-yl]benzothiazol-6-yloxy}butan-2-ol The title compound was prepared in the same manner as in Reference Example 12 using suitable starting materials.

Yellow Amorphous

Reference Example 104

Preparation of (R)-4-(2-chloro-4-nitroimidazol-1-yl)-1-{2-[4-(4-trifluoromethoxybenzyl)piperazin-1-yl]benzothiazol-6-yloxy}butan-2-ol The title compound was prepared in the same manner as in Reference Example 12 using suitable starting materials.

Yellow Amorphous

Reference Example 105

Preparation of 4-{6-[(R)-4-(2-chloro-4-nitroimidazol-1-yl)-2-hydroxybutoxy]benzothiazol-2-yl}piperazine-1-carboxylic acid tert-butyl ester The title compound was prepared in the same manner as in Reference Example 12 using suitable starting materials.

White Powder

Reference Example 106

Preparation of (R)-4-(2-chloro-4-nitroimidazol-1-yl)-1-[4-(4,4-dimethoxypiperidin-1-yl)phenoxy]butan-2-ol The title compound was prepared in the same manner as in Reference Example 12 using suitable starting materials.

Orange Amorphous

Reference Example 107

Preparation of (R)-4-(2-chloro-4-nitroimidazol-1-yl)-1-(6-{4-[2-(4-trifluoromethoxyphenyl)ethyl]piperidin-1-yl}-naphthalen-2-yloxy)butan-2-ol The title compound was prepared in the same manner as in Reference Example 12 using suitable starting materials.

Pale Yellow Solid

Reference Example 108

Preparation of (R)-4-(2-chloro-4-nitroimidazol-1-yl)-1-(4-{4-[2-(4-trifluoromethoxyphenoxy)ethyl]piperidin-1-yl}phenoxy)butan-2-ol The title compound was prepared in the same manner as in Reference Example 12 using suitable starting materials.

Pale Yellow Powder

Reference Example 109

Preparation of (R)-4-(2-chloro-4-nitroimidazol-1-yl)-1-(4-{4-[3-(4-trifluoromethoxyphenyl)propyl]piperidin-1-yl}phenoxy)butan-2-ol The title compound was prepared in the same manner as in Reference Example 12 using suitable starting materials.

Pale Yellow Powder

Reference Example 110

Preparation of (R)-4-(2-chloro-4-nitroimidazol-1-yl)-1-(4-{4-[2-(3,4-dichlorophenoxy)ethyl]piperidin-1-yl}phenoxy)butan-2-ol The title compound was prepared in the same manner as in Reference Example 12 using suitable starting materials.

Yellow Amorphous

Reference Example 111

Preparation of (R)-4-(2-chloro-4-nitroimidazol-1-yl)-1-(4-{4-[2-(3-chloro-5-trifluoromethylpyridin-2-yloxy)ethyl]piperidin-1-yl}phenoxy)butan-2-ol The title compound was prepared in the same manner as in Reference Example 12 using suitable starting materials.

Yellow Amorphous

Reference Example 112

Preparation of (R)-4-(2-chloro-4-nitroimidazol-1-yl)-1-(4-{4-[2-(3,5-dichloropyridin-2-yloxy)ethyl]piperidin-1-yl}phenoxy)butan-2-ol The title compound was prepared in the same manner as in Reference Example 12 using suitable starting materials.

Brown Amorphous

Reference Example 113

Preparation of (R)-4-(2-chloro-4-nitroimidazol-1-yl)-1-(4-{4-[2-(4-chloro-3-trifluoromethylphenoxy)ethyl]piperidin-1-yl}phenoxy)butan-2-ol The title compound was prepared in the same manner as in Reference Example 12 using suitable starting materials.

Brown Amorphous

Reference Example 114

Preparation of (R)-4-(2-chloro-4-nitroimidazol-1-yl)-1-(4-{4-[2-(tetrahydropyran-2-yloxy)-2-(4-trifluoromethoxyphenyl)ethyl]piperidin-1-yl}phenoxy)butan-2-ol The title compound was prepared in the same manner as in Reference Example 12 using suitable starting materials.

Yellow Amorphous

Reference Example 115

Preparation of (R)-4-(2-chloro-4-nitroimidazol-1-yl)-1-(4-{4-[2-(2,4-dichlorophenoxy)ethyl]piperidin-1-yl}phenoxy)butan-2-ol The title compound was prepared in the same manner as in Reference Example 12 using suitable starting materials.

Reference Example 116

Preparation of (R)-4-(2-chloro-4-nitroimidazol-1-yl)-1-(4-{4-[4-(4-trifluoromethoxybenzyloxy)phenyl]piperazin-1-yl}phenoxy)butan-2-ol The title compound was prepared in the same manner as in Reference Example 12 using suitable starting materials.

Yellow Solid

Reference Example 117

Preparation of (R)-1-(4-{4-[2-(4-chloro-3-methylphenoxy)ethyl]piperidin-1-yl}phenoxy)-4-(2-chloro-4-nitroimidazol-1-yl)butan-2-ol The title compound was prepared in the same manner as in Reference Example 12 using suitable starting materials.

Yellow Amorphous

Reference Example 118

Preparation of (R)-4-(2-chloro-4-nitroimidazol-1-yl)-1-(4-{4-[2-(3-trifluoromethylphenoxy)ethyl]piperidin-1-yl}phenoxy)butan-2-ol The title compound was prepared in the same manner as in Reference Example 12 using suitable starting materials.

Pale Yellow Powder

Reference Example 119

Preparation of (R)-1-(4-{4-[2-(3-chloro-4-fluorophenoxy)ethyl]piperidin-1-yl}phenoxy)-4-(2-chloro-4-nitroimidazol-1-yl)butan-2-ol The title compound was prepared in the same manner as in Reference Example 12 using suitable starting materials.

Yellow Amorphous

Reference Example 120

Preparation of (4-{4-[(R)-4-(2-chloro-4-nitroimidazol-1-yl)-2-hydroxybutoxy]phenyl}piperazin-1-yl)-carbamic acid tert-butyl ester The title compound was prepared in the same manner as in Reference Example 12 using suitable starting materials.

Yellow Amorphous

Reference Example 121

Preparation of (R)-4-(2-chloro-4-nitroimidazol-1-yl)-1-(4-{4-[4-(4-trifluoromethoxyphenoxy)phenyl]piperazin-1-yl}phenoxy)butan-2-ol The title compound was prepared in the same manner as in Reference Example 12 using suitable starting materials.

Pale Brown Solid

Reference Example 122

Preparation of (R)-4-(2-chloro-4-nitroimidazol-1-yl)-1-{2-[4-(4-trifluoromethoxyphenoxy)piperidin-1-yl]benzooxazol-5-yloxy}butan-2-ol The title compound was prepared in the same manner as in Reference Example 12 using suitable starting materials.

Pale Yellow Powder

Reference Example 123

Preparation of (R)-4-(2-chloro-4-nitroimidazol-1-yl)-1-(4-{4-[3-(4-trifluoromethoxyphenoxy)propyl]piperidin-1-yl}phenoxy)butan-2-ol The title compound was prepared in the same manner as in Reference Example 12 using suitable starting materials.

White Powder

Reference Example 124

Preparation of (R)-4-(2-chloro-4-nitroimidazol-1-yl)-1-(4-{4-[2-(5-trifluoromethylpyridin-2-yloxy)ethyl]piperidin-1-yl}phenoxy)butan-2-ol The title compound was prepared in the same manner as in Reference Example 12 using suitable starting materials.

Pale Yellow Powder

Reference Example 125

Preparation of 4-{4-[(R)-4-(2-chloro-4-nitroimidazol-1-yl)-2-hydroxybutoxy]phenyl}piperidine-1-carboxylic acid tert-butyl ester The title compound was prepared in the same manner as in Reference Example 12 using suitable starting materials.

Pale Yellow Amorphous

Reference Example 126

Preparation of (R)-4-(2-chloro-4-nitroimidazol-1-yl)-1-(4-{4-[4-(4-trifluoromethoxyphenoxy)butyl]piperidin-1-yl}phenoxy)butan-2-ol The title compound was prepared in the same manner as in Reference Example 12 using suitable starting materials.

Pale Yellow Powder

Reference Example 127

Preparation of 4-{4-[(R)-4-(2-chloro-4-nitroimidazol-1-yl)-2-hydroxybutoxy]phenyl}piperazine-1-carboxylic acid tert-butyl ester The title compound was prepared in the same manner as in Reference Example 88 using suitable starting materials.

Orange Amorphous

Reference Example 128

Preparation of (R)-4-(2-chloro-4-nitroimidazol-1-yl)-1-[4-(3-trifluoromethyl-5,6-dihydro-8H-imidazo[1,2-a]pyrazin-7-yl)phenoxy]butan-2-ol The title compound was prepared in the same manner as in Reference Example 12 using suitable starting materials.

Yellow Solid

Reference Example 129

Preparation of (S)-4-(2-chloro-4-nitroimidazol-1-yl)-1-(4-{4-[4-(4-trifluoromethoxybenzyloxy)phenoxy]piperidin-1-yl}phenoxy)butan-2-ol The title compound was prepared in the same manner as in Reference Example 12 using suitable starting materials.

Orange Amorphous

Reference Example 130

Preparation of (R)-4-(2-chloro-4-nitroimidazol-1-yl)-1-(4-{4-[4-(4-trifluoromethoxybenzyloxy)phenoxy]piperidin-1-yl}phenoxy)butan-2-ol The title compound was prepared in the same manner as in Reference Example 12 using suitable starting materials.

Brown Amorphous

Reference Example 131

Preparation of (R)-4-(2-chloro-4-nitroimidazol-1-yl)-1-[4-(3-trifluoromethyl-5,6-dihydro-8H-[1,2,4]triazolo[4,3-a]pyrazin-7-yl)phenoxy]butan-2-ol The title compound was prepared in the same manner as in Reference Example 12 using suitable starting materials.

Pale Yellow Amorphous

Reference Example 132

Preparation of (R)-4-(2-chloro-4-nitroimidazol-1-yl)-1-(4-{4-[4-(4-trifluoromethoxyphenoxymethyl)phenyl]piperazin-1-yl}phenoxy)butan-2-ol The title compound was prepared in the same manner as in Reference Example 12 using suitable starting materials.

Brown Amorphous

Reference Example 133

Preparation of (R)-4-(2-chloro-4-nitroimidazol-1-yl)-1-[4-(4-{4-[N-methyl-N-(4-trifluoromethylbenzyl)amino]phenyl}piperazin-1-yl)phenoxy]butan-2-ol The title compound was prepared in the same manner as in Reference Example 12 using suitable starting materials.

Pale Brown Solid

Reference Example 134

Preparation of (S)-4-(2-chloro-4-nitroimidazol-1-yl)-1-(4-{4-[4-(4-trifluoromethylbenzyloxy)phenoxy]piperidin-1-yl}phenoxy)butan-2-ol The title compound was prepared in the same manner as in Reference Example 12 using suitable starting materials.

Yellow Powder

Reference Example 135

Preparation of 4-{4-[(S)-4-(2-chloro-4-nitroimidazol-1-yl)-2-hydroxybutoxy]phenoxy}piperidine-1-carboxylic acid tert-butyl ester The title compound was prepared in the same manner as in Reference Example 12 using suitable starting materials.

Yellow Solid

Reference Example 136

Preparation of (R)-4-(2-chloro-4-nitroimidazol-1-yl)-1-(4-{4-[4-(4-trifluoromethylbenzyloxy)phenoxy]piperidin-1-yl}phenoxy)butan-2-ol The title compound was prepared in the same manner as in Reference Example 12 using suitable starting materials.

Red Powder

Reference Example 137

Preparation of 4-{5-[(S)-4-(2-chloro-4-nitroimidazol-1-yl)-2-hydroxybutoxy]benzooxazol-2-yl}piperazine-1-carboxylic acid tert-butyl ester The title compound was prepared in the same manner as in Reference Example 12 using suitable starting materials.

Pale Yellow Powder

Reference Example 138

Preparation of 4-{5-[(R)-4-(2-chloro-4-nitroimidazol-1-yl)-2-hydroxybutoxy]benzooxazol-2-yl}piperazine-1-carboxylic acid tert-butyl ester The title compound was prepared in the same manner as in Reference Example 12 using suitable starting materials.

White Powder

Reference Example 139

Preparation of (S)-4-(2-chloro-4-nitroimidazol-1-yl)-1-[4-(4,4-dimethoxypiperidin-1-yl)phenoxy]butan-2-ol The title compound was prepared in the same manner as in Reference Example 12 using suitable starting materials.

Pale Yellow Powder

Reference Example 140

Preparation of 5-[(S)-4-(2-chloro-4-nitroimidazol-1-yl)-2-hydroxybutoxy]-1,3-dihydroisoindole-2-carboxylic acid tert-butyl ester The title compound was prepared in the same manner as in Reference Example 12 using suitable starting materials.

Pale Brown Amorphous

Reference Example 141

Preparation of 5-[(R)-4-(2-chloro-4-nitroimidazol-1-yl)-2-hydroxybutoxy]-1,3-dihydroisoindole-2-carboxylic acid tert-butyl ester The title compound was prepared in the same manner as in Reference Example 12 using suitable starting materials.

Pale Yellow Amorphous

Reference Example 142

Preparation of (R)-4-(2-chloro-4-nitroimidazol-1-yl)-1-(4-{4-[4-(4-trifluoromethoxybenzyloxy)phenoxymethyl]piperidin-1-yl}phenoxy)butan-2-ol The title compound was prepared in the same manner as in Reference Example 12 using suitable starting materials.

Yellow Powder

Reference Example 143

Preparation of (S)-4-(2-chloro-4-nitroimidazol-1-yl)-1-(4-{4-[4-(4-trifluoromethoxybenzyloxy)phenoxymethyl]piperidin-1-yl}phenoxy)butan-2-ol The title compound was prepared in the same manner as in Reference Example 12 using suitable starting materials.

Yellow Powder

Reference Example 144

Preparation of (S)-4-(2-chloro-4-nitroimidazol-1-yl)-1-(2-{4-[4-(4-trifluoromethoxybenzyloxy)benzyl]piperidin-1-yl}benzothiazol-6-yloxy)butan-2-ol The title compound was prepared in the same manner as in Reference Example 12 using suitable starting materials.

Yellow Amorphous

Reference Example 145

Preparation of (R)-4-(2-chloro-4-nitroimidazol-1-yl)-1-(4'-diethoxymethylbiphenyl-4-yloxy)butan-2-ol The title compound was prepared in the same manner as in Reference Example 12 using suitable starting materials.

Brown Oil

Reference Example 146

Preparation of (R)-4-(2-chloro-4-nitroimidazol-1-yl)-1-(2-{4-[4-(4-trifluoromethoxybenzyloxy)benzyl]piperidin-1-yl}benzothiazol-6-yloxy)butan-2-ol The title compound was prepared in the same manner as in Reference Example 12 using suitable starting materials.

Yellow Amorphous

Reference Example 147

Preparation of 7-[(S)-4-(2-chloro-4-nitroimidazol-1-yl)-2-hydroxybutoxy]-3,4-dihydro-1H-isoquinoline-2-carboxylic acid tert-butyl ester The title compound was prepared in the same manner as in Reference Example 12 using suitable starting materials.

Reference Example 148

Preparation of 7-[(R)-4-(2-chloro-4-nitroimidazol-1-yl)-2-hydroxybutoxy]-3,4-dihydro-1H-isoquinoline-2-carboxylic acid tert-butyl ester The title compound was prepared in the same manner as in Reference Example 12 using suitable starting materials.

Pale Yellow Amorphous

Reference Example 149

Preparation of 6-[(S)-4-(2-chloro-4-nitroimidazol-1-yl)-2-hydroxybutoxy]-3,4-dihydro-1H-isoquinoline-2-carboxylic acid tert-butyl ester The title compound was prepared in the same manner as in Reference Example 12 using suitable starting materials.

Yellow Amorphous

Reference Example 150

Preparation of 6-[(R)-4-(2-chloro-4-nitroimidazol-1-yl)-2-hydroxybutoxy]-3,4-dihydro-1H-isoquinoline-2-carboxylic acid tert-butyl ester The title compound was prepared in the same manner as in Reference Example 12 using suitable starting materials.

Yellow Amorphous

Reference Example 151

Preparation of 7-[(S)-4-(2-chloro-4-nitroimidazol-1-yl)-2-hydroxybutoxy]-1,3,4,5-tetrahydrobenzo[c]azepine-2-carboxylic acid tert-butyl ester The title compound was prepared in the same manner as in Reference Example 12 using suitable starting materials.

White Amorphous

Reference Example 152

Preparation of 7-[(R)-4-(2-chloro-4-nitroimidazol-1-yl)-2-hydroxybutoxy]-1,3,4,5-tetrahydrobenzo[c]azepine-2-carboxylic acid tert-butyl ester The title compound was prepared in the same manner as in Reference Example 12 using suitable starting materials.

White Amorphous

Reference Example 153

Preparation of (2R,5S)-4-{4-[(S)-4-(2-chloro-4-nitroimidazol-1-yl)-2-hydroxybutoxy]phenyl}-2,5-dimethylpiperazine-1-carboxylic acid tert-butyl ester The title compound was prepared in the same manner as in Reference Example 12 using suitable starting materials.

Reference Example 154

Preparation of (2R,5S)-4-{4-[(R)-4-(2-chloro-4-nitroimidazol-1-yl)-2-hydroxybutoxy]phenyl}-2,5-dimethylpiperazine-1-carboxylic acid tert-butyl ester The title compound was prepared in the same manner as in Reference Example 12 using suitable starting materials.

Amorphous

Reference Example 155

Preparation of 4-{5-[(R)-4-(2-chloro-4-nitroimidazol-1-yl)-2-hydroxybutoxy]pyridin-2-yl}piperazine-1-carboxylic acid tert-butyl ester The title compound was prepared in the same manner as in Reference Example 12 using suitable starting materials.

Pale Brown Amorphous

Reference Example 156

Preparation of 4-{5-[(S)-4-(2-chloro-4-nitroimidazol-1-yl)-2-hydroxybutoxy]pyridin-2-yl}piperazine-1-carboxylic acid tert-butyl ester The title compound was prepared in the same manner as in Reference Example 12 using suitable starting materials.

Pale Brown Amorphous

Reference Example 157

Preparation of 5-{4-[(S)-4-(2-chloro-4-nitroimida-zol-1-yl)-2-hydroxybutoxy]phenyl}-2,5-diaza-bicyclo[2.2.1]heptane-2-carboxylic acid tert-butyl ester The title compound was prepared in the same manner as in Reference Example 12 using suitable starting materials.

Orange Amorphous

Reference Example 158

Preparation of 4-{4'-[(R)-4-(2-chloro-4-nitroimida-zol-1-yl)-2-hydroxybutoxy]biphenyl-4-yl}piperazine-1-carboxylic acid tert-butyl ester The title compound was prepared in the same manner as in Reference Example 12 using suitable starting materials.

Pale Yellow Solid

Reference Example 159

Preparation of 4-{4'-[(S)-4-(2-chloro-4-nitroimida-zol-1-yl)-2-hydroxybutoxy]biphenyl-4-yl}piperazine-1-carboxylic acid tert-butyl ester The title compound was prepared in the same manner as in Reference Example 12 using suitable starting materials.

Pale Yellow Solid

Reference Example 160

Preparation of (R)-4-(2-chloro-4-nitroimidazol-1-yl)-1-{4-[4-({N-methyl-N-[4-(4-trifluoromethoxybenzy-loxy)phenyl]-amino}-methyl)piperidin-1-yl]phenoxy}butan-2-ol The title compound was prepared in the same manner as in Reference Example 12 using suitable starting materials.

Brown Amorphous

Reference Example 161

Preparation of (S)-4-(2-chloro-4-nitroimidazol-1-yl)-1-{4-[4-({N-methyl-N-[4-(4-trifluoromethoxybenzy-loxy)phenyl]-amino}-methyl)piperidin-1-yl]phenoxy}butan-2-ol The title compound was prepared in the same manner as in Reference Example 12 using suitable starting materials.

Brown Amorphous

Reference Example 162

Preparation of 5-{4-[(R)-4-(2-chloro-4-nitroimida-zol-1-yl)-2-hydroxybutoxy]phenyl}-2,5-diaza-bicyclo[2.2.1]heptane-2-carboxylic acid tert-butyl ester The title compound was prepared in the same manner as in Reference Example 12 using suitable starting materials.

Brown Amorphous

Reference Example 163

Preparation of 4-{4-[(R)-4-(2-chloro-4-nitroimida-zol-1-yl)-2-hydroxybutoxy]phenyl}piperidine-1-carboxylic acid tert-butyl ester The title compound was prepared in the same manner as in Reference Example 12 using suitable starting materials.

Yellow Amorphous

Reference Example 164

Preparation of (R)-4-(2-chloro-4-nitroimidazol-1-yl)-1-{4-[4-(4-trifluoromethylphenoxymethyl)piperidin-1-yl]phenoxy}butan-2-ol The title compound was prepared in the same manner as in Reference Example 12 using suitable starting materials.

Brown Solid

Reference Example 165

Preparation of (R)-4-(2-chloro-4-nitroimidazol-1-yl)-1-{4-[4-(4-trifluoromethoxybenzyloxymethyl)piperi-din-1-yl]phenoxy}butan-2-ol The title compound was prepared in the same manner as in Reference Example 12 using suitable starting materials.

Brown Oil

Reference Example 166

Preparation of 4-(2-chloro-4-nitroimidazol-1-yl)-2-methyl-1-(4-{4-[2-(4-trifluoromethoxyphenyl)ethyl]piperidin-1-yl}phenoxy)butan-2-ol The title compound was prepared in the same manner as in Reference Example 88 using suitable starting materials.
Brown Amorphous
MS (m/z): 596[M]+

Reference Example 167

Preparation of (R)-4-(2-chloro-4-nitroimidazol-1-yl)-1-{4-[4-(4-trifluoromethoxybenzyl)piperidin-1-yl]phenoxy}butan-2-ol The title compound was prepared in the same manner as in Reference Example 12 using suitable starting materials.

Reddish Brown Amorphous

Reference Example 168

Preparation of (R)-4-(2-chloro-4-nitroimidazol-1-yl)-1-{4-[4-(4-trifluoromethylbenzyl)piperidin-1-yl]phenoxy}butan-2-ol The title compound was prepared in the same manner as in Reference Example 12 using suitable starting materials.

Yellow-Red Amorphous

Reference Example 169

Preparation of (R)-1-{4-[4-(4-chlorobenzyl)piperidin-1-yl]phenoxy}-4-(2-chloro-4-nitroimidazol-1-yl)butan-2-ol The title compound was prepared in the same manner as in Reference Example 12 using suitable starting materials.

Yellow-Red Amorphous

Reference Example 170

Preparation of (R)-4-(2-chloro-4-nitroimidazol-1-yl)-1-{4-[4-(4-trifluoromethoxyphenyl)piperidin-1-yl]phenoxy}butan-2-ol The title compound was prepared in the same manner as in Reference Example 12 using suitable starting materials.

Orange Amorphous

Reference Example 171

Preparation of (R)-4-(2-chloro-4-nitroimidazol-1-yl)-1-{4-[4-(4-trifluoromethylphenyl)piperidin-1-yl]phenoxy}butan-2-ol The title compound was prepared in the same manner as in Reference Example 12 using suitable starting materials.

Orange Amorphous

Reference Example 172

Preparation of (R)-4-(2-chloro-4-nitroimidazol-1-yl)-1-{4-[1-(4-trifluoromethoxyphenyl)piperidin-4-yloxy]phenoxy}butan-2-ol The title compound was prepared in the same manner as in Reference Example 12 using suitable starting materials.

Yellow Amorphous

Reference Example 173

Preparation of (R)-4-(2-chloro-4-nitroimidazol-1-yl)-1-{4-[1-(4-trifluoromethylphenyl)piperidin-4-yloxy]phenoxy}butan-2-ol The title compound was prepared in the same manner as in Reference Example 12 using suitable starting materials.

Yellow-Red Amorphous

Reference Example 174

Preparation of 4-(2-chloro-4-nitroimidazol-1-yl)-2-methyl-1-{4-[4-(4-trifluoromethoxybenzyl)piperidin-1-yl]phenoxy}butan-2-ol The title compound was prepared in the same manner as in Reference Example 88 using suitable starting materials.
Yellow Oil
MS (m/z): 582[M]$^+$

Reference Example 175

Preparation of 4-(2-chloro-4-nitroimidazol-1-yl)-2-methyl-1-(4-{4-[3-(4-trifluoromethoxyphenyl)propyl]piperidin-1-yl}phenoxy)butan-2-ol The title compound was prepared in the same manner as in Reference Example 88 using suitable starting materials.

Yellow Oil

Reference Example 176

Preparation of (R)-4-(2-chloro-4-nitroimidazol-1-yl)-1-(4-{4-[3-(4-trifluoromethylphenyl)propyl]piperidin-1-yl}phenoxy)butan-2-ol The title compound was prepared in the same manner as in Reference Example 12 using suitable starting materials.

Pale Brown Oil

Reference Example 177

Preparation of (R)-4-(2-chloro-4-nitroimidazol-1-yl)-1-{4-[4-(5-trifluoromethylpyridin-2-yloxymethyl)piperidin-1-yl]phenoxy}butan-2-ol The title compound was prepared in the same manner as in Reference Example 12 using suitable starting materials.

Pale Yellow Powder

Reference Example 178

Preparation of (R)-4-(2-chloro-4-nitroimidazol-1-yl)-1-(4-{N-ethyl-N-[1-(4-trifluoromethoxyphenyl)piperidin-4-yl]amino}phenoxy)butan-2-ol The title compound was prepared in the same manner as in Reference Example 12 using suitable starting materials.

Pale Yellow Powder

Reference Example 179

Preparation of (R)-4-(2-chloro-4-nitroimidazol-1-yl)-1-(4-{N-methyl-N-[1-(4-trifluoromethoxyphenyl)piperidin-4-yl]amino}phenoxy)butan-2-ol The title compound was prepared in the same manner as in Reference Example 12 using suitable starting materials.

Orange Powder

Reference Example 180

Preparation of (R)-4-(2-chloro-4-nitroimidazol-1-yl)-1-{4-[4-(4-trifluoromethylbenzyloxymethyl)piperidin-1-yl]phenoxy}butan-2-ol The title compound was prepared in the same manner as in Reference Example 12 using suitable starting materials.

Red Amorphous

Reference Example 181

Preparation of (R)-4-(2-chloro-4-nitroimidazol-1-yl)-1-{4-[4-(2,2,2-trifluoro-ethyl)piperazin-1-yl]phenoxy}butan-2-ol The title compound was prepared in the same manner as in Reference Example 12 using suitable starting materials.
Brown Oil
MS (m/z): 477[M]$^+$

Reference Example 182

Preparation of (R)-4-(2-chloro-4-nitroimidazol-1-yl)-1-[4-(4-{2-[N-methyl-N-(4-trifluoromethoxyphenyl)amino]-ethyl}piperidin-1-yl)phenoxy]butan-2-ol Toluene-4-sulfonic acid (R)-4-(2-chloro-4-nitroimidazol-1-yl)-2-hydroxybutyl ester (988 mg) and 4-(4-{2-[N-methyl-N-(4-trifluoromethoxyphenyl)amino]ethyl}piperidin-1-yl)phenol (1.0 g) were suspended in ethanol (30 ml). Tripotassium phosphate (1.08 g) and sodium iodide (418 mg) were added to the suspension, and the mixture was stirred at 80° C. under a nitrogen atmosphere for 4.5 hours. After being cooled to room temperature, ethyl acetate (20 ml) was added to the reaction mixture, insoluble matter was removed by filtration, and the filtrate was concentrated under reduced pressure. The residue was purified by silica gel column chromatography (hexane:ethyl acetate=3:1→methylene chloride:methanol=97:3) to afford the title compound as a reddish brown oil (1.17 g).

Reference Example 183

Preparation of (R)-4-(2-chloro-4-nitroimidazol-1-yl)-1-[4-(4-{[N-methyl-N-(4-trifluoromethoxybenzyl)amino]methyl}piperidin-1-yl)phenoxy]butan-2-ol The title compound was prepared in the same manner as in Reference Example 182 using suitable starting materials.

Orange Amorphous

Reference Example 184

Preparation of (R)-4-(2-chloro-4-nitroimidazol-1-yl)-1-{4-[4-(4-trifluoromethylsulfanylbenzyl)piperidin-1-yl]phenoxy}butan-2-ol Sodium tert-butoxide (0.412 g) was added to an ethanol solution (20 ml) of toluene-4-sulfonic acid (R)-4-(2-chloro-4-nitroimidazol-1-yl)-2-hydroxybutyl ester (1.671 g) under an argon atmosphere in an ice water bath, and the mixture was stirred at room temperature for 30 minutes. Subsequently, 4-[4-(4-trifluoromethylsulfanylbenzyl)piperidin-1-yl]phenol (1.50 g) and tripotassium phosphate (0.867 g) were added thereto, and then the mixture was heated at reflux for 4 hours. Thereafter the reaction mixture was poured into water, followed by extraction with ethyl acetate. The organic layer was washed with a saturated sodium chloride aqueous solution, dried over sodium sulfate, and concentrated under reduced pressure. The residue was purified by silica gel column chromatography (hexane:ethyl acetate=10:0→0:10) to afford the title compound as a brown oil (1.47 g).
MS (m/z): 584[M]$^+$

Reference Example 185

Preparation of (R)-1-{4-[4-(tert-butyl-dimethylsilanyloxy)-[1,4']bipiperidinyl-1'-yl]phenoxy}-4-(2-chloro-4-nitroimidazol-1-yl)butan-2-ol Toluene-4-sulfonic acid (R)-4-(2-chloro-4-nitroimidazol-1-yl)-2-hydroxybutyl ester (848 mg) and 4-[4-(tert-butyl-dimethylsilanyloxy)[1,4']bipiperidinyl-1'-yl]phenol (850 mg) were suspended in ethanol (30 ml). Tripotassium phosphate (1.02 g) and sodium iodide (359 mg) were added to the suspension, and the mixture was stirred at 75° C. for 3 hours under a nitrogen atmosphere. After being cooled to room temperature, the reaction mixture was concentrated under reduced pressure, and water was added to the resulting residue, followed by extraction with ethyl acetate. The organic layer was dried over sodium sulfate and concentrated under reduced pressure. Insoluble matter that was precipitated by adding isopropyl ether to the residue was collected by filtration to afford the title compound as a pale brown powder (470 mg).

Reference Example 186

Preparation of 4-(4-hydroxyphenyl)piperazine-1-carboxylic acid tert-butyl ester 1-(4-Hydroxyphenyl)piperazine (5.0 g) was suspended in methanol (50 ml). Di-tert-butyl dicarbonate (6.8 ml) was added to the suspension, and stirred at room temperature for 2 hours. The mixture was concentrated under reduced pressure, and the residue was purified by silica gel column chromatography (dichloromethane:methanol=50:1) to afford the title compound as a white powder (7.88 g).
1H NMR (CDCl3) δ 1.49 (9H, s), 2.95-3.00 (4H, m), 3.55-3.60 (4H, m), 5.77 (1H, s), 6.74-6.86 (4H, m).

Reference Example 187

Preparation of 4-[4-(4-trifluoromethoxybenzyloxy)piperidin-1-yl]phenol

Pyridinium p-toluenesulfonate (81 mg) was added to an ethanol solution (3 ml) of 1-[4-(tetrahydropyran-2-yloxy)phenyl]-4-(4-trifluoromethoxybenzyloxy)piperidine (507 mg) and the mixture was stirred at 70 to 80° C. for 24 hours. After being cooled to room temperature, the reaction mixture was concentrated under reduced pressure, ethyl acetate and a saturated sodium hydrogen carbonate aqueous solution were added to the residue, and the result was separated into layers. The organic layer was washed with a saturated sodium chloride aqueous solution and dried over magnesium sulfate. After being concentrated under reduced pressure, the residue was purified by silica gel column chromatography (hexane:ethyl acetate=2:1) to afford the title compound as a pale purple solid (305 mg).
1H NMR (CDCl3) δ 1.76-1.90 (2H, m), 2.00-2.10 (2H, m), 2.84 (2H, m), 3.33-3.42 (2H, m), 3.51-3.60 (1H, m), 4.53 (1H, brs), 4.63 (2H, s), 6.74 (2H, d, J=9.0 Hz), 6.87 (2H, d, J=9.0 Hz), 7.48 (2H, d, J=8.1 Hz), 7.60 (2H, d, J=8.2 Hz).

Reference Example 188

Preparation of 4-[4-(4-trifluoromethylbenzyloxy)piperidin-1-yl]phenol

The title compound was prepared in the same manner as in Reference Example 187 using suitable starting materials.
Colorless Solid
1H NMR (CDCl3) δ 1.71-1.93 (2H, m), 1.95-2.15 (2H, m), 2.71-2.93 (2H, m), 3.26-3.46 (2H, m), 3.46-3.63 (1H, m), 4.50 (1H, s), 4.57 (2H, s), 6.74 (2H, d, J=9.0 Hz), 6.87 (2H, d, J=8.9 Hz), 7.19 (2H, d, J=8.5 Hz), 7.39 (2H, d, J=8.4 Hz).

Reference Example 189

Preparation of 4-[4-(4-trifluoromethylphenylamino)piperidin-1-yl]phenol

The title compound was prepared in the same manner as in Reference Example 187 using suitable starting materials.
Colorless Amorphous
1H NMR (CDCl3) δ 1.56-1.72 (2H, m), 2.13-2.20 (2H, m), 2.77-2.88 (2H, m), 3.44-3.51 (3H, m), 3.92 (1H, d, J=7.94 Hz), 4.86 (1H, s), 6.59-6.63 (2H, m), 6.72-6.79 (2H, m), 6.85-6.92 (2H, m), 7.38-7.42 (2H, m).

Reference Example 190

Preparation of 4-[4-(4-trifluoromethoxyphenoxymethyl)piperidin-1-yl]phenol

The title compound was prepared in the same manner as in Reference Example 187 using suitable starting materials.
Pale Yellow Solid
1H NMR (CDCl3) δ 1.48-1.63 (2H, m), 1.87-1.98 (3H, m), 2.62-2.72 (2H, m), 3.51-3.57 (2H, m), 3.83 (2H, d, J=5.88 Hz), 4.50 (1H, brs), 6.73-6.78 (2H, m), 6.84-6.91 (4H, m), 7.12-7.16 (2H, m).

Reference Example 191

Preparation of 4-[4-(4-trifluoromethoxybenzyl)piperidin-1-yl]phenol

10% palladium on carbon (64 mg) was added to an ethanol solution (13 ml) of 4-(4-trifluoromethoxybenzyl)piperidine (1.28 g) and 1,4-cyclohexanedione (1.19 g), and the mixture was stirred at 70 to 80° C. for 8.5 hours. After being cooled to room temperature, the catalyst was removed by filtration, and the filtrate was concentrated under reduced pressure. After being dissolved in ethyl acetate, the residue was washed with a saturated sodium chloride aqueous solution and dried over magnesium sulfate. After being concentrated under reduced pressure, the residue was purified by silica gel column chromatography (hexane:ethyl acetate=10:0→6:4) to afford the title compound as a black oil (305 mg).
MS (m/z): 351[M]+

Reference Example 192

Preparation of 4-[4-(3,4-dichlorobenzyl)piperidin-1-yl]phenol

The title compound was prepared in the same manner as in Reference Example 191 using suitable starting materials.
Brown Oil
MS (m/z): 335[M]+

Reference Example 193

Preparation of 4-[4-(4-trifluoromethylbenzyloxymethyl)piperidin-1-yl]phenol

The title compound was prepared in the same manner as in Reference Example 187 using suitable starting materials.
Pale Yellow Oil
1H NMR (CDCl3) δ 1.37-1.54 (2H, m), 1.68-1.90 (3H, m), 2.57-2.68 (2H, m), 3.39 (2H, d, J=6.29 Hz), 3.46-3.52 (2H, m), 4.57 (2H, s), 5.28 (1H, s), 6.67-6.74 (2H, m), 6.83-6.89 (2H, m), 7.43-7.47 (2H, m), 7.58-7.62 (2H, m).

Reference Example 194

Preparation of 4-[3-(4-trifluoromethoxyphenoxy)-8-azabicyclo[3.2.1]oct-8-yl]phenol The title compound was prepared in the same manner as in Reference Example 191 using suitable starting materials.
Gray Powder
MS (m/z): 379[M]+

Reference Example 195

Preparation of 1-(4-hydroxyphenyl)-4-(4-trifluoromethoxyphenyl)piperidin-4-ol

The title compound was prepared in the same manner as in Reference Example 191 using suitable starting materials.
Black Powder
MS (m/z): 353[M]+

Reference Example 196

Preparation of 4-{4-[3-(4-trifluoromethoxyphenyl)propyl]piperidin-1-yl}phenol

The title compound was prepared in the same manner as in Reference Example 191 using suitable starting materials.
Black Oil
MS (m/z): 379[M]+

Reference Example 197

Preparation of 4-{4-[2-(4-trifluoromethoxybenzyloxy)ethyl]piperidin-1-yl}phenol

6 N hydrochloric acid (1 ml) was added to an ethanol solution (15 ml) of 1-(4-methoxymethoxyphenyl)-4-[2-(4-trifluoromethoxybenzyloxy)ethyl]piperidine (1.51 g) and stirred at 60° C. for 2 hours. The mixture was cooled to room temperature and concentrated under reduced pressure. A saturated sodium hydrogen carbonate aqueous solution was added to the residue, followed by extraction with dichloromethane. The organic layer was dried over magnesium sulfate and concentrated under reduced pressure to afford the title compound as a pink solid (1.34 g).
1H NMR (CDCl3) δ 1.37-1.66 (5H, m), 1.75-1.81 (2H, m), 2.55-2.65 (2H, m), 3.44-3.50 (2H, m), 3.55 (2H, t, J=6.3 Hz), 4.44 (1H, s), 4.50 (2H, s), 6.72-6.78 (2H, m), 6.83-6.89 (2H, m), 7.18-7.22 (2H, m), 7.35-7.39 (2H, m)

Reference Example 198

Preparation of 4-{4-[2-(4-trifluoromethylbenzyloxy)ethyl]piperidin-1-yl}phenol

The title compound was prepared in the same manner as in Reference Example 191 using suitable starting materials.
Gray Solid
1H NMR (CDCl3) δ 1.35-1.67 (5H, m), 1.76-1.82 (2H, m), 2.55-2.66 (2H, m), 3.44-3.50 (2H, m), 3.57 (2H, t, J=6.3 Hz), 4.38 (1H, s), 4.57 (2H, s), 6.72-6.78 (2H, m), 6.84-6.89 (2H, m), 7.43-7.48 (2H, m), 7.59-7.62 (2H, m)

Reference Example 199

Preparation of 4-[4-(5-trifluoromethylbenzofuran-2-ylmethyl)piperidin-1-yl]phenol 1 N hydrochloric acid was added to an ethanol solution of 1-[4-(tetrahydropyran-2-yloxy)phenyl]-4-(5-trifluoromethylbenzofuran-2-ylmethyl)piperidine (2.3 g) and stirred at 80° C. for 1 hour. After being cooled to room temperature, a saturated sodium hydrogen carbonate aqueous solution was added to the mixture and concentrated under reduced pressure. The residue was subjected to extraction with ethyl acetate. The organic layer was dried over sodium sulfate, and then concentrated under reduced pressure. The residue was purified by silica gel column chromatography (hexane:ethyl acetate=3:1) to afford the title compound as a pinkish white amorphous compound (1.15 g).

Reference Example 200

Preparation of 4-[4-(3-trifluoromethylphenoxymethyl)piperidin-1-yl]phenol

The title compound was prepared in the same manner as in Reference Example 191 using suitable starting materials.
Brown Solid Reference Example 201

Preparation of 4-{4-[2-(4-trifluoromethylphenoxy)ethyl]piperidin-1-yl}phenol

The title compound was prepared in the same manner as in Reference Example 191 using suitable starting materials.
Brown Solid Reference Example 202

Preparation of 4-{4-[3-(4-trifluoromethylphenoxy)propyl]piperidin-1-yl}phenol

The title compound was prepared in the same manner as in Reference Example 191 using suitable starting materials.
Brown Solid Reference Example 203

Preparation of 4-[2-(4-chlorophenoxymethyl)oxazol-4-yl]phenol

2-Bromo-1-(4-hydroxyphenyl)ethanone (2.90 g) and 2-(4-chlorophenoxy)acetamide (5.0 g) were added to N-methylpyrrolidone (5 ml), and the mixture was stirred at 100° C. under a nitrogen atmosphere. After being cooled to room temperature, ethyl acetate and a saturated sodium hydrogen carbonate aqueous solution were added to the reaction mixture and separated into layers. The organic layer was washed with water, dried over sodium sulfate, and then concentrated under reduced pressure. Sodium acetate (11.1 g) in DMF (20 ml) were added to the residue and then stirred at room temperature for 2 hours. The reaction mixture was diluted with ethyl acetate and the prepared insoluble matter was removed by filtration, and the filtrate was concentrated under reduced pressure. The residue was purified by silica gel column chromatography (hexane:ethyl acetate=2:1→1:1) and recrystallized from hexane-ethyl acetate to afford the title compound as a pale yellow powder (1.63 g).

Reference Example 204

Preparation of 4-{4-[2-(4-trifluoromethylphenyl)ethyl]piperidin-1-yl}phenol

The title compound was prepared in the same manner as in Reference Example 191 using suitable starting materials.
White Powder Reference Example 205

Preparation of 4-{4-[4-(4-trifluoromethoxybenzyloxy)benzyl]piperidin-1-yl}phenol The title compound was prepared in the same manner as in Reference Example 191 using suitable starting materials.
Brown Powder
MS (m/z): 457[M]$^+$ Reference Example 206

Preparation of 4-{4-[2-(4-trifluoromethylphenyl)ethyl]piperazin-1-yl}phenol 1-(4-Benzyloxyphenyl)-4-[2-(4-trifluoromethylphenyl)ethyl]piperazine (0.94 g) was dissolved in ethanol (19 ml) and THF (19 ml). 10% palladium on carbon (94 mg) was added to the mixture and stirred at 50 to 60° C. under a hydrogen atmosphere for 8 hours. After being cooled to room temperature, the catalyst was removed by filtration, and the filtrate was concentrated under reduced pressure to afford the title compound as a gray powder (0.72 g).
MS (m/z): 349[M−H]

Reference Example 207

Preparation of 4-{4-[2-(4-trifluoromethoxyphenyl)ethyl]piperazin-1-yl}phenol

The title compound was prepared in the same manner as in Reference Example 206 using suitable starting materials.
Gray Powder
MS (m/z): 366[M]$^+$

Reference Example 208

Preparation of 4-{4-[4-(4-trifluoromethylbenzyloxy)benzyl]piperidin-1-yl}phenol

The title compound was prepared in the same manner as in Reference Example 191 using suitable starting materials.
Brown Amorphous
MS (m/z): 411[M]$^+$

Reference Example 209

Preparation of 3-fluoro-4-[4-(4-trifluoromethoxyphenoxy)piperidin-1-yl]phenol

The title compound was prepared in the same manner as in Reference Example 206 using suitable starting materials.

Pale Brown Powder

Reference Example 210

Preparation of 4-{4-[4-(4-trifluoromethoxyphenoxy)benzyl]piperidin-1-yl}phenol

The title compound was prepared in the same manner as in Reference Example 199 using suitable starting materials.

Amorphous

Reference Example 211

Preparation of 4-{3,5-dimethyl-4-[3-(4-trifluoromethylphenyl)propyl]piperazin-1-yl}phenol The title compound was prepared in the same manner as in Reference Example 191 using suitable starting materials.
Pale brown powder
MS (m/z): 392[M]$^+$

Reference Example 212

Preparation of 4-{(3R,5S)-3,5-dimethyl-4-[4-(4-trifluoromethoxybenzyloxy)benzyl]piperazin-1-yl}phenol The title compound was prepared in the same manner as in Reference Example 191 using suitable starting materials.
Brown Amorphous
MS (m/z): 486[M]$^+$

Reference Example 213

Preparation of 4'-[4-(4-trifluoromethoxyphenoxy)piperidin-1-ylmethyl]-biphenyl-4-ol Sodium triacetoxyborohydride (1.69 g) was added to a 1,2-dichloroethane solution (11 ml) of 4'-hydroxybiphenyl-4-carbaldehyde (1.13 g) and 4-(4-trifluoromethoxyphenoxy)piperidine (1.78 g) and stirred at room temperature overnight. A potassium carbonate aqueous solution was added to the reaction mixture, followed by extraction with dichloromethane. The organic layer was washed with water, dried over sodium sulfate, and concentrated under reduced pressure. The residue was purified by silica gel column chromatography (hexane:ethyl acetate=10:0→0:10) to afford the title compound as a yellow powder (1.73 g).
MS (m/z): 443[M]$^+$

Reference Example 214

Preparation of 4-{3,5-dimethyl-4-[4-(4-trifluoromethylbenzyloxy)benzyl]piperazin-1-yl}phenol The title compound was prepared in the same manner as in Reference Example 187 using suitable starting materials.
Brown Powder
MS (m/z): 470[M]$^+$

Reference Example 215

Preparation of 4-{(R)-3-methyl-4-[4-(4-trifluoromethylbenzyloxy)benzyl]piperazin-1-yl}phenol The title compound was prepared in the same manner as in Reference Example 187 using suitable starting materials.
Brown Amorphous
MS (m/z): 456[M]$^+$

Reference Example 216

Preparation of (R)-4-(4-hydroxyphenyl)-3-methylpiperazine-1-carboxylic acid tert-butyl ester The title compound was prepared in the same manner as in Reference Example 187 using suitable starting materials.
Yellow Oil
MS (m/z): 292[M]$^+$

Reference Example 217

Preparation of 4-{(S)-3-methyl-4-[4-(4-trifluoromethylbenzyloxy)benzyl]piperazin-1-yl}phenol The title compound was prepared in the same manner as in Reference Example 187 using suitable starting materials.
Brown Amorphous
MS (m/z): 456[M]$^+$

Reference Example 218

Preparation of (S)-4-(4-hydroxyphenyl)-3-methylpiperazine-1-carboxylic acid tert-butyl ester The title compound was prepared in the same manner as in Reference Example 206 using suitable starting materials.
Brown Oil
MS (m/z): 292[M]$^+$

Reference Example 219

Preparation of 1-(4'-hydroxybiphenyl-4-yl)-4-trifluoromethylpiperidin-4-ol

The title compound was prepared in the same manner as in Reference Example 206 using suitable starting materials.

White Powder

Reference Example 220

Preparation of 4-{4-[3-(3-trifluoromethylphenoxy) propyl]piperidin-1-yl}phenol

The title compound was prepared in the same manner as in Reference Example 187 using suitable starting materials.

Yellow Solid

Reference Example 221

Preparation of 4-{4-[3-(5-trifluoromethylpyridin-2-yloxy)propyl]piperidin-1-yl}phenol The title compound was prepared in the same manner as in Reference Example 187 using suitable starting materials.

White Solid

Reference Example 222

Preparation of 4-{4-[4-(4-trifluoromethylbenzyloxy) benzyl]-3,6-dihydro-2H-pyridin-1-yl}phenol The title compound was prepared in the same manner as in Reference Example 199 using suitable starting materials.

Brown Powder

Reference Example 223

Preparation of 4-[4-(4-trifluoromethoxyphenyl)-3,6-dihydro-2H-pyridin-1-yl]phenol The title compound was prepared in the same manner as in Reference Example 187 using suitable starting materials.

Pink Powder

Reference Example 224

Preparation of 4-[4-(4-trifluoromethoxybenzyl)-3,6-dihydro-2H-pyridin-1-yl]phenol The title compound was prepared in the same manner as in Reference Example 187 using suitable starting materials.

Yellow Oil

Reference Example 225

Preparation of 2-hydroxy-4-(4-trifluoromethylbenzyloxy)benzaldehyde

Potassium carbonate (16.51 g) and 4-trifluoromethylbenzylbromide (18.47 ml) were added to an acetone solution of 2,4-dihydroxybenzaldehyde (15 g). The mixture was stirred at room temperature for 15 hours and further stirred at 60° C. for 7 hours. After being cooled to room temperature, the mixture was concentrated under reduced pressure. Water was added to the residue, followed by extraction with ethyl acetate. The organic layer was washed with water and a saturated sodium chloride aqueous solution, dried over sodium sulfate, and then concentrated under reduced pressure. The residue was purified by silica gel column chromatography (hexane:ethyl acetate=9:1) to afford the title compound as a white powder (12.76 g).

Reference Example 226

Preparation of 4-[4-(4-trifluoromethylsulfanylphenoxy)piperidin-1-yl]phenol

The title compound was prepared in the same manner as in Reference Example 187 using suitable starting materials.
Yellow Powder
MS (m/z): 369[M]$^+$

Reference Example 227

Preparation of 4-[4-(5-trifluoromethylbenzofuran-2-ylmethoxy)piperidin-1-yl]phenol p-Toluenesulfonic acid monohydrate (0.84 g) was added to an ethanol solution (40 ml) of 1-[4-(tetrahydropyran-2-yloxy)phenyl]-4-(5-trifluoromethylbenzofuran-2-yl-methoxy)piperidine (2.1 g) and the mixture was heated at reflux for 1 hour. After being cooled to room temperature, water was added to the reaction mixture and filtered through Celite, followed by extraction with ethyl acetate. The organic layer was washed with a saturated sodium chloride aqueous solution, dried over sodium sulfate, and then concentrated under reduced pressure. The residue was washed with ether and dried to afford the title compound as a white powder (1.4 g).
1H NMR (CDCl3) δ 1.80-1.87 (2H, m), 2.03-2.09 (2H, m), 2.83 (2H, dt, J=9.5, 2.9 Hz), 3.35-3.39 (2H, m), 3.60-3.66 (1H, m), 4.69 (2H, s), 5.23 (1H, brs), 6.70-6.76 (3H, m), 6.85-6.88 (2H, m), 7.52-7.56 (2H, m), 7.84 (1H, s).

Reference Example 228

Preparation of 4-[4-(4-trifluoromethoxyphenylsulfanyl)piperidin-1-yl]phenol

The title compound was prepared in the same manner as in Reference Example 227 using suitable starting materials.
White Powder
1H NMR (CDCl3) δ 1.76-1.84 (2H, m), 2.05-2.09 (2H, m), 2.74 (2H, dt, J=9.5, 2.6 Hz), 3.13-3.19 (1H, m), 3.42-3.46 (2H, m), 5.23 (1H, brs), 6.70-6.76 (2H, m), 6.82-6.86 (2H, m), 7.15 (2H, d, J=8.6 Hz), 7.44-7.47 (2H, m).

Reference Example 229

Preparation of 4-{4-[2-(4-trifluoromethoxyphenylsulfanyl)ethyl]piperidin-1-yl}phenol The title compound was prepared in the same manner as in Reference Example 227 using suitable starting materials.
White Powder
1H NMR (CDCl3) δ 1.36-1.46 (2H, m), 1.48-1.58 (1H, m), 1.64 (2H, dt, J=7.0, 7.5 Hz), 1.76-1.83 (2H, m), 2.56-2.65 (2H, m), 2.96 (2H, t, J=7.5 Hz), 3.43-3.49 (2H, m), 5.30 (1H, brs), 6.70 (2H, d, J=9.0 Hz), 6.85 (2H, d, J=9.0 Hz), 7.12-7.16 (2H, m), 7.31-7.35 (2H, m).

Reference Example 230

Preparation of 4-[4-(3,4-dichlorophenoxy)piperidin-1-yl]phenol

10% palladium on carbon (350 mg) was added to an ethanol solution (50 ml) of 4-(3,4-dichlorophenoxy)piperidine (7.1 g) and 1,4-cyclohexanedione (6.47 g), and the mixture was stirred at 50 to 60° C. for 5 hours. After being cooled to room temperature, the catalyst was removed by filtration, and the filtrate was concentrated under reduced pressure. The residue was dissolved in ethyl acetate, washed with a saturated sodium chloride aqueous solution, and dried over magnesium sulfate. After being concentrated under reduced pressure, the residue was purified by silica gel column chromatography (hexane:ethyl acetate=9:1→3:1) to afford the title compound as a pale brown powder (5.2 g).

1H NMR (CDCl3) δ 1.91-1.98 (2H, m), 2.05-2.13 (2H, m), 2.94-3.01 (2H, m), 3.29-3.34 (2H, m), 4.36-4.41 (1H, m), 5.25 (1H, brs), 6.72-6.79 (3H, m), 6.87-6.90 (2H, m), 7.02 (1H, d, J=0.7 Hz), 7.31 (1H, d, J=8.9 Hz).

Reference Example 231

Preparation of 1-(4-hydroxyphenyl)-4-(4-trifluoromethylphenyl)piperidin-4-ol 1-(4-Benzyloxyphenyl)-4-(4-trifluoromethylphenyl)piperidin-4-ol (2 g) was dissolved in ethanol (20 ml) and ethyl acetate (20 ml). 20% palladium hydroxide on carbon (0.2 g) was added to the mixture and stirred at room temperature under a hydrogen atmosphere for 1.5 hours. The mixture was filtered through Celite to remove the catalyst, and the filtrate was concentrated under reduced pressure. The residue was washed with an ether-hexane mixed solvent to afford the title compound as a pale pink powder (1.43 g).

Reference Example 232

Preparation of 4-[4-methoxy-4-(4-trifluoromethylphenyl)piperidin-1-yl]phenol

The title compound was prepared in the same manner as in Reference Example 231 using suitable starting materials.

White Powder

Reference Example 233

Preparation of 4-[4-methoxy-4-(4-trifluoromethoxyphenyl)piperidin-1-yl]phenol

The title compound was prepared in the same manner as in Reference Example 231 using suitable starting materials.

Pale Pink Powder

Reference Example 234

Preparation of 4-[4-(4-hydroxybenzyl)piperidin-1-yl]phenol

48% hydrobromic acid (300 ml) was added to 4-(4-methoxybenzyl)-1-(4-methoxyphenyl)piperidine (10.58 g) and heated at 100° C. for 21 hours. After being cooled to room temperature, the reaction mixture was diluted with water and neutralized by adding a sodium hydroxide aqueous solution and a sodium hydrogen carbonate aqueous solution. The insoluble matter formed was collected by filtration and dried to afford the title compound as a grayish brown powder (10.46 g).

Reference Example 235

Preparation of 4-(4-{1-methyl-1-[4-(4-trifluoromethylbenzyloxy)phenyl]-ethyl}piperazin-1-yl)phenol The title compound was prepared in the same manner as in Reference Example 227 using suitable starting materials.

White Powder

Reference Example 236

Preparation of 4-{4-[4-(4-trifluoromethylphenoxy)benzyl]piperidin-1-yl}phenol

The title compound was prepared in the same manner as in Reference Example 187 using suitable starting materials.

Pale Red Solid

Reference Example 237

Preparation of 4-[2-(4-trifluoromethoxyphenoxymethyl)thiazol-4-yl]phenol

A solution of 2-Bromo-1-(4-hydroxyphenyl)ethanone (4.09 g) and 4-(4-trifluoromethoxyphenoxy)-thiobutyramide (5.31 g) in ethanol (100 ml) was heated at reflux overnight. The mixture was concentrated under reduced pressure. The residue was purified by silica gel column chromatography (dichloromethane) to afford the title compound as a yellow oil (2.60 g, 6.57 mmol, 34.6%).

Reference Example 238

Preparation of 4-(4-hydroxyphenyl)piperidine-1-carboxylic acid tert-butyl ester

The title compound was prepared in the same manner as in Reference Example 206 using suitable starting materials.

Reference Example 239

Preparation of 4-[4-(4-trifluoromethoxyphenoxy)piperidin-1-yl]phenol

The title compound was prepared in the same manner as in Reference Example 187 using suitable starting materials.

Reference Example 240

Preparation of 4-[4-(4-chlorophenoxy)piperidin-1-yl]phenol

The title compound was prepared in the same manner as in Reference Example 187 using suitable starting materials.

Reference Example 241

Preparation of 4-[4-(4-trifluoromethylphenoxy)piperidin-1-yl]phenol

The title compound was prepared in the same manner as in Reference Example 187 using suitable starting materials.

Reference Example 242

Preparation of 4-[4-(4-chlorobenzyloxy)piperidin-1-yl]phenol

The title compound was prepared in the same manner as in Reference Example 187 using suitable starting materials.

Reference Example 243

Preparation of 4-{4-[N-(4-chlorophenyl)-N-methylamino]piperidin-1-yl}phenol

The title compound was prepared in the same manner as in Reference Example 187 using suitable starting materials.

Reference Example 244

Preparation of 4-[4-(4-trifluoromethoxybenzyloxymethyl)piperidin-1-yl]phenol

The title compound was prepared in the same manner as in Reference Example 187 using suitable starting materials.

Reference Example 245

Preparation of 4-[4-(4-trifluoromethylbenzyl)piperidin-1-yl]phenol

The title compound was prepared in the same manner as in Reference Example 191 using suitable starting materials.

Reference Example 246

Preparation of 4-[4-(4-chlorobenzyl)piperidin-1-yl]phenol

The title compound was prepared in the same manner as in Reference Example 191 using suitable starting materials.

Reference Example 247

Preparation of 4-[4-(4-trifluoromethylphenoxymethyl)piperidin-1-yl]phenol

The title compound was prepared in the same manner as in Reference Example 187 using suitable starting materials.

Reference Example 248

Preparation of 4-[4-(4-chlorobenzyloxymethyl)piperidin-1-yl]phenol

The title compound was prepared in the same manner as in Reference Example 187 using suitable starting materials.

Reference Example 249

Preparation of 4-[4-(4-trifluoromethoxyphenyl)piperidin-1-yl]phenol

The title compound was prepared in the same manner as in Reference Example 191 using suitable starting materials.

Reference Example 250

Preparation of 4-{4-[N-methyl-N-(4-trifluoromethylphenyl)amino]piperidin-1-yl}phenol The title compound was prepared in the same manner as in Reference Example 191 using suitable starting materials.

Reference Example 251

Preparation of 4-[1-(4-trifluoromethoxyphenyl)piperidin-4-yloxy]phenol

The title compound was prepared in the same manner as in Reference Example 206 using suitable starting materials.

Reference Example 252

Preparation of 4-(4-hydroxyphenoxy)piperidine-1-carboxylic acid tert-butyl ester The title compound was prepared in the same manner as in Reference Example 206 using suitable starting materials.

Reference Example 253

Preparation of 4-[1-(4-trifluoromethylphenyl)piperidin-4-yloxy]phenol

The title compound was prepared in the same manner as in Reference Example 206 using suitable starting materials.

Reference Example 254

Preparation of 4-{4-[N-methyl-N-(4-trifluoromethoxyphenyl)amino]piperidin-1-yl}phenol The title compound was prepared in the same manner as in Reference Example 191 using suitable starting materials.

Reference Example 255

Preparation of 4-{4-[N-(4-chlorophenyl)-N-ethylamino]piperidin-1-yl}phenol

The title compound was prepared in the same manner as in Reference Example 191 using suitable starting materials.

Reference Example 256

Preparation of 4-(4'-hydroxybiphenyl-4-yl)piperazin-1-carboxylic acid tert-butyl ester The title compound was prepared in the same manner as in Reference Example 187 using suitable starting materials.

Reference Example 257

Preparation of 4-{4-[2-(4-trifluoromethoxyphenyl)ethyl]piperidin-1-yl}phenol

The title compound was prepared in the same manner as in Reference Example 191 using suitable starting materials.

Reference Example 258

Preparation of 4-(4-hydroxyphenyl)[1,4]diazepane-1-carboxylic acid tert-butyl ester The title compound was prepared in the same manner as in Reference Example 191 using suitable starting materials.

Reference Example 259

Preparation of 4-(4,4-dimethoxypiperidin-1-yl)phenol

The title compound was prepared in the same manner as in Reference Example 206 using suitable starting materials.

Reference Example 260

Preparation of 4-[4-(5-chlorobenzofuran-2-ylmethyl)piperidin-1-yl]phenol

The title compound was prepared in the same manner as in Reference Example 191 using suitable starting materials.

Reference Example 261

Preparation of 4-[2-(4-trifluoromethoxyphenyl)oxazol-4-yl]phenol

2-Bromo-1-(4-hydroxyphenyl)ethanone (0.39 g) and 4-trifluoromethoxybenzamide (0.39 g) were dissolved in N,N-dimethylformamide (10 ml) and stirred at 140° C. for 2 hours. After cooling the reaction mixture to room temperature, water was added thereto, followed by extraction with ethyl acetate. The organic layer was washed with water and a saturated sodium chloride aqueous solution, dried over sodium sulfate, and then concentrated under reduced pressure. The residue was purified by silica gel column chromatography (hexane:ethyl acetate=75:25). The result was concentrated to dryness under reduced pressure to afford the title compound as a pale yellow solid (70 mg).

Reference Example 262

Preparation of 4-[4-(4-trifluoromethoxyphenyl)oxazol-2-ylmethyl]phenol

The title compound was prepared in the same manner as in Reference Example 261 using suitable starting materials.

Reference Example 263

Preparation of [4-(4-hydroxyphenyl)piperazin-1-yl]carbamic acid tert-butyl ester The title compound was prepared in the same manner as in Reference Example 191 using suitable starting materials.

Reference Example 264

Preparation of 4-[2-(4-trifluoromethoxybenzyl)thiazol-4-yl]phenol

The title compound was prepared in the same manner as in Reference Example 237 using suitable starting materials.

Reference Example 265

Preparation of 4-{4-[2-(4-chlorophenoxy)ethyl]piperidin-1-yl}phenol

The title compound was prepared in the same manner as in Reference Example 191 using suitable starting materials.

Reference Example 266

Preparation of 4-{4-[2-(4-trifluoromethoxyphenoxy)ethyl]piperidin-1-yl}phenol

The title compound was prepared in the same manner as in Reference Example 191 using suitable starting materials.

Reference Example 267

Preparation of 4-[4-(5-trifluoromethylpyridin-2-yloxymethyl)piperidin-1-yl]phenol The title compound was prepared in the same manner as in Reference Example 197 using suitable starting materials.

Reference Example 268

Preparation of 4-[2-(4-trifluoromethoxyphenoxymethyl)oxazol-4-yl]phenol

The title compound was prepared in the same manner as in Reference Example 261 using suitable starting materials.

Reference Example 269

Preparation of 4-{4-[3-(4-trifluoromethoxyphenoxy)propyl]piperidin-1-yl}phenol

The title compound was prepared in the same manner as in Reference Example 197 using suitable starting materials.

Reference Example 270

Preparation of 4-[4-(5-trifluoromethylpyridin-2-yloxy)piperidin-1-yl]phenol

The title compound was prepared in the same manner as in Reference Example 199 using suitable starting materials.

Reference Example 271

Preparation of 4-{4-[2-(5-trifluoromethylpyridin-2-yloxy)ethyl]piperidin-1-yl}phenol The title compound was prepared in the same manner as in Reference Example 199 using suitable starting materials.

Reference Example 272

Preparation of 4-{4-[N-ethyl-N-(4-trifluoromethylphenyl)amino]piperidin-1-yl}phenol The title compound was prepared in the same manner as in Reference Example 191 using suitable starting materials.

Reference Example 273

Preparation of 4-[4-(3-trifluoromethylphenoxy)piperidin-1-yl]phenol

The title compound was prepared in the same manner as in Reference Example 191 using suitable starting materials.

Reference Example 274

Preparation of 4-[4-(3,5-bis-trifluoromethylphenoxy)piperidin-1-yl]phenol

The title compound was prepared in the same manner as in Reference Example 191 using suitable starting materials.

Reference Example 275

Preparation of 4-{4-[N-ethyl-N-(4-trifluoromethoxyphenyl)amino]piperidin-1-yl}phenol The title compound was prepared in the same manner as in Reference Example 191 using suitable starting materials.

Reference Example 276

Preparation of 4-[1-(4-trifluoromethoxyphenyl)piperidin-4-yl]phenol

The title compound was prepared in the same manner as in Reference Example 234 using suitable starting materials.

Reference Example 277

Preparation of 4-[1-(4-trifluoromethylphenyl)piperidin-4-yl]phenol

The title compound was prepared in the same manner as in Reference Example 234 using suitable starting materials.

Reference Example 278

Preparation of 1-(4-hydroxyphenyl)-4-trifluoromethylpiperidin-4-ol

The title compound was prepared in the same manner as in Reference Example 206 using suitable starting materials.

Reference Example 279

Preparation of 4-[2-(4-trifluoromethoxyphenyl)thiazol-4-yl]phenol

The title compound was prepared in the same manner as in Reference Example 237 using suitable starting materials.

Reference Example 280

Preparation of 4-(4-methoxy-4-trifluoromethylpiperidin-1-yl)phenol

Boron trichloride (1 M dichloromethane solution, 2.3 ml) was added to a solution (50 ml) of 1-(4-benzyloxyphenyl)-4-methoxy-4-trifluoromethylpiperidine (0.7 g) in dichloromethane (50 ml) at 0° C. and stirred for 20 minutes. A sodium hydrogen carbonate aqueous solution was added to the reaction mixture, followed by extraction with dichloromethane. The organic layer was washed with water and dried over sodium sulfate. The result was concentrated under reduced pressure, and the residue was washed with diethylether and then dried to afford the title compound as a pale yellow powder (508 mg).

Reference Example 281

Preparation of 4-(4-propoxy-4-trifluoromethylpiperidin-1-yl)phenol

The title compound was prepared in the same manner as in Reference Example 206 using suitable starting materials.

Reference Example 282

Preparation of 4-[4-(3-chloro-5-trifluoromethylpyridin-2-yloxy)piperidin-1-yl]phenol The title compound was prepared in the same manner as in Reference Example 199 using suitable starting materials.

Reference Example 283

Preparation of 4-[1-(4-trifluoromethoxyphenyl)piperidin-4-ylmethyl]phenol

The title compound was prepared in the same manner as in Reference Example 234 using suitable starting materials.

Reference Example 284

Preparation of 4-(4-hydroxybenzyl)piperidine-1-carboxylic acid tert-butyl ester

The title compound was prepared in the same manner as in Reference Example 186 using suitable starting materials.

Reference Example 285

Preparation of 4-[1-(4-trifluoromethylphenyl)piperidin-4-ylmethyl]phenol

The title compound was prepared in the same manner as in Reference Example 234 using suitable starting materials.

Reference Example 286

Preparation of 4-{4-[3-(4-trifluoromethylphenyl)propyl]piperidin-1-yl}phenol

The title compound was prepared in the same manner as in Reference Example 199 using suitable starting materials.

Reference Example 287

Preparation of 4-[2-(4-hydroxyphenyl)ethyl]piperidine-1-carboxylic acid tert-butyl ester The title compound was prepared in the same manner as in Reference Example 186 using suitable starting materials.

Reference Example 288

Preparation of 2-chloro-4-[4-(4-trifluoromethoxyphenoxy)piperidin-1-yl]phenol

The title compound was prepared in the same manner as in Reference Example 199 using suitable starting materials.

Reference Example 289

Preparation of 4-{4-[2-(4-chlorophenyl)ethyl]piperidin-1-yl}phenol

The title compound was prepared in the same manner as in Reference Example 199 using suitable starting materials.

Reference Example 290

Preparation of 4-[4-(5-chlorobenzofuran-2-ylmethoxy)piperidin-1-yl]phenol

The title compound was prepared in the same manner as in Reference Example 199 using suitable starting materials.

Reference Example 291

Preparation of 4-{4-[3-(4-chlorophenoxy)propyl]piperidin-1-yl}phenol

The title compound was prepared in the same manner as in Reference Example 199 using suitable starting materials.

Reference Example 292

Preparation of 4-{4-[3-(4-chlorophenyl)propyl]piperidin-1-yl}phenol

The title compound was prepared in the same manner as in Reference Example 199 using suitable starting materials.

Reference Example 293

Preparation of 4-[4-(5-trifluoromethoxybenzofuran-2-ylmethyl)piperidin-1-yl]phenol The title compound was prepared in the same manner as in Reference Example 199 using suitable starting materials.

Reference Example 294

Preparation of 4-[4-(5-chlorobenzofuran-2-ylmethoxymethyl)piperidin-1-yl]phenol

The title compound was prepared in the same manner as in Reference Example 199 using suitable starting materials.

Reference Example 295

Preparation of 4-{4-[4-(4-trifluoromethoxybenzyloxy)phenyl]piperazin-1-yl}phenol p-toluenesulfonate The title compound was prepared in the same manner as in Reference Example 191 using suitable starting materials.

Reference Example 296

Preparation of 4-{4-[2-(3,4-dichlorophenoxy)ethyl]piperidin-1-yl}phenol

The title compound was prepared in the same manner as in Reference Example 199 using suitable starting materials.

Reference Example 297

Preparation of 4-{4-[2-(3-chloro-5-trifluoromethylpyridin-2-yloxy)ethyl]piperidin-1-yl}phenol The title compound was prepared in the same manner as in Reference Example 199 using suitable starting materials.

Reference Example 298

Preparation of 4-{4-[2-(3,5-dichloropyridin-2-yloxy)ethyl]piperidin-1-yl}phenol

The title compound was prepared in the same manner as in Reference Example 199 using suitable starting materials.

Reference Example 299

Preparation of 4-{4-[2-(4-chloro-3-trifluoromethylphenoxy)ethyl]piperidin-1-yl}phenol The title compound was prepared in the same manner as in Reference Example 199 using suitable starting materials.

Reference Example 300

Preparation of 4-{4-[2-(2,4-dichlorophenoxy)ethyl]piperidin-1-yl}phenol

The title compound was prepared in the same manner as in Reference Example 199 using suitable starting materials.

Reference Example 301

Preparation of 4-{4-[2-(tetrahydropyran-2-yloxy)-2-(4-trifluoromethoxyphenyl)ethyl]piperidin-1-yl}phenol The title compound was prepared in the same manner as in Reference Example 206 using suitable starting materials.

Reference Example 302

Preparation of 4-{4-[2-(4-chloro-3-methylphenoxy)ethyl]piperidin-1-yl}phenol

The title compound was prepared in the same manner as in Reference Example 199 using suitable starting materials.

Reference Example 303

Preparation of 4-{4-[2-(3-trifluoromethylphenoxy)ethyl]piperidin-1-yl}phenol

The title compound was prepared in the same manner as in Reference Example 199 using suitable starting materials.

Reference Example 304

Preparation of 4-{4-[2-(3-chloro-4-fluorophenoxy)ethyl]piperidin-1-yl}phenol

The title compound was prepared in the same manner as in Reference Example 199 using suitable starting materials.

Reference Example 305

Preparation of 4-{4-[4-(4-trifluoromethoxyphenoxy)phenyl]piperazin-1-yl}phenol

The title compound was prepared in the same manner as in Reference Example 191 using suitable starting materials.

Reference Example 306

Preparation of 4-{4-[4-(4-trifluoromethoxyphenoxy)butyl]piperidin-1-yl}phenol

The title compound was prepared in the same manner as in Reference Example 199 using suitable starting materials.

Reference Example 307

Preparation of 4-{4-[4-(4-trifluoromethoxyphenoxymethyl)phenyl]piperazin-1-yl}phenol The title compound was prepared in the same manner as in Reference Example 197 using suitable starting materials.

Reference Example 308

Preparation of 4-(4-{4-[N-methyl-N-(4-trifluoromethylbenzyl)amino]phenyl}piperazin-1-yl)phenol The title compound was prepared in the same manner as in Reference Example 197 using suitable starting materials.

Reference Example 309

Preparation of 4-{4-[4-(4-trifluoromethoxybenzyloxy)phenoxy]piperidin-1-yl}phenol The title compound was prepared in the same manner as in Reference Example 199 using suitable starting materials.

Reference Example 310

Preparation of 4-(3-trifluoromethyl-5,6-dihydro-8H-imidazo[1,2-a]pyrazin-7-yl)phenol The title compound was prepared in the same manner as in Reference Example 199 using suitable starting materials.

Reference Example 311

Preparation of 4-{4-[4-(4-trifluoromethylbenzyloxy)phenoxy]piperidin-1-yl}phenol The title compound was prepared in the same manner as in Reference Example 199 using suitable starting materials.

Reference Example 312

Preparation of 4-(3-trifluoromethyl-5,6-dihydro-8H-[1,2,4]triazolo[4,3-a]pyrazin-7-yl)phenol The title compound was prepared in the same manner as in Reference Example 206 using suitable starting materials.

Reference Example 313

Preparation of 4-{4-[4-(4-trifluoromethoxybenzyloxy)phenoxymethyl]piperidin-1-yl}phenol The title compound was prepared in the same manner as in Reference Example 199 using suitable starting materials.

Reference Example 314

Preparation of 4'-diethoxymethylbiphenyl-4-ol

The title compound was prepared in the same manner as in Reference Example 206 using suitable starting materials.

Reference Example 315

Preparation of (2R,5S)-4-(4-hydroxyphenyl)-2,5-dimethylpiperazine-1-carboxylic acid tert-butyl ester The title compound was prepared in the same manner as in Reference Example 186 using suitable starting materials.

Reference Example 316

Preparation of (1R,4R)-5-(4-hydroxyphenyl)-2,5-diaza-bicyclo[2.2.1]heptane-2-carboxylic acid tert-butyl ester The title compound was prepared in the same manner as in Reference Example 186 using suitable starting materials.

Reference Example 317

Preparation of 4-[4-([N-methyl-N-[4-(4-trifluoromethoxybenzyloxy)phenyl]amino]methyl)piperidin-1-yl]phenol The title compound was prepared in the same manner as in Reference Example 187 using suitable starting materials.

Reference Example 318

Preparation of 4-[4-(4-trifluoromethylphenyl)piperidin-1-yl]phenol

The title compound was prepared in the same manner as in Reference Example 187 using suitable starting materials.

Reference Example 319

Preparation of 4-(4-trifluoromethoxyphenoxy)-3,4,5,6-tetrahydro-2H-[1,2']bipyridinyl-5'-ol 5'-Benzyloxy-4-(4-trifluoromethoxyphenoxy)-3,4,5,6-tetrahydro-2H-[1,2']bipyridinyl (0.93 g) and 10% palladium on carbon (93 mg) were added to ethanol (9.3 ml), and the mixture was stirred at room temperature under a hydrogen atmosphere (atmospheric pressure) for 1 hour. The catalyst was removed by filtration, and the filtrate was concentrated under reduced pressure. The residue was purified by silica gel column chromatography (hexane:ethyl acetate=10:0→6:4). The result was concentrated to dryness under reduced pressure to afford the title compound as a pale yellow powder (0.55 g).

Reference Example 320

Preparation of 4-(4-trifluoromethoxybenzyl)-3,4,5,6-tetrahydro-2H-[1,2']bipyridinyl-5'-ol The title compound was prepared in the same manner as in Reference Example 319 using suitable starting materials.

Reference Example 321

Preparation of 4-(5-hydroxypyridin-2-yl)piperazine-1-carboxylic acid tert-butyl ester The title compound was prepared in the same manner as in Reference Example 319 using suitable starting materials.

Reference Example 322

Preparation of 4-(4-trifluoromethoxyphenoxymethyl)-3,4,5,6-tetrahydro-2H-[1,2']bipyridinyl-5'-ol Pyridinium p-toluenesulfonate (PPTS) (0.917 g) was added to an ethanol solution (20 ml) of 5'-(tetrahydropyran-2-yloxy)-4-(4-trifluoromethoxyphenoxymethyl)-3,4,5,6-tetrahydro-2H-[1,2']bipyridinyl (1.65 g), and the mixture was stirred for 4 hours while heating under reflux. After cooling the reaction mixture to room temperature, a sodium hydrogen carbonate aqueous solution was added thereto, and ethanol was distilled off under reduced pressure, followed by extraction with ethyl acetate. The organic layer was washed with a saturated sodium chloride aqueous solution and dried over sodium sulfate. The solvent was distilled off and the precipitated solid was collected by filtration. The solid was then washed with diisopropyl ether and dried to afford the title compound as a yellow powder (0.94 g).

Reference Example 323

Preparation of 4-[2-(4-trifluoromethoxyphenoxy)ethyl]-3,4,5,6-tetrahydro-2H-[1,2']bipyridinyl-5'-ol The title compound was prepared in the same manner as in Reference Example 322 using suitable starting materials.

Reference Example 324

Preparation of 4-(4-chlorophenoxy)-3,4,5,6-tetrahydro-2H-[1,2']bipyridinyl-5'-ol The title compound was prepared in the same manner as in Reference Example 322 using suitable starting materials.

Reference Example 325

Preparation of 4-(4-trifluoromethoxybenzyloxy)-3,4,5,6-tetrahydro-2H-[1,2']bipyridinyl-5'-ol The title compound was prepared in the same manner as in Reference Example 322 using suitable starting materials.

Reference Example 326

Preparation of 4-(4-trifluoromethylphenoxy)-3,4,5,6-tetrahydro-2H-[1,2']bipyridinyl-5'-ol The title compound was prepared in the same manner as in Reference Example 322 using suitable starting materials.

Reference Example 327

Preparation of 4-[3-(4-trifluoromethoxyphenyl)propyl]-3,4,5,6-tetrahydro-2H-[1,2']bipyridinyl-5'-ol The title compound was prepared in the same manner as in Reference Example 322 using suitable starting materials.

Reference Example 328

Preparation of 6-(4-trifluoromethoxybenzyloxymethyl)pyridin-3-ol

2 N hydrogen chloride-ethyl acetate solution (20 ml) was added to an ethanol solution (20 ml) of 5-methoxymethoxy-2-(4-trifluoromethoxybenzyloxymethyl)pyridine (2.3 g) and stirred at room temperature for 16 hours. The reaction mixture was concentrated under reduced pressure and a sodium hydrogen carbonate aqueous solution was added to the residue, followed by extraction with ethyl acetate. The organic layer was washed with water and a saturated sodium chloride aqueous solution and dried over sodium sulfate. The result was concentrated under reduced pressure, and the residue was purified by silica gel column chromatography (hexane:ethyl acetate=4:1→2:1). The result was concentrated to dryness under reduced pressure to afford the title compound as a white solid (2.4 g).

Reference Example 329

Preparation of 2-[4-(4-trifluoromethoxybenzyl)piperazin-1-yl]benzothiazol-6-ol

Methanol (1 ml) and a catalytic amount of acetic acid and sodium triacetoxyborohydride (0.14 g) were added to a 1,2-dichloroethane solution (5 ml) of 2-piperazin-1-yl-benzothiazol-6-ol (0.1 g) and 4-trifluoromethoxybenzaldehyde (0.067 ml) and stirred at room temperature overnight. Water was added to the reaction mixture, followed by extraction with dichloromethane. The organic layer was washed with water, dried over sodium sulfate, and then concentrated under reduced pressure to afford the title compound as a colorless amorphous compound (80 mg).

Reference Example 330

Preparation of 4-(6-hydroxyquinolin-2-yl)piperazine-1-carboxylic acid tert-butyl ester 2-Chloro-6-(tetrahydropyran-2-yloxy)quinoline (1.00 g) and piperazine-1-carboxylic acid tert-butyl ester (0.76 g) were heated to 140° C. in the absence of solvent under an argon atmosphere and stirred for 2 hours. After cooling the reaction mixture to room temperature, a sodium hydrogen carbonate aqueous solution was added thereto, followed by extraction with dichloromethane. The organic layer was washed with a saturated sodium chloride aqueous solution and dried over magnesium sulfate. The result was concen-

Reference Example 331

Preparation of 2-[4-(4-trifluoromethoxyphenoxy)piperidin-1-yl]quinolin-6-ol

The title compound was prepared in the same manner as in Reference Example 330 using suitable starting materials.

Reference Example 332

Preparation of 6-hydroxy-3,4-dihydro-1H-isoquinoline-2-carboxylic acid tert-butyl ester 1,2,3,4-Tetrahydro-isoquinolin-6-ol hydrobromide (8.3 g) and sodium hydroxide (4.35 g) were dissolved in a mixed solvent of 1,4-dioxane (50 ml) and water (50 ml). Under ice cooling, di-tert-butyl dicarbonate ($Boc_2O$) (8.7 g) was added thereto dropwise and stirred at 0 to 10° C. for 2 hours. The result was made hydrochloric acidic, followed by extraction with dichloromethane. The organic layer was washed with a saturated sodium chloride aqueous solution, dried over sodium sulfate, and then concentrated under reduced pressure to afford the title compound as a brown oil (4.1 g).

Reference Example 333

Preparation of 5-hydroxy-1,3-dihydroisoindole-2-carboxylic acid tert-butyl ester The title compound was prepared in the same manner as in Reference Example 332 using suitable starting materials.

Reference Example 334

Preparation of 2-[4-(4-trifluoromethoxyphenoxy)piperidin-1-yl]benzothiazol-5-ol

The title compound was prepared in the same manner as in Reference Example 330 using suitable starting materials.

Reference Example 335

Preparation of 1-[3-(4-trifluoromethoxyphenoxy)propyl]-1,2,3,4-tetrahydroquinolin-6-ol 6-Benzyloxy-1-[3-(4-trifluoromethoxy-phenoxy)propyl]-1,2,3,4-tetrahydro-quinoline (2.13 g) was dissolved in ethanol (10 ml). 10% palladium on carbon (0.2 g) was added thereto and stirred at room temperature under a hydrogen atmosphere for 4 hours. The mixture was filtered through Celite to remove the catalyst, and then the filtrate was concentrated under reduced pressure. The residue was purified by silica gel column chromatography (hexane:ethyl acetate=4:1) and concentrated under reduced pressure to afford the title compound (1.45 g).

Reference Example 336

Preparation of 1-[3-(4-trifluoromethoxyphenoxy)propyl]-1H-indol-5-ol

The title compound was prepared in the same manner as in Reference Example 335 using suitable starting materials.

Reference Example 337

Preparation of 1-[3-(4-trifluoromethoxyphenoxy)propyl]-2,3,4,5-tetrahydro-1H-benzo[b]azepin-7-ol The title compound was prepared in the same manner as in Reference Example 335 using suitable starting materials.

Reference Example 338

Preparation of 1-[3-(4-trifluoromethoxyphenoxy)propyl]-1,2,3,4-tetrahydroquinolin-5-ol A 1 N hydrochloric acid aqueous solution (10 ml) was added to an ethanol solution (15 ml) of 5-(tetrahydropyran-2-yloxy)-1-[3-(4-trifluoromethoxyphenoxy)propyl]-1,2,3,4-tetrahydroquinoline (1.71 g) and stirred at room temperature overnight. A saturated sodium hydrogen carbonate aqueous solution was added thereto, and the mixture was concentrated under reduced pressure. The residue was subjected to extraction with ethyl acetate. The organic layer was dried over sodium sulfate and concentrated under reduced pressure. The residue was purified by silica gel column chromatography (hexane:ethyl acetate=6:1) to afford the title compound as a colorless oil (0.62 g).

Reference Example 339

Preparation of 1-[4-(4-trifluoromethoxyphenoxy)benzyl]-1,2,3,4-tetrahydroquinolin-6-ol The title compound was prepared in the same manner as in Reference Example 335 using suitable starting materials.

Reference Example 340

Preparation of 1-[4-(4-trifluoromethoxyphenoxy)benzyl]-2,3,4,5-tetrahydro-1H-benzo[b]azepin-7-ol The title compound was prepared in the same manner as in Reference Example 335 using suitable starting materials.

Reference Example 341

Preparation of 4-(6-hydroxybenzothiazol-2-yl)piperazine-1-carboxylic acid tert-butyl ester The title compound was prepared in the same manner as in Reference Example 332 using suitable starting materials.

Reference Example 342

Preparation of 6-{4-[2-(4-trifluoromethoxyphenyl)ethyl]piperidin-1-yl}naphthalen-2-ol The title compound was prepared in the same manner as in Reference Example 338 using suitable starting materials.

Reference Example 343

Preparation of 2-[4-(4-trifluoromethoxyphenoxy)piperidin-1-yl]benzooxazol-5-ol hydrochloride The title compound was prepared in the same manner as in Reference Example 330 using suitable starting materials.

Reference Example 344

Preparation of 4-(5-hydroxybenzoxazol-2-yl)piperazine-1-carboxylic acid tert-butyl ester The title compound was prepared in the same manner as in Reference Example 332 using suitable starting materials.

Reference Example 345

Preparation of 7-hydroxy-3,4-dihydro-1H-isoquinoline-2-carboxylic acid tert-butyl ester The title compound was prepared in the same manner as in Reference Example 332 using suitable starting materials.

Reference Example 346

Preparation of 2-{4-[4-(4-trifluoromethoxybenzyloxy)benzyl]piperidin-1-yl}-benzothiazol-6-ol Potassium carbonate (1.02 g) and 4-[4-(4-trifluoromethoxybenzyloxy)benzyl]piperidine were added to an N,N-dimethylformamide solution (10 ml) of 2-chlorobenzothiazol-6-ol (1.37 g) and the mixture was stirred at 80° C. for 2 days. After being cooled to room temperature, the mixture was concentrated under reduced pressure. Water was added to the residue, followed by extraction with ethyl acetate. The organic layer was washed with water and a saturated sodium chloride aqueous solution, dried over sodium sulfate, and then concentrated under reduced pressure. The residue was purified by silica gel column chromatography (hexane:ethyl acetate=4:1→2:1) to afford the title compound as a white powder (2.1 g).

Reference Example 347

Preparation of 7-hydroxy-1,3,4,5-tetrahydrobenzo[c]azepin-2-carboxylic acid tert-butyl ester The title compound was prepared in the same manner as in Reference Example 332 using suitable starting materials.

Reference Example 348

Preparation of 2-chloro-6-(tetrahydropyran-2-yloxy)-quinoline

2-Chloroquinolin-6-ol (36 g, 0.20 mol) was dissolved in dichloromethane (500 ml) and tetrahydrofuran (500 ml). 3,4-dihydro-2H-pyran (74 ml, 0.81 mol) and p-toluenesulfonic acid (0.49 g, 0.005 mol) were added to the mixture in ice cooling water bath, followed by stirring at room temperature overnight. A 10% sodium hydroxide aqueous solution was added to the reaction mixture, followed by extraction with dichloromethane. The result was dried over potassium carbonate and subjected to filtration, and then the filtrate was concentrated under reduced pressure. The crude crystal thus obtained was recrystallized from ethanol to afford the title compound as a colorless granular compound (47 g, yield 89%).

Melting point: 122-124° C.

Reference Example 349

Preparation of (4-trifluoromethoxyphenoxy)acetic acid methyl ester

Bromoacetic acid methyl ester (8 ml, 84.2 mmol) was added to a mixture of 4-(trifluoromethoxy)phenol (10 g, 56.1 mmol) and potassium carbonate (11.6 g, 84.2 mmol) in N,N-Dimethylformamide (50 ml) and stirred at room temperature overnight. The reaction mixture was poured into water and neutralized with a 1 N hydrochloric acid aqueous solution, followed by extraction with diethylether. The result was concentrated and used for the subsequent reaction.

1H NMR (CDCl$_3$) δ 3.80 (s, 3H), 4.63 (s, 2H), 6.89-6.92 (m, 2H), 7.15-7.16 (m, 2H).

Reference Example 350

Preparation of 2-(4-trifluoromethoxyphenoxy)acetamide

A 25% ammonia aqueous solution (20 ml) was added to (4-trifluoromethoxyphenoxy)acetic acid methyl ester in methanol (40 ml) and the mixture was stirred at room temperature overnight. After distilling the solvent off, the residue was washed with water and dried to afford the title compound as a white solid (12.1 g, yield 91%).

1H NMR (CDCl$_3$) δ 4.50 (s, 2H), 5.66 (br, 1H), 6.50 (br, 1H), 6.92-6.94 (m, 2H), 7.18-7.20 (m, 2H).

Reference Example 351

Preparation of 1-(3-chloropropoxy)-4-trifluoromethoxybenzene

1-Bromo-3-chloropropane (2.37 ml, 24 mmol), 4-(trifluoromethoxy)phenol (3.56 g, 20 mmol) and potassium carbonate (4.15 g, 30 mmol) were stirred in NMP (30 ml) overnight. After removing potassium carbonate by filtration, water was added to the mixture, followed by extraction with ethyl acetate. The organic layer was washed with water and dried over sodium sulfate. The solvent was distilled off, and the residue was fractionated and purified by silica gel column chromatography (hexane:ethyl acetate=89:11) to afford the title compound as a colorless oil (5.09 g, yield 99%).

1H NMR (CDCl$_3$) δ 2.23-2.25 (m, 2H), 3.75 (t, J=6.3 Hz, 2H), 4.11 (t, J=5.8 Hz, 2H), 6.89 (d, J=9.1 Hz, 2H), 7.14 (d, J=8.9 Hz, 2H).

Reference Example 352

Preparation of 4'-[4-(4-trifluoromethoxyphenoxy)piperidin-1-yl]biphenyl-4-ol

The title compound was prepared in the same manner as in Reference Example 199 using suitable starting materials.

1H NMR (CDCl$_3$) δ 1.85-2.04 (m, 2H), 2.04-2.22 (m, 2H), 3.07-3.23 (m, 2H), 3.45-3.63 (m, 2H), 4.38-4.53 (m, 1H), 4.74 (s, 1H), 6.81-6.96 (m, 4H), 7.01 (d, J=8.8 Hz, 2H), 7.08-7.20 (m, 2H), 7.38-7.51 (m, 4H).

Reference Example 353

Preparation of 4-[2-(4-trifluoromethoxyphenoxy) ethyl]piperidine-1-carboxylic acid tert-butyl ester Sodium hydride (60% in oil, 2.12 g) wad added to an N,N-dimethylformamide solution (100 ml) of 4-trifluoromethoxyphenol (9.0 g) under ice cooling and stirred for 30 minutes. After adding 4-[2-(toluene-4-sulfonyloxy)ethyl]piperidine-1-carboxylic acid tert-butyl ester (17.7 g), the mixture was heated to room temperature and stirred. The mixture was further stirred at 50° C. for 1 hour. After cooling the reaction mixture to room temperature, water was added thereto, followed by extraction with ethyl acetate. The organic layer was washed with a saturated sodium chloride aqueous solution and dried over sodium sulfate. The result was concentrated under reduced pressure, and the residue was purified by silica gel column chromatography (hexane:ethyl acetate=67:33) to afford the title compound as a pale yellow oil (18.64 g).

Reference Example 354

Preparation of 4-[2-(4-trifluoromethoxyphenoxy)ethyl]piperidine

Trifluoroacetic acid (40 ml) was added to a dichloromethane solution (40 ml) of 4-[2-(4-trifluoromethoxyphenoxy)ethyl]piperidine-1-carboxylic acid tert-butyl ester (18.6 g), and the mixture was stirred at room temperature for 5 hours. The mixture was concentrated under reduced pressure, and ice water was added to the resulting residue. The result was treated with 6 N sodium hydroxide aqueous solution, followed by extraction with ethyl acetate. The organic layer was washed with a saturated sodium chloride aqueous solution and dried over magnesium sulfate. The solvent was concentrated to dryness under reduced pressure to afford the title compound as a white powder (14 g).

Reference Example 355

Preparation of 6-(4-trifluoromethoxyphenoxy)nicotinic acid ethyl ester

Ethyl 6-chloro nicotinate (5.00 g, 26.9 mmol), 4-(trifluoromethoxy)phenol (5.28 g, 29.6 mmol), potassium carbonate (4.84 g, 35.0 mmol) and N,N-dimethylformamide (50 ml) were mixed and stirred at 100 to 110° C. overnight. The reaction mixture was poured into water, followed by extraction with ethyl acetate. The organic layer was washed with a saturated sodium chloride aqueous solution and dried over magnesium sulfate. The organic layer was concentrated under reduced pressure. The residue was purified by silica gel column chromatography (hexane:ethyl acetate=100:0→70:30) to afford the title compound as a colorless oil (7.48 g, 85%).
Mass: [M]$^+$=327.

Reference Example 356

Preparation of [6-(4-trifluoromethoxyphenoxy)pyridin-3-yl]methanol 6-(4-Trifluoromethoxyphenoxy)nicotinic acid ethyl ester (7.48 g, 22.9 mmol) was dissolved in tetrahydrofuran (75 ml) and cooled to −78° C. A toluene solution (100.6 ml, 100.6 mmol) of diisobutylaluminium hydride was added thereto and the mixture was stirred at the same temperature for 1 hour. The reaction mixture was poured into a 1 N sodium hydroxide aqueous solution, followed by extraction with dichloromethane. The organic layer was washed with a saturated sodium chloride aqueous solution and dried over magnesium sulfate. The organic layer was concentrated and purified by silica gel column chromatography (hexane:ethyl acetate=100:0→0:100) to afford the title compound as a colorless oil (6.15 g, 94%).
Mass: [M]$^+$=285.

Reference Example 357

Preparation of 6-(4-trifluoromethoxyphenoxy)pyridine-3-carbaldehyde

{6-[(4-Trifluoromethoxy)phenoxy]pyridine-3-yl}methanol (3.00 g, 10.5 mmol), dimethylsulfoxide (90 ml) and 2-iodoxybenzoic acid (3.53 g, 12.6 mmol) were mixed and stirred at room temperature overnight. After adding water and ethyl acetate to the reaction mixture, insoluble matter was removed and the filtrate was separated into layers. The organic layer was washed with water, dried over magnesium sulfate, and then concentrated. The residue was purified by silica gel column chromatography (hexane:ethyl acetate=100:0→70:30) to afford the title compound as a colorless oil (2.96 g, 99%).
Mass: [M]$^+$=283

Reference Example 358

Preparation of 5'-(tetrahydropyran-2-yloxy)-4-[2-(4-trifluoromethoxyphenoxy)ethyl]-3,4,5,6-tetrahydro-2H-[1,2']bipyridinyl Toluene (15 ml) was added to a mixture of 2-bromo-5-(tetrahydropyran-2-yloxy)pyridine (2.58 g, 10 mmol), 4-[2-(4-trifluoromethoxyphenoxy)ethyl]piperidine (3.18 g, 11 mmol) and sodium tert-butoxide (1.35 g, 14 mmol), and then the atmosphere was replaced with nitrogen. Bis(dibenzylideneacetone)palladium (Pd$_2$(dba)$_3$ complex) (0.23 g, 0.25 mmol) and 9,9-dimethyl-4,5-bis(diphenylphosphino)xanthine (xantphos) (0.36 g, 0.63 mmol) were added to the mixture, and the reaction mixture was heated at 100° C. for 3 hours under a nitrogen atmosphere. After being cooled to room temperature, the reaction mixture was poured into water, followed by extraction with ethyl acetate. The organic layer was washed with a saturated sodium chloride aqueous solution, dried over sodium sulfate, and concentrated. The result was purified by silica gel column chromatography (ethyl acetate:hexane=10:90→25:75) to afford the title compound as a pale brown powder (4.45 g, 95%).
1H NMR (CDCl$_3$) δ 1.34-1.38 (m, 2H), 1.52-1.85 (m, 10H), 1.97-1.99 (m, 1H), 2.75-2.80 (m, 2H), 3.57-3.60 (m, 1H), 3.91-3.95 (m, 1H), 3.99-4.03 (m, 2H), 4.13-4.16 (m, 2H), 5.21 (s, 1H), 6.62-6.64 (m, 1H), 6.86-6.89 (m, 2H), 7.13-7.14 (m, 2H), 7.28 (m, 1H), 8.04-8.05 (m, 1H).

Reference Example 359

Preparation of 4-[(E)-3-(4-trifluoromethylphenyl)allyl]piperidine-1-carboxylic acid tert-butyl ester Potassium tert-butoxide (5.78 g, 50.0 mmol) was added to a solution of 4-(trifluoromethyl)benzylphosphonic acid diethyl ester (14.8 g, 50.0 mmol) in tetrahydrofuran solution (40 ml) under ice cooling, and the mixture was stirred at the same temperature for 30 minutes. Subsequently, a tetrahydrofuran solution (10 ml) of 4-(2-oxoethyl)piperidine-1-carboxylic acid tert-butyl ester (11.4 g, 50.0 mmol) was added thereto dropwise at 0° C., warmed to room temperature, and then stirred overnight. Water was added to the reaction mixture, followed by extraction with ethyl acetate. The organic layer was washed with a saturated sodium chloride aqueous solution and dried over sodium sulfate. After filtering, the filtrate was concentrated under reduced pressure. The residue thus obtained was purified by silica gel column chromatography (hexane:ethyl acetate=86:14) to afford the title compound as a colorless oil (8.6 g, yield 47%).

1H NMR (CDCl$_3$) δ 1.10-1.22 (m, 2H), 1.44 (s, 9H), 1.66-1.81 (m, 2H), 2.17-2.25 (m, 2H), 2.60-2.78 (m, 2H), 4.00-4.22 (m, 3H), 6.25-6.33 (m, 1H), 6.37-6.44 (m, 1H), 7.40-7.46 (m, 2H), 7.52-7.56 (m, 2H)

Reference Example 360

Preparation of 4-[3-(4-trifluoromethylphenyl)propyl]piperidine-1-carboxylic acid tert-butyl ester 4-[(E)-3-(4-Trifluoromethylphenyl)allyl]piperidine-1-carboxylic acid tert-butyl ester (13.4 g, 36.2 mmol) and 10% palladium on carbon (1.4 g, 1.3 mmol) were suspended in ethanol (120 ml), followed by stirring under a hydrogen atmosphere (atmospheric pressure) at room temperature for 5 hours. Thereafter the insoluble matter was removed by filtration, and the resulting solution was concentrated to afford the title compound as a colorless oil (crude).

1H NMR (CDCl$_3$) δ 1.05-1.08 (m, 2H), 1.25-1.30 (m, 2H), 1.37-1.41 (m, 1H), 1.45 (s, 9H), 1.59-1.68 (m, 4H), 2.64-2.67 (m, 4H), 4.11-4.13 (m, 2H), 7.26-7.28 (d, J=9.2 Hz, 2H), 7.52-7.54 (d, J=8.1, 2H).

Reference Example 361

Preparation of 4-[3-(4-trifluoromethylphenyl)propyl]piperidine

4-[3-(4-Trifluoromethylphenyl)propyl]piperidine-1-carboxylic acid tert-butyl ester (13.45 g, 36.2 mmol) prepared in Reference Example 360 was dissolved in dichloromethane (50 ml). Trifluoroacetic acid (25 ml, 324 mmol) was added thereto and stirred at room temperature overnight. The reaction mixture was concentrated under reduced pressure and adjusted to a pH of 10 using a 5 N sodium hydroxide aqueous solution. The mixture was subjected to extraction with dichloromethane 4 times. The result was dried over anhydrous sodium sulfate and then concentrated to afford the title compound as a pale brown oil (10.2 g, quant).

1H NMR (CDCl$_3$) δ 1.09-1.51 (m, 2H), 1.25-1.29 (m, 2H), 1.37 (m, 1H), 1.61-1.69 (m, 4H), 2.11 (br, 1H), 2.56-2.66 (m, 4H), 3.06-3.08 (m, 2H), 7.27-7.28 (d, J=7.8 Hz, 2H), 7.52-7.53 (d, J=8.1, 2H).

Reference Example 362

Preparation of 1-[4-(tetrahydropyran-2-yloxy)phenyl]-4-[3-(4-trifluoromethylphenyl)propyl]piperidine 2-(4-Iodophenoxy)tetrahydropyran (1.12 g, 3.7 mmol) and 4-[3-(4-trifluoromethylphenyl)propyl]piperidine (1 g, 3.7 mmol) were dissolved in degassed anhydrous toluene (10 ml). Sodium tert-butoxide (0.50 g, 5.2 mmol), tri-tert-butylphosphine tetrafluoroborate (tBu$_3$P.HBF$_4$) (0.09 g, 0.3 mmol) and palladium acetate (0.03 g, 0.15 mmol) were added thereto, and the mixture was heated at reflux under a nitrogen atmosphere for 5 hours. After being allowed to cool to room temperature, water (10 ml) was added to the mixture, followed by extraction with ethyl acetate. The organic layers were combined and washed with water and a saturated sodium chloride aqueous solution, and dried over anhydrous sodium sulfate. After removing insoluble matter by filtration, the solvent was distilled off. The residue was purified by silica gel column chromatography (hexane:ethyl acetate=80:20) to afford the title compound as a pale yellow solid (1.42 g, 86%).

1H NMR (CDCl$_3$) δ 1.32-1.35 (m, 4H), 1.59-1.85 (m, 10H), 1.93-2.05 (m, 1H), 2.58 (t, J=11.7 Hz, 2H), 2.65-2.68 (t, J=7.7 Hz, 2H), 3.50-3.52 (d, J=11.4 Hz, 2H), 3.57-3.59 (m, 1H), 3.92-3.96 (t, J=9.3 Hz, 1H), 5.29-5.30 (m, 1H), 6.87-6.89 (d, J=9.1 Hz, 2H), 6.96-6.97 (d, J=9.1, 2H) 7.28-7.30 (d, J=7.9 Hz, 2H), 7.52-7.54 (d, J=8.05, 2H).

Reference Example 363

Preparation of 4-[4-(4-trifluoromethylbenzyloxy)benzyl]piperidine-1-carboxylic acid tert-butyl ester tert-Butyl 4-(4-hydroxybenzyl)piperidine-1-carboxylate (1.78 g, 6.1 mmol), potassium carbonate (1.27 g, 9.2 mmol), N,N-dimethylformamide (18 ml) and 4-(trifluoromethyl)benzylbromide (1.75 g, 7.3 mmol) were mixed and stirred at room temperature overnight. The reaction mixture was poured into water, followed by extraction with ethyl acetate. The organic layer was washed with water, dried over magnesium sulfate, and then concentrated. The residue was purified by silica gel column chromatography (hexane:ethyl acetate=100:0→60:40) to afford the title compound as a colorless powder (2.64 g, 96%).

Mass: [M]$^+$=449.

Reference Example 364

Preparation of 4-[4-(4-trifluoromethylbenzyloxy)benzyl]piperidine

4-{4-[4-(Trifluoromethyl)benzyloxy]benzyl}piperidine-1-carboxylic acid tert-butyl ester (2.64 g, 5.9 mmol), dichloromethane (5 ml) and trifluoroacetic acid (5 ml) were mixed and stirred at room temperature for 2 hours. After concentrating the reaction mixture, dichloromethane was added to the residue, and 5 N sodium hydroxide was further added, followed by vigorous stirring. The organic layer was separated, washed with water, dried over sodium sulfate, and then concentrated to afford the title compound as a colorless powder (2.06 g, 100%).

Mass: [M]$^+$=349.

Reference Example 365

Preparation of 4-(4-benzyloxybenzylidene)piperidine 4-(4-Benzyloxybenzylidene)piperidine-1-carboxylic acid tert-butyl ester (3.80 g, 10 mmol), ethanol (40 ml) and 1 N hydrochloric acid (25 ml) were mixed and stirred at 80° C. for 1 hour. Ethanol was distilled off under reduced pressure and neutralized with sodium hydroxide. The organic layer was dried over sodium sulfate and concentrated to afford the title compound as a pale yellow powder (2.32 g, 83%).

1H NMR (CDCl$_3$) δ 2.30 (t, J=5.2 Hz, 2H), 2.44 (t, J=5.2 Hz, 2H), 2.84 (t, J=5.5 Hz, 2H), 2.94 (t, J=5.5 Hz, 2H), 5.05 (s, 2H), 6.22 (s, 1H), 6.92-6.94 (m, 2H), 7.13 (d, J=8.6 Hz, 2H), 7.32-7.44 (m, 5H).

Reference Example 366

Preparation of 4-(4-benzyloxybenzylidene)-1-[4-(tetrahydropyran-2-yloxy)phenyl]piperidine 4-[4-(Benzyloxy)benzylidene]piperidine (2.32 g, 8.3 mmol), 1-bromo-4-(tetrahydro-2H-pyran-2-yloxy)benzene (2.35 g, 9.1 mmol), toluene (20 ml), sodium tert-butoxide (1.12 g, 11.6 mmol), palladium acetate (0.075 g, 0.3 mmol) and tri-tert-butylphosphine tetrafluoroborate (0.19 g, 0.7 mmol) were mixed and stirred at 100° C. overnight. Water was poured into the reaction mixture, followed by extraction with ethyl acetate. The organic layer was washed with water, dried over sodium sulfate, and concentrated. The residue was purified by silica gel column chromatography (hexane:ethyl acetate=80:20→50:50) to afford the title compound as a colorless powder.

TLC:Rf=0.6 (hexane:ethyl acetate=1:1)

Reference Example 367

Preparation of 6-benzyloxy-1-[3-(4-trifluoromethoxyphenoxy)propyl]-1,2,3,4-tetrahydro-quinoline 6-Benzyloxy-1,2,3,4-tetrahydro-quinoline (1.20 g, 5 mmol), 1-(3-chloropropoxy)-4-trifluoromethoxybenzene (1.42 g, 5.58 mmol), potassium carbonate (1.04 g, 7.5 mmol) and sodium iodide (0.90 g, 6 mmol) were heated and stirred at 90° C. in NMP (10 ml) overnight. Water was added thereto, followed by extraction with ethyl acetate. The organic layer was washed with water and dried over sodium sulfate. The result was concentrated and purified by silica gel column chromatography (hexane:ethyl acetate=75:25) to afford the title compound as a yellow oil (2.13 g, 93%).

1H NMR (CDCl$_3$) δ 1.91-1.94 (m, 2H), 2.03-2.06 (m, 2H), 2.73 (t, J=6.4 Hz, 2H), 3.21 (t, J=5.6 Hz, 2H), 3.41 (t, J=7.0 Hz, 2H), 4.01 (t, J=5.9 Hz, 2H), 4.96 (s, 2H), 6.53-6.55 (m, 1H), 6.66-6.70 (m, 2H), 6.88-6.90 (m, 2H), 7.13-7.14 (m, 2H), 7.30-7.32 (m, 1H), 7.35-7.38 (m, 2H), 7.41-7.42 (m, 2H).

Reference Example 368

Preparation of 4-{1-[4-(tetrahydropyran-2-yloxy)phenyl]piperidin-4-ylmethyl}phenol Ethanol (20 ml) and ethyl acetate (10 ml) were added to 4-[4-(benzyloxy)benzylidene]-1-[4-(tetrahydro-2H-pyran-2-yloxy)phenyl]piperidine prepared in Reference Example 366. A palladium on carbon (0.378 g) was added to the mixture, and stirred at 50° C. for 4 hours under a hydrogen atmosphere. The insoluble matter was removed by filtration, and the filtrate was concentrated. The residue was purified by silica gel column chromatography (hexane:ethyl acetate=6:1→4:1) to afford the title compound as a colorless amorphous compound (1.10 g).

Reference Example 369

Preparation of 1-[4-(tetrahydropyran-2-yloxy)phenyl]-4-[4-(4-trifluoromethoxyphenoxy)benzyl]piperidine 4-({1-[4-(Tetrahydro-2H-pyran-2-yloxy)phenyl]piperidin-4-yl}methyl)phenol (1.10 g, 3.0 mmol), cesium carbonate (0.977 g, 3.0 mmol), N-methylpyrrolidinone (5 ml), 1-bromo-4-(trifluoromethoxy)benzene (0.723 g, 2.99 mmol) and dipivaloylmethane (0.3 g, 1.5 mmol) were mixed, and the atmosphere was replaced with nitrogen. Copper chloride (0.030 g, 0.3 mmol) was added thereto and stirred at 120° C. for 24 hours. An ammonium chloride aqueous solution was added to the reaction mixture, followed by extraction with ethyl acetate. The organic layer was dried over sodium sulfate and concentrated. The residue was purified by silica gel column chromatography (hexane:ethyl acetate=75:25) to afford the title compound as a colorless powder (0.84 g, 53%).

TLC:Rf=0.2 (hexane:ethyl acetate=4:1)

Reference Example 370

Preparation of 6-(tetrahydropyran-2-yloxy)-2-(4-trifluoromethoxybenzyloxy)-quinoline To a solution of (4-(trifluoromethoxy)phenyl)methanol (1.65 ml, 11.4 mmol) in DMF (40 ml) was added 60% sodium hydride (0.46 g, 11.4 mmol) at 0° C. and further stirred for 20 minutes. While stirring the resulting mixture under ice cooling, 2-chloro-6-(tetrahydropyran-2-yloxy)-quinoline (3.0 g, 11.4 mmol) was added thereto and warmed to room temperature, followed by further stirring for 5 hours. A saturated ammonium chloride aqueous solution was added to the reaction mixture, followed by extraction with ethyl acetate. The organic layer was washed with a saturated sodium chloride aqueous solution and then dried over sodium sulfate. After filtering, the filtrate was concentrated under reduced pressure. The residue thus obtained was purified by silica gel column chromatography (hexane:ethyl acetate=80:20). The resulting crude crystal was washed with hexane-diethylether to afford the title compound as a white powder (3.84 g, yield 81%).

1H NMR (CDCl$_3$) δ 1.65-1.94 (m, 6H), 3.45-3.58 (m, 1H), 3.86-3.94 (m, 1H), 5.51 (s, 2H), 5.51-5.53 (m, 1H), 6.92 (d, J=9.0 Hz, 1H), 7.22 (d, J=8.5 Hz, 2H), 7.34 (d, J=3.0 Hz, 1H), 7.39 (dd, J=9.0, 3.0 Hz, 1H), 7.55 (d, J=8.5 Hz, 2H), 7.77 (d, J=9.0 Hz, 1H), 7.92 (d, J=9.0 Hz, 1H)

Reference Example 371

Preparation of 2-(4-trifluoromethoxybenzyloxy)-quinolin-6-ol

A 1 N hydrochloric acid ethanol solution (40 ml) was added to an ethanol (10 ml) solution of 6-(Tetrahydro-2H-pyran-2-yloxy)-2-[4-(trifluoromethoxy)benzyloxy]quinoline (3.5 g, 8.3 mmol) and then stirred at room temperature for 2 hours. A saturated sodium hydrogen carbonate aqueous solution was added to the reaction mixture, followed by extraction with ethyl acetate. The organic layer was washed with a saturated sodium chloride aqueous solution and dried over sodium sulfate. After filtering, the filtrate was concentrated under reduced pressure, and the resulting crude crystal was washed with hexane-diethylether to afford the title compound as a white powder (2.52 g, yield 90%).

1H NMR (CDCl$_3$) δ 5.17 (brs, 1H), 5.51 (s, 2H), 6.93 (d, J=8.8 Hz, 1H), 7.08 (d, J=2.8 Hz, 1H), 7.22 (d, J=8.4 Hz, 2H), 7.23 (dd, J=9.1, 2.8 Hz, 1H), 7.54 (d, J=8.4 Hz, 2H), 7.57 (d, J=9.1 Hz, 1H), 7.87 (d, J=8.9 Hz, 1H).

Reference Example 372

Preparation of 4-benzyloxy-1-bromo-2-fluorobenzene

The title compound was prepared in the same manner as in Example 363 using suitable starting materials.

Reference Example 373

Preparation of 1-(4-benzyloxy-2-fluoro-phenyl)-4-(4-trifluoromethoxyphenoxy)piperidine 4-Benzyloxy-1-bromo-2-fluorobenzene (3.55 g, 12.6 mmol), 4-(4-trifluoromethoxyphenoxy)piperidine (3.0 g, 11.5 mmol), sodium tert-butoxide (1.55 g, 16.1 mmol) and toluene (60 ml) were mixed. Palladium acetate (0.10 g, 0.46 mmol) and 2,2'-bis(diphenylphosphino)-1,1'-binaphthyl (0.57 g, 0.92 mmol) were added thereto. The mixture was heated and refluxed under a nitrogen atmosphere for 4 hours. A saturated ammonium chloride aqueous solution was added to the reaction mixture, followed by extraction with ethyl acetate. The organic layer was washed with a saturated sodium chloride aqueous solution and dried over sodium sulfate. After filtering, the filtrate was concentrated under reduced pressure. The residue thus obtained was purified by silica gel column chromatography (hexane:ethyl acetate=80: 20→60:40), and the resulting crude crystal was washed with hexane-diethylether to afford the title compound as a white powder (3.76 g, yield 71%).
1H NMR (CDCl$_3$) δ 1.90-2.02 (m, 2H), 2.05-2.15 (m, 2H), 2.89-2.94 (m, 2H), 3.21-3.26 (m, 2H), 4.40-4.45 (m, 1H), 5.01 (s, 2H), 6.65-6.75 (m, 2H), 6.93 (d, J=8.5 Hz, 2H), 6.92-6.98 (m, 1H), 7.14 (d, J=8.5 Hz, 2H), 7.24-7.42 (m, 5H).

Reference Example 374

Preparation of 4-[4-(4-benzyloxy-2-hydroxy-2-methylbutoxy)phenyl]piperazine-1-carboxylic acid tert-butyl ester 2-[2-(Benzyloxy)ethyl]-2-methyloxirane (2.60 g, 13.5 mmol), 4-(4-hydroxyphenyl)piperazine-1-carboxylic acid tert-butyl ester (4.14 g, 14.9 mmol), tripotassium phosphate (1.15 g, 5.4 mmol) and ethanol (26 ml) were mixed and stirred at 80 to 90° C. overnight. The reaction mixture was poured into water, followed by extraction with ethyl acetate. The organic layer was washed with a saturated sodium chloride aqueous solution, dried over sodium sulfate, and concentrated. The residue was purified by silica gel column chromatography (hexane:ethyl acetate=100:0→30:70) to afford the title compound as a pale yellow oil (6.16 g).
Mass: [M]$^+$=470.

Reference Example 375

Preparation of 4-[4-(2,4-dihydroxy-2-methylbutoxy)phenyl]piperazine-1-carboxylic acid tert-butyl ester 4-[4-(4-Benzyloxy-2-hydroxy-2-methylbutoxy)phenyl]piperazine-1-carboxylic acid tert-butyl ester (6.16 g, 13.1 mmol), palladium hydroxide on carbon (0.62 g) and ethanol (62 ml) were mixed and stirred at 50 to 60° C. under a hydrogen atmosphere for 9 hours. The mixture was filtered through Celite to remove the catalyst, and the filtrate was concentrated. The residue was purified by silica gel column chromatography (hexane:ethyl acetate=100:0→0:100) to afford the title compound as a colorless powder (3.75 g).
Mass: [M]$^+$=380.

Reference Example 376

Preparation of 4-{4-[2-hydroxy-2-methyl-4-(toluene-4-sulfonyloxy)butoxy]phenyl}piperazine-1-carboxylic acid tert-butyl ester 4-[4-(2,4-Dihydroxy-2-methylbutoxy)phenyl]piperazine-1-carboxylic acid tert-butyl ester (3.75 g, 9.9 mmol), tosyl chloride (2.07 g, 10.8 mmol), dichloromethane (38 ml) and triethylamine (2.75 ml, 19.7 mmol) were mixed and ice-cooled. 1,1,3,3,-Tetramethylpropanediamine (0.16 ml, 1.0 mmol) was added thereto and stirred at room temperature overnight. The reaction mixture was washed with a saturated sodium chloride aqueous solution and dried over magnesium sulfate. The organic layer was concentrated, and the residue was purified by silica gel column chromatography (hexane: ethyl acetate=100:0→40:60) to afford the title compound as a colorless oil (4.69 g, 89%).
Mass: [M]$^+$=534.

Reference Example 377

Preparation of 4'-(tetrahydropyran-2-yloxy)biphenyl-4-carbaldehyde 2-(4-Bromophenoxy)tetrahydropyran (3.0 g) was dissolved in N,N-dimethylformamide (30 ml). 4-Formylphenylboronic acid (2.1 g), tetrakis(triphenylphosphine)palladium (0) (1.35 g) and tripotassium phosphate (4.95 g) were added thereto, and the resulting mixture was heated at 90 to 100° C. under a nitrogen atmosphere for 3 hours. After completion of the reaction, ethyl acetate was added to the reaction mixture and filtered through Celite. The filtrate was separated into layers. The organic layer was washed with a saturated sodium chloride aqueous solution and dried over sodium sulfate. The solvent was distilled off under reduced pressure, and the residue was purified by silica gel column chromatography (hexane:ethyl acetate=100:0→50:50) to afford the title compound as a white powder (1.49 g).

Reference Example 378

Preparation of (R)-4-(4-benzyloxyphenyl)-3-methylpiperazine-1-carboxylic acid tert-butyl ester (3R)-1-tert-Butoxycarbonyl-3-methylpiperazine (3.0 g, 15.0 mmol), 4-benzyloxybromobenzene (4.73 g, 18.0 mmol), sodium tert-butoxide (2.02 g, 21.0 mmol) and toluene (30 ml) were mixed, and the atmosphere was replaced with nitrogen. tri-tert-Butylphosphine tetrafluoroborate (0.52 g, 1.8 mmol) and palladium acetate (0.34 g, 1.5 mmol) were added thereto and heated at 90 to 100° C. for 4 hours. Water and ethyl acetate were added to the brown reaction mixture, and insoluble matter was removed by filtration. The filtrate was separated into layers. The organic layer was washed with a saturated sodium chloride aqueous solution, dried over magnesium sulfate and concentrated. The residue was purified by silica gel column chromatography (hexane:ethyl acetate=100:0→50:50) to afford the title compound as a colorless oil (5.29 g, 92%).
Mass: [M+1]$^+$=383.

Reference Example 379

Preparation of (R)-4-(4-benzyloxyphenyl)-2-methylpiperazine-1-carboxylic acid benzyl ester (R)-2-Methylpiperazine-1-carboxylic acid benzyl ester (4.42 g, 18.9 mmol), 1-benzyloxy-4-bromobenzene (5.95 g, 22.6 mmol), cesium carbonate (8.60 g, 26.4 mmol) and toluene (49 ml) were mixed, and the atmosphere was replaced with nitrogen. Palladium acetate (0.42 g, 1.9 mmol) and tri-tert-butylphosphine tetrafluoroborate (0.66 g, 2.3 mmol) were added thereto and stirred at 90 to 100° C. for 2 days. Water and ethyl acetate were added to the reaction mixture, the mixture was filtered through Celite to remove insoluble matter. The filtrate was separated into layers. The organic layer was washed with a saturated sodium chloride aqueous solution, dried over magnesium sulfate and concentrated. The residue was purified by silica gel column chromatography (hexane:ethyl acetate=100:0→70:30) to afford the title compound as a brown oil (6.18 g, 79%).
Mass: $[M]^+=416$.

Reference Example 380

Preparation of (R)-4-(4-hydroxyphenyl)-2-methylpiperazine-1-carboxylic acid tert-butyl ester (R)-4-(4-Benzyloxyphenyl)-2-methylpiperazine-1-carboxylic acid benzyl ester (6.18 g, 14.8 mmol), acetic acid (62 ml) and 10% palladium on carbon (0.62 g) were mixed and stirred at room temperature under the hydrogen pressure of 1 atm for 8 hours. The mixture was filtered through Celite to remove the catalyst, and the filtrate was concentrated. Methanol (62 ml), triethylamine (10 ml) and di-tert-butyl dicarbonate (3.89 g, 17.8 mmol) were added to the residue and stirred at room temperature overnight. The reaction mixture was concentrated, and water was added to the residue, followed by extraction with ethyl acetate.

The organic layer was washed with a saturated sodium chloride aqueous solution, dried over sodium sulfate, and concentrated. The residue was purified by silica gel column chromatography (hexane:ethyl acetate=100:0→60:40) to afford the title compound as a pale brown oil (4.65 g, 100%).
Mass: $[M]^+=292$.

Reference Example 381

Preparation of 1'-[4-(tetrahydropyran-2-yloxy)phenyl]-[4,4']bipiperidinyl-1-carboxylic acid tert-butyl ester The title compound was prepared in the same manner as in Reference Example 362 using suitable starting materials.
1H NMR (CDCl$_3$) δ 1.11-1.32 (m, 4H), 1.38-1.52 (m, 2H), 1.46 (s, 9H), 1.55-1.74 (m, 5H), 1.75-1.89 (m, 4H), 1.95-2.05 (m, 1H), 2.56 (dd, J=12.0, 2.0 Hz, 2H), 2.60-2.75 (m, 2H), 3.52-3.63 (m, 3H), 3.91-4.01 (m, 1H), 4.02-4.22 (m, 2H), 5.31 (d, J=2.0 Hz, 1H), 6.86-6.90 (m, 2H), 6.94-6.98 (m, 2H).

Reference Example 382

Preparation of 1'-(4-hydroxyphenyl)-[4,4']bipiperidinyl-1-carboxylic acid tert-butyl ester The title compound was prepared in the same manner as in Reference Example 187 using suitable starting materials.
1H NMR (CDCl$_3$) δ 1.08-1.30 (m, 4H), 1.46 (s, 9H), 1.54-1.69 (m, 4H), 1.77-1.85 (m, 2H), 2.59-2.72 (m, 2H), 2.72 (t, J=12.0, 2H), 3.53 (d, J=12.0, 2H), 4.00-4.25 (m, 2H), 6.79 (d, J=9.0 Hz, 2H), 7.00 (d, J=9.0 Hz, 2H).

Reference Example 383

Preparation of 4-trifluoromethylcyclohexane carbaldehyde

After dissolving [cis-4-(trifluoromethyl)cyclohexyl]methanol (2.04 g, 10.2 mmol) in dimethylsulfoxide (30 ml), 2-iodoxybenzoic acid (4.00 g, 14.3 mmol) was added thereto and stirred at room temperature overnight. Water and ethyl acetate were added to the reaction mixture, the insoluble matter was removed by filtration, and then the filtrate was separated into layers. The organic layer was washed with water and a saturated sodium chloride aqueous solution, dried over sodium sulfate, and concentrated to afford the title compound as a colorless oil (2.3 g, 100%).
1H NMR (CDCl$_3$) δ 1.28-1.39 (m, 2H), 1.53-1.65 (m, 2H), 1.78-1.88 (m, 2H), 1.95-2.10 (m, 1H), 2.30 (dd, J=14.1 Hz, 2.8 Hz, 2H), 2.45-2.52 (m, 1H), 9.71 (s, 1H).

Reference Example 384

Preparation of 1-(4'-benzyloxybiphenyl-4-yl)-4,4'-diethoxy-piperidine 4-(Benzyloxy)-4'-bromobiphenyl (10.0 g, 29.5 mmol), 4,4-diethoxypiperidine (5.62 g, 32.4 mmol), sodium tert-butoxide (3.97 g, 41.3 mmol) and toluene (150 ml) were mixed. Palladium acetate (0.20 g, 0.88 mmol) and tri-tert-butylphosphine tetrafluoroborate (0.39 g, 1.33 mmol) were added thereto and heated and refluxed under a nitrogen atmosphere for 2 hours. A saturated ammonium chloride aqueous solution was added to the reaction mixture, and the precipitated crystal was collected by filtration. The obtained crude crystal was washed with acetone-hexane to afford the title compound as a white powder (10.4 g, yield 82%).

Reference Example 385

Preparation of 1-(4'-benzyloxybiphenyl-4-yl)piperidin-4-one 1-(4'-Benzyloxybiphenyl-4-yl)-4,4-diethoxy-piperidine (10.0 g, 23.2 mmol), acetone (100 ml) and a 5 N hydrochloric acid aqueous solution (35 ml) were mixed and heated under reflux for 5 hours. 1 N sodium hydroxide was added to the residue obtained by removing the solvent by distillation, followed by extraction with dichloromethane. The organic layer was washed with water and then dried over sodium sulfate. After filtering, the filtrate was concentrated under reduced pressure. The resulting crude crystal was washed with diethylether to afford the title compound as a white powder (7.2 g, yield 87%).
1H NMR (CDCl$_3$) δ 2.57 (t, J=6.1 Hz, 4H), 3.64 (t, J=6.1 Hz, 4H), 5.10 (s, 2H), 7.00-7.06 (m, 4H), 7.33-7.39 (m, 1H), 7.40-7.45 (m, 2H), 7.46-7.52 (m, 6H).

Reference Example 386

Preparation of 4-benzyloxy-2-methyl-1-(4-{4-[2-(4-trifluoromethoxyphenyl)ethyl]piperidin-1-yl}phenoxy)butan-2-ol A tripotassium phosphate (0.44 g, 2.1 mmol) was added to a solution of 2-[2-(Benzyloxy)ethyl]-2-methyloxirane (1.00 g, 5.2 mmol) and 4-{4-[4-(trifluoromethoxy)phenethyl]piperidin-1-yl}phenol (2.28 g, 6.2 mmol) in ethanol (10 ml), and then the mixture was heated at reflux overnight. Water was added to the reaction mixture, followed by extraction with ethyl acetate. The organic layer was washed with a saturated sodium chloride aqueous solution, dried over sodium sulfate, and concentrated. The residue was purified by silica gel column chromatography (hexane:ethyl acetate=100:0→50:50) to afford the title compound as a brown powder (2.43 g, 86%).

1H NMR (CDCl$_3$) δ 1.32 (s, 3H), 1.34-1.49 (m, 3H), 1.53-1.65 (m, 3H), 1.78-1.89 (m, 2H), 1.89-2.08 (m, 2H), 2.53-2.63 (m, 2H), 2.63-2.70 (m, 2H), 3.42-3.55 (m, 2H), 3.66-3.83 (m, 4H), 4.51 (s, 2H), 6.81 (d, J=9.1 Hz, 2H), 6.90 (d, J=9.1 Hz, 2H), 7.13 (d, J=8.0 Hz, 2H), 7.20 (d, J=8.6 Hz, 2H), 7.27-7.41 (m, 5H).

Reference Example 387

Preparation of 3-methyl-4-(4-{4-[2-(4-trifluoromethoxyphenyl)ethyl]piperidin-1-yl}phenoxy)butane-1,3-diol 4-Benzyloxy-2-methyl-1-(4-{4-[4-(trifluoromethoxy)phenethyl]piperidin-1-yl}phenoxy)butan-2-ol (2.43 g, 4.5 mmol), ethanol (24 ml) and 20% palladium hydroxide on carbon (0.24 g) were mixed and stirred at 50 to 60° C. under the hydrogen pressure of 1 atm for 4 hours. The mixture was filtered through Celite to remove the catalyst, and the filtrate was concentrated. The residue was purified by silica gel column chromatography (hexane:ethyl acetate=100:0→0:100) to afford the title compound as a colorless powder (1.68 g, 80%).

Mass: [M]$^+$=467.

Reference Example 388

Preparation of toluene-4-sulfonic acid 3-hydroxy-3-methyl-4-(4-{4-[2-(4-trifluoromethoxyphenyl)ethyl]piperidin-1-yl}phenoxy)butyl ester 3-Methyl-4-(4-{4-[2-(4-trifluoromethoxyphenyl)ethyl]piperidin-1-yl}phenoxy)butane-1,3-diol (1.68 g, 3.6 mmol), dichloromethane (17 ml), triethylamine (1.00 ml, 7.2 mmol) and p-toluenesulfonyl chloride (0.82 g, 4.3 mmol) were mixed and ice-cooled. 1,1,3,3,-Tetramethylpropanediamine (0.12 ml, 0.7 mmol) was added thereto and stirred at room temperature for 1 hour. The reaction mixture was washed with a saturated sodium chloride aqueous solution and dried over sodium sulfate. The organic layer was concentrated, and the residue was purified by silica gel column chromatography (hexane:ethyl acetate=100:0, 50:50) to afford the title compound as a colorless powder (2.03 g, 91%).

Mass: [M]$^+$=621.

Reference Example 389

Preparation of 4-[3-(3-trifluoromethylphenoxy)propyl]piperidine-1-carboxylic acid tert-butyl ester 4-(3-Hydroxypropyl)piperidine-1-carboxylic acid tert-butyl ester (15.0 g, 61.6 mmol), 3-trifluoromethylphenol (19.4 g, 64.7 mmol), triphenylphosphine (1.40 g, 73.9 mmol) and tetrahydrofuran (200 ml) were mixed. While stirring the mixture at room temperature, DEAD (21.1 ml, 80.0 mmol) was added thereto dropwise and heated at reflux for 2 days. Water was added to the reaction mixture, followed by extraction with ethyl acetate. The organic layer was washed with a saturated sodium chloride aqueous solution and dried over sodium sulfate. After filtering, the filtrate was concentrated under reduced pressure. The resulting residue was purified by silica gel column chromatography (hexane:ethyl acetate=87:13) to afford the title compound as a pale yellow oil (20.5 g, yield 86%).

1H NMR (CDCl$_3$) δ 1.05-1.21 (m, 2H), 1.40-1.57 (m, 3H), 1.46 (s, 9H), 1.65-1.76 (m, 2H), 1.81-1.89 (m, 2H), 2.65-2.80 (m, 2H), 3.98 (t, J=6.4, 2H), 3.94-4.24 (m, 2H), 7.04 (dd, J=8.3, 2.4 Hz, 1H), 7.11 (d, J=2.4, 1H), 7.19 (d, J=7.7, 1H), 7.38 (ddd, J=8.3, 7.7, 2.4, 1H).

Reference Example 390

Preparation of 1-(4'-benzyloxybiphenyl-4-yl)-4-trifluoromethylpiperidin-4-ol 1-(4'-Benzyloxybiphenyl-4-yl)piperidin-4-one (7.1 g, 19.9 mmol), tetrabutylammonium acetate (0.3 g, 1.0 mmol) and 1,2-dimethoxethane (100 ml) were mixed. While stirring the mixture under ice cooling, trifluoromethyltrimethylsilane (4.11 ml, 27.8 mmol) was added to the mixture and warmed to room temperature, followed by stirring for 6 hours. The residue obtained by distilling off the solvent was dissolved in tetrahydrofuran (100 ml). While stirring at room temperature, 1 mol/l tetrabutylammonium fluoride in tetrahydrofuran (23.8 ml, 23.8 mmol) was added thereto and stirred at room temperature overnight. Water was added to the residue obtained by distilling off the solvent, followed by extraction with dichloromethane. The organic layer was washed with water and dried over sodium sulfate. After filtering, the filtrate was concentrated under reduced pressure. The resulting crude crystal was washed with diethylether to afford the title compound as a white powder (7.6 g, yield 90%).

1H NMR (CDCl$_3$) δ 1.83 (dd, J=14.0, 2.4 Hz, 2H), 2.08 (dt, J=13.5, 4.5 Hz, 2H), 3.11 (dd, J=12.6, 2.4 Hz, 2H), 3.60-3.66 (m, 2H), 5.10 (s, 2H), 6.99-7.05 (m, 4H), 7.34-7.39 (m, 1H), 7.40-7.46 (m, 2H), 7.47-7.54 (m, 6H).

Reference Example 391

Preparation of 4-[3-(3-trifluoromethylphenoxy)propyl]piperidine

The title compound was prepared in the same manner as in Reference Example 354 using suitable starting materials.

1H NMR (CDCl$_3$) δ 1.42-1.63 (m, 5H), 1.80-1.90 (m, 4H), 2.75-2.83 (m, 2H), 3.24-3.33 (m, 2H), 3.98 (t, J=6.3, 2H), 7.04 (dd, J=8.2, 2.3 Hz, 1H), 7.10 (d, J=2.3, 1H), 7.19 (d, J=7.7, 1H), 7.39 (ddd, J=8.2, 7.7, 2.3, 1H).

Reference Example 392

Preparation of 1-[4-(tetrahydropyran-2-yloxy)phenyl]-4-[3-(3-trifluoromethylphenoxy)propyl]piperidine The title compound was prepared in the same manner as in Reference Example 362 using suitable starting materials.

1H NMR (CDCl$_3$) δ 1.37-1.55 (m, 5H), 1.60-1.75 (m, 3H), 1.83-1.90 (m, 6H), 1.95-2.08 (m, 1H), 2.63 (t, J=10.0, 2H), 3.55-3.65 (m, 3H), 3.91-3.98 (m, 1H), 4.00 (t, J=6.5, 2H), 5.31 (t, J=2.0, 1H), 6.87-6.92 (m, 2H), 6.96-6.99 (m, 2H), 7.06 (dd, J=8.3, 2.4 Hz, 1H), 7.13 (d, J=2.4, 1H), 7.20 (d, J=7.7, 1H), 7.38 (ddd, J=8.3, 7.7, 2.4, 1H).

Reference Example 393

Preparation of 1-[4-(tetrahydropyran-2-yloxy)phenyl]-4-(4-trifluoromethylsulfanylphenoxy)piperidine The title compound was prepared in the same manner as in Reference Example 379 using suitable starting materials.
Mass: [M]+=453.

Reference Example 394

Preparation of cis-(4-trifluoromethylcyclohexyl)methanol cis-4-(Trifluoromethyl)cyclohexanecarboxylic acid (1.05 g, 5.4 mmol) and tetrahydrofuran (20 ml) were mixed and ice-cooled. A borane-tetrahydrofuran complex (10.71 ml, 10.7 mmol) was added to the mixture dropwise. After the completion of dropwise addition, the reaction mixture was stirred at room temperature overnight. 1 N hydrochloric acid was added to the reaction mixture, followed by extraction with ethyl acetate. The organic layer was washed with water and a saturated sodium chloride aqueous solution, dried over sodium sulfate, and concentrated to afford the title compound as a colorless oil (0.92 g, 94%).
1H NMR (CDCl$_3$) δ 1.32 (t, J=4.7 Hz, 1H), 1.48-1.62 (m, 4H), 1.64-1.74 (m, 4H), 1.76-1.82 (m, 1H), 2.05-2.17 (m, 1H), 3.62 (dd, J=4.5 Hz, 7.1 Hz, 2H).

Reference Example 395

Preparation of 1-(4-benzyloxyphenyl)-4-(4-trifluoromethylphenyl)piperidin-4-ol

Isopropylmagnesium chloride (2M tetrahydrofuran solution) (11.73 ml) was added to a tetrahydrofuran solution (20 ml) of 4-iodobenzotrifluoride (3.45 ml, 23.5 mmol) dropwise at −10° C. under an argon atmosphere. The mixture was stirred at the same temperature for 5 minutes and further stirred at room temperature for 2 hours. After cooling the mixture to −10° C., a tetrahydrofuran solution (40 ml) of 1-(4-benzyloxyphenyl)piperidin-4-one (6 g, 21.3 mmol) was added thereto dropwise. While gradually returning to room temperature, the mixture was stirred. After 10 hours, a saturated ammonium chloride aqueous solution/ice water was poured into the mixture, followed by extraction with ethyl acetate. The result was washed with water and a saturated sodium chloride aqueous solution and dried over sodium sulfate. After removing the desiccant by filtration, the solvent was distilled off. The residue was purified by silica gel column chromatography (hexane:ethyl acetate=75:25→66:34). The resultant was washed with a mixed solvent of isopropyl ether and hexane and filtered to afford the title compound as a white powder (6.69 g, 73%).
1H NMR (CDCl$_3$) δ=1.65 (s, 1H), 1.82-1.88 (m, 2H), 2.31 (dt, J=4.6 Hz, 13.3 Hz, 2H), 3.14 (dt, J=2.5 Hz, 12.3 Hz, 2H), 3.40-3.47 (m, 2H), 5.03 (s, 2H), 6.92-6.96 (m, 2H), 6.96-7.01 (m, 2H), 7.30-7.35 (m, 1H), 7.36-7.41 (m, 2H), 7.42-7.45 (m, 2H), 7.63 (d, J=8.6 Hz, 2H), 7.67 (d, J=8.6 Hz, 2H).

Reference Example 396

Preparation of 1-(4-benzyloxyphenyl)-4-methoxy-4-(4-trifluoromethylphenyl)piperidine 60% sodium hydride (0.225 g, 5.2 mmol) was added to an N,N-dimethylformamide solution (20 ml) of 1-(4-benzyloxyphenyl)-4-(4-trifluoromethylphenyl)piperidin-4-ol (2 g, 4.7 mmol) and iodomethane (0.585 ml, 9.4 mmol) under an argon atmosphere while ice cooling, followed by stirring at the same temperature. After 2 hours, the mixture was poured into ice water, and the precipitate was collected by filtration. The resulting solid was dissolved in ethyl acetate/dichloromethane and dried over sodium sulfate. After removing the desiccant by filtration, the solvent was distilled off. The residue was purified by silica gel column chromatography (dichloromethane:ethyl acetate=100:0→95:5) to afford the title compound as a white powder (1.64 g, 79%).
1H NMR (CDCl$_3$) δ=2.10-2.18 (m, 4H), 3.02 (s, 3H), 3.05-3.15 (m, 2H), 3.35-3.43 (m, 2H), 5.03 (s, 2H), 6.91-6.94 (m, 2H), 6.94-6.98 (m, 2H), 7.29-7.34 (m, 1H), 7.36-7.41 (m, 2H), 7.42-7.45 (m, 2H), 7.56 (d, J=8.2 Hz, 2H), 7.64 (d, J=8.2 Hz, 2H).

Reference Example 397

Preparation of 2-methyl-2-[4-(4-trifluoromethylbenzyloxy)phenyl]propionic acid

Iodomethane (4.63 ml, 74.0 mmol) was added to an N,N-dimethylformamide solution (80 ml) of [4-(4-trifluoromethylbenzyloxy)phenyl]acetic acid methyl ester (8 g, 24.7 mmol) under an argon atmosphere. Subsequently, sodium hydride (2.37 g, 54.3 mmol) was gradually added thereto under ice cooling. After stirring at the same temperature for 30 minutes, the mixture was further stirred at room temperature. After 2 hours, iodomethane (3.09 ml, 49.3 mmol) was added thereto, and sodium hydride (1.08 g, 24.7 mmol) was further added 1 hour later. Thereafter, the mixture was stirred at room temperature overnight. Because a monomethylated compound still remained, the mixture was ice-cooled again. Sodium hydride (1.08 g, 24.7 mmol) was added thereto and stirred for 5 minutes. Iodomethane (3.09 ml, 49.3 mmol) was added to the mixture and stirred at room temperature. The reaction mixture was poured into a mixture of ice water (500 ml) and acetic acid (6 ml), followed by stirring. Ethyl acetate was added thereto, and the mixture was neutralized with a saturated sodium hydrogen carbonate aqueous solution, followed by extraction with ethyl acetate. The result was washed with water and a saturated sodium chloride aqueous solution and dried over sodium sulfate. After distilling the solvent off, the residue was dissolved in an N,N-dimethylformamide solution (80 ml) again. Sodium hydride (1.08 g, 24.7 mmol) was added to the result under an argon atmosphere while ice cooling, followed by stirring at the same temperature for 30 minutes. Thereafter, iodomethane (3.09 ml, 49.3 mmol) was added to the mixture and stirred while returning the mixture to room temperature. After 10 hours, the reaction mixture was poured into ice water/acetic acid (1.5 ml) and stirred for a while, and the precipitate was collected by filtration. The resulting solid was dissolved in ethyl acetate and dried over sodium sulfate. The solvent was then distilled off.
Because a monomethylated compound still remained, the mixture was dissolved in an N,N-dimethylformamide (80 ml) again, and sodium hydride (1.08 g, 24.7 mmol) was added thereto under an argon atmosphere while ice cooling. The mixture was stirred at the same temperature for 30 minutes, iodomethane (3.09 ml, 49.3 mmol) was added thereto and stirred while returning the mixture to room temperature. After 9 hours, the mixture was poured into ice water/acetic acid (1.5 ml) and stirred for a while. The precipitate was collected by filtration, and the resulting solid was dissolved in ethyl acetate and dried over sodium sulfate. Thereafter, the solvent was distilled off.

Because a monomethylated compound still remained, the mixture was dissolved in an N,N-dimethylformamide (80 ml) again, and sodium hydride (1.08 g, 24.7 mmol) was added thereto under an argon atmosphere while ice cooling. After stirring at the same temperature for 30 minutes, iodomethane (3.09 ml, 49.3 mmol) was added thereto and stirred while returning the mixture to room temperature. After 10 hours, the mixture was poured into ice water/acetic acid (1.5 ml) and the resulting mixture was stirred for a while. Thereafter, the precipitate was collected by filtration. The resulting solid was dissolved in ethyl acetate and dried over sodium sulfate. The solvent was then distilled off.

The resultant was dissolved in methanol (80 ml), and 5 N sodium hydroxide (25 ml) was added thereto and stirred under reflux. After 2 hours, the mixture was returned to room temperature, and the solvent was distilled off. The residue was dissolved in water and washed with hexane. The pH value of the water layer was adjusted to 1 to 2 using a concentrated hydrochloric acid under ice cooling, and the precipitate was collected by filtration. The solid thus obtained was dissolved in ethyl acetate and dried over sodium sulfate. After removing the desiccant by filtration, the solvent was distilled of to afford the title compound as a white powder (7.03 g, 84%).

1H NMR (CDCl$_3$) δ=1.59 (s, 6H), 5.11 (s, 2H), 6.91-6.95 (m, 2H), 7.32-7.36 (m, 2H), 7.54 (d, J=8.1 Hz, 2H), 7.64 (d, J=8.1 Hz, 2H).

Reference Example 398

Preparation of 1-(2-isocyanatopropan-2-yl)-4-[4-(trifluoromethyl)benzyloxy]benzene Triethylamine (2.90 ml, 20.8 mmol) and diphenylphosphorylazide (4.48 ml, 20.8 mmol) were added to a 1,4-dioxane solution (70 ml) of 2-methyl-2-[4-(4-trifluoromethylbenzyloxy)phenyl]propionic acid (7.03 g, 10.8 mmol) and heated at reflux. After 2 hours, the solvent was distilled off, and diethylether and water were added to the residue, followed by extraction with diethylether. The result was washed with water and a saturated sodium chloride aqueous solution and dried over sodium sulfate. After removing the desiccant by filtration, the solvent was distilled off to afford the title compound as a pale brown oil (6.89 g, 99%).

1H NMR (CDCl$_3$) δ=1.70 (s, 6H), 5.13 (s, 2H), 6.90-6.96 (m, 2H), 7.33-7.39 (m, 2H), 7.55 (d, J=8.1 Hz, 2H), 7.65 (d, J=8.1 Hz, 2H).

Reference Example 399

Preparation of 1-methyl-1-[4-(4-trifluoromethylbenzyloxy)phenyl]ethylamine

Concentrated hydrochloric acid (18 ml) was added to an acetic acid solution (24 ml) of 1-(2-isocyanatopropan-2-yl)-4-[4-(trifluoromethyl)benzyloxy]benzene (4.35 g, 13.0 mmol) and stirred at room temperature. After 2.5 hours, the mixture was heated to 80° C. and stirred for 1 hour. The solvent was then distilled off. Ice and a 5 N sodium hydroxide aqueous solution were sequentially added to the residue and stirred, followed by extraction with ethyl acetate. The resultant was washed with a saturated sodium chloride aqueous solution and dried over sodium sulfate. After removing the desiccant, the solvent was distilled off to afford the title compound as a brown solid (3.3 g, 82%).

1H NMR (CDCl$_3$) δ=1.48 (s, 6H), 1.76 (brs, 2H), 5.12 (s, 2H), 6.90-6.94 (m, 2H), 7.41-7.46 (m, 2H), 7.55 (d, J=8.0 Hz, 2H), 7.64 (d, J=8.0 Hz, 2H).

Reference Example 400

Preparation of 1-{1-methyl-1-[4-(4-trifluoromethylbenzyloxy)phenyl]ethyl}-4-(toluene-4-sulfonyl]piperazine N,N-bis-2-(Chloro-ethyl)-4-methylbenzenesulfonamide (4.74 g, 16.0 mmol) was added to a disopropylethylamine suspension (40 ml) of 1-methyl-1-[4-(4-trifluoromethylbenzyloxy)phenyl]ethylamine (3.3 g, 10.7 mmol) and stirred at 130° C. After 24 hours, heating was stopped. The solvent was distilled off, and a dilute sodium hydroxide aqueous solution was added to the residue, followed by extraction with ethyl acetate. The result was washed with water and a saturated sodium chloride aqueous solution and dried over sodium sulfate (30 g of silica gel was added at the same time). After removing the desiccant and silica gel by filtration, the solvent was distilled off. The residue was purified by silica gel column chromatography (hexane:ethyl acetate=90:10→85:15→80:20) to afford the title compound as a white solid (2.67 g, 47%).

1H NMR (CDCl$_3$) δ=1.29 (s, 6H), 2.45 (s, 2H), 2.54 (t, J=4.7 Hz, 4H), 2.87-3.02 (m, 4H), 6.82-6.87 (m, 2H), 7.30-7.36 (m, 4H), 7.54 (d, J=8.1 Hz, 2H), 7.60-7.66 (m, 4H).

Reference Example 401

Preparation of 1-{1-methyl-1-[4-(4-trifluoromethylbenzyloxy)phenyl]ethyl}piperazine Magnesium (1.83 g, 75.0 mmol) was added to a methanol solution (50 ml) of 1-{1-methyl-1-[4-(4-trifluoromethylbenzyloxy)phenyl]ethyl}-4-(toluene-4-sulfonyl]piperazine (2.67 g, 5.0 mmol) and stirred at 60° C. After hours, magnesium (0.61 g, 25.1 mmol) was added thereto and further stirred. After 1 hour, heating was stopped and the solvent was distilled off. Ice and 10% hydrochloric acid (100 ml) were added to the residue and stirred. Ethyl acetate was added and further stirred. The mixture was separated into layers, and the water layer was made basic using a 25% sodium hydroxide aqueous solution. Ethyl acetate was added to the mixture, followed by stirring. The mixture was filtered through Celite to remove the insoluble matter. The filtrate was subjected to extraction with ethyl acetate. The organic layer was dried over sodium sulfate. After removing the desiccant by filtration, the solvent was distilled off to afford the title compound as a slightly yellow oil (1.05 g, 55%).

1H NMR (CDCl$_3$) δ=1.32 (s, 6H), 2.38-2.49 (m, 4H), 2.84 (t, J=4.8 Hz, 4H), 5.11 (s, 2H), 6.87-6.92 (m, 2H), 7.42-7.48 (m, 2H), 7.56 (d, J=8.0 Hz, 2H), 7.64 (d, J=8.0 Hz, 2H).

Reference Example 402

Preparation of 1-{1-methyl-1-[4-(4-trifluoromethylbenzyloxy)phenyl]ethyl}-4-[4-(tetrahydropyran-2-yloxy)phenyl]piperazine The title compound was prepared in the same manner as in Reference Example 362 using suitable starting materials.

1H NMR (CDCl$_3$) δ=1.36 (s, 6H), 1.53-1.73 (m, 3H), 1.78-1.90 (m, 2H), 1.94-2.04 (m, 1H), 2.62 (t, J=4.8 Hz, 4H), 3.05 (t, J=4.8 Hz, 4H), 3.54-3.63 (m, 1H), 3.90-3.98 (m, 1H), 5.12 (s, 2H), 5.30 (t, J=3.4 Hz, 1H), 6.83-6.88 (m, 2H), 6.89-6.93 (m, 2H), 6.95-6.99 (m, 2H), 7.45-7.50 (m, 2H), 7.56 (d, J=8.2 Hz, 2H), 7.65 (d, J=8.2 Hz, 2H).

Example 1

Preparation of 2-nitro-7-{4-[4-(4-trifluoromethoxyphenoxy)piperidin-1-yl]phenoxymethyl}-6,7-dihydro-5H-imidazo[2,1-b][1,3]oxazine 60% sodium hydride (70 mg) was added to an N,N-dimethylformamide solution (10 ml) of 4-(2-chloro-4-nitroimidazol-1-yl)-1-{4-[4-(4-trifluoromethoxyphenoxy)piperidin-1-yl]phenoxy}butan-2-ol (0.9 g) under ice cooling, and the mixture was stirred at room temperature for 3 days. A saturated ammonium chloride aqueous solution was added to the reaction mixture, followed by extraction with ethyl acetate. The organic layer was washed with a saturated sodium chloride aqueous solution and dried over sodium sulfate. After filtering, the filtrate was concentrated under reduced pressure. The residue thus obtained was purified by silica gel column chromatography (methylene chloride:ethyl acetate=8:2→methylene chloride:ethyl acetate=2:8) and recrystallized from methylene chloride-ethyl acetate-isopropyl ether to afford the title compound as a pale yellow powder (158 mg).

Melting point: 186.8-187.8° C.

Example 2

Preparation of 4-[4-(2-nitro-6,7-dihydro-5H-imidazo[2,1-b][1,3]oxazin-7-ylmethoxy)phenyl]piperazine-1-carboxylic acid tert-butyl ester The title compound was prepared in the same manner as in Example 1 using suitable starting materials.
White Powder
Melting point: 199.5-200.3° C.

Example 3

Preparation of 2-nitro-7-{4-[4-(4-trifluoromethoxybenzyl)piperazin-1-yl]phenoxymethyl}-6,7-dihydro-5H-imidazo[2,1-b][1,3]oxazine Trifluoroacetic acid (6.0 ml) was added to 4-[4-(2-nitro-6,7-dihydro-5H-imidazo[2,1-b][1,3]oxazin-7-ylmethoxy)phenyl]piperazine-1-carboxylic acid tert-butyl ester (200 mg), and the mixture was stirred at room temperature for 3 hours. The reaction mixture was concentrated under reduced pressure, and methylene chloride (2.0 ml) and triethylamine (2.0 ml) were added to the residue, followed by stirring at room temperature for 5 minutes. The reaction mixture was reconcentrated under reduced pressure. 1,2-Dichloroethane (5 ml), 4-(trifluoromethoxy)benzaldehyde (124 µl) and sodium triacetoxyborohydride (185 mg) were added to the residue, and the mixture was stirred at room temperature overnight. Water was added to the reaction mixture, and the resulting mixture was subjected to extraction with ethyl acetate. The organic layer was washed with a saturated sodium chloride aqueous solution and dried over sodium sulfate. After filtering, the filtrate was concentrated under reduced pressure. The residue was purified by silica gel column chromatography (methylene chloride:methanol=10:0→methylene chloride:methanol=9:1) and recrystallized from methylene chloride-isopropyl ether to afford the title compound as a white powder (211 mg).

Melting point: 171.8-173.3° C.

Example 4

Preparation of N-(4-chlorophenyl)-N-methyl-N-{1-[4-(2-nitro-6,7-dihydro-5H-imidazo[2,1-b][1,3]oxazin-7-ylmethoxy)phenyl]piperidin-4-yl}amine The title compound was prepared in the same manner as in Example 1 using suitable starting materials.
Pale Yellow Powder
Melting point: 212.0-213.6° C.

Example 5

Preparation of 2-nitro-7-{4-[4-(4-trifluoromethylbenzyloxymethyl)piperidin-1-yl]phenoxymethyl}-6,7-dihydro-5H-imidazo[2,1-b][1,3]oxazine The title compound was prepared in the same manner as in Example 1 using suitable starting materials.
Pale Yellow Powder
Melting point: 141-143° C.

Example 6

Preparation of 2-nitro-7-{4-[4-(4-trifluoromethylphenoxymethyl)piperidin-1-yl]phenoxymethyl}-6,7-dihydro-5H-imidazo[2,1-b][1,3]oxazine The title compound was prepared in the same manner as in Example 1 using suitable starting materials.
Yellow Solid
Melting point: 199.8-200.8° C.

Example 7

Preparation of 7-{4-[4-(4'-chlorobiphenyl-4-ylmethyl)piperazin-1-yl]phenoxymethyl}-2-nitro-6,7-dihydro-5H-imidazo[2,1-b][1,3]oxazine The title compound was prepared in the same manner as in Example 3 using suitable starting materials.
Pale Yellow Powder
Melting point: 276.4-277.1° C.

Example 8

Preparation of 2-nitro-7-(4-{4-[4-(4-trifluoromethoxyphenoxy)benzyl]piperazin-1-yl}phenoxymethyl)-6,7-dihydro-5H-imidazo[2,1-b][1,3]oxazine The title compound was prepared in the same manner as in Example 3 using suitable starting materials.
Pale Brown Powder
Melting point: 164.0-164.4° C.

Example 9

Preparation of 2-nitro-7-{4-[4-(4-trifluoromethoxybenzyloxy)piperidin-1-yl]phenoxymethyl}-6,7-dihydro-5H-imidazo[2,1-b][1,3]oxazine The title compound was prepared in the same manner as in Example 1 using suitable starting materials.
Pale Yellow Powder
Melting point: 189-190° C.

Example 10

Preparation of N-methyl-N-(4-trifluoromethoxyphenyl)-{1-[4-(2-nitro-6,7-dihydro-5H-imidazo[2,1-b][1,3]oxazin-7-ylmethoxy)phenyl]piperidin-4-yl}amine The title compound was prepared in the same manner as in Example 1 using suitable starting materials.
Pale Yellow Powder
Melting point: 188-189° C.

Example 11

Preparation of 2-nitro-7-{4-[4-(4-trifluoromethoxybenzyl)piperidin-1-yl]phenoxymethyl}-6,7-dihydro-5H-imidazo[2,1-b][1,3]oxazine The title compound was prepared in the same manner as in Example 1 using suitable starting materials.
White Powder
Melting point: 174-175° C.

Example 12

Preparation of 2-nitro-7-(4-{4-[2-(4-trifluoromethoxyphenyl)ethyl]piperidin-1-yl}phenoxymethyl)-6,7-dihydro-5H-imidazo[2,1-b][1,3]oxazine The title compound was prepared in the same manner as in Example 1 using suitable starting materials.
Pale Yellow Powder
Melting point: 204-205° C.

Example 13

Preparation of (S)-2-nitro-7-{4-[4-(4-trifluoromethoxyphenoxy)piperidin-1-yl]phenoxymethyl}-6,7-dihydro-5H-imidazo[2,1-b][1,3]oxazine The title compound was prepared in the same manner as in Example 1 using suitable starting materials.
White Powder
Melting point: 165-166° C.

Example 14

Preparation of 2-nitro-7-{4-[4-(4-trifluoromethoxybenzyloxymethyl)piperidin-1-yl]phenoxymethyl}-6,7-dihydro-5H-imidazo[2,1-b][1,3]oxazine The title compound was prepared in the same manner as in Example 1 using suitable starting materials.
White Powder
Melting point: 156-157° C.

Example 15

Preparation of 2-nitro-7-{4-[4-(4-trifluoromethoxyphenoxymethyl)piperidin-1-yl]phenoxymethyl}-6,7-dihydro-5H-imidazo[2,1-b][1,3]oxazine The title compound was prepared in the same manner as in Example 1 using suitable starting materials.
Pale Yellow Powder
Melting point: 202-203° C.

Example 16

Preparation of 7-{4-[4-(4-chlorobenzyloxymethyl)piperidin-1-yl]phenoxymethyl}-2-nitro-6,7-dihydro-5H-imidazo[2,1-b][1,3]oxazine The title compound was prepared in the same manner as in Example 1 using suitable starting materials.
Pale Yellow Powder
Melting point: 149-150° C.

Example 17

Preparation of 7-{4-[4-(4-chlorobenzyloxy)piperidin-1-yl]phenoxymethyl}-2-nitro-6,7-dihydro-5H-imidazo[2,1-b][1,3]oxazine The title compound was prepared in the same manner as in Example 1 using suitable starting materials.
White Powder
Melting point: 200-201° C.

Example 18

Preparation of (R)-2-nitro-7-{4-[4-(4-trifluoromethoxyphenoxy)piperidin-1-yl]phenoxymethyl}-6,7-dihydro-5H-imidazo[2,1-b][1,3]oxazine The title compound was prepared in the same manner as in Example 1 using suitable starting materials.
White Powder
Melting point: 163-164° C.

Example 19

Preparation of 2-nitro-7-{4-[4-(4-trifluoromethylphenoxy)piperidin-1-yl]phenoxymethyl}-6,7-dihydro-5H-imidazo[2,1-b][1,3]oxazine The title compound was prepared in the same manner as in Example 1 using suitable starting materials.
Pale Yellow Powder
Melting point: 207-209° C.

Example 20

Preparation of 7-{4-[4-(4-chlorophenoxy)piperidin-1-yl]phenoxymethyl}-2-nitro-6,7-dihydro-5H-imidazo[2,1-b][1,3]oxazine The title compound was prepared in the same manner as in Example 1 using suitable starting materials.
Pale Yellow Powder
Melting point: 183-185° C.

Example 21

Preparation of 2-nitro-7-{4-[4-(4-trifluoromethoxyphenyl)piperidin-1-yl]phenoxymethyl}-6,7-dihydro-5H-imidazo[2,1-b][1,3]oxazine The title compound was prepared in the same manner as in Example 1 using suitable starting materials.
Pale Yellow Powder
Melting point: 214-216° C.

Example 22

Preparation of N-methyl-N-{1-[4-(2-nitro-6,7-dihydro-5H-imidazo[2,1-b][1,3]oxazin-7-ylmethoxy)phenyl]piperidin-4-yl}-N-(4-trifluoromethylphenyl)amine The title compound was prepared in the same manner as in Example 1 using suitable starting materials.
Pale Yellow Powder
Melting point: 208-209° C.

Example 23

Preparation of 2-nitro-7-{4-[4-(3-trifluoromethylphenoxy)piperidin-1-yl]phenoxymethyl}-6,7-dihydro-5H-imidazo[2,1-b][1,3]oxazine The title compound was prepared in the same manner as in Example 1 using suitable starting materials.
Pale Yellow Powder
Melting point: 189-190° C.

Example 24

Preparation of 7-{4-[4-(3,5-bis-trifluoromethylphenoxy)piperidin-1-yl]phenoxymethyl}-2-nitro-6,7-dihydro-5H-imidazo[2,1-b][1,3]oxazine The title compound was prepared in the same manner as in Example 1 using suitable starting materials.
Pale Yellow Powder
Melting point: 199-200° C.

Example 25

Preparation of 2-nitro-7-(4-{4-[4-(4-trifluoromethoxybenzyl)benzyl]piperazin-1-yl}phenoxymethyl)-6,7-dihydro-5H-imidazo[2,1-b][1,3]oxazine The title compound was prepared in the same manner as in Example 3 using suitable starting materials.
Pale Yellow Powder
Melting point: 213.9-214.0° C.

Example 26

Preparation of 2-nitro-7-{4-[1-(4-trifluoromethoxyphenyl)piperidin-4-yl]phenoxymethyl}-6,7-dihydro-5H-imidazo[2,1-b][1,3]oxazine The title compound was prepared in the same manner as in Example 1 using suitable starting materials.
White Powder
Melting point: 200-201° C.

Example 27

Preparation of 2-nitro-7-{4-[1-(4-trifluoromethylphenyl)piperidin-4-yl]phenoxymethyl}-6,7-dihydro-5H-imidazo[2,1-b][1,3]oxazine The title compound was prepared in the same manner as in Example 1 using suitable starting materials.
White Powder
Melting point: 219-221° C.

Example 28

Preparation of 2-nitro-7-(4-{4-[4-(4-trifluoromethylbenzyl)benzyl]piperazin-1-yl}phenoxymethyl)-6,7-dihydro-5H-imidazo[2,1-b][1,3]oxazine The title compound was prepared in the same manner as in Example 3 using suitable starting materials.
Pale Yellow Powder
Melting point: 213.3-214.4° C.

Example 29

Preparation of 4-[4-(2-nitro-6,7-dihydro-5H-imidazo[2,1-b][1,3]oxazin-7-ylmethoxy)phenyl]piperidine-1-carboxylic acid tert-butyl ester The title compound was prepared in the same manner as in Example 1 using suitable starting materials.
Pale Yellow Powder
Melting point: 182-183° C.

Example 30

Preparation of 2-nitro-7-{4-[4-(4-trifluoromethylbenzyl)piperidin-1-yl]phenoxymethyl}-6,7-dihydro-5H-imidazo[2,1-b][1,3]oxazine The title compound was prepared in the same manner as in Example 1 using suitable starting materials.
White Powder
Melting point: 179-180° C.

Example 31

Preparation of 7-{4-[4-(4-chlorobenzyl)piperidin-1-yl]phenoxymethyl}-2-nitro-6,7-dihydro-5H-imidazo[2,1-b][1,3]oxazine The title compound was prepared in the same manner as in Example 1 using suitable starting materials.
Pale Yellow Powder
Melting point: 175-176° C.

Example 32

Preparation of 7-(4-{4-[4-(4-chlorobenzyl)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Pale Yellow Powder
Melting point: 205.7-206.2° C.

Example 33

Preparation of N-(4-chlorophenyl)-N-ethyl-N-{1-[4-(2-nitro-6,7-dihydro-5H-imidazo[2,1-b][1,3]oxazin-7-ylmethoxy)phenyl]piperidin-4-yl}amine The title compound was prepared in the same manner as in Example 1 using suitable starting materials.
Pale Yellow Powder
Melting point: 195.2° C.

Example 34

Preparation of N-ethyl-N-{1-[4-(2-nitro-6,7-dihydro-5H-imidazo[2,1-b][1,3]oxazin-7-ylmethoxy)phenyl]piperidin-4-yl}-N-(4-trifluoromethylphenyl)amine The title compound was prepared in the same manner as in Example 1 using suitable starting materials.
Pale Yellow Powder
Melting point: 206.2° C.

Example 35

Preparation of N-ethyl-N-{1-[4-(2-nitro-6,7-dihydro-5H-imidazo[2,1-b][1,3]oxazin-7-ylmethoxy)phenyl]piperidin-4-yl}-N-(4-trifluoromethoxyphenyl)amine The title compound was prepared in the same manner as in Example 1 using suitable starting materials.
Pale Yellow Powder
Melting point: 184.8-185.3° C.

Example 36

Preparation of 2-nitro-7-{4-[4-(4'-trifluoromethoxybiphenyl-4-ylmethyl)piperazin-1-yl]phenoxymethyl}-6,7-dihydro-5H-imidazo[2,1-b][1,3]oxazine The title compound was prepared in the same manner as in Example 3 using suitable starting materials.
Pale Yellow Powder
Melting point: 236.0-236.8° C.

Example 37

Preparation of 2-nitro-7-(4-{4-[4-(4-trifluoromethoxybenzyloxy)benzyl]piperazin-1-yl}phenoxymethyl)-6,7-dihydro-5H-imidazo[2,1-b][1,3]oxazine The title compound was prepared in the same manner as in Example 3 using suitable starting materials.
Pale Yellow Powder
Melting point: 196.3-196.8° C.

Example 38

Preparation of 2-nitro-7-(4-{4-[4-(4-trifluoromethylbenzyloxy)benzyl]piperazin-1-yl}phenoxymethyl)-6,7-dihydro-5H-imidazo[2,1-b][1,3]oxazine The title compound was prepared in the same manner as in Example 3 using suitable starting materials.
Pale Yellow Powder
Melting point: 205.2-205.4° C.

Example 39

Preparation of 2-nitro-7-(4-{4-[3-(4-trifluoromethylphenyl)propyl]piperazin-1-yl}phenoxymethyl)-6,7-dihydro-5H-imidazo[2,1-b][1,3]oxazine The title compound was prepared in the same manner as in Example 3 using suitable starting materials.
Pale Yellow Powder
Melting point: 172.5-173.2° C.

Example 40

Preparation of 2-nitro-7-(4-{4-[(E)-3-(4-trifluoromethoxyphenyl)allyl]piperazin-1-yl}phenoxymethyl)-6,7-dihydro-5H-imidazo[2,1-b][1,3]oxazine The title compound was prepared in the same manner as in Example 3 using suitable starting materials.
Pale Yellow Powder
Melting point: 203.6-204.3° C.

Example 41

Preparation of 7-(4-{4-[4-(4-chlorobenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Pale Yellow Powder
Melting point: 231.3-232.2° C.

Example 42

Preparation of 2-nitro-7-(4-{4-[3-(4-trifluoromethylphenyl)propyl]-[1,4]diazepan-1-yl}phenoxymethyl)-6,7-dihydro-5H-imidazo[2,1-b][1,3]oxazine The title compound was prepared in the same manner as in Example 3 using suitable starting materials.
Pale Yellow Powder
Melting point: 157.8-158.0° C.

Example 43

Preparation of 2-nitro-7-(4-{4-[2-(4-trifluoromethoxyphenoxy)ethyl]piperidin-1-yl}phenoxymethyl)-6,7-dihydro-5H-imidazo[2,1-b][1,3]oxazine The title compound was prepared in the same manner as in Example 1 using suitable starting materials.
White Powder
Melting point: 167-168° C.

Example 44

Preparation of 2-nitro-7-(4-{4-[3-(4-trifluoromethoxyphenoxy)propyl]piperidin-1-yl}phenoxymethyl)-6,7-dihydro-5H-imidazo[2,1-b][1,3]oxazine The title compound was prepared in the same manner as in Example 1 using suitable starting materials.
White Powder
Melting point: 180-181° C.

Example 45

Preparation of 4-{4-[4-(2-nitro-6,7-dihydro-5H-imidazo[2,1-b][1,3]oxazin-7-ylmethoxy)phenyl]piperazin-1-ylmethyl}piperidine-1-carboxylic acid tert-butyl ester The title compound was prepared in the same manner as in Example 3 using suitable starting materials.
Pale Yellow Powder
Melting point: 217.5-217.8° C.

Example 46

Preparation of 4-[4-(2-nitro-6,7-dihydro-5H-imidazo[2,1-b][1,3]oxazin-7-ylmethoxy)phenyl]-[1,4]diazepane-1-carboxylic acid tert-butyl ester The title compound was prepared in the same manner as in Example 1 using suitable starting materials.
Pale Yellow Powder
Melting point: 176.7-177.1° C.

Example 47

Preparation of 2-nitro-7-{4-[2-(4-trifluoromethoxyphenyl)oxazol-4-yl]phenoxymethyl}-6,7-dihydro-5H-imidazo[2,1-b][1,3]oxazine The title compound was prepared in the same manner as in Example 1 using suitable starting materials.
Pale Yellow Powder
Melting point: 238-239° C.

Example 48

Preparation of 2-nitro-7-(4-{4-[3-(4-trifluoromethoxyphenyl)propyl]piperidin-1-yl}phenoxymethyl)-6,7-dihydro-5H-imidazo[2,1-b][1,3]oxazine The title compound was prepared in the same manner as in Example 1 using suitable starting materials.
White Powder
Melting point: 172-174° C.

Example 49

Preparation of 1-[4-(2-nitro-6,7-dihydro-5H-imidazo[2,1-b][1,3]oxazin-7-ylmethoxy)phenyl]-4-trifluoromethylpiperidin-4-ol The title compound was prepared in the same manner as in Example 1 using suitable starting materials.
White Powder
Melting point: 209-211° C.

Example 50

Preparation of 2-nitro-7-(4-{4-[1-(4-trifluoromethylbenzyl)piperidin-4-ylmethyl]piperazin-1-yl}phenoxymethyl)-6,7-dihydro-5H-imidazo[2,1-b][1,3]oxazine Trifluoroacetic acid (1.5 ml) was added to a methylene chloride solution (1.5 ml) of 4-{4-[4-(2-nitro-6,7-dihydro-5H-imidazo[2,1-b][1,3]oxazin-7-ylmethoxy)phenyl]piperazin-1-ylmethyl}piperidine-1-carboxylic acid tert-butyl ester (300 mg), and the mixture was stirred at room temperature for 1 hour. The reaction mixture was concentrated under reduced pressure, methylene chloride (1.5 ml) and triethylamine (1.5 ml) were added to the residue, and the result was stirred at room temperature for 5 minutes. After concentrating the reaction mixture under reduced pressure, methanol (3 ml), 4-(trifluoromethyl)benzaldehyde (130 mg), sodium cyanoborohydride (160 mg) and acetic acid (1 ml) were added to the residue in this order, and the mixture was stirred at room temperature overnight. The resulting reaction mixture was added to a potassium carbonate aqueous solution, followed by extraction with methylene chloride. The organic layer was washed with a saturated sodium chloride aqueous solution and dried over sodium sulfate. After filtering, the filtrate was concentrated under reduced pressure, the residue was purified by silica gel column chromatography (methylene chloride:methanol=1:0→methylene chloride:methanol=9:1) and recrystallized from methanol to afford the title compound as a pale yellow powder (50 mg).
Melting point: 214.3-217.2° C.

Example 51

Preparation of 7-(4-{4-[1-(4-chlorobenzyl)piperidin-4-ylmethyl]piperazin-1-yl}phenoxymethyl)-2-nitro-6,7-dihydro-5H-imidazo[2,1-b][1,3]oxazine The title compound was prepared in the same manner as in Example 50 using suitable starting materials.
Pale Yellow Powder
Melting point: 211.1-213.2° C.

Example 52

Preparation of 2-nitro-7-(4-{4-[1-(4-trifluoromethoxybenzyl)piperidin-4-ylmethyl]piperazin-1-yl}phenoxymethyl)-6,7-dihydro-5H-imidazo[2,1-b][1,3]oxazine The title compound was prepared in the same manner as in Example 50 using suitable starting materials.
Pale Yellow Powder
Melting point: 207.6° C.

Example 53

Preparation of 2-nitro-7-{4-[2-(4-trifluoromethoxyphenoxymethyl)oxazol-4-yl]phenoxymethyl}-6,7-dihydro-5H-imidazo[2,1-b][1,3]oxazine The title compound was prepared in the same manner as in Example 1 using suitable starting materials.
Pale Yellow Powder
Melting point: 171-172° C.

Example 54

Preparation of 2-nitro-7-(4-{4-[6-(4-trifluoromethoxyphenoxy)pyridin-3-ylmethyl]piperazin-1-yl}phenoxymethyl)-6,7-dihydro-5H-imidazo[2,1-b][1,3]oxazine The title compound was prepared in the same manner as in Example 3 using suitable starting materials.
Pale Yellow Powder
Melting point: 190.7° C.

Example 55

Preparation of 2-nitro-7-{4-[2-(4-trifluoromethoxyphenoxymethyl)thiazol-4-yl]phenoxymethyl}-6,7-dihydro-5H-imidazo[2,1-b][1,3]oxazine The title compound was prepared in the same manner as in Example 1 using suitable starting materials.
Pale Yellow Powder
Melting point: 219-220° C.

Example 56

Preparation of 2-nitro-7-{4-[2-(4-trifluoromethoxyphenyl)thiazol-4-yl]phenoxymethyl}-6,7-dihydro-5H-imidazo[2,1-b][1,3]oxazine The title compound was prepared in the same manner as in Example 1 using suitable starting materials.
Slightly Yellow Powder
Melting point: 235-236° C.

Example 57

Preparation of 2-nitro-7-(4-{4-[2-(5-trifluoromethylpyridin-2-yloxy)ethyl]piperidin-1-yl}phenoxymethyl)-6,7-dihydro-5H-imidazo[2,1-b][1,3]oxazine The title compound was prepared in the same manner as in Example 1 using suitable starting materials.
White Powder
Melting point: 156-158° C.

Example 58

Preparation of 2-nitro-7-{4-[4-(5-trifluoromethylpyridin-2-yloxymethyl)piperidin-1-yl]phenoxymethyl}-6,7-dihydro-5H-imidazo[2,1-b][1,3]oxazine The title compound was prepared in the same manner as in Example 1 using suitable starting materials.
Pale Yellow Powder
Melting point: 206-207° C.

Example 59

Preparation of 7-[4-(4-methoxy-4-trifluoromethylpiperidin-1-yl)phenoxymethyl]-2-nitro-6,7-dihydro-5H-imidazo[2,1-b][1,3]oxazine The title compound was prepared in the same manner as in Example 1 using suitable starting materials.
White Powder
Melting point: 167-168° C.

Example 60

Preparation of 2-nitro-7-{4-[4-(4-trifluoromethoxyphenyl)oxazol-2-ylmethyl]phenoxymethyl}-6,7-dihydro-5H-imidazo[2,1-b][1,3]oxazine The title compound was prepared in the same manner as in Example 1 using suitable starting materials.
Pale Yellow Powder
Melting point: 87-89° C.

Example 61

Preparation of 2-nitro-7-{4-[4-(5-trifluoromethylpyridin-2-yloxy)piperidin-1-yl]phenoxymethyl}-6,7-dihydro-5H-imidazo[2,1-b][1,3]oxazine The title compound was prepared in the same manner as in Example 1 using suitable starting materials.
White Powder
Melting point: 186-187° C.

Example 62

Preparation of 2-nitro-7-(4-{4-[6-(4-trifluoromethylphenoxy)pyridin-3-ylmethyl]piperazin-1-yl}phenoxymethyl)-6,7-dihydro-5H-imidazo[2,1-b][1,3]oxazine The title compound was prepared in the same manner as in Example 3 using suitable starting materials.
White Powder
Melting point: 197.5-197.9° C.

Example 63

Preparation of 7-(4-{4-[6-(4-chlorophenoxy)pyridin-3-ylmethyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
White Powder
Melting point: 199.1-200.6° C.

Example 64

Preparation of 2-nitro-7-[4-(4-{3-[4-(4-trifluoromethoxyphenoxy)phenyl]propyl}piperazin-1-yl)phenoxymethyl]-6,7-dihydro-5H-imidazo[2,1-b][1,3]oxazine The title compound was prepared in the same manner as in Example 3 using suitable starting materials.
Pale Yellow Powder
Melting point: 140.6-142.4° C.

Example 65

Preparation of 2-nitro-7-(6-{4-[4-(4-trifluoromethoxyphenoxy)benzyl]piperazin-1-yl}pyridin-3-yloxymethyl)-6,7-dihydro-5H-imidazo[2,1-b][1,3]oxazine The title compound was prepared in the same manner as in Example 3 using suitable starting materials.
White Powder
Melting point: 167.0-167.1° C.

Example 66

Preparation of 2-nitro-7-(6-{4-[6-(4-trifluoromethoxyphenoxy)pyridin-3-ylmethyl]piperazin-1-yl}pyridin-3-yloxymethyl)-6,7-dihydro-5H-imidazo[2,1-b][1,3]oxazine The title compound was prepared in the same manner as in Example 3 using suitable starting materials.
White Powder
Melting point: 186.0-186.1° C.

Example 67

Preparation of 2-nitro-7-(4-{4-[2-(4-trifluoromethylbenzyloxy)ethyl]piperazin-1-yl}phenoxymethyl)-6,7-dihydro-5H-imidazo[2,1-b][1,3]oxazine The title compound was prepared in the same manner as in Example 3 using suitable starting materials.
Pale Yellow Powder
Melting point: 156.0-158.2° C.

Example 68

Preparation of 4-[5-(2-nitro-6,7-dihydro-5H-imidazo[2,1-b][1,3]oxazin-7-ylmethoxy)pyridin-2-yl]piperazine-1-carboxylic acid tert-butyl ester The title compound was prepared in the same manner as in Example 1 using suitable starting materials.
Pale Yellow Powder
Melting point: 205.4-205.7° C.

Example 69

Preparation of 2-nitro-7-{4-[2-(4-trifluoromethoxybenzyl)thiazol-4-yl]phenoxymethyl}-6,7-dihydro-5H-imidazo[2,1-b][1,3]oxazine Sodium tert-butoxide (62 mg) was added to a dimethyl formaldehyde solution (5 ml) of 4-(2-chloro-4-nitroimidazol-1-yl)-1-{4-[2-(4-trifluoromethoxybenzyl)thiazol-4-yl]phenoxy}butan-2-ol (334 mg), and the mixture was stirred at room temperature. While confirming the progress of the reaction, sodium tert-butoxide (62 mg) was added 3 times, and the resulting mixture was stirred overnight. A saturated ammonium chloride aqueous solution was added to the reaction mixture, and the precipitated solid was sequentially washed with water and diisopropyl ether. The residue was purified by silica gel column chromatography (ethyl acetate:n-hexane=1:1→ethyl acetate) to afford the title compound as a pale brown powder (69 mg).
Melting point: 222-224° C.

Example 70

Preparation of 2-nitro-7-{6-[4-(4-trifluoromethoxyphenoxy)piperidin-1-yl]pyridin-3-yloxymethyl}-6,7-dihydro-5H-imidazo[2,1-b][1,3]oxazine The title compound was prepared in the same manner as in Example 69 using suitable starting materials.
White Powder
Melting point: 181-182° C.

Example 71

Preparation of 2-nitro-7-(4-{4-[3-(5-trifluoromethylpyridin-2-yl)propyl]piperazin-1-yl}phenoxymethyl)-6,7-dihydro-5H-imidazo[2,1-b][1,3]oxazine The title compound was prepared in the same manner as in Example 3 using suitable starting materials.
Pale Yellow Powder
Melting point: 173.3-173.4° C.

Example 72

Preparation of 2-nitro-7-{6-[4-(4-trifluoromethoxybenzyl)piperidin-1-yl]pyridin-3-yloxymethyl}-6,7-dihydro-5H-imidazo[2,1-b][1,3]oxazine The title compound was prepared in the same manner as in Example 69 using suitable starting materials.
Pale Yellow Powder
Melting point: 184-185° C.

Example 73

Preparation of 2-nitro-7-(6-{4-[3-(5-trifluoromethylpyridin-2-yl)propyl]piperazin-1-yl}pyridin-3-yloxymethyl)-6,7-dihydro-5H-imidazo[2,1-b][1,3]oxazine The title compound was prepared in the same manner as in Example 3 using suitable starting materials.
Pale Yellow Powder
Melting point: 164.2-164.7° C.

Example 74

Preparation of 2-nitro-7-(4-{4-[3-(5-trifluoromethylpyridin-2-yl)propyl]-[1,4]diazepan-1-yl}phenoxymethyl)-6,7-dihydro-5H-imidazo[2,1-b][1,3]oxazine The title compound was prepared in the same manner as in Example 3 using suitable starting materials.
Pale Yellow Powder
Melting point: 177.4° C.

Example 75

Preparation of 7-(4-{4-[5-(1-methyl-5-trifluoromethyl-1H-pyrazol-3-yl)thiophen-2-ylmethyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Pale Yellow Powder
Melting point: 204.6° C.

Example 76

Preparation of 2-nitro-7-{6-[4-(4-trifluoromethoxyphenoxymethyl)piperidin-1-yl]pyridin-3-yloxymethyl}-6,7-dihydro-5H-imidazo[2,1-b][1,3]oxazine The title compound was prepared in the same manner as in Example 69 using suitable starting materials.
White Powder
Melting point: 181-182° C.

Example 77

Preparation of 7-{4-[4-(4-benzyloxybenzyl)piperazin-1-yl]phenoxymethyl}-2-nitro-6,7-dihydro-5H-imidazo[2,1-b][1,3]oxazine The title compound was prepared in the same manner as in Example 3 using suitable starting materials.
Pale Yellow Powder
Melting point: 219.5-220.5° C.

Example 78

Preparation of 2-nitro-7-(4-{4-[2-(4-trifluoromethylphenoxy)ethyl]piperazin-1-yl}phenoxymethyl)-6,7-dihydro-5H-imidazo[2,1-b][1,3]oxazine The title compound was prepared in the same manner as in Example 3 using suitable starting materials.
Pale Yellow Powder
Melting point: 166.5-168.8° C.

Example 79

Preparation of 2-nitro-7-(6-{4-[2-(4-trifluoromethoxyphenoxy)ethyl]piperidin-1-yl}pyridin-3-yloxymethyl)-6,7-dihydro-5H-imidazo[2,1-b][1,3]oxazine The title compound was prepared in the same manner as in Example 69 using suitable starting materials.
White Powder
Melting point: 140-141° C.

Example 80

Preparation of 2-nitro-7-[4-(4-propoxy-4-trifluoromethylpiperidin-1-yl)phenoxymethyl]-6,7-dihydro-5H-imidazo[2,1-b][1,3]oxazine The title compound was prepared in the same manner as in Example 1 using suitable starting materials.
Pale Yellow Powder
Melting point: 157-158° C.

Example 81

Preparation of 4-[4-((S)-2-nitro-6,7-dihydro-5H-imidazo[2,1-b][1,3]oxazin-7-ylmethoxy)phenyl]piperazine-1-carboxylic acid tert-butyl ester An ethanol solution (25.00 ml) of 20% sodium ethoxide was added to an ethanol solution (250 ml) of toluene-4-sulfonic acid (S)-4-(2-chloro-4-nitro-imidazol-1-yl)-2-hydroxybutyl ester (25.00 g), and the mixture was stirred at room temperature for 30 minutes. 4-(4-Hydroxyphenyl)piperazine-1-carboxylic acid tert-butyl ester (19.63 g) and tripotassium phosphate (13.61 g) were added to the reaction mixture, followed by heating under reflux for 4 hours. The reaction mixture was then concentrated under reduced pressure, and water was added to the residue, followed by extraction with methylene chloride. The organic layer was washed with a saturated sodium chloride aqueous solution and dried over sodium sulfate. After filtering, the filtrate was concentrated under reduced pressure. The residue was purified by silica gel column chromatography (methylene chloride:ethyl acetate=1:0→methylene chloride:ethyl acetate=0:1) and concentrated under reduced pressure. Sodium hydride (3.08 g) was added to a dimethylformamide solution (269 ml) of residue and the mixture was stirred at room temperature for 1 hour. Water was added to the reaction mixture, followed by extraction with methylene chloride. The organic layer was dried over magnesium sulfate. After filtering, the filtrate was concentrated under reduced pressure. The residue was purified by silica gel column chromatography (methylene chloride:ethyl acetate=1:0→methylene chloride:ethyl acetate=0:1) to afford the title compound as a yellow powder (16.57 g).
Melting point: 201.0-202.7° C.

Example 82

Preparation of (S)-2-nitro-7-(4-{4-[2-(4-trifluoromethoxyphenyl)ethyl]piperidin-1-yl}phenoxymethyl)-6,7-dihydro-5H-imidazo[2,1-b][1,3]oxazine The title compound was prepared in the same manner as in Example 69 using suitable starting materials.
Pale Yellow Powder
Melting point: 201-202° C.

Example 83

Preparation of N-methyl-N-{1-[4-((S)-2-nitro-6,7-dihydro-5H-imidazo[2,1-b][1,3]oxazin-7-ylmethoxy)phenyl]piperidin-4-yl}-N-(4-trifluoromethoxyphenyl)amine The title compound was prepared in the same manner as in Example 69 using suitable starting materials.
Pale Yellow Powder
Melting point: 186-187° C.

Example 84

Preparation of 7-{4-[4-(3-chloro-5-trifluoromethylpyridin-2-yloxy)piperidin-1-yl]phenoxymethyl}-2-nitro-6,7-dihydro-5H-imidazo[2,1-b][1,3]oxazine The title compound was prepared in the same manner as in Example 1 using suitable starting materials.
Pale Yellow Powder
Melting point: 185-186° C.

Example 85

Preparation of 7-(4-{4-[5-(2-methyl-5-trifluoromethyl-2H-pyrazol-3-yl)thiophen-2-ylmethyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Pale Yellow Powder (acetone-methanol)
Melting point: 180.3-180.8° C.

Example 86

Preparation of 4-[4-((R)-2-nitro-6,7-dihydro-5H-imidazo[2,1-b][1,3]oxazin-7-ylmethoxy)phenyl]piperazine-1-carboxylic acid tert-butyl ester An ethanol solution (3.02 ml) of 20% sodium ethoxide was added to an ethanol solution (30 ml) of toluene-4-sulfonic acid (R)-4-(2-chloro-4-nitroimidazol-1-yl)-2-hydroxybutyl ester (3.00 g), and the mixture was stirred at room temperature for 30 minutes. 4-(4-Hydroxyphenyl)piperazine-1-carboxylic acid tert-butyl ester (2.36 g) and tripotassium phosphate (1.80 g) were added to the reaction mixture and heated under reflux for 4 hours. Water was added to the reaction mixture, followed by extraction with methylene chloride. The organic layer was washed with water and dried over sodium sulfate. After filtering, the filtrate was concentrated under reduced pressure. The residue thus obtained was dissolved in dimethylformamide (46 ml), sodium hydride (0.31 g) was added thereto, and the resulting mixture was stirred at room temperature for 30 minutes. Water was added to the reaction mixture, followed by extraction with methylene chloride. The organic layer was dried over magnesium sulfate. After filtering, the filtrate was concentrated under reduced pressure. The residue was purified by silica gel column chromatography (methylene chloride:ethyl acetate=1:0→methylene chloride:ethyl acetate=0:1) and recrystallized from acetone to afford the title compound as a yellow powder (0.72 g).
Melting point: 206.7-208.0° C.

Example 87

Preparation of (S)-2-nitro-7-(4-{4-[4-(4-trifluoromethoxyphenoxy)benzyl]piperazin-1-yl}phenoxymethyl)-6,7-dihydro-5H-imidazo[2,1-b][1,3]oxazine The title compound was prepared in the same manner as in Example 3 using suitable starting materials.
Pale Yellow Powder
Melting point: 161.2-163.8° C.

Example 88

Preparation of (R)-2-nitro-7-(4-{4-[4-(4-trifluoromethoxyphenoxy)benzyl]piperazin-1-yl}phenoxymethyl)-6,7-dihydro-5H-imidazo[2,1-b][1,3]oxazine The title compound was prepared in the same manner as in Example 3 using suitable starting materials.
Pale Yellow Powder
Melting point: 162.6-163.2° C.

Example 89

Preparation of (R)-2-nitro-7-(4-{4-[2-(4-trifluoromethoxyphenyl)ethyl]piperidin-1-yl}phenoxymethyl)-6,7-dihydro-5H-imidazo[2,1-b][1,3]oxazine The title compound was prepared in the same manner as in Example 69 using suitable starting materials.
Pale Yellow Needle
Melting point: 201-202° C.

Example 90

Preparation of N-methyl-N-{1-[4-((R)-2-nitro-6,7-dihydro-5H-imidazo[2,1-b][1,3]oxazin-7-ylmethoxy)phenyl]piperidin-4-yl}-N-(4-trifluoromethoxyphenyl)amine The title compound was prepared in the same manner as in Example 69 using suitable starting materials.
Yellow Needle
Melting point: 186-187° C.

Example 91

Preparation of 2-nitro-7-{6-[4-(4-chlorophenoxy)piperidin-1-yl]pyridin-3-yloxymethyl}-6,7-dihydro-5H-imidazo[2,1-b][1,3]oxazine The title compound was prepared in the same manner as in Example 69 using suitable starting materials.
White Powder
Melting point: 171-172° C.

Example 92

Preparation of 2-nitro-7-{4-[1-(4-trifluoromethoxyphenyl)piperidin-4-ylmethyl]phenoxymethyl}-6,7-dihydro-5H-imidazo[2,1-b][1,3]oxazine The title compound was prepared in the same manner as in Example 1 using suitable starting materials.
White Powder
Melting point: 193-194° C.

Example 93

Preparation of 7-{4-[4-(5-chlorothiophen-2-ylmethyl)piperazin-1-yl]phenoxymethyl}-2-nitro-6,7-dihydro-5H-imidazo[2,1-b][1,3]oxazine The title compound was prepared in the same manner as in Example 3 using suitable starting materials.
Pale Yellow Powder
Melting point: 182.5-183.3° C.

Example 94

Preparation of 2-nitro-7-{6-[4-(4-trifluoromethoxybenzyloxy)piperidin-1-yl]pyridin-3-yloxymethyl}-6,7-dihydro-5H-imidazo[2,1-b][1,3]oxazine The title compound was prepared in the same manner as in Example 69 using suitable starting materials.
Pale Yellow Powder
Melting point: 168-169° C.

Example 95

Preparation of 2-nitro-7-{6-[4-(4-trifluoromethylphenoxy)piperidin-1-yl]pyridin-3-yloxymethyl}-6,7-dihydro-5H-imidazo[2,1-b][1,3]oxazine The title compound was prepared in the same manner as in Example 69 using suitable starting materials.
Pale Yellow Powder
Melting point: 199-200° C.

Example 96

Preparation of 2-nitro-7-{4-[1-(4-trifluoromethylphenyl)piperidin-4-ylmethyl]phenoxymethyl}-6,7-dihydro-5H-imidazo[2,1-b][1,3]oxazine The title compound was prepared in the same manner as in Example 1 using suitable starting materials.
Pale Yellow Powder
Melting point: 186-188° C.

Example 97

Preparation of 7-{4-[4-(2,2-difluorobenzo[1,3]dioxol-5-ylmethyl)piperazin-1-yl]phenoxymethyl}-2-nitro-6,7-dihydro-5H-imidazo[2,1-b][1,3]oxazine The title compound was prepared in the same manner as in Example 3 using suitable starting materials.
Pale Yellow Powder
Melting point: 195.8-196.5° C.

Example 98

Preparation of 2-nitro-7-{4-[1-(4-trifluoromethoxybenzyl)piperidin-4-ylmethyl]phenoxymethyl}-6,7-dihydro-5H-imidazo[2,1-b][1,3]oxazine The title compound was prepared in the same manner as in Example 3 using suitable starting materials.
White Powder
Melting point: 185-186° C.

Example 99

Preparation of 2-nitro-7-{4-[4-(4-trifluoromethyl-benzyl)piperazin-1-yl]phenoxymethyl}-6,7-dihydro-5H-imidazo[2,1-b][1,3]oxazine The title compound was prepared in the same manner as in Example 3 using suitable starting materials.
Pale Yellow Powder
Melting point: 170.7-171.0° C.

Example 100

Preparation of 7-{4-[4-(4-chlorobenzyl)piperazin-1-yl]phenoxymethyl}-2-nitro-6,7-dihydro-5H-imidazo[2,1-b][1,3]oxazine The title compound was prepared in the same manner as in Example 3 using suitable starting materials.
Yellow Powder
Melting point: 188.8-189.5° C.

Example 101

Preparation of 2-nitro-7-{4-[1-(4-trifluoromethyl-benzyl)piperidin-4-ylmethyl]phenoxymethyl}-6,7-dihydro-5H-imidazo[2,1-b][1,3]oxazine The title compound was prepared in the same manner as in Example 3 using suitable starting materials.
White Powder
Melting point: 180-181° C.

Example 102

Preparation of 2-nitro-7-(4-{1-[4-(4-trifluoromethoxyphenoxy)benzyl]piperidin-4-ylmethyl}phenoxymethyl)-6,7-dihydro-5H-imidazo[2,1-b][1,3]oxazine The title compound was prepared in the same manner as in Example 3 using suitable starting materials.
White Powder
Melting point: 197-198° C.

Example 103

Preparation of 7-{4-[1-(4-chlorobenzyl)piperidin-4-ylmethyl]phenoxymethyl}-2-nitro-6,7-dihydro-5H-imidazo[2,1-b][1,3]oxazine The title compound was prepared in the same manner as in Example 3 using suitable starting materials.
White Powder
Melting point: 194-195° C.

Example 104

Preparation of 2-nitro-7-(6-{4-[3-(4-trifluoromethoxyphenyl)propyl]piperidin-1-yl}pyridin-3-yloxymethyl)-6,7-dihydro-5H-imidazo[2,1-b][1,3]oxazine The title compound was prepared in the same manner as in Example 69 using suitable starting materials.
Pale Yellow Powder
Melting point: 162-163° C.

Example 105

Preparation of 7-{4-[4-(4-methylsulfanylbenzyl)piperazin-1-yl]phenoxymethyl}-2-nitro-6,7-dihydro-5H-imidazo[2,1-b][1,3]oxazine The title compound was prepared in the same manner as in Example 3 using suitable starting materials.
Pale Yellow Powder
Melting point: 191.1-191.5° C.

Example 106

Preparation of 2-nitro-7-{4-[4-(5-trifluoromethyl-benzofuran-2-ylmethyl)piperazin-1-yl]phenoxymethyl}-6,7-dihydro-5H-imidazo[2,1-b][1,3]oxazine The title compound was prepared in the same manner as in Example 3 using suitable starting materials.
Pale Yellow Powder
Melting point: 181.0-181.6° C.

Example 107

Preparation of 2-nitro-7-(4-{4-[3-(4-trifluoromethoxyphenyl)propyl]piperazin-1-yl}phenoxymethyl)-6,7-dihydro-5H-imidazo[2,1-b][1,3]oxazine The title compound was prepared in the same manner as in Example 3 using suitable starting materials.
Yellow Powder
Melting point: 168.5-168.8° C.

Example 108

Preparation of 2-nitro-7-[6-(4-trifluoromethoxybenzyloxymethyl)pyridin-3-yloxymethyl]-6,7-dihydro-5H-imidazo[2,1-b][1,3]oxazine The title compound was prepared in the same manner as in Example 1 using suitable starting materials.
Pale Yellow Powder
Melting point: 105-106° C.

Example 109

Preparation of 2-nitro-7-(4-{4-[2-(4-trifluoromethylphenyl)ethyl]piperidin-1-yl}phenoxymethyl)-6,7-dihydro-5H-imidazo[2,1-b][1,3]oxazine The title compound was prepared in the same manner as in Example 1 using suitable starting materials.
Pale Yellow Powder
Melting point: 210-211° C.

Example 110

Preparation of 2-nitro-7-(4-{4-[2-(4-trifluoromethylphenoxy)ethyl]piperidin-1-yl}phenoxymethyl)-6,7-dihydro-5H-imidazo[2,1-b][1,3]oxazine The title compound was prepared in the same manner as in Example 69 using suitable starting materials.
Pale Yellow Powder
Melting point: 171-172° C.

Example 111

Preparation of 7-(4-{4-[2-(4-chlorophenoxy)ethyl]piperidin-1-yl}phenoxymethyl)-2-nitro-6,7-dihydro-5H-imidazo[2,1-b][1,3]oxazine The title compound was prepared in the same manner as in Example 69 using suitable starting materials.
Pale Yellow Powder
Melting point: 174-175° C.

Example 112

Preparation of 2-{4-[4-(2-nitro-6,7-dihydro-5H-imidazo[2,1-b][1,3]oxazin-7-ylmethoxy)phenyl]piperazin-1-yl}-1-(4-trifluoromethylphenyl)ethanol 1) Trifluoroacetic acid (1.5 ml) and methylene chloride (1.5 ml) were added to 4-[4-(2-nitro-6,7-dihydro-5H-imidazo[2,1-b][1,3]oxazin-7-ylmethoxy)phenyl]piperazine-1-carboxylic acid tert-butyl ester (300 mg), and the mixture was stirred at room temperature for 3 hours. The reaction mixture was concentrated under reduced pressure. Methylene chloride (1.5 ml) and triethylamine (1.5 ml) were added to the residue, and the mixture was stirred at room temperature for 5 minutes. The reaction mixture was reconcentrated under reduced pressure.

2) 2,2,6,6-Tetramethyl-1-piperidinyloxy radical (TEMPO) (13 mg) and trichloroisocyanuric acid (1.93 g) were added to a methylene chloride solution (15 ml) of 4-trifluoromethyl phenethyl alcohol (1.5 g) under ice cooling and the mixture was stirred at the same temperature for 1 hour. After removing insoluble matter by filtration, the filtrate was washed with water, dried over magnesium sulfate, and then concentrated under reduced pressure. The residue was purified by silica gel column chromatography (hexane:ethyl acetate=1:0-1; 1) and then concentrated under reduced pressure.

3) The residues obtained in Step 1) and Step 2) above were dissolved in 1,2-dichloroethane (5 ml). Sodium triacetoxyborohydride (0.39 g) was added thereto, and the mixture was stirred at room temperature overnight. After adding methylene chloride, the reaction mixture was washed with a potassium carbonate aqueous solution and water, dried over sodium sulfate, and then concentrated under reduced pressure. The residue was purified by silica gel column chromatography (ethyl acetate:methanol=1:0→9; 1) and concentrated under reduced pressure. The residue was recrystallized from methanol to afford the title compound as a pale yellow powder (69 mg).
Melting point: 223.8-225.3° C.

Example 113

Preparation of 2-nitro-7-(4-{4-[4-(4-trifluoromethylphenoxy)benzyl]piperazin-1-yl}phenoxymethyl)-6,7-dihydro-5H-imidazo[2,1-b][1,3]oxazine The title compound was prepared in the same manner as in Example 3 using suitable starting materials.
Pale Yellow Powder
Melting point: 149.9-151.9° C.

Example 114

Preparation of 7-(4-{4-[4-(4-chlorophenoxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Pale Yellow Powder
Melting point: 134.7° C.

Example 115

Preparation of 2-nitro-7-(4-{4-[4-(4-trifluoromethoxyphenyl)butyl]piperazin-1-yl}phenoxymethyl)-6,7-dihydro-5H-imidazo[2,1-b][1,3]oxazine The title compound was prepared in the same manner as in Example 3 using suitable starting materials.
Yellow Powder
Melting point: 186.3-186.5° C.

Example 116

Preparation of 7-{2-chloro-4-[4-(4-trifluoromethoxyphenoxy)piperidin-1-yl]phenoxymethyl}-2-nitro-6,7-dihydro-5H-imidazo[2,1-b][1,3]oxazine The title compound was prepared in the same manner as in Example 1 using suitable starting materials.
Pale Yellow Powder
Melting point: 108-110° C.

Example 117

Preparation of 7-(4-{4-[2-(4-chlorophenyl)ethyl]piperidin-1-yl}phenoxymethyl)-2-nitro-6,7-dihydro-5H-imidazo[2,1-b][1,3]oxazine The title compound was prepared in the same manner as in Example 1 using suitable starting materials.
Pale Yellow Powder
Melting point: 212-214° C.

Example 118

Preparation of 2-nitro-7-(4-{4-[3-(4-trifluoromethylphenyl)propyl]piperidin-1-yl}phenoxymethyl)-6,7-dihydro-5H-imidazo[2,1-b][1,3]oxazine The title compound was prepared in the same manner as in Example 69 using suitable starting materials.
Pale Yellow Powder
Melting point: 180-181° C.

Example 119

Preparation of 2-nitro-7-(4-{4-[3-(4-trifluoromethylphenoxy)propyl]piperidin-1-yl}phenoxymethyl)-6,7-dihydro-5H-imidazo[2,1-b][1,3]oxazine The title compound was prepared in the same manner as in Example 69 using suitable starting materials.
Pale Yellow Powder
Melting point: 184-185° C.

Example 120

Preparation of 7-{4-[4-(5-chlorobenzofuran-2-ylmethyl)piperidin-1-yl]phenoxymethyl}-2-nitro-6,7-dihydro-5H-imidazo[2,1-b][1,3]oxazine The title compound was prepared in the same manner as in Example 69 using suitable starting materials.
White Powder
Melting point: 157-158° C.

Example 121

Preparation of 7-{4-[4-(5-chlorobenzofuran-2-yl-methoxy)piperidin-1-yl]phenoxymethyl}-2-nitro-6,7-dihydro-5H-imidazo[2,1-b][1,3]oxazine The title compound was prepared in the same manner as in Example 69 using suitable starting materials.
Pale Yellow Powder
Melting point: 198-200° C.

Example 122

Preparation of 7-{4-[4-(4-fluoro-naphthalen-1-ylmethyl)piperazin-1-yl]phenoxymethyl}-2-nitro-6,7-dihydro-5H-imidazo[2,1-b][1,3]oxazine The title compound was prepared in the same manner as in Example 3 using suitable starting materials.
Pale Yellow Powder
Melting point: 182.9-184.4° C.

Example 123

Preparation of 2-nitro-7-(4-{4-[2-(4-trifluoromethylphenyl)ethyl]piperazin-1-yl}phenoxymethyl)-6,7-dihydro-5H-imidazo[2,1-b][1,3]oxazine Toluene-4-sulfonic acid 4-(2-chloro-4-nitroimidazol-1-yl)-2-hydroxybutyl ester (1.12 g) was suspended in an ethanol (14 ml). An ethanol solution (1.13 ml) of 20% sodium ethoxide was added to the suspension, and the mixture was stirred at room temperature for 30 minutes. 4-{4-[2-(4-Trifluoromethylphenyl)ethyl]piperazin-1-yl}phenol (0.72 g) and tripotassium phosphate (0.61 g) were added to the reaction mixture and heated for 4 hours under reflux. After the reaction mixture was cooled to room temperature, water was added thereto, followed by extraction with methylene chloride. The organic layer was washed with water, dried over sodium sulfate, and concentrated under reduced pressure. The residue was purified by silica gel column chromatography (hexane:ethyl acetate=1:0→hexane:ethyl acetate=0:1) and recrystallized from methanol to afford the title compound as a pale yellow powder (0.72 g).
Melting point: 213.6-213.7° C.

Example 124

Preparation of 7-(4-{4-[3-(4-chlorophenoxy)propyl]piperidin-1-yl}phenoxymethyl)-2-nitro-6,7-dihydro-5H-imidazo[2,1-b][1,3]oxazine The title compound was prepared in the same manner as in Example 69 using suitable starting materials.
White Powder
Melting point: 196-198° C.

Example 125

Preparation of 2-nitro-7-{4-[3-(4-trifluoromethoxyphenoxy)-8-azabicyclo[3.2.1]oct-8-yl]phenoxymethyl}-6,7-dihydro-5H-imidazo[2,1-b][1,3]oxazine The title compound was prepared in the same manner as in Example 123 using suitable starting materials.
Pale Brown Powder
Melting point: 220.5-222.6° C.

Example 126

Preparation of 2-nitro-7-(4-{4-[4-(4-trifluoromethoxybenzyloxy)benzyl]piperidin-1-yl}phenoxymethyl)-6,7-dihydro-5H-imidazo[2,1-b][1,3]oxazine The title compound was prepared in the same manner as in Example 123 using suitable starting materials.
Yellow Powder
Melting point: 214.6° C.

Example 127

Preparation of 2-nitro-7-{4-[4-(5-trifluoromethyl-benzofuran-2-ylmethyl)piperidin-1-yl]phenoxymethyl}-6,7-dihydro-5H-imidazo[2,1-b][1,3]oxazine The title compound was prepared in the same manner as in Example 69 using suitable starting materials.
White Powder
Melting point: 171-172° C.

Example 128

Preparation of 7-(4-{4-[3-(4-chlorophenyl)propyl]piperidin-1-yl}phenoxymethyl)-2-nitro-6,7-dihydro-5H-imidazo[2,1-b][1,3]oxazine The title compound was prepared in the same manner as in Example 69 using suitable starting materials.
Pale Yellow Powder
Melting point: 170-171° C.

Example 129

Preparation of 2-nitro-7-(4-{4-[2-(4-trifluoromethoxyphenyl)ethyl]piperazin-1-yl}phenoxymethyl)-6,7-dihydro-5H-imidazo[2,1-b][1,3]oxazine The title compound was prepared in the same manner as in Example 123 using suitable starting materials.
White Powder
Melting point: 206.0-206.1° C.

Example 130

Preparation of (R)-2-nitro-7-(4-{4-[4-(4-trifluoromethoxybenzyloxy)benzyl]piperidin-1-yl}phenoxymethyl)-6,7-dihydro-5H-imidazo[2,1-b][1,3]oxazine The title compound was prepared in the same manner as in Example 123 using suitable starting materials.
Pale Yellow Powder
Melting point: 209.5-210.4° C.

Example 131

Preparation of (R)-2-nitro-7-(4-{4-[4-(4-trifluoromethoxybenzyloxy)benzyl]piperazin-1-yl}phenoxymethyl)-6,7-dihydro-5H-imidazo[2,1-b][1,3]oxazine The title compound was prepared in the same manner as in Example 3 using suitable starting materials.
White Powder
Melting point: 194.0-194.4° C.

Example 132

Preparation of 2-nitro-7-{4-[4-(5-trifluoromethoxy-benzofuran-2-ylmethyl)piperidin-1-yl]phenoxymethyl}-6,7-dihydro-5H-imidazo[2,1-b][1,3]oxazine Sodium tert-butoxide (81 mg) was added to an N-methylpyrrolidone solution (5 ml) of 4-(2-chloro-4-nitroimidazol-1-yl)-1-{4-[4-(5-trifluoromethoxybenzofuran-2-ylmethyl)piperidin-1-yl]phenoxy}butan-2-ol (469 mg), and the mixture was stirred at room temperature for 1 hour. A saturated ammonium chloride aqueous solution was added to the reaction mixture, and precipitated solid was sequentially washed with water and diisopropyl ether. The crude product formed was purified by silica gel column chromatography (ethyl acetate:n-hexane=1:1→3:1) to afford the title compound as a white powder (181 mg).
Melting point: 142-143° C.

Example 133

Preparation of (R)-2-nitro-7-(4-{4-[4-(4-trifluoromethylbenzyloxy)benzyl]piperidin-1-yl}phenoxymethyl)-6,7-dihydro-5H-imidazo[2,1-b][1,3]oxazine The title compound was prepared in the same manner as in Example 123 using suitable starting materials.
Pale Yellow Powder
Melting point: 217.0-220.3° C.

Example 134

Preparation of 2-nitro-7-(4-{4-[4-(4-trifluoromethylbenzyloxy)benzyl]piperidin-1-yl}phenoxymethyl)-6,7-dihydro-5H-imidazo[2,1-b][1,3]oxazine The title compound was prepared in the same manner as in Example 123 using suitable starting materials.
Pale Yellow Powder
Melting point: 217.2-217.3° C.

Example 135

Preparation of 7-{4-[4-(5-chlorobenzofuran-2-ylmethoxymethyl)piperidin-1-yl]phenoxymethyl}-2-nitro-6,7-dihydro-5H-imidazo[2,1-b][1,3]oxazine The title compound was prepared in the same manner as in Example 132 using suitable starting materials.
Pale Yellow Powder
Melting point: 130-132° C.

Example 136

Preparation of 7-{4-[4-(4'-fluoro-3'-trifluoromethylbiphenyl-4-ylmethyl)piperazin-1-yl]phenoxymethyl}-2-nitro-6,7-dihydro-5H-imidazo[2,1-b][1,3]oxazine The title compound was prepared in the same manner as in Example 3 using suitable starting materials.
Yellow Powder
Melting point: 187.4-187.7° C.

Example 137

Preparation of 7-{4-[4-(4'-fluorobiphenyl-4-ylmethyl)piperazin-1-yl]phenoxymethyl}-2-nitro-6,7-dihydro-5H-imidazo[2,1-b][1,3]oxazine The title compound was prepared in the same manner as in Example 3 using suitable starting materials.
Pale Yellow Powder
Melting point: 232.4-233.0° C.

Example 138

Preparation of 7-{4-[4-(4'-methylsulfanylbiphenyl-4-ylmethyl)piperazin-1-yl]phenoxymethyl}-2-nitro-6,7-dihydro-5H-imidazo[2,1-b][1,3]oxazine The title compound was prepared in the same manner as in Example 3 using suitable starting materials.
Pale Brown Powder
Melting point: 258.2-259.1° C.

Example 139

Preparation of 2-nitro-7-(4-{4-[4-(5-trifluoromethylpyridin-2-yl)benzyl]piperazin-1-yl}phenoxymethyl)-6,7-dihydro-5H-imidazo[2,1-b][1,3]oxazine The title compound was prepared in the same manner as in Example 3 using suitable starting materials.
Pale Yellow Powder
Melting point: 243.0-243.9° C.

Example 140

Preparation of 7-{4-[4-(3-fluoro-4'-trifluoromethoxybiphenyl-4-ylmethyl)piperazin-1-yl]phenoxymethyl}-2-nitro-6,7-dihydro-5H-imidazo[2,1-b][1,3]oxazine The title compound was prepared in the same manner as in Example 3 using suitable starting materials.
Pale Yellow Powder
Melting point: 179.0-180.4° C.

Example 141

Preparation of 7-{4-[4-(3-fluoro-4'-trifluoromethylbiphenyl-4-ylmethyl)piperazin-1-yl]phenoxymethyl}-2-nitro-6,7-dihydro-5H-imidazo[2,1-b][1,3]oxazine The title compound was prepared in the same manner as in Example 3 using suitable starting materials.
Pale Yellow Powder
Melting point: 211.6-212.9° C.

Example 142

Preparation of 7-{4-[4-(4'-chloro-3-fluorobiphenyl-4-ylmethyl)piperazin-1-yl]phenoxymethyl}-2-nitro-6,7-dihydro-5H-imidazo[2,1-b][1,3]oxazine The title compound was prepared in the same manner as in Example 3 using suitable starting materials.
Pale Yellow Powder
Melting point: 234.5-235.1° C.

Example 143

Preparation of 6-(2-nitro-6,7-dihydro-5H-imidazo[2,1-b][1,3]oxazin-7-ylmethoxy)-1-[3-(4-trifluoromethoxyphenoxy)propyl]-1,2,3,4-tetrahydroquinoline The title compound was prepared in the same manner as in Example 132 using suitable starting materials.
Pale Yellow Powder
Melting point: 175-176° C.

Example 144

Preparation of 2-nitro-7-(4-{4-[(E)-3-(5-trifluoromethylbenzofuran-2-yl)allyl]piperazin-1-yl}phenoxymethyl)-6,7-dihydro-5H-imidazo[2,1-b][1,3]oxazine The title compound was prepared in the same manner as in Example 3 using suitable starting materials.
Pale Yellow Powder
Melting point: 196.6-197.4° C.

Example 145

Preparation of 2-nitro-7-{4-[4-(5-trifluoromethoxybenzofuran-2-ylmethyl)piperazin-1-yl]phenoxymethyl}-6,7-dihydro-5H-imidazo[2,1-b][1,3]oxazine The title compound was prepared in the same manner as in Example 3 using suitable starting materials.
Yellow Powder
Melting point: 185.5-185.6° C.

Example 146

Preparation of 2-nitro-7-(4-{4-[(E)-3-(4-trifluoromethylphenyl)allyl]piperazin-1-yl}phenoxymethyl)-6,7-dihydro-5H-imidazo[2,1-b][1,3]oxazine The title compound was prepared in the same manner as in Example 3 using suitable starting materials.
Pale Yellow Powder
Melting point: 206.0-206.4° C.

Example 147

Preparation of 7-{3-fluoro-4-[4-(4-trifluoromethoxyphenoxy)piperidin-1-yl]phenoxymethyl}-2-nitro-6,7-dihydro-5H-imidazo[2,1-b][1,3]oxazine The title compound was prepared in the same manner as in Example 86 using suitable starting materials.
White Powder
Melting point: 186-187° C.

Example 148

Preparation of 7-{3-chloro-4-[4-(4-trifluoromethoxyphenoxy)piperidin-1-yl]phenoxymethyl}-2-nitro-6,7-dihydro-5H-imidazo[2,1-b][1,3]oxazine The title compound was prepared in the same manner as in Example 1 using suitable starting materials.
White Powder
Melting point: 143-144° C.

Example 149

Preparation of 7-{3-methyl-4-[4-(4-trifluoromethoxyphenoxy)piperidin-1-yl]phenoxymethyl}-2-nitro-6,7-dihydro-5H-imidazo[2,1-b][1,3]oxazine The title compound was prepared in the same manner as in Example 1 using suitable starting materials.
White Powder
Melting point: 199-200° C.

Example 150

Preparation of 7-{2-methyl-4-[4-(4-trifluoromethoxyphenoxy)piperidin-1-yl]phenoxymethyl}-2-nitro-6,7-dihydro-5H-imidazo[2,1-b][1,3]oxazine The title compound was prepared in the same manner as in Example 1 using suitable starting materials.
White Powder
Melting point: 156-157° C.

Example 151

Preparation of 6-((R)-2-nitro-6,7-dihydro-5H-imidazo[2,1-b][1,3]oxazin-7-ylmethoxy)-2-[2-(4-trifluoromethoxyphenoxy)ethoxy]quinoline The title compound was prepared in the same manner as in Example 1 using suitable starting materials.
White Powder
Melting point: 156-157° C.

Example 152

Preparation of 6-((R)-2-nitro-6,7-dihydro-5H-imidazo[2,1-b][1,3]oxazin-7-ylmethoxy)-2-[3-(4-trifluoromethoxyphenoxy)propoxy]quinoline The title compound was prepared in the same manner as in Example 1 using suitable starting materials.
White Powder
Melting point: 172-173° C.

Example 153

Preparation of 6-((R)-2-nitro-6,7-dihydro-5H-imidazo[2,1-b][1,3]oxazin-7-ylmethoxy)-2-(4-trifluoromethoxybenzyloxy)quinoline The title compound was prepared in the same manner as in Example 1 using suitable starting materials.
White Powder
Melting point: 203-204° C.

Example 154

Preparation of 6-((R)-2-nitro-6,7-dihydro-5H-imidazo[2,1-b][1,3]oxazin-7-ylmethoxy)-1-[3-(4-trifluoromethoxyphenoxy)propyl]-1,2,3,4-tetrahydroquinoline The title compound was prepared in the same manner as in Example 132 using suitable starting materials.
Pale Yellow Powder
Melting point: 183-185° C.

Example 155

Preparation of (R)-2-nitro-7-{1-[3-(4-trifluoromethoxyphenoxy)propyl]-1H-indol-5-yloxymethyl}-6,7-dihydro-5H-imidazo[2,1-b][1,3]oxazine The title compound was prepared in the same manner as in Example 132 using suitable starting materials.
Pale Yellow Powder
Melting point: 129-131° C.

Example 156

Preparation of 7-((R)-2-nitro-6,7-dihydro-5H-imidazo[2,1-b][1,3]oxazin-7-ylmethoxy)-1-[3-(4-trifluoromethoxyphenoxy)propyl]-2,3,4,5-tetrahydro-1H-benzo[b]azepine The title compound was prepared in the same manner as in Example 132 using suitable starting materials.
White Powder
Melting point: 159-160° C.

Example 157

Preparation of 6-((R)-2-nitro-6,7-dihydro-5H-imidazo[2,1-b][1,3]oxazin-7-ylmethoxy)-1-[4-(4-trifluoromethoxyphenoxy)benzyl]-1,2,3,4-tetrahydroquinoline The title compound was prepared in the same manner as in Example 132 using suitable starting materials.
Pale Brown Powder
Melting point: 194-196° C.

Example 158

Preparation of 7-((R)-2-nitro-6,7-dihydro-5H-imidazo[2,1-b][1,3]oxazin-7-ylmethoxy)-1-[4-(4-trifluoromethoxyphenoxy)benzyl]-2,3,4,5-tetrahydro-1H-benzo[b]azepine The title compound was prepared in the same manner as in Example 132 using suitable starting materials.
Powder
Melting point: 133-134° C.

Example 159

Preparation of 6-((R)-2-nitro-6,7-dihydro-5H-imidazo[2,1-b][1,3]oxazin-7-ylmethoxy)-2-[4-(4-trifluoromethoxyphenoxy)piperidin-1-yl]quinoline The title compound was prepared in the same manner as in Example 132 using suitable starting materials.
Yellow Powder
Melting point: 193-195° C.

Example 160

Preparation of (R)-7-(2-methyl-4-{4-[2-(4-trifluoromethoxyphenyl)ethyl]piperidin-1-yl}phenoxymethyl)-2-nitro-6,7-dihydro-5H-imidazo[2,1-b][1,3]oxazine The title compound was prepared in the same manner as in Example 1 using suitable starting materials.
White Powder
Melting point: 181-182° C.

Example 161

Preparation of (R)-7-(2-chloro-4-{4-[2-(4-trifluoromethoxyphenyl)ethyl]piperidin-1-yl}phenoxymethyl)-2-nitro-6,7-dihydro-5H-imidazo[2,1-b][1,3]oxazine The title compound was prepared in the same manner as in Example 1 using suitable starting materials.
White Powder
Melting point: 160-162° C.

Example 162

Preparation of (R)-2-nitro-7-(6-{4-[2-(4-trifluoromethoxyphenyl)ethyl]piperidin-1-yl}naphthalen-2-yloxymethyl)-6,7-dihydro-5H-imidazo[2,1-b][1,3]oxazine The title compound was prepared in the same manner as in Example 1 using suitable starting materials.
Pale Yellow Powder
Melting point: 234-235° C.

Example 163

Preparation of 2-nitro-7-{4-[4-(4'-trifluoromethylbiphenyl-4-ylmethyl)piperazin-1-yl]phenoxymethyl}-6,7-dihydro-5H-imidazo[2,1-b][1,3]oxazine The title compound was prepared in the same manner as in Example 3 using suitable starting materials.
Pale Yellow Powder
Melting point: 256.9-257.9° C.

Example 164

Preparation of 2-nitro-7-(4-{4-[6-(4-trifluoromethoxyphenyl)pyridin-3-ylmethyl]piperazin-1-yl}phenoxymethyl)-6,7-dihydro-5H-imidazo[2,1-b][1,3]oxazine The title compound was prepared in the same manner as in Example 3 using suitable starting materials.
White Powder
Melting point: 201.2-203.7° C.

Example 165

Preparation of 6-((R)-2-nitro-6,7-dihydro-5H-imidazo[2,1-b][1,3]oxazin-7-ylmethoxy)-2-[4-(4-trifluoromethoxybenzyl)piperazin-1-yl]quinoline The title compound was prepared in the same manner as in Example 3 using suitable starting materials.
Yellow Powder
Melting point: 218-221° C.

Example 166

Preparation of 6-((R)-2-nitro-6,7-dihydro-5H-imidazo[2,1-b][1,3]oxazin-7-ylmethoxy)-2-{4-[4-(4-trifluoromethoxyphenoxy)benzyl]piperazin-1-yl}quinoline The title compound was prepared in the same manner as in Example 3 using suitable starting materials.
White Powder
Melting point: 208-211° C.

Example 167

Preparation of 6-((R)-2-nitro-6,7-dihydro-5H-imidazo[2,1-b][1,3]oxazin-7-ylmethoxy)-2-{4-[4-(4-trifluoromethoxybenzyloxy)benzyl]piperazin-1-yl}quinoline The title compound was prepared in the same manner as in Example 3 using suitable starting materials.
Yellow Powder
Melting point: 226-230° C.

Example 168

Preparation of (R)-2-nitro-7-{2-[4-(4-trifluoromethoxyphenoxy)piperidin-1-yl]benzothiazol-6-yloxymethyl}-6,7-dihydro-5H-imidazo[2,1-b][1,3]oxazine The title compound was prepared in the same manner as in Example 132 using suitable starting materials.
Yellow Powder
Melting point: 189-191° C.

Example 169

Preparation of (R)-2-nitro-7-{2-[4-(4-trifluoromethoxybenzyl)piperazin-1-yl]benzothiazol-6-yloxymethyl}-6,7-dihydro-5H-imidazo[2,1-b][1,3]oxazine Sodium tert-butoxide (112 mg) was added to a dimethylsulfoxide solution (6 ml) of (R)-4-(2-chloro-4-nitroimidazol-1-yl)-1-{2-[4-(4-trifluoromethoxybenzyl)piperazin-1-yl]benzothiazol-6-yloxy}butan-2-ol (662 mg), and the mixture was stirred at room temperature for 3 hours. A saturated ammonium chloride aqueous solution was added to the reaction mixture, and precipitated solid was sequentially washed with water and diisopropyl ether. The crude product was purified by silica gel column chromatography (ethyl acetate: n-hexane=2:1→ethyl acetate) to afford the title compound as a pale yellow powder (60 mg).
Melting point: 157-159° C.

Example 170

Preparation of (R)-2-nitro-7-[4-(4-{4-[2-(4-trifluoromethoxyphenyl)ethoxy]benzyl}piperazin-1-yl)phenoxymethyl]-6,7-dihydro-5H-imidazo[2,1-b][1,3]oxazine The title compound was prepared in the same manner as in Example 3 using suitable starting materials.
White Powder
Melting point: 157.7° C.

Example 171

Preparation of (S)-2-nitro-7-(4-{4-[4-(4-trifluoromethoxybenzyloxy)benzyl]piperazin-1-yl}phenoxymethyl)-6,7-dihydro-5H-imidazo[2,1-b][1,3]oxazine The title compound was prepared in the same manner as in Example 3 using suitable starting materials.
White Powder
Melting point: 193.4-193.9° C.

Example 172

Preparation of (R)-2-nitro-7-(4-{4-[2-(4-trifluoromethoxyphenoxy)ethyl]piperidin-1-yl}phenoxymethyl)-6,7-dihydro-5H-imidazo[2,1-b][1,3]oxazine The title compound was prepared in the same manner as in Example 1 using suitable starting materials.
White Powder
Melting point: 152-153° C.

Example 173

Preparation of 2-nitro-7-(2-{4-[4-(4-trifluoromethoxybenzyloxy)benzyl]piperazin-1-yl}benzothiazol-6-yloxymethyl)-6,7-dihydro-5H-imidazo[2,1-b][1,3]oxazine The title compound was prepared in the same manner as in Example 3 using suitable starting materials.
Pale Yellow Powder
Melting point: 203-205° C.

Example 174

Preparation of (R)-2-nitro-7-[4-(4-{4-[3-(4-trifluoromethoxyphenyl)propoxy]benzyl}piperazin-1-yl)phenoxymethyl]-6,7-dihydro-5H-imidazo[2,1-b][1,3]oxazine The title compound was prepared in the same manner as in Example 3 using suitable starting materials.
Yellow Powder
Melting point: 158.2-158.4° C.

Example 175

Preparation of (R)-2-nitro-7-[4-(4-{4-[(E)-3-(4-trifluoromethoxyphenyl)allyloxy]benzyl}piperazin-1-yl)phenoxymethyl]-6,7-dihydro-5H-imidazo[2,1-b][1,3]oxazine The title compound was prepared in the same manner as in Example 3 using suitable starting materials.
Yellow Powder
Melting point: 183.0-183.9° C.

Example 176

Preparation of (R)-7-[4-(4-{4-[2-(4-chlorophenyl)ethoxy]benzyl}piperazin-1-yl)phenoxymethyl]-2-nitro-6,7-dihydro-5H-imidazo[2,1-b][1,3]oxazine The title compound was prepared in the same manner as in Example 3 using suitable starting materials.
Yellow Powder
Melting point: 150.0-152.2° C.

Example 177

Preparation of (R)-2-nitro-7-[4-(4-{4-[3-(4-trifluoromethylphenyl)propoxy]benzyl}piperazin-1-yl)phenoxymethyl]-6,7-dihydro-5H-imidazo[2,1-b][1,3]oxazine The title compound was prepared in the same manner as in Example 3 using suitable starting materials.
Yellow Powder
Melting point: 155.0-155.9° C.

Example 178

Preparation of (R)-2-nitro-7-[4-(4-{4-[(E)-3-(4-trifluoromethylphenyl)allyloxy]benzyl}piperazin-1-yl)phenoxymethyl]-6,7-dihydro-5H-imidazo[2,1-b][1,3]oxazine The title compound was prepared in the same manner as in Example 3 using suitable starting materials.
Yellow Powder
Melting point: 196.1-199.1° C.

Example 179

Preparation of (R)-2-nitro-7-[4-(4-{4-[4-(4-trifluoromethoxyphenoxy)piperidin-1-yl]benzyl}piperazin-1-yl)phenoxymethyl]-6,7-dihydro-5H-imidazo[2,1-b][1,3]oxazine The title compound was prepared in the same manner as in Example 3 using suitable starting materials.
Yellow Solid
Melting point: 168.3-169.5° C.

Example 180

Preparation of N-{1-[4-((R)-2-nitro-6,7-dihydro-5H-imidazo[2,1-b][1,3]oxazin-7-ylmethoxy)phenyl]piperidin-4-yl}-N-[4-(4-trifluoromethoxyphenoxy)phenyl]amine 1-[4-((R)-2-Nitro-6,7-dihydro-5H-imidazo[2,1-b][1,3]oxazin-7-ylmethoxy)phenyl]piperidin-4-one (700 mg) and 4-(4-trifluoromethoxyphenoxy)phenylamine (557 mg) were suspended in 1,2-dichloroethane (20 ml) and tetrahydrofuran (20 ml). Sodium triacetoxyborohydride (558 mg) and acetic acid (0.13 ml) were added to the suspension, and stirred at room temperature for 20 hours. The reaction mixture was concentrated under reduced pressure and the remaining water layer was ice-cooled. A 20% sodium carbonate aqueous solution was added thereto, followed by extraction with methylene chloride. The organic layer was washed with a saturated sodium chloride aqueous solution and dried over sodium sulfate. After filtering, the filtrate was concentrated under reduced pressure. The residue was then purified by silica gel column chromatography (methylene chloride:methanol=100:1→methylene chloride:methanol=40:1) and recrystallized from isopropyl alcohol-isopropyl ether to afford the title compound as a yellow solid (226 mg).
Melting point: 119.6-121° C.

Example 181

Preparation of N-(4'-chlorobiphenyl-4-ylmethyl)-N-methyl-N-{1-[4-NR)-2-nitro-6,7-dihydro-5H-imidazo[2,1-b][1,3]oxazin-7-ylmethoxy)phenyl]piperidin-4-yl}amine The title compound was prepared in the same manner as in Example 180 using suitable starting materials.
Colorless Solid
Melting point: 256.5-258° C.

Example 182

Preparation of (R)-2-nitro-7-(4-{4-[4-(4-trifluoromethylbenzyloxy)benzyl]piperazin-1-yl}phenoxymethyl)-6,7-dihydro-5H-imidazo[2,1-b][1,3]oxazine The title compound was prepared in the same manner as in Example 3 using suitable starting materials.
Yellow Powder
Melting point: 198.8-200.8° C.

Example 183

Preparation of (R)-7-(4-{4-[4-(4-chlorobenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Yellow Powder
Melting point: 225.5-229.0° C.

Example 184

Preparation of (R)-7-(4-{4-[2-(3,4-dichlorophenoxy)ethyl]piperidin-1-yl}phenoxymethyl)-2-nitro-6,7-dihydro-5H-imidazo[2,1-b][1,3]oxazine The title compound was prepared in the same manner as in Example 132 using suitable starting materials.
Yellow Powder
Melting point: 152-153° C.

Example 185

Preparation of (R)-7-(4-{4-[2-(3-chloro-5-trifluoromethylpyridin-2-yloxy)ethyl]piperidin-1-yl}phenoxymethyl)-2-nitro-6,7-dihydro-5H-imidazo[2,1-b][1,3]oxazine The title compound was prepared in the same manner as in Example 132 using suitable starting materials.
Yellow Powder
Melting point: 140-143° C.

Example 186

Preparation of (R)-2-nitro-7-(4-{4-[3-(4-trifluoromethoxyphenyl)propyl]piperidin-1-yl}phenoxymethyl)-6,7-dihydro-5H-imidazo[2,1-b][1,3]oxazine The title compound was prepared in the same manner as in Example 1 using suitable starting materials.
White Powder
Melting point: 171-172° C.

Example 187

Preparation of (R)-2-nitro-7-(4-{4-[2-(tetrahydropyran-2-yloxy)-2-(4-trifluoromethoxyphenyl)ethyl]piperidin-1-yl}phenoxymethyl)-6,7-dihydro-5H-imidazo[2,1-b][1,3]oxazine The title compound was prepared in the same manner as in Example 1 using suitable starting materials.
Pale Yellow Powder
Melting point: 172-175° C.

Example 188

Preparation of 2-{1-[4-((R)-2-nitro-6,7-dihydro-5H-imidazo[2,1-b][1,3]oxazin-7-ylmethoxy)phenyl]piperidin-4-yl}-1-(4-trifluoromethoxyphenyl)ethanol A 1 N HCl ethanol solution (6 ml) was added to (R)-2-nitro-7-(4-{4-[2-(tetrahydropyran-2-yloxy)-2-(4-trifluoromethoxyphenyl)ethyl]piperidin-1-yl}phenoxymethyl)-6,7-dihydro-5H-imidazo[2,1-b][1,3]oxazine (0.20 g), and the mixture was stirred at room temperature for 3 hours. A saturated sodium hydrogen carbonate aqueous solution was added to the residue obtained by distilling the solvent off, followed by extraction with ethyl acetate. The organic layer was washed with a saturated sodium chloride aqueous solution and dried over sodium sulfate. After filtering, the filtrate was concentrated under reduced pressure. The crystal thus obtained was washed with methylene chloride-ether and dried to afford the title compound as a white powder (0.16 g).
Melting point: 186-187° C.

Example 189

Preparation of (R)-7-(4-{4-[2-(3,5-dichloropyridin-2-yloxy)ethyl]piperidin-1-yl}phenoxymethyl)-2-nitro-6,7-dihydro-5H-imidazo[2,1-b][1,3]oxazine The title compound was prepared in the same manner as in Example 69 using suitable starting materials.
Yellow Powder
Melting point: 143-145° C.

Example 190

Preparation of N-{1-[4-((R)-2-nitro-6,7-dihydro-5H-imidazo[2,1-b][1,3]oxazin-7-ylmethoxy)phenyl]piperidin-4-yl}-N-[4-(4-trifluoromethoxybenzyloxy)phenyl]amine Sodium triacetoxyborohydride (0.32 g) and acetic acid (1 ml) were added to a 1,2-dichloroethane solution (8 ml) of 1-[4-((R)-2-nitro-6,7-dihydro-5H-imidazo[2,1-b][1,3]oxazin-7-ylmethoxy)phenyl]piperidin-4-one (0.40 g) and 4-(4-trifluoromethoxybenzyloxy)phenylamine (0.33 g), and the mixture was stirred at room temperature for 5 days. The reaction mixture was diluted with methylene chloride. The result was washed with a potassium carbonate aqueous solution and water in this order, and then dried over magnesium sulfate. After filtering, the filtrate was concentrated under reduced pressure. The residue was purified by silica gel column chromatography (methylene chloride:methanol=1:0→methylene chloride:methanol=9:1) to afford the title compound as a yellow powder (0.46 g).
Melting point: 226.9-228.6° C.

Example 191

Preparation of (R)-7-(4-{4-[2-(4-chloro-3-trifluoromethylphenoxy)ethyl]piperidin-1-yl}phenoxymethyl)-2-nitro-6,7-dihydro-5H-imidazo[2,1-b][1,3]oxazine The title compound was prepared in the same manner as in Example 69 using suitable starting materials.
Yellow Powder
Melting point: 116-118° C.

Example 192

Preparation of (R)-2-nitro-7-(4-{4-[3-(4-trifluoromethoxybenzyloxy)benzyl]piperazin-1-yl}phenoxymethyl)-6,7-dihydro-5H-imidazo[2,1-b][1,3]oxazine The title compound was prepared in the same manner as in Example 3 using suitable starting materials.
Yellow Powder
Melting point: 155.6-156.5° C.

Example 193

Preparation of (R)-7-(4-{4-[2-(2,4-dichlorophenoxy)ethyl]piperidin-1-yl}phenoxymethyl)-2-nitro-6,7-dihydro-5H-imidazo[2,1-b][1,3]oxazine The title compound was prepared in the same manner as in Example 69 using suitable starting materials.
Pale Yellow Powder
Melting point: 164-166° C.

Example 194

Preparation of (R)-7-(4-{4-[2-(4-chloro-3-methylphenoxy)ethyl]piperidin-1-yl}phenoxymethyl)-2-nitro-6,7-dihydro-5H-imidazo[2,1-b][1,3]oxazine The title compound was prepared in the same manner as in Example 69 using suitable starting materials.
Pale Yellow Powder
Melting point: 166-168° C.

Example 195

Preparation of (R)-2-nitro-7-(4-{4-[2-(3-trifluoromethylphenoxy)ethyl]piperidin-1-yl}phenoxymethyl)-6,7-dihydro-5H-imidazo[2,1-b][1,3]oxazine The title compound was prepared in the same manner as in Example 69 using suitable starting materials.
Yellow Powder
Melting point: 148-149° C.

Example 196

Preparation of (R)-2-nitro-7-(4-{4-[3-(4-trifluoromethoxyphenoxy)propyl]piperidin-1-yl}phenoxymethyl)-6,7-dihydro-5H-imidazo[2,1-b][1,3]oxazine The title compound was prepared in the same manner as in Example 1 using suitable starting materials.
Pale Yellow Powder
Melting point: 176-177° C.

Example 197

Preparation of (R)-2-nitro-7-(4-{4-[2-(5-trifluoromethylpyridin-2-yloxy)ethyl]piperidin-1-yl}phenoxymethyl)-6,7-dihydro-5H-imidazo[2,1-b][1,3]oxazine The title compound was prepared in the same manner as in Example 1 using suitable starting materials.
White Powder
Melting point: 162-163° C.

Example 198

Preparation of (R)-2-nitro-7-(4-{4-[4-(4-trifluoromethoxybenzyloxy)phenyl]piperazin-1-yl}phenoxymethyl)-6,7-dihydro-5H-imidazo[2,1-b][1,3]oxazine The title compound was prepared in the same manner as in Example 1 using suitable starting materials.
Yellow Solid
Melting point: 261-262° C.

Example 199

Preparation of (R)-7-(4-{4-[2-(3-chloro-4-fluorophenoxy)ethyl]piperidin-1-yl}phenoxymethyl)-2-nitro-6,7-dihydro-5H-imidazo[2,1-b][1,3]oxazine The title compound was prepared in the same manner as in Example 69 using suitable starting materials.
Yellow Powder
Melting point: 144-145° C.

Example 200

Preparation of (R)-2-nitro-7-{2-[4-(4-trifluoromethoxyphenoxy)piperidin-1-yl]benzooxazol-5-yloxymethyl}-6,7-dihydro-5H-imidazo[2,1-b][1,3]oxazine hydrochloride The title compound was prepared in the same manner as in Example 69 using suitable starting materials.
Pale Yellow Powder
Melting point: 146-149° C.

Example 201

Preparation of (R)-2-nitro-7-(4-{4-[4-(4-trifluoromethoxyphenoxy)phenyl]piperazin-1-yl}phenoxymethyl)-6,7-dihydro-5H-imidazo[2,1-b][1,3]oxazine The title compound was prepared in the same manner as in Example 1 using suitable starting materials.
Colorless Solid
Melting point: 207.6-208.2° C.

Example 202

Preparation of (R)-2-nitro-7-(4-{4-[3-(4-trifluoromethylphenyl)propyl]piperazin-1-yl}phenoxymethyl)-6,7-dihydro-5H-imidazo[2,1-b][1,3]oxazine The title compound was prepared in the same manner as in Example 3 using suitable starting materials.
Pale Brown Powder
Melting point: 190.9° C.

Example 203

Preparation of (R)-7-[4-(4-{4-[(E)-3-(4-chlorophenyl)allyloxy]benzyl}piperazin-1-yl)phenoxymethyl]-2-nitro-6,7-dihydro-5H-imidazo[2,1-b][1,3]oxazine The title compound was prepared in the same manner as in Example 3 using suitable starting materials.
Pale Yellow Powder
Melting point: 210.6-213.6° C.

Example 204

Preparation of N-{4-[4-((R)-2-nitro-6,7-dihydro-5H-imidazo[2,1-b][1,3]oxazin-7-ylmethoxy)phenyl]piperazin-1-yl}-N-(4'-trifluoromethylbiphenyl-4-ylmethyl)amine Trifluoroacetic acid (3.0 ml) was added to a mixture of {4-[4-((R)-2-nitro-6,7-dihydro-5H-imidazo[2,1-b][1,3]oxazin-7-ylmethoxy)phenyl]piperazin-1-yl}carbamic acid tert-butyl ester (600 mg) and methylene chloride (3.0 ml), and the mixture was stirred at room temperature for 40 minutes. The reaction mixture was concentrated under reduced pressure, and methylene chloride (3.0 ml) and triethylamine (3.0 ml) were added to the residue, followed by stirring at room temperature for 5 minutes. The reaction mixture was concentrated under reduced pressure, and the resulting residue was dissolved in acetic acid (8 ml). 4'-Trifluoromethylbiphenyl-4-carbaldehyde (316 mg) and sodium cyanoborohydride (239 mg) were added thereto, and the mixture was stirred at room temperature for 2 hours. The reaction mixture was added to a 20% sodium carbonate aqueous solution, followed by extraction with methylene chloride. The organic layer was washed with a saturated sodium chloride aqueous solution and then dried over sodium sulfate. After filtering, the filtrate was concentrated under reduced pressure. The residue was purified by silica gel column chromatography (methylene chloride:methanol=100:1→methylene chloride:methanol=40:1) and washed with ethyl acetate-isopropyl ether to afford the title compound as a colorless solid (265 mg).
Melting point: 294-295° C.

Example 205

Preparation of (R)-2-nitro-7-{4-[1-(4-trifluoromethoxybenzyl)piperidin-4-yloxy]phenoxymethyl}-6,7-dihydro-5H-imidazo[2,1-b][1,3]oxazine The title compound was prepared in the same manner as in Example 3 using suitable starting materials.
White Powder
Melting point: 151-152° C.

Example 206

Preparation of (R)-2-nitro-7-(4-{1-[4-(4-trifluoromethoxybenzyloxy)benzyl]piperidin-4-yloxy}phenoxymethyl)-6,7-dihydro-5H-imidazo[2,1-b][1,3]oxazine The title compound was prepared in the same manner as in Example 3 using suitable starting materials.
White Powder
Melting point: 163-164° C.

Example 207

Preparation of (R)-2-nitro-7-(4-{1-[4-(4-trifluoromethoxyphenoxy)benzyl]piperidin-4-yloxy}phenoxymethyl)-6,7-dihydro-5H-imidazo[2,1-b][1,3]oxazine The title compound was prepared in the same manner as in Example 3 using suitable starting materials.
White Powder
Melting point: 127-128° C.

Example 208

Preparation of N-methyl-N-{1-[4-((R)-2-nitro-6,7-dihydro-5H-imidazo[2,1-b][1,3]oxazin-7-ylmethoxy)phenyl]piperidin-4-yl}-N-[4-(4-trifluoromethoxybenzyloxy)phenyl]amine N-{1-[4-((R)-2-Nitro-6,7-dihydro-5H-imidazo[2,1-b][1,3]oxazin-7-ylmethoxy)phenyl]piperidin-4-yl}-N-[4-(4-trifluoromethoxybenzyloxy)phenyl]amine (0.30 g) was suspended in methanol (3 ml). A 37% formaldehyde aqueous solution (0.11 g), sodium cyanoborohydride (89 mg) and acetic acid (1 ml) were added to the suspension and stirred at room temperature for 1 day. A 37% formaldehyde aqueous solution (0.22 g), sodium cyanoborohydride (178 mg) and acetic acid (2 ml) were further added to the mixture and stirred at room temperature for 1 day. The reaction mixture was gradually added to a potassium carbonate aqueous solution, followed by extraction with methylene chloride. The organic layer was washed with a saturated sodium chloride aqueous solution and dried over sodium sulfate, and the filtrate was concentrated under reduced pressure. The resulting residue was purified by medium pressure silica gel column chromatography (methylene chloride:methanol=10:0→methylene chloride:methanol=9:1) and recrystallized from methanol to afford the title compound as a pale brown powder (0.20 g).
Melting point: 142.0-143.7° C.

Example 209

Preparation of (R)-2-nitro-7-(4-{4-[4-(4-trifluoromethoxyphenoxy)butyl]piperidin-1-yl}phenoxymethyl)-6,7-dihydro-5H-imidazo[2,1-b][1,3]oxazine The title compound was prepared in the same manner as in Example 69 using suitable starting materials.
White Powder
Melting point: 160-162° C.

Example 210

Preparation of (R)-7-[4-(4-{4-[3-(4-chlorophenyl)propoxy]benzyl}piperazin-1-yl)phenoxymethyl]-2-nitro-6,7-dihydro-5H-imidazo[2,1-b][1,3]oxazine The title compound was prepared in the same manner as in Example 3 using suitable starting materials.
Yellow Powder
Melting point: 200.7-200.9° C.

Example 211

Preparation of (R)-2-nitro-7-[4-(4-{4-[2-(4-trifluoromethoxyphenyl)ethyl]benzyl}piperazin-1-yl)phenoxymethyl]-6,7-dihydro-5H-imidazo[2,1-b][1,3]oxazine The title compound was prepared in the same manner as in Example 3 using suitable starting materials.
Gray Powder
Melting point: 147.3-150.0° C.

Example 212

Preparation of N-{1-[4-((R)-2-nitro-6,7-dihydro-5H-imidazo[2,1-b][1,3]oxazin-7-ylmethoxy)phenyl]piperidin-4-yl}-N-[4-(4-trifluoromethylbenzyloxy)phenyl]amine The title compound was prepared in the same manner as in Example 190 using suitable starting materials.
Yellow Powder
Melting point: 233.2-235.6° C.

Example 213

Preparation of N-methyl-N-{1-[4-((R)-2-nitro-6,7-dihydro-5H-imidazo[2,1-b][1,3]oxazin-7-ylmethoxy)phenyl]piperidin-4-yl}-N-[4-(4-trifluoromethylbenzyloxy)phenyl]amine N-{1-[4-((R)-2-Nitro-6,7-dihydro-5H-imidazo[2,1-b][1,3]oxazin-7-ylmethoxy)phenyl]piperidin-4-yl}-N-[4-(4-trifluoromethylbenzyloxy)phenyl]amine (0.40 g) and methanol (3 ml) were mixed. A 37% formaldehyde aqueous solution (0.47 g), sodium cyanoborohydride (0.36 g) and acetic acid (3 ml) were added to the mixture and stirred at room temperature overnight. The reaction mixture was added to a potassium carbonate aqueous solution, followed by extraction with methylene chloride. The organic layer was washed with water and dried over sodium sulfate. After filtering, the filtrate was concentrated under reduced pressure. The residue was purified by silica gel column chromatography (methylene chloride:methanol=1:0→methylene chloride:methanol=9:1) to afford the title compound as a yellow powder (0.26 g).
Melting point: 170.6° C.

Example 214

Preparation of N-[4-(4-chlorobenzyloxy)phenyl]-N-{1-[4-((R)-2-nitro-6,7-dihydro-5H-imidazo[2,1-b][1,3]oxazin-7-ylmethoxy)phenyl]piperidin-4-yl}amine The title compound was prepared in the same manner as in Example 190 using suitable starting materials.
Yellow Powder
Melting point: 236.5-237.1° C.

Example 215

Preparation of N-[4-(4-chlorobenzyloxy)phenyl]-N-methyl-N-{1-[4-((R)-2-nitro-6,7-dihydro-5H-imidazo[2,1-b][1,3]oxazin-7-ylmethoxy)phenyl]piperidin-4-yl}amine The title compound was prepared in the same manner as in Example 213 using suitable starting materials.
Yellow Powder
Melting point: 205.6-206.5° C.

Example 216

Preparation of (R)-2-nitro-7-(4-{4-[3-(4-trifluoromethylbenzyloxy)benzyl]piperazin-1-yl}phenoxymethyl)-6,7-dihydro-5H-imidazo[2,1-b][1,3]oxazine The title compound was prepared in the same manner as in Example 3 using suitable starting materials.
Pale Gray Powder
Melting point: 161.9-163.5° C.

Example 217

Preparation of (R)-7-(4-{4-[3-(4-chlorobenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Yellow Powder
Melting point: 167.8-167.9° C.

Example 218

Preparation of (R)-2-nitro-7-[4-(3-trifluoromethyl-5,6-dihydro-8H-imidazo[1,2-a]pyrazin-7-yl)phenoxymethyl]-6,7-dihydro-5H-imidazo[2,1-b][1,3]oxazine The title compound was prepared in the same manner as in Example 1 using suitable starting materials.
Pale Yellow Powder
Melting point: 239-240° C.

Example 219

Preparation of (R)-2-nitro-7-(4-{4-[4-(4-trifluoromethoxyphenoxymethyl)benzyl]piperazin-1-yl}phenoxymethyl)-6,7-dihydro-5H-imidazo[2,1-b][1,3]oxazine The title compound was prepared in the same manner as in Example 3 using suitable starting materials.
Yellow Powder
Melting point: 174.2-174.4° C.

Example 220

Preparation of (R)-2-nitro-7-(4-{4-[4-(4-trifluoromethylphenoxymethyl)benzyl]piperazin-1-yl}phenoxymethyl)-6,7-dihydro-5H-imidazo[2,1-b][1,3]oxazine The title compound was prepared in the same manner as in Example 3 using suitable starting materials.
Yellow Powder
Melting point: 207.2-208.2° C.

Example 221

Preparation of 4-[4-(7-methyl-2-nitro-6,7-dihydro-5H-imidazo[2,1-b][1,3]oxazin-7-ylmethoxy)phenyl]piperazine-1-carboxylic acid tert-butyl ester 4-{4-[4-(2-Chloro-4-nitroimidazol-1-yl)-2-hydroxy-2-methylbutoxy]phenyl}piperazine-1-carboxylic acid tert-butyl ester (2.12 g) was dissolved in dimethylformamide (21 ml). 60% sodium hydride (0.24 g) was added thereto, and the mixture was stirred at room temperature for 3 hours. Water was added to the reaction mixture, the mixture was subjected to extraction with methylene chloride, and then dried over sodium sulfate. After filtering, the filtrate was concentrated under reduced pressure. The residue was purified by silica gel column chromatography (methylene chloride:ethyl acetate=1:0→methylene chloride:ethyl acetate=1:1) to afford the title compound as a colorless powder (1.05 g).
Melting point: 208.2-208.8° C.

Example 222

Preparation of (R)-2-nitro-7-[4-(4-{4-[2-(4-trifluoromethylphenyl)ethoxy]benzyl}piperazin-1-yl)phenoxymethyl]-6,7-dihydro-5H-imidazo[2,1-b][1,3]oxazine The title compound was prepared in the same manner as in Example 3 using suitable starting materials.
Yellow Powder
Melting point: 149.1° C.

Example 223

Preparation of (R)-7-(4-{4-[3-(4-chlorophenoxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Yellow Powder
Melting point: 185.2-186.1° C.

Example 224

Preparation of (R)-2-nitro-7-(4-{1-[4-(4-trifluoromethylbenzyloxy)benzyl]piperidin-4-yloxy}phenoxymethyl)-6,7-dihydro-5H-imidazo[2,1-b][1,3]oxazine The title compound was prepared in the same manner as in Example 3 using suitable starting materials.
White Powder
Melting point: 177-178° C.

Example 225

Preparation of 7-[4-((R)-2-nitro-6,7-dihydro-5H-imidazo[2,1-b][1,3]oxazin-7-ylmethoxy)phenyl]-3-trifluoromethyl-5,6,7,8-tetrahydro-[1,2,4]triazolo[4,3-a]pyrazine The title compound was prepared in the same manner as in Example 1 using suitable starting materials.
Pale Yellow Powder
Melting point: 145-146° C.

Example 226

Preparation of 7-methyl-2-nitro-7-(4-{4-[4-(4-trifluoromethoxybenzyloxy)benzyl]piperazin-1-yl}phenoxymethyl)-6,7-dihydro-5H-imidazo[2,1-b][1,3]oxazine The title compound was prepared in the same manner as in Example 3 using suitable starting materials.
Yellow Powder
Melting point: 178.7-178.8° C.

Example 227

Preparation of 7-methyl-2-nitro-7-(4-{4-[4-(4-trifluoromethoxyphenoxy)benzyl]piperazin-1-yl}phenoxymethyl)-6,7-dihydro-5H-imidazo[2,1-b][1,3]oxazine The title compound was prepared in the same manner as in Example 3 using suitable starting materials.
Yellow Powder
Melting point: 162.1-162.7° C.

Example 228

Preparation of (R)-2-nitro-7-(4-{4-[4-(4-trifluoromethoxyphenoxy)benzyl]piperidin-1-yl}phenoxymethyl)-6,7-dihydro-5H-imidazo[2,1-b][1,3]oxazine The title compound was prepared in the same manner as in Example 86 using suitable starting materials.
Pale Gray Powder
Melting point: 143.2-144.9° C.

Example 229

Preparation of (S)-2-nitro-7-(4-{4-[4-(4-trifluoromethoxyphenoxy)benzyl]piperidin-1-yl}phenoxymethyl)-6,7-dihydro-5H-imidazo[2,1-b][1,3]oxazine The title compound was prepared in the same manner as in Example 86 using suitable starting materials.
Pale Gray Powder
Melting point: 143.5-146.9° C.

Example 230

Preparation of (S)-2-nitro-7-(4-{4-[4-(4-trifluoromethoxybenzyloxy)phenoxy]piperidin-1-yl}phenoxymethyl)-6,7-dihydro-5H-imidazo[2,1-b][1,3]oxazine The title compound was prepared in the same manner as in Example 69 using suitable starting materials.
White Powder
Melting point: 189-191° C.

Example 231

Preparation of (R)-2-nitro-7-(4-{4-[4-(4-trifluoromethoxybenzyloxy)phenoxy]piperidin-1-yl}phenoxymethyl)-6,7-dihydro-5H-imidazo[2,1-b][1,3]oxazine The title compound was prepared in the same manner as in Example 169 using suitable starting materials.
White Powder
Melting point: 190-191° C.

Example 232

Preparation of (S)-2-nitro-7-(4-{4-[4-(3-trifluoromethylphenoxy)benzyl]piperazin-1-yl}phenoxymethyl)-6,7-dihydro-5H-imidazo[2,1-b][1,3]oxazine The title compound was prepared in the same manner as in Example 3 using suitable starting materials.
Yellow Powder
Melting point: 155.5-156.4° C.

Example 233

Preparation of (S)-7-(4-{4-[4-(4-chlorophenoxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Yellow Powder
Melting point: 135.7-138.7° C.

Example 234

Preparation of (S)-2-nitro-7-[4-(4-{4-[2-(4-trifluoromethoxyphenyl)ethoxy]benzyl}piperazin-1-yl)phenoxymethyl]-6,7-dihydro-5H-imidazo[2,1-b][1,3]oxazine The title compound was prepared in the same manner as in Example 3 using suitable starting materials.
Yellow Powder
Melting point: 147.8-149.5° C.

Example 235

Preparation of (S)-2-nitro-7-[4-(4-{4-[2-(4-trifluoromethylphenyl)ethoxy]benzyl}piperazin-1-yl)phenoxymethyl]-6,7-dihydro-5H-imidazo[2,1-b][1,3]oxazine The title compound was prepared in the same manner as in Example 3 using suitable starting materials.
Yellow Powder
Melting point: 169.8-170.6° C.

Example 236

Preparation of (S)-7-[4-(4-{4-[2-(4-chlorophenyl)ethoxy]benzyl}piperazin-1-yl)phenoxymethyl]-2-nitro-6,7-dihydro-5H-imidazo[2,1-b][1,3]oxazine The title compound was prepared in the same manner as in Example 3 using suitable starting materials.
Yellow Powder
Melting point: 153.6° C.

Example 237

Preparation of (S)-2-nitro-7-(4-{4-[4-(4-trifluoromethoxyphenoxymethyl)benzyl]piperazin-1-yl}phenoxymethyl)-6,7-dihydro-5H-imidazo[2,1-b][1,3]oxazine The title compound was prepared in the same manner as in Example 3 using suitable starting materials.
Yellow Powder
Melting point: 174.1-174.5° C.

Example 238

Preparation of (S)-2-nitro-7-(4-{4-[4-(4-trifluoromethylphenoxymethyl)benzyl]piperazin-1-yl}phenoxymethyl)-6,7-dihydro-5H-imidazo[2,1-b][1,3]oxazine The title compound was prepared in the same manner as in Example 3 using suitable starting materials.
Yellow Powder
  Melting point: 208° C.

Example 239

Preparation of (S)-7-(4-{4-[4-(4-chlorophenoxymethyl)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Yellow Powder
  Melting point: 228.6° C.

Example 240

Preparation of (S)-2-nitro-7-(4-{4-[3-(4-trifluoromethoxybenzyloxy)benzyl]piperazin-1-yl}phenoxymethyl)-6,7-dihydro-5H-imidazo[2,1-b][1,3]oxazine The title compound was prepared in the same manner as in Example 3 using suitable starting materials.
Yellow Powder
  Melting point: 156.6-158.3° C.

Example 241

Preparation of (S)-2-nitro-7-(4-{4-[3-(4-trifluoromethylbenzyloxy)benzyl]piperazin-1-yl}phenoxymethyl)-6,7-dihydro-5H-imidazo[2,1-b][1,3]oxazine The title compound was prepared in the same manner as in Example 3 using suitable starting materials.
Yellow Powder
  Melting point: 188.0-188.5° C.

Example 242

Preparation of (R)-7-(4-{1-[4-(4-chlorobenzyloxy)benzyl]piperidin-4-yloxy}phenoxymethyl)-2-nitro-6,7-dihydro-5H-imidazo[2,1-b][1,3]oxazine The title compound was prepared in the same manner as in Example 3 using suitable starting materials.
White Powder
  Melting point: 176-177° C.

Example 243

Preparation of (S)-2-nitro-7-(4-{1-[4-(4-trifluoromethoxybenzyloxy)benzyl]piperidin-4-yloxy}phenoxymethyl)-6,7-dihydro-5H-imidazo[2,1-b][1,3]oxazine The title compound was prepared in the same manner as in Example 3 using suitable starting materials.
White Powder
  Melting point: 162-164° C.

Example 244

Preparation of (S)-2-nitro-7-(4-{1-[4-(4-trifluoromethylbenzyloxy)benzyl]piperidin-4-yloxy}phenoxymethyl)-6,7-dihydro-5H-imidazo[2,1-b][1,3]oxazine The title compound was prepared in the same manner as in Example 3 using suitable starting materials.
White Powder
  Melting point: 156-158° C.

Example 245

Preparation of (S)-7-(4-{1-[4-(4-chlorobenzyloxy)benzyl]piperidin-4-yloxy}phenoxymethyl)-2-nitro-6,7-dihydro-5H-imidazo[2,1-b][1,3]oxazine The title compound was prepared in the same manner as in Example 3 using suitable starting materials.
White Powder
  Melting point: 146-148° C.

Example 246

Preparation of (S)-2-nitro-7-(4-{4-[4-(4-trifluoromethylbenzyloxy)phenoxy]piperidin-1-yl}phenoxymethyl)-6,7-dihydro-5H-imidazo[2,1-b][1,3]oxazine The title compound was prepared in the same manner as in Example 69 using suitable starting materials.
White Powder
  Melting point: 187-188° C.

Example 247

Preparation of (R)-2-nitro-7-(4-{4-[4-(4-trifluoromethylbenzyloxy)phenoxy]piperidin-1-yl}phenoxymethyl)-6,7-dihydro-5H-imidazo[2,1-b][1,3]oxazine The title compound was prepared in the same manner as in Example 69 using suitable starting materials.
White Powder
  Melting point: 187-189° C.

Example 248

Preparation of (R)-2-nitro-7-(4-{4-[4-(4-trifluoromethoxyphenoxymethyl)phenyl]piperazin-1-yl}phenoxymethyl)-6,7-dihydro-5H-imidazo[2,1-b][1,3]oxazine The title compound was prepared in the same manner as in Example 1 using suitable starting materials.
Pale Brown Solid
  Melting point: 199-201° C.

Example 249

Preparation of N-methyl-N-(4-{4-[4-((R)-2-nitro-6, 7-dihydro-5H-imidazo[2,1-b][1,3]oxazin-7-yl-methoxy)phenyl]piperazin-1-yl}phenyl)-N-(4-trifluoromethylbenzyl)amine The title compound was prepared in the same manner as in Example 1 using suitable starting materials.
Colorless Solid
Melting point: 229-230° C.

Example 250

Preparation of (S)-7-(4-{4-[3-(4-chlorobenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Pale Yellow Powder
Melting point: 186.1-186.2° C.

Example 251

Preparation of (S)-2-nitro-7-(2-{4-[4-(4-trifluoromethoxyphenoxy)benzyl]piperazin-1-yl}benzooxazol-5-yloxymethyl)-6,7-dihydro-5H-imidazo[2,1-b][1,3]oxazine The title compound was prepared in the same manner as in Example 3 using suitable starting materials.
White Powder
Melting point: 165-167° C.

Example 252

Preparation of (S)-2-nitro-7-(2-{4-[4-(4-trifluoromethoxybenzyloxy)benzyl]piperazin-1-yl}benzooxazol-5-yloxymethyl)-6,7-dihydro-5H-imidazo[2,1-b][1,3]oxazine The title compound was prepared in the same manner as in Example 3 using suitable starting materials.
White Powder
Melting point: 174-176° C.

Example 253

Preparation of (R)-2-nitro-7-(2-{4-[4-(4-trifluoromethoxybenzyloxy)benzyl]piperazin-1-yl}benzooxazol-5-yloxymethyl)-6,7-dihydro-5H-imidazo[2,1-b][1,3]oxazine The title compound was prepared in the same manner as in Example 3 using suitable starting materials.
White Powder
Melting point: 175-176° C.

Example 254

Preparation of (S)-2-nitro-7-(4-{4-[4-(4-trifluoromethylbenzyloxy)benzyl]piperidin-1-yl}phenoxymethyl)-6,7-dihydro-5H-imidazo[2,1-b][1,3]oxazine The title compound was prepared in the same manner as in Example 86 using suitable starting materials.
Brown Powder
Melting point: 217.9-220.1° C.

Example 255

Preparation of (S)-7-(4-{(3R,5S)-3,5-dimethyl-4-[4-(4-trifluoromethoxybenzyloxy)benzyl]piperazin-1-yl}phenoxymethyl)-2-nitro-6,7-dihydro-5H-imidazo[2,1-b][1,3]oxazine The title compound was prepared in the same manner as in Example 86 using suitable starting materials.
Pale Brown Powder
Melting point: 122.1-122.6° C.

Example 256

Preparation of (R)-7-(4-{(3R,5S)-3,5-dimethyl-4-[4-(4-trifluoromethoxybenzyloxy)benzyl]piperazin-1-yl}phenoxymethyl)-2-nitro-6,7-dihydro-5H-imidazo[2,1-b][1,3]oxazine The title compound was prepared in the same manner as in Example 86 using suitable starting materials.
Pale Brown Powder
Melting point: 125.1° C.

Example 257

Preparation of (S)-2-nitro-7-[4-(4-{4-[2-(4-trifluoromethoxyphenyl)ethyl]benzyl}piperazin-1-yl)phenoxymethyl]-6,7-dihydro-5H-imidazo[2,1-b][1,3]oxazine The title compound was prepared in the same manner as in Example 3 using suitable starting materials.
Pale Yellow Powder
Melting point: 178.0-178.6° C.

Example 258

Preparation of (S)-2-nitro-7-[4-(4-{4-[2-(4-trifluoromethylphenyl)ethyl]benzyl}piperazin-1-yl)phenoxymethyl]-6,7-dihydro-5H-imidazo[2,1-b][1,3]oxazine The title compound was prepared in the same manner as in Example 3 using suitable starting materials.
Pale Yellow Powder
Melting point: 193.8° C.

Example 259

Preparation of (S)-2-nitro-7-[4-(4-{4-[3-(4-trifluoromethylphenyl)propoxy]benzyl}piperazin-1-yl)phenoxymethyl]-6,7-dihydro-5H-imidazo[2,1-b][1,3]oxazine The title compound was prepared in the same manner as in Example 3 using suitable starting materials.
Pale Yellow Powder
Melting point: 164.7-164.8° C.

Example 260

Preparation of (S)-7-[4-(4-{4-[3-(4-chlorophenyl) propoxy]benzyl}piperazin-1-yl)phenoxymethyl]-2-nitro-6,7-dihydro-5H-imidazo[2,1-b][1,3]oxazine The title compound was prepared in the same manner as in Example 3 using suitable starting materials.
Pale Yellow Powder
Melting point: 200.2-200.6° C.

Example 261

Preparation of (S)-2-nitro-7-(4-{4-[4-(4-trifluoromethylbenzyloxy)benzyl]piperazin-1-yl}phenoxymethyl)-6,7-dihydro-5H-imidazo[2,1-b][1,3]oxazine The title compound was prepared in the same manner as in Example 3 using suitable starting materials.
Pale Yellow Powder
Melting point: 208° C.

Example 262

Preparation of (S)-7-(4-{4-[4-(4-chlorobenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Pale Yellow Powder
Melting point: 229.9° C.

Example 263

Preparation of N-{1-[4-((S)-2-nitro-6,7-dihydro-5H-imidazo[2,1-b][1,3]oxazin-7-ylmethoxy)phenyl]piperidin-4-yl}-N-[4-(4-trifluoromethoxybenzyloxy)phenyl]amine The title compound was prepared in the same manner as in Example 3 using suitable starting materials.
Powder
Melting point: 228-229° C.

Example 264

Preparation of (S)-2-nitro-7-[4-(4-{4-[3-(4-trifluoromethoxyphenyl)propoxy]benzyl}piperazin-1-yl)phenoxymethyl]-6,7-dihydro-5H-imidazo[2,1-b][1,3]oxazine The title compound was prepared in the same manner as in Example 3 using suitable starting materials.
Yellow Powder
Melting point: 159.4-161.7° C.

Example 265

Preparation of (4-{4-[4-((S)-2-nitro-6,7-dihydro-5H-imidazo[2,1-b][1,3]oxazin-7-ylmethoxy)phenyl]piperazin-1-ylmethyl}phenyl)carbamic acid tert-butyl ester The title compound was prepared in the same manner as in Example 3 using suitable starting materials.
White Powder
Melting point: 191.4-191.9° C.

Example 266

Preparation of N-methyl-N-{1-[4-((S)-2-nitro-6,7-dihydro-5H-imidazo[2,1-b][1,3]oxazin-7-ylmethoxy)phenyl]piperidin-4-yl}-N-[4-(4-trifluoromethoxybenzyloxy)phenyl]amine N-{1-[4-((S)-2-Nitro-6,7-dihydro-5H-imidazo[2,1-b][1,3]oxazin-7-ylmethoxy)phenyl]piperidin-4-yl}-N-[4-(4-trifluoromethoxybenzyloxy)phenyl]amine (0.30 g) was suspended in 1,2-dichloroethane (2 ml). A 37% formaldehyde aqueous solution (0.362 ml) and sodium triacetoxyborohydride (149 mg) were added to the suspension and stirred at room temperature overnight. A 37% formaldehyde aqueous solution (0.362 ml) and sodium triacetoxyborohydride (149 mg) were further added thereto and stirred at room temperature for 1 day. A sodium hydrogen carbonate aqueous solution was added to the reaction mixture, followed by extraction with ethyl acetate. The organic layer was dried over sodium sulfate and concentrated under reduced pressure. The residue was purified by silica gel column chromatography (ethyl acetate:hexane=2:1→methylene chloride:methanol=4:1) and crystallized from ether to afford the title compound as a pale yellow powder (130 mg).
Melting point: 143-145° C.

Example 267

Preparation of N-ethyl-N-{1-[4-((S)-2-nitro-6,7-dihydro-5H-imidazo[2,1-b][1,3]oxazin-7-ylmethoxy)phenyl]piperidin-4-yl}-N-[4-(4-trifluoromethoxybenzyloxy)phenyl]amine The title compound was prepared in the same manner as in Example 226 using suitable starting materials.
Pale Yellow Powder
Melting point: 147-150° C.

Example 268

Preparation of (R)-7-(4-{(3R,5S)-3,5-dimethyl-4-[3-(4-trifluoromethylphenyl)propyl]piperazin-1-yl}phenoxymethyl)-2-nitro-6,7-dihydro-5H-imidazo[2,1-b][1,3]oxazine The title compound was prepared in the same manner as in Example 86 using suitable starting materials.
Yellow Powder
Melting point: 190.6-191.4° C.

Example 269

Preparation of (S)-7-(4-{(3R,5S)-3,5-dimethyl-4-[3-(4-trifluoromethylphenyl)propyl]piperazin-1-yl}phenoxymethyl)-2-nitro-6,7-dihydro-5H-imidazo[2,1-b][1,3]oxazine The title compound was prepared in the same manner as in Example 86 using suitable starting materials.
Yellow Powder
Melting point: 190.6-191.5° C.

Example 270

Preparation of (S)-2-nitro-7-(4-{4-[5-(4-trifluoromethoxyphenyl)pentyl]piperazin-1-yl}phenoxymethyl)-6,7-dihydro-5H-imidazo[2,1-b][1,3]oxazine The title compound was prepared in the same manner as in Example 3 using suitable starting materials.
Pale Yellow Powder
Melting point: 165-168° C.

Example 271

Preparation of (R)-2-nitro-7-(4-{4-[5-(4-trifluoromethoxyphenyl)pentyl]piperazin-1-yl}phenoxymethyl)-6,7-dihydro-5H-imidazo[2,1-b][1,3]oxazine The title compound was prepared in the same manner as in Example 3 using suitable starting materials.
Pale Yellow Powder
Melting point: 166-168° C.

Example 272

Preparation of (S)-2-nitro-7-{2-[4-(4-trifluoromethoxyphenoxy)benzyl]-2,3-dihydro-1H-isoindol-5-yloxymethyl}-6,7-dihydro-5H-imidazo[2,1-b][1,3]oxazine The title compound was prepared in the same manner as in Example 3 using suitable starting materials.
White Powder
Melting point: 160-162° C.

Example 273

Preparation of (S)-2-nitro-7-{2-[4-(4-trifluoromethoxybenzyloxy)benzyl]-2,3-dihydro-1H-isoindol-5-yloxymethyl}-6,7-dihydro-5H-imidazo[2,1-b][1,3]oxazine The title compound was prepared in the same manner as in Example 3 using suitable starting materials.
White Powder
Melting point: 161-163° C.

Example 274

Preparation of (S)-2-nitro-7-(4-{4-[4-(4-trifluoromethoxybenzyloxy)benzyl]piperidin-1-yl}phenoxymethyl)-6,7-dihydro-5H-imidazo[2,1-b][1,3]oxazine The title compound was prepared in the same manner as in Example 86 using suitable starting materials.
Yellow Powder
Melting point: 210.2-212.2° C.

Example 275

Preparation of N-ethyl-N-{1-[4-((R)-2-nitro-6,7-dihydro-5H-imidazo[2,1-b][1,3]oxazin-7-ylmethoxy)phenyl]piperidin-4-yl}-N-[4-(4-trifluoromethoxybenzyloxy)phenyl]amine N-{1-[4-((R)-2-Nitro-6,7-dihydro-5H-imidazo[2,1-b][1,3]oxazin-7-ylmethoxy)phenyl]piperidin-4-yl}-N-[4-(4-trifluoromethoxybenzyloxy)phenyl]amine (0.47 g) was suspended in 1,2-dichloroethane (5 ml). Acetaldehyde (0.41 ml) and sodium triacetoxyborohydride (0.46 g) were added to the suspension, and the mixture was stirred at room temperature for 3 days. A potassium carbonate aqueous solution was added to the reaction mixture, followed by extraction with methylene chloride. The organic layer was washed with a saturated sodium chloride aqueous solution, dried over sodium sulfate, and then concentrated under reduced pressure. The residue was purified by medium pressure silica gel column chromatography (methylene chloride:methanol=10:0→methylene chloride:methanol=9:1) and recrystallized from methanol to afford the title compound as a yellow powder (0.25 g).
Melting point: 95.2-97.0° C.

Example 276

Preparation of N-ethyl-N-{1-[4-((R)-2-nitro-6,7-dihydro-5H-imidazo[2,1-b][1,3]oxazin-7-ylmethoxy)phenyl]piperidin-4-yl}-N-[4-(4-trifluoromethylbenzyloxy)phenyl]amine The title compound was prepared in the same manner as in Example 275 using suitable starting materials.
Brown Solid
Melting point: 88.7-90.2° C.

Example 277

Preparation of (R)-2-nitro-7-{2-[4-(4-trifluoromethoxyphenoxy)benzyl]-2,3-dihydro-1H-isoindol-5-yloxymethyl}-6,7-dihydro-5H-imidazo[2,1-b][1,3]oxazine The title compound was prepared in the same manner as in Example 3 using suitable starting materials.
White Powder
Melting point: 161-164° C.

Example 278

Preparation of (R)-2-nitro-7-{2-[4-(4-trifluoromethoxybenzyloxy)benzyl]-2,3-dihydro-1H-isoindol-5-yloxymethyl}-6,7-dihydro-5H-imidazo[2,1-b][1,3]oxazine The title compound was prepared in the same manner as in Example 3 using suitable starting materials.
White Powder
Melting point: 160-163° C.

Example 279

Preparation of (R)-2-nitro-7-(4-{4-[4-(4-trifluoromethoxybenzyloxy)phenoxymethyl]piperidin-1-yl}phenoxymethyl)-6,7-dihydro-5H-imidazo[2,1-b][1,3]oxazine The title compound was prepared in the same manner as in Example 69 using suitable starting materials.
Pale Yellow Powder
Melting point: 210-215° C.

Example 280

Preparation of (R)-2-nitro-7-[4-(4-{4-[2-(4-trifluoromethylphenyl)ethyl]benzyl}piperazin-1-yl)phenoxymethyl]-6,7-dihydro-5H-imidazo[2,1-b][1,3]oxazine The title compound was prepared in the same manner as in Example 3 using suitable starting materials.
Yellow Powder
Melting point: 187.6-188.8° C.

Example 281

Preparation of (R)-2-nitro-7-{4'-[4-(4-trifluoromethoxyphenoxy)piperidin-1-ylmethyl]biphenyl-4-yloxymethyl}-6,7-dihydro-5H-imidazo[2,1-b][1,3]oxazine The title compound was prepared in the same manner as in Example 86 using suitable starting materials.
Pale Brown Powder
Melting point: 200.4-201.4° C.

Example 282

Preparation of (S)-2-nitro-7-{4'-[4-(4-trifluoromethoxyphenoxy)piperidin-1-ylmethyl]biphenyl-4-yloxymethyl}-6,7-dihydro-5H-imidazo[2,1-b][1,3]oxazine The title compound was prepared in the same manner as in Example 86 using suitable starting materials.
Pale Brown Powder
Melting point: 196.9-198.0° C.

Example 283

Preparation of (S)-2-nitro-7-(4-{4-[4-(4-trifluoromethoxybenzyloxy)phenoxymethyl]piperidin-1-yl}phenoxymethyl)-6,7-dihydro-5H-imidazo[2,1-b][1,3]oxazine The title compound was prepared in the same manner as in Example 69 using suitable starting materials.
Brown Powder
Melting point: 193-196° C.

Example 284

Preparation of (R)-7-(4-{(3R,5S)-3,5-dimethyl-4-[4-(4-trifluoromethylbenzyloxy)benzyl]piperazin-1-yl}phenoxymethyl)-2-nitro-6,7-dihydro-5H-imidazo[2,1-b][1,3]oxazine The title compound was prepared in the same manner as in Example 86 using suitable starting materials.
Brown Powder
Melting point: 112.8° C.

Example 285

Preparation of (S)-7-(4-{(3R,5S)-3,5-dimethyl-4-[4-(4-trifluoromethylbenzyloxy)benzyl]piperazin-1-yl}phenoxymethyl)-2-nitro-6,7-dihydro-5H-imidazo[2,1-b][1,3]oxazine The title compound was prepared in the same manner as in Example 86 using suitable starting materials.
Brown Powder
Melting point: 111.5° C.

Example 286

Preparation of (S)-2-nitro-7-(2-{4-[4-(4-trifluoromethoxybenzyloxy)benzyl]piperidin-1-yl}benzothiazol-6-yloxymethyl)-6,7-dihydro-5H-imidazo[2,1-b][1,3]oxazine The title compound was prepared in the same manner as in Example 69 using suitable starting materials.
Pale Yellow Powder
Melting point: 190-191° C.

Example 287

Preparation of (R)-2-nitro-7-(2-{4-[4-(4-trifluoromethoxybenzyloxy)benzyl]piperidin-1-yl}benzothiazol-6-yloxymethyl)-6,7-dihydro-5H-imidazo[2,1-b][1,3]oxazine The title compound was prepared in the same manner as in Example 69 using suitable starting materials.
Pale Yellow Powder
Melting point: 190-191° C.

Example 288

Preparation of 7-((S)-2-nitro-6,7-dihydro-5H-imidazo[2,1-b][1,3]oxazin-7-ylmethoxy)-2-[4-(4-trifluoromethoxyphenoxy)benzyl]-1,2,3,4-tetrahydroisoquinoline The title compound was prepared in the same manner as in Example 3 using suitable starting materials.
White Powder
Melting point: 147-150° C.

Example 289

Preparation of 7-((S)-2-nitro-6,7-dihydro-5H-imidazo[2,1-b][1,3]oxazin-7-ylmethoxy)-2-[4-(4-trifluoromethoxybenzyloxy)benzyl]-1,2,3,4-tetrahydroisoquinoline The title compound was prepared in the same manner as in Example 3 using suitable starting materials.
Pale Yellow Powder
Melting point: 150-154° C.

Example 290

Preparation of N-(4-{4-[4-((S)-2-nitro-6,7-dihydro-5H-imidazo[2,1-b][1,3]oxazin-7-ylmethoxy)phenyl]piperazin-1-ylmethyl}phenyl)-N-(4-trifluoromethylbenzyl)amine The title compound was prepared in the same manner as in Example 3 using suitable starting materials.
Yellow Powder
Melting point: 215.8-217.1° C.

Example 291

Preparation of 7-((R)-2-nitro-6,7-dihydro-5H-imidazo[2,1-b][1,3]oxazin-7-ylmethoxy)-2-[4-(4-trifluoromethoxyphenoxy)benzyl]-1,2,3,4-tetrahydroisoquinoline The title compound was prepared in the same manner as in Example 3 using suitable starting materials.
White Powder
Melting point: 149-151° C.

Example 292

Preparation of 7-((R)-2-nitro-6,7-dihydro-5H-imidazo[2,1-b][1,3]oxazin-7-ylmethoxy)-2-[4-(4-trifluoromethoxybenzyloxy)benzyl]-1,2,3,4-tetrahydroisoquinoline The title compound was prepared in the same manner as in Example 3 using suitable starting materials.
Pale Yellow Powder
Melting point: 149-152° C.

Example 293

Preparation of N-methyl-N-(4-{4-[4-((S)-2-nitro-6,7-dihydro-5H-imidazo[2,1-b][1,3]oxazin-7-ylmethoxy)phenyl]piperazin-1-ylmethyl}phenyl)-N-(4-trifluoromethylbenzyl)amine The title compound was prepared in the same manner as in Example 213 using suitable starting materials.
White Powder
Melting point: 168.5-169.0° C.

Example 294

Preparation of (R)-7-(4-{4-[4-(2,4-bis-trifluoromethylbenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Yellow Powder
Melting point: 185.4-186.3° C.

Example 295

Preparation of (S)-7-(4-{4-[4-(2,4-bis-trifluoromethylbenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Yellow Powder
Melting point: 184.5-185.8° C.

Example 296

Preparation of (R)-2-nitro-7-(4-{4-[4-(4-trifluoromethoxybenzyloxy)phenyl]piperazin-1-ylmethyl}phenoxymethyl)-6,7-dihydro-5H-imidazo[2,1-b][1,3]oxazine The title compound was prepared in the same manner as in Example 190 using suitable starting materials.
Yellow Powder
Melting point: 212-214° C.

Example 297

Preparation of (R)-2-nitro-7-(4-{4-[4-(4-trifluoromethoxyphenoxy)phenyl]piperazin-1-ylmethyl}phenoxymethyl)-6,7-dihydro-5H-imidazo[2,1-b][1,3]oxazine The title compound was prepared in the same manner as in Example 190 using suitable starting materials.
Yellow Powder
Melting point: 140-142° C.

Example 298

Preparation of (4-{4-[4-((R)-2-nitro-6,7-dihydro-5H-imidazo[2,1-b][1,3]oxazin-7-ylmethoxy)phenyl]piperazin-1-ylmethyl}phenyl)carbamic acid tert-butyl ester The title compound was prepared in the same manner as in Example 3 using suitable starting materials.
Pale Yellow Powder
Melting point: 190.5-190.7° C.

Example 299

Preparation of (R)-7-(4-{(R)-3-methyl-4-[4-(4-trifluoromethylbenzyloxy)benzyl]piperazin-1-yl}phenoxymethyl)-2-nitro-6,7-dihydro-5H-imidazo[2,1-b][1,3]oxazine The title compound was prepared in the same manner as in Example 86 using suitable starting materials.
Pale Brown Powder
Melting point: 151.0-152.2° C.

Example 300

Preparation of (S)-7-(4-{(R)-3-methyl-4-[4-(4-trifluoromethylbenzyloxy)benzyl]piperazin-1-yl}phenoxymethyl)-2-nitro-6,7-dihydro-5H-imidazo[2,1-b][1,3]oxazine The title compound was prepared in the same manner as in Example 86 using suitable starting materials.
Pale Brown Powder
Melting point: 156.8-158.3° C.

Example 301

Preparation of 6-((S)-2-nitro-6,7-dihydro-5H-imidazo[2,1-b][1,3]oxazin-7-ylmethoxy)-2-[4-(4-trifluoromethoxyphenoxy)benzyl]-1,2,3,4-tetrahydroisoquinoline The title compound was prepared in the same manner as in Example 3 using suitable starting materials.
White Powder
Melting point: 196-198° C.

Example 302

Preparation of (R)-3-methyl-4-[4-((R)-2-nitro-6,7-dihydro-5H-imidazo[2,1-b][1,3]oxazin-7-ylmethoxy)phenyl]piperazine-1-carboxylic acid tert-butyl ester The title compound was prepared in the same manner as in Example 86 using suitable starting materials.
Brown Powder
Melting point: 196.4° C.

Example 303

Preparation of 6-((R)-2-nitro-6,7-dihydro-5H-imidazo[2,1-b][1,3]oxazin-7-ylmethoxy)-2-[4-(4-trifluoromethoxybenzyloxy)benzyl]-1,2,3,4-tetrahydroisoquinoline The title compound was prepared in the same manner as in Example 3 using suitable starting materials.
White Powder
Melting point: 212-215° C.

Example 304

Preparation of 6-((R)-2-nitro-6,7-dihydro-5H-imidazo[2,1-b][1,3]oxazin-7-ylmethoxy)-2-[4-(4-trifluoromethylbenzyloxy)benzyl]-1,2,3,4-tetrahydroisoquinoline The title compound was prepared in the same manner as in Example 3 using suitable starting materials.
White Powder
Melting point: 209-211° C.

Example 305

Preparation of 7-((S)-2-nitro-6,7-dihydro-5H-imidazo[2,1-b][1,3]oxazin-7-ylmethoxy)-2-[4-(4-trifluoromethoxyphenoxy)benzyl]-2,3,4,5-tetrahydro-1H-benzo[c]azepine The title compound was prepared in the same manner as in Example 3 using suitable starting materials.
White Powder
Melting point: 196-198° C.

Example 306

Preparation of 7-((S)-2-nitro-6,7-dihydro-5H-imidazo[2,1-b][1,3]oxazin-7-ylmethoxy)-2-[4-(4-trifluoromethoxybenzyloxy)benzyl]-2,3,4,5-tetrahydro-1H-benzo[c]azepine The title compound was prepared in the same manner as in Example 3 using suitable starting materials.
White Powder
Melting point: 216-218° C.

Example 307

Preparation of N-(4-{4-[4-((R)-2-nitro-6,7-dihydro-5H-imidazo[2,1-b][1,3]oxazin-7-ylmethoxy)phenyl]piperazin-1-ylmethyl}phenyl)-N-(4-trifluoromethylbenzyl)amine The title compound was prepared in the same manner as in Example 3 using suitable starting materials.
Yellow Powder
Melting point: 216.0-217.7° C.

Example 308

Preparation of (R)-7-(4-{(S)-3-methyl-4-[4-(4-trifluoromethylbenzyloxy)benzyl]piperazin-1-yl}phenoxymethyl)-2-nitro-6,7-dihydro-5H-imidazo[2,1-b][1,3]oxazine The title compound was prepared in the same manner as in Example 86 using suitable starting materials.
Pale Brown Powder
Melting point: 155.9° C.

Example 309

Preparation of (S)-7-(4-{(S)-3-methyl-4-[4-(4-trifluoromethylbenzyloxy)benzyl]piperazin-1-yl}phenoxymethyl)-2-nitro-6,7-dihydro-5H-imidazo[2,1-b][1,3]oxazine The title compound was prepared in the same manner as in Example 86 using suitable starting materials.
Pale Brown Powder
Melting point: 150.6° C.

Example 310

Preparation of (R)-7-(4-{(R)-2-methyl-4-[4-(4-trifluoromethoxybenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Pale Yellow Powder
Melting point: 164.5° C.

Example 311

Preparation of (R)-7-(4-{(R)-2-methyl-4-[4-(4-trifluoromethylbenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Pale Yellow Powder
Melting point: 154.3° C.

Example 312

Preparation of (R)-7-(4-{4-[4-(2-fluoro-4-trifluoromethylbenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Pale Brown Powder
Melting point: 166.4-167.2° C.

Example 313

Preparation of (S)-7-(4-{4-[4-(2-fluoro-4-trifluoromethylbenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Pale Brown Powder
Melting point: 166.4-167.8° C.

Example 314

Preparation of N-(4-{4-[4-((R)-2-nitro-6,7-dihydro-5H-imidazo[2,1-b][1,3]oxazin-7-ylmethoxy)phenyl]piperazin-1-ylmethyl}phenyl)-N-(4-trifluoromethoxybenzyl)amine The title compound was prepared in the same manner as in Example 3 using suitable starting materials.
Yellow Powder
Melting point: 226.3-228.2° C.

Example 315

Preparation of N-methyl-N-(4-{4-[4-((R)-2-nitro-6,7-dihydro-5H-imidazo[2,1-b][1,3]oxazin-7-ylmethoxy)phenyl]piperazin-1-ylmethyl}phenyl)-N-(4-trifluoromethylbenzyl)amine The title compound was prepared in the same manner as in Example 213 using suitable starting materials.
Yellow Powder
Melting point: 179.6-179.7° C.

Example 316

Preparation of 7-((R)-2-nitro-6,7-dihydro-5H-imidazo[2,1-b][1,3]oxazin-7-ylmethoxy)-2-[4-(4-trifluoromethoxyphenoxy)benzyl]-2,3,4,5-tetrahydro-1H-benzo[c]azepine The title compound was prepared in the same manner as in Example 3 using suitable starting materials.
White Powder
Melting point: 195-196° C.

Example 317

Preparation of 7-((R)-2-nitro-6,7-dihydro-5H-imidazo[2,1-b][1,3]oxazin-7-ylmethoxy)-2-[4-(4-trifluoromethoxybenzyloxy)benzyl]-2,3,4,5-tetrahydro-1H-benzo[c]azepine The title compound was prepared in the same manner as in Example 3 using suitable starting materials.
White Powder
Melting point: 215-217° C.

Example 318

Preparation of (S)-3-methyl-4-[4-((R)-2-nitro-6,7-dihydro-5H-imidazo[2,1-b][1,3]oxazin-7-ylmethoxy)phenyl]piperazine-1-carboxylic acid tert-butyl ester The title compound was prepared in the same manner as in Example 86 using suitable starting materials.
Yellow Powder
Melting point: 167.6° C.

Example 319

Preparation of (S)-3-methyl-4-[4-((S)-2-nitro-6,7-dihydro-5H-imidazo[2,1-b][1,3]oxazin-7-ylmethoxy)phenyl]piperazine-1-carboxylic acid tert-butyl ester The title compound was prepared in the same manner as in Example 86 using suitable starting materials.
Yellow Powder
Melting point: 195.0-195.4° C.

Example 320

Preparation of N-methyl-N-(4-{4-[4-((R)-2-nitro-6,7-dihydro-5H-imidazo[2,1-b][1,3]oxazin-7-ylmethoxy)phenyl]piperazin-1-ylmethyl}phenyl)-N-(4-trifluoromethoxybenzyl)amine The title compound was prepared in the same manner as in Example 213 using suitable starting materials.
Yellow Powder
Melting point: 184.8-184.9° C.

Example 321

Preparation of (R)-7-(4-{(S)-2-methyl-4-[4-(4-trifluoromethoxybenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Yellow Powder
Melting point: 132.5-132.8° C.

Example 322

Preparation of (R)-7-(4-{(S)-2-methyl-4-[4-(4-trifluoromethylbenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Yellow Powder
Melting point: 155.6-155.8° C.

Example 323

Preparation of (S)-7-(4-{(S)-2-methyl-4-[4-(4-trifluoromethoxybenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
White Powder
Melting point: 148.0-148.3° C.

Example 324

Preparation of (S)-7-(4-{(S)-2-methyl-4-[4-(4-trifluoromethylbenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Yellow Powder
Melting point: 163.7-164.2° C.

Example 325

Preparation of (R)-2-nitro-7-(4-{4-[4-(2,3,5,6-tetrafluoro-4-trifluoromethylbenzyloxy)benzyl]piperazin-1-yl}phenoxymethyl)-6,7-dihydro-5H-imidazo[2,1-b][1,3]oxazine The title compound was prepared in the same manner as in Example 3 using suitable starting materials.
Yellow Powder
Melting point: 172.0-172.5° C.

Example 326

Preparation of (S)-2-nitro-7-(4-{4-[4-(2,3,5,6-tetrafluoro-4-trifluoromethylbenzyloxy)benzyl]piperazin-1-yl}phenoxymethyl)-6,7-dihydro-5H-imidazo[2,1-b][1,3]oxazine The title compound was prepared in the same manner as in Example 3 using suitable starting materials.
Yellow Powder
Melting point: 171.9-172.2° C.

Example 327

Preparation of (R)-2-nitro-7-(4-{4-[4-(4-trifluoromethylphenoxy)benzyl]piperazin-1-yl}phenoxymethyl)-6,7-dihydro-5H-imidazo[2,1-b][1,3]oxazine The title compound was prepared in the same manner as in Example 3 using suitable starting materials.
Yellow Powder
Melting point: 184.6-184.9° C.

Example 328

Preparation of (R)-7-(4-[(S)-2-methyl-4-[4-(4-trifluoromethoxyphenoxy)benzyl]piperazin-1-yl]phenoxymethyl)-2-nitro-6,7-dihydro-5H-imidazo[2,1-b][1,3]oxazine The title compound was prepared in the same manner as in Example 3 using suitable starting materials.
Yellow Powder
Melting point: 147.0-147.4° C.

Example 329

Preparation of (R)-7-(4-[(S)-2-methyl-4-[4-(4-trifluoromethylphenoxy)benzyl]piperazin-1-yl]phenoxymethyl)-2-nitro-6,7-dihydro-5H-imidazo[2,1-b][1,3]oxazine The title compound was prepared in the same manner as in Example 3 using suitable starting materials.
Yellow Powder
Melting point: 158.8° C.

Example 330

Preparation of (R)-3-methyl-4-[4-((S)-2-nitro-6,7-dihydro-5H-imidazo[2,1-b][1,3]oxazin-7-ylmethoxy)phenyl]piperazine-1-carboxylic acid tert-butyl ester The title compound was prepared in the same manner as in Example 86 using suitable starting materials.
Yellow Powder
Melting point: 164.3-164.9° C.

Example 331

Preparation of N-methyl-N-{1-[4-((R)-2-nitro-6,7-dihydro-5H-imidazo[2,1-b][1,3]oxazin-7-ylmethoxy)phenyl]piperidin-4-yl}-N-[4-(4-trifluoromethoxybenzyloxy)benzyl]amine The title compound was prepared in the same manner as in Example 180 using suitable starting materials.
Pale Yellow Solid
Melting point: 181.4-184.1° C.

Example 332

Preparation of N-methyl-N-{1-[4-((S)-2-nitro-6,7-dihydro-5H-imidazo[2,1-b][1,3]oxazin-7-ylmethoxy)phenyl]piperidin-4-yl}-N-[4-(4-trifluoromethoxybenzyloxy)benzyl]amine The title compound was prepared in the same manner as in Example 180 using suitable starting materials.
Pale Yellow Solid
Melting point: 181.6-185.2° C.

Example 333

Preparation of (S)-7-(4-{(S)-2-methyl-4-[4-(4-trifluoromethoxyphenoxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Yellow Powder
Melting point: 150.0-150.3° C.

Example 334

Preparation of (S)-7-(4-{(S)-2-methyl-4-[4-(4-trifluoromethylphenoxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Yellow Powder
Melting point: 158.0-159.1° C.

Example 335

Preparation of (R)-7-(4-{(R)-2-methyl-4-[4-(4-trifluoromethoxyphenoxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Yellow Powder
Melting point: 150.2-150.6° C.

Example 336

Preparation of (R)-7-(4-{(R)-2-methyl-4-[4-(4-trifluoromethylphenoxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Yellow Powder
Melting point: 158.6-160.6° C.

Example 337

Preparation of (R)-2-nitro-7-(6-{4-[4-(4-trifluoromethoxybenzyloxy)benzyl]piperazin-1-yl}pyridin-3-yloxymethyl)-6,7-dihydro-5H-imidazo[2,1-b][1,3]oxazine The title compound was prepared in the same manner as in Example 3 using suitable starting materials.
Pale Brown Solid
Melting point: 197.7-198.0° C.

Example 338

Preparation of (S)-2-nitro-7-(6-{4-[4-(4-trifluoromethoxybenzyloxy)benzyl]piperazin-1-yl}pyridin-3-yloxymethyl)-6,7-dihydro-5H-imidazo[2,1-b][1,3]oxazine The title compound was prepared in the same manner as in Example 3 using suitable starting materials.
Pale Brown Solid
Melting point: 197-198° C.

Example 339

Preparation of (S)-7-(4-{(2S,5R)-2,5-dimethyl-4-[4-(4-trifluoromethoxyphenoxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Pale Yellow Powder
Melting point: 95-97° C.

Example 340

Preparation of (S)-7-(4-{(2S,5R)-2,5-dimethyl-4-[4-(4-trifluoromethoxybenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Pale Yellow Powder
Melting point: 127.8-129.8° C.

Example 341

Preparation of (S)-7-(4-{(2S,5R)-2,5-dimethyl-4-[4-(4-trifluoromethylbenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Pale Yellow Powder
Melting point: 124.2-125.2° C.

Example 342

Preparation of (S)-7-(4-{(R)-2-methyl-4-[4-(4-trifluoromethoxyphenoxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Yellow Powder
Melting point: 145.7-146.3° C.

Example 343

Preparation of (S)-7-(4-{(R)-2-methyl-4-[4-(4-trifluoromethylphenoxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Yellow Powder
Melting point: 153.6-154.3° C.

Example 344

Preparation of (S)-7-(4-{(R)-2-methyl-4-[4-(4-trifluoromethoxybenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
White Powder
Melting point: 151.0-151.7° C.

Example 345

Preparation of (S)-7-(4-{(R)-2-methyl-4-[4-(4-trifluoromethylbenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
Yellow Powder
Melting point: 155.1-157.2° C.

Example 346

Preparation of (R)-7-(4-{4-[3-methyl-4-(4-trifluoromethoxybenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
White Powder
Melting point: 172.9-173.8° C.

Example 347

Preparation of (R)-7-(4-{4-[3-methyl-4-(4-trifluoromethylbenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
White Powder
Melting point: 199.4-206.5° C.

Example 348

Preparation of (S)-7-(4-{4-[3-methyl-4-(4-trifluoromethoxybenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
White Powder
Melting point: 169.8-170.2° C.

Example 349

Preparation of (S)-7-(4-{4-[3-methyl-4-(4-trifluoromethylbenzyloxy)benzyl]piperazin-1-yl}phenoxymethyl)-2-nitro-6,7-dihydro-5H-imidazo[2,1-b][1,3]oxazine The title compound was prepared in the same manner as in Example 3 using suitable starting materials.
White Powder
Melting point: 161.2-162.8° C.

Example 350

Preparation of (R)-7-(4-{(2S,5R)-2,5-dimethyl-4-[4-(4-trifluoromethoxyphenoxy)benzyl]piperazin-1-yl}phenoxymethyl)-2-nitro-6,7-dihydro-5H-imidazo[2,1-b][1,3]oxazine Potassium carbonate (135 mg) and sodium iodide (146 mg) were added to an N-methylpyrrolidone solution (6 ml) of (R)-7-[4-((2S,5R)-2,5-dimethyl-piperazin-1-yl)phenoxymethyl]-2-nitro-6,7-dihydro-5H-imidazo[2,1-b][1,3]oxazine trifluoroacetate (343 mg) and 1-(chloromethyl)-4-[4-(trifluoromethoxy)phenoxy]benzene (269 mg), and the mixture was stirred at 60° C. for 3 hours. Sodium tert-butoxide (112 mg) was added to the mixture and stirred at room temperature for 3 hours. Water was added thereto, followed by extraction with ethyl acetate. The organic layer was washed with a saturated sodium chloride aqueous solution and then dried over sodium sulfate. After filtering, the filtrate was concentrated under reduced pressure. The residue was purified by silica gel column chromatography (ethyl acetate:n-hexane=1:1→ethyl acetate:n-hexane=3:1) to afford the title compound as a pale brown amorphous compound (200 mg).
1H NMR (CDCl3) δ 0.83 (d, J=6.1 Hz, 3H), 1.14 (d, J=6.3 Hz, 3H), 2.04 (t, J=8.9 Hz, 1H), 2.26-2.54 (m, 2H), 2.55-2.73 (m, 2H), 2.82 (dd, J=12.0 Hz, 2.9 Hz, 1H), 2.93-3.17 (m, 2H), 3.22 (d, J=13.4 Hz, 1H), 4.02 (d, J=13.4 Hz, 1H), 4.06-4.35 (m, 4H), 4.65-4.78 (m, 1H), 6.84 (d, J=8.9 Hz, 2H), 6.90-7.11 (m, 6H), 7.18 (d, J=8.8 Hz, 2H), 7.34 (d, J=8.5 Hz, 2H), 7.44 (s, 1H).

Example 351

Preparation of (R)-7-(4-{(2S,5R)-2,5-dimethyl-4-[4-(4-trifluoromethoxybenzyloxy)benzyl]piperazin-1-yl}phenoxymethyl)-2-nitro-6,7-dihydro-5H-imidazo[2,1-b][1,3]oxazine The title compound was prepared in the same manner as in Example 350 using suitable starting materials.
Pale Brown Amorphous
Melting point: 119.5-121.5° C.

1H NMR (CDCl3) δ 0.81 (d, J=6.1 Hz, 3H), 1.13 (d, J=5.9 Hz, 3H), 1.91-2.06 (m, 1H), 2.22-2.54 (m, 2H), 2.54-2.83 (m, 3H), 2.94-3.10 (m, 2H), 3.19 (d, J=13.1 Hz, 1H), 3.89-4.34 (m, 5H), 4.62-4.77 (m. 1H), 5.06 (s, 2H), 6.84 (d, J=8.9 Hz, 2H), 6.93 (d, J=8.6 Hz, 2H), 7.04 (d, J=8.9 Hz, 2H), 7.18-7.32 (m, 4H), 7.40-7.55 (m, 3H).

Example 352

Preparation of (R)-7-(4-{(2S,5R)-2,5-dimethyl-4-[4-(4-trifluoromethylbenzyloxy)benzyl]piperazin-1-yl}phenoxymethyl)-2-nitro-6,7-dihydro-5H-imidazo[2,1-b][1,3]oxazine The title compound was prepared in the same manner as in Example 350 using suitable starting materials.
Pale Brown Amorphous
Melting point: 108-110° C.
1H NMR (CDCl3) δ 0.81 (d, J=6.1 Hz, 3H), 1.13 (d, J=6.0 Hz, 3H), 1.93-2.07 (m, 1H), 2.26-2.52 (m, 2H), 2.56-2.83 (m, 3H), 2.92-3.14 (m, 2H), 3.19 (d, J=13.2 Hz, 1H), 3.99 (d, J=13.2 Hz, 1H), 4.05-4.34 (m, 4H), 4.66-4.79 (m, 1H), 5.13 (s, 2H), 6.83 (d, J=8.9 Hz, 2H), 6.93 (d, J=8.6 Hz, 2H), 7.04 (d, J=8.9 Hz, 2H), 7.18-7.28 (m, 2H), 7.45 (s, 1H), 7.56 (d, J=8.2 Hz, 2H), 7.65 (d, J=8.2 Hz, 2H).

Example 353

Preparation of (R)-2-nitro-7-(4'-{4-[4-(4-trifluoromethoxybenzyloxy)benzyl]piperazin-1-yl}biphenyl-4-yloxymethyl)-6,7-dihydro-5H-imidazo[2,1-b][1,3]oxazine The title compound was prepared in the same manner as in Example 3 using suitable starting materials.
Pale Yellow Solid
Melting point: 249.6-252.8° C.

Example 354

Preparation of (S)-2-nitro-7-(4'-{4-[4-(4-trifluoromethoxybenzyloxy)benzyl]piperazin-1-yl}biphenyl-4-yloxymethyl)-6,7-dihydro-5H-imidazo[2,1-b][1,3]oxazine The title compound was prepared in the same manner as in Example 3 using suitable starting materials.
Pale Yellow Solid
Melting point: 222.6-222.9° C.

Example 355

Preparation of N-methyl-N-{1-[4-((R)-2-nitro-6,7-dihydro-5H-imidazo[2,1-b][1,3]oxazin-7-ylmethoxy)phenyl]piperidin-4-ylmethyl}-N-[4-(4-trifluoromethoxybenzyloxy)phenyl]amine The title compound was prepared in the same manner as in Example 1 using suitable starting materials.
Pale Yellow Solid
Melting point: 167.0-170.1° C.

Example 356

Preparation of N-methyl-N-{1-[4-((S)-2-nitro-6,7-dihydro-5H-imidazo[2,1-b][1,3]oxazin-7-ylmethoxy)phenyl]piperidin-4-ylmethyl}-N-[4-(4-trifluoromethoxybenzyloxy)phenyl]amine The title compound was prepared in the same manner as in Example 1 using suitable starting materials.
Pale Yellow Solid
Melting point: 170-171° C.

Example 357

Preparation of (S)-2-nitro-7-(4-{5-[4-(4-trifluoromethoxyphenoxy)benzyl]-2,5-diazabicyclo[2.2.1]hept-2-yl}phenoxymethyl)-6,7-dihydro-5H-imidazo[2,1-b][1,3]oxazine The title compound was prepared in the same manner as in Example 350 using suitable starting materials.
Pale Brown Powder
Melting point: 127-129° C.

Example 358

Preparation of (S)-2-nitro-7-(4-{5-[4-(4-trifluoromethoxybenzyloxy)benzyl]-2,5-diazabicyclo[2.2.1]hept-2-yl}phenoxymethyl)-6,7-dihydro-5H-imidazo[2,1-b][1,3]oxazine The title compound was prepared in the same manner as in Example 350 using suitable starting materials.
Powder
Melting point: 142-145° C.

Example 359

Preparation of (R)-2-nitro-7-(4-{5-[4-(4-trifluoromethoxyphenoxy)benzyl]-2,5-diazabicyclo[2.2.1]hept-2-yl}phenoxymethyl)-6,7-dihydro-5H-imidazo[2,1-b][1,3]oxazine The title compound was prepared in the same manner as in Example 350 using suitable starting materials.
Pale Brown Powder
Melting point: 165-168° C.

Example 360

Preparation of (R)-2-nitro-7-(4-{5-[4-(4-trifluoromethoxybenzyloxy)benzyl]-2,5-diazabicyclo[2.2.1]hept-2-yl}phenoxymethyl)-6,7-dihydro-5H-imidazo[2,1-b][1,3]oxazine The title compound was prepared in the same manner as in Example 350 using suitable starting materials.
Pale Brown Powder
Melting point: 172-174° C.

Example 361

Preparation of 7-{4-[2-(4-chlorophenoxymethyl)oxazol-4-yl]phenoxymethyl}-2-nitro-6,7-dihydro-5H-imidazo[2,1-b][1,3]oxazine An ethanol solution (0.45 ml) of 20% sodium ethoxide was added to an ethanol solution (10 ml) of toluene-4-sulfonic acid 4-(2-chloro-4-nitroimidazol-1-yl)-2-hydroxybutyl ester (0.52 g), and the mixture was stirred at room temperature for 30 minutes. 4-[2-(4-Chlorophenoxymethyl)oxazol-4-yl]phenol (0.40 g) and tripotassium phosphate (0.34 g) were added to the reaction mixture, and the resulting mixture was heated under reflux for 2 hours. Water was added thereto and the precipitated solid was collected by filtration and dried at 60° C. The residue thus obtained was dissolved in dimethylformamide (3 ml), and sodium hydride (53 mg) was added thereto, followed by stirring at room temperature for 1 hour. Water was added to the reaction mixture, followed by extraction with methylene chloride. The organic layer was dried over magnesium sulfate. After filtering, the filtrate was concentrated under reduced pressure. The residue was purified by silica gel column chromatography (methylene chloride:methanol=10:0→methylene chloride:methanol=9:1) to afford the title compound as a pale yellow powder (0.34 g).
Melting point: 199-200° C.

Example 362

Preparation of (R)-7-{4-[2-(4-chlorophenoxymethyl)oxazol-4-yl]phenoxymethyl}-2-nitro-6,7-dihydro-5H-imidazo[2,1-b][1,3]oxazine The title compound was prepared in the same manner as in Example 361 using suitable starting materials.
Pale Yellow Powder
Melting point: 214-215° C.

Example 363

Preparation of (R)-2-nitro-7-{4-[1-(4-trifluoromethoxybenzyl)piperidin-4-yl]phenoxymethyl}-6,7-dihydro-5H-imidazo[2,1-b][1,3]oxazine Trifluoroacetic acid (6 ml) was added to 4-[4-((R)-2-nitro-6,7-dihydro-5H-imidazo[2,1-b][1,3]oxazin-7-ylmethoxy)phenyl]piperidine-1-carboxylic acid tert-butyl ester (2.0 g), and the mixture was stirred at room temperature for 40 minutes. The reaction mixture was concentrated under reduced pressure. Methylene chloride (6 ml) and triethylamine (6 ml) were added to the residue, and the mixture was stirred at room temperature for 10 minutes. The reaction mixture was reconcentrated under reduced pressure. N-Methylpyrrolidone (6 ml), 4-(trifluoromethoxy)benzaldehyde (0.93 ml) and sodium triacetoxyborohydride (1.39 g) were added to the residue, and the mixture was stirred at room temperature for 3 hours. A 20% sodium carbonate aqueous solution (20 ml) and water (20 ml) were added to the reaction mixture, followed by stirring. The insoluble matter generated was collected by filtration. The residue thus obtained was washed with water and hexane, and then dried. Subsequently, the residue was suspended in ethyl acetate-isopropyl ether (1:1), and the suspension was stirred at room temperature, followed by collection by filtration. The residue was then dried to afford the title compound as a reddish brown solid (2.39 g).
Melting point: 183-184° C.

Example 364

Preparation of 2-nitro-7-{4-[1-(4-trifluoromethoxybenzyl)piperidin-4-yl]phenoxymethyl}-6,7-dihydro-5H-imidazo[2,1-b][1,3]oxazine The title compound was prepared in the same manner as in Example 363 using suitable starting materials.
Pale Yellow Solid
Melting point: 178.6-180.2° C.

Example 365

Preparation of N-{1-[4-((R)-2-nitro-6,7-dihydro-5H-imidazo[2,1-b][1,3]oxazin-7-ylmethoxy)phenyl]piperidin-4-yl}-N-(4-trifluoromethylphenyl)amine The title compound was prepared in the same manner as in Example 86 using suitable starting materials.
Yellowish Orange Powder
Melting point: 214-216° C.

Example 366

Preparation of (R)-2-nitro-7-(4-{4-[2-(4-trifluoromethylphenoxy)ethyl]piperidin-1-yl}phenoxymethyl)-6,7-dihydro-5H-imidazo[2,1-b][1,3]oxazine The title compound was prepared in the same manner as in Example 86 using suitable starting materials.
Yellow Solid
Melting point: 172.9-173.1° C.

Example 367

Preparation of (R)-2-nitro-7-{4-[4-(4-trifluoromethylbenzyloxy)piperidin-1-yl]phenoxymethyl}-6,7-dihydro-5H-imidazo[2,1-b][1,3]oxazine The title compound was prepared in the same manner as in Example 86 using suitable starting materials.
Yellow Solid
Melting point: 186.6-197.0° C.

Example 368

Preparation of (R)-2-nitro-7-{4-[4-(4-trifluoromethylbenzyl)piperazin-1-yl]phenoxymethyl}-6,7-dihydro-5H-imidazo[2,1-b][1,3]oxazine The title compound was prepared in the same manner as in Example 363 using suitable starting materials.
Slightly Yellow Powder
Melting point: 162-164° C.

Example 369

Preparation of (R)-2-nitro-7-{4-[4-(4-trifluoromethoxybenzyl)piperazin-1-yl]phenoxymethyl}-6,7-dihydro-5H-imidazo[2,1-b][1,3]oxazine The title compound was prepared in the same manner as in Example 363 using suitable starting materials.
Pale Yellow Powder
Melting point: 188-189° C.

Example 370

Preparation of N-ethyl-N-{1-[4-((R)-2-nitro-6,7-dihydro-5H-imidazo[2,1-b][1,3]oxazin-7-ylmethoxy)phenyl]piperidin-4-yl}-N-(4-trifluoromethylphenyl)amine Acetaldehyde (2.2 ml) was added to an acetic acid solution (11 ml) of N-{1-[4-((R)-2-nitro-6,7-dihydro-5H-imidazo[2,1-b][1,3]oxazin-7-ylmethoxy)phenyl]piperidin-4-yl}-N-(4-trifluoromethylphenyl)amine (2.2 g). Subsequently, sodium triacetoxyborohydride (2.52 g) was added thereto, and the mixture was stirred at room temperature for 3 hours. The reaction mixture was poured into ice water, and neutralized with a 5 N sodium hydroxide aqueous solution and a saturated sodium hydrogen carbonate aqueous solution. The resulting precipitate was collected by filtration and dried. The solid thus obtained was purified by silica gel column chromatography (methylene chloride:ethyl acetate=50:50) and recrystallized from acetone-ethyl acetate to afford the title compound as a yellow powder (1.96 g).

Melting point: 206° C.

Example 371

Preparation of N-methyl-N-{1-[4-((R)-2-nitro-6,7-dihydro-5H-imidazo[2,1-b][1,3]oxazin-7-ylmethoxy)phenyl]piperidin-4-yl}-N-(4-trifluoromethylphenyl)amine The title compound was prepared in the same manner as in Example 370 using suitable starting materials.
Yellow Powder
Melting point: 208-209° C.

Example 372

Preparation of (R)-2-nitro-7-(4-{4-[(E)-3-(4-trifluoromethylphenyl)allyl]piperazin-1-yl}phenoxymethyl)-6,7-dihydro-5H-imidazo[2,1-b][1,3]oxazine The title compound was prepared in the same manner as in Example 363 using suitable starting materials.
White Powder
Melting point: 207-210° C.

Example 373

Preparation of N-{1-[4-((R)-2-nitro-6,7-dihydro-5H-imidazo[2,1-b][1,3]oxazin-7-ylmethoxy)phenyl]piperidin-4-yl}-N-(4-trifluoromethoxyphenyl)amine 4-(Trifluoromethoxy)aniline (1.271 ml) was added to a 1,2-dichloroethane solution (50 ml) of 1-[4-((R)-2-nitro-6,7-dihydro-5H-imidazo[2,1-b][1,3]oxazin-7-ylmethoxy)phenyl]piperidin-4-one (2.5 g). Subsequently, sodium triacetoxyborohydride (1.992 g) and acetic acid (0.538 ml) were added thereto and the mixture was stirred at room temperature for 21 hours. A saturated sodium hydrogen carbonate aqueous solution was added to the reaction mixture, followed by extraction with methylene chloride. The organic layer was washed with a saturated sodium chloride aqueous solution and dried over anhydrous sodium sulfate. Thereafter, the solvent was distilled off under reduced pressure. The resulting residue was purified by silica gel column chromatography (ethyl acetate:n-hexane=1:1) and recrystallized from ethyl acetate to afford the title compound as a yellow powder (2.55 g).

Melting point: 189-190° C.

Example 374

Preparation of N-ethyl-N-{1-[4-((R)-2-nitro-6,7-dihydro-5H-imidazo[2,1-b][1,3]oxazin-7-ylmethoxy)phenyl]piperidin-4-yl}-N-(4-trifluoromethoxyphenyl)amine The title compound was prepared in the same manner as in Example 370 using suitable starting materials.
Yellow Powder
Melting point: 184-185° C.

Example 375

Preparation of (R)-2-nitro-7-(4-{4-[(E)-3-(4-trifluoromethoxyphenyl)allyl]piperazin-1-yl}phenoxymethyl)-6,7-dihydro-5H-imidazo[2,1-b][1,3]oxazine The title compound was prepared in the same manner as in Example 363 using suitable starting materials.
Slightly Yellow Powder
Melting point: 208-209° C.

Example 376

Preparation of (R)-2-nitro-7-{4-[4-(4-trifluoromethylbenzyloxymethyl)piperidin-1-yl]phenoxymethyl}-6,7-dihydro-5H-imidazo[2,1-b][1,3]oxazine The title compound was prepared in the same manner as in Example 86 using suitable starting materials.
Yellow Solid
Melting point: 137.7-139.8° C.

Example 377

Preparation of (R)-2-nitro-7-{4-[4-(4-trifluoromethylphenoxymethyl)piperidin-1-yl]phenoxymethyl}-6,7-dihydro-5H-imidazo[2,1-b][1,3]oxazine The title compound was prepared in the same manner as in Example 1 using suitable starting materials.
Yellow Solid
Melting point: 198.5-200° C.

Example 378

Preparation of (R)-2-nitro-7-{4-[4-(4-trifluoromethoxybenzyloxymethyl)piperidin-1-yl]phenoxymethyl}-6,7-dihydro-5H-imidazo[2,1-b][1,3]oxazine The title compound was prepared in the same manner as in Example 1 using suitable starting materials.
Orange Solid
Melting point: 123-127° C.

Example 379

Preparation of 1-[4'-((R)-2-nitro-6,7-dihydro-5H-imidazo[2,1-b][1,3]oxazin-7-ylmethoxy)biphenyl-4-yl]-4-trifluoromethylpiperidin-4-ol The title compound was prepared in the same manner as in Example 86 using suitable starting materials.
Pale Yellow Powder
Melting point: 225-230° C.

Example 380

Preparation of (R)-2-nitro-7-{4-[4-(nonafluorobutane-1-sulfonyl)piperazin-1-yl]phenoxymethyl}-6,7-dihydro-5H-imidazo[2,1-b][1,3]oxazine Triethylamine (0.35 ml) was added to a methylene chloride suspension (6 ml) of (R)-2-nitro-7-(4-piperazin-1-ylphenoxymethyl)-6,7-dihydro-5H-imidazo[2,1-b][1,3]oxazine (0.30 g). Subsequently, bis(nonafluoro-1-butanesulfonic)anhydride (0.31 ml) was added thereto dropwise under ice cooling. The mixture was stirred for 7.5 hours while it gradually returned to room temperature. A saturated sodium hydrogen carbonate aqueous solution was added to the reaction mixture, followed by extraction with methylene chloride. The organic layer was washed with a saturated sodium chloride aqueous solution and dried over anhydrous sodium sulfate, and the solvent was then distilled off under reduced pressure. The residue thus obtained was purified by silica gel column chromatography (methylene chloride:ethyl acetate=1:1) and recrystallized from acetone-water to afford the title compound as a pale orange powder (0.19 g).
Melting point: 235-236° C.

Example 381

Preparation of (R)-2-nitro-7-[4-(4-trifluoromethanesulfonylpiperazin-1-yl)phenoxymethyl]-6,7-dihydro-5H-imidazo[2,1-b][1,3]oxazine The title compound was prepared in the same manner as in Example 380 using suitable starting materials.
Beige Needle
Melting point: 225-227° C.

Example 382

Preparation of 7-methyl-2-nitro-7-(4-{4-[2-(4-trifluoromethoxyphenyl)ethyl]piperidin-1-yl}phenoxymethyl)-6,7-dihydro-5H-imidazo[2,1-b][1,3]oxazine The title compound was prepared in the same manner as in Example 1 using suitable starting materials.
Yellow Powder
Melting point: 216.6-218.2° C.

Example 383

Preparation of (R)-2-nitro-7-{4-[4-(4-trifluoromethoxybenzyl)piperidin-1-yl]phenoxymethyl}-6,7-dihydro-5H-imidazo[2,1-b][1,3]oxazine The title compound was prepared in the same manner as in Example 1 using suitable starting materials.
Pale Yellow Solid
Melting point: 172-173° C.

Example 384

Preparation of (R)-2-nitro-7-{4-[4-(4-trifluoromethylbenzyl)piperidin-1-yl]phenoxymethyl}-6,7-dihydro-5H-imidazo[2,1-b][1,3]oxazine The title compound was prepared in the same manner as in Example 1 using suitable starting materials.
Pale Yellow Solid
Melting point: 178-179° C.

Example 385

Preparation of (R)-7-{4-[4-(4-chlorobenzyl)piperidin-1-yl]phenoxymethyl}-2-nitro-6,7-dihydro-5H-imidazo[2,1-b][1,3]oxazine The title compound was prepared in the same manner as in Example 1 using suitable starting materials.
Colorless Solid
Melting point: 176.5-178° C.

Example 386

Preparation of (R)-2-nitro-7-{4-[4-(4-trifluoromethoxyphenoxymethyl)piperidin-1-yl]phenoxymethyl}-6,7-dihydro-5H-imidazo[2,1-b][1,3]oxazine The title compound was prepared in the same manner as in Example 86 using suitable starting materials.
Orange Solid
Melting point: 199.3-199.5° C.

Example 387

Preparation of (R)-2-nitro-7-{4-[4-(4-trifluoromethoxyphenyl)piperidin-1-yl]phenoxymethyl}-6,7-dihydro-5H-imidazo[2,1-b][1,3]oxazine The title compound was prepared in the same manner as in Example 1 using suitable starting materials.
Reddish Yellow Solid
Melting point: 206.5-207.5° C.

Example 388

Preparation of (R)-2-nitro-7-{4-[4-(4-trifluoromethylphenyl)piperidin-1-yl]phenoxymethyl}-6,7-dihydro-5H-imidazo[2,1-b][1,3]oxazine The title compound was prepared in the same manner as in Example 1 using suitable starting materials.
Yellow Solid
Melting point: 229-230° C.

Example 389

Preparation of (R)-2-nitro-7-{4-[4-(5-trifluoromethylpyridin-2-yloxy)piperidin-1-yl]phenoxymethyl}-6,7-dihydro-5H-imidazo[2,1-b][1,3]oxazine The title compound was prepared in the same manner as in Example 86 using suitable starting materials.
White Powder
Melting point: 183.2-186.6° C.

Example 390

Preparation of (S)-2-nitro-7-(4-{4-[3-(4-trifluoromethoxyphenyl)propyl]piperidin-1-yl}phenoxymethyl)-6,7-dihydro-5H-imidazo[2,1-b][1,3]oxazine The title compound was prepared in the same manner as in Example 86 using suitable starting materials.
Pale Yellow Powder
Melting point: 171-173° C.

Example 391

Preparation of 7-methyl-2-nitro-7-{4-[4-(4-trifluoromethoxybenzyl)piperidin-1-yl]phenoxymethyl}-6,7-dihydro-5H-imidazo[2,1-b][1,3]oxazine The title compound was prepared in the same manner as in Example 1 using suitable starting materials.
Yellow Powder
Melting point: 170.4-171.6° C.

Example 392

Preparation of (R)-2-nitro-7-{4-[1-(4-trifluoromethoxyphenyl)piperidin-4-yloxy]phenoxymethyl}-6,7-dihydro-5H-imidazo[2,1-b][1,3]oxazine The title compound was prepared in the same manner as in Example 1 using suitable starting materials.
Pale Yellow Solid
Melting point: 155-157° C.

Example 393

Preparation of (R)-2-nitro-7-{4-[1-(4-trifluoromethylphenyl)piperidin-4-yloxy]phenoxymethyl}-6,7-dihydro-5H-imidazo[2,1-b][1,3]oxazine The title compound was prepared in the same manner as in Example 1 using suitable starting materials.
Pale Yellow Solid
Melting point: 162.5-164° C.

Example 394

Preparation of (R)-2-nitro-7-{4-[4-(4-trifluoromethoxybenzyloxy)piperidin-1-yl]phenoxymethyl}-6,7-dihydro-5H-imidazo[2,1-b][1,3]oxazine The title compound was prepared in the same manner as in Example 86 using suitable starting materials.
Yellow Powder
Melting point: 180.0-180.3° C.

Example 395

Preparation of (R)-2-nitro-7-(4-{4-[3-(3-trifluoromethylphenoxy)propyl]piperidin-1-yl}phenoxymethyl)-6,7-dihydro-5H-imidazo[2,1-b][1,3]oxazine The title compound was prepared in the same manner as in Example 86 using suitable starting materials.
Orange Solid
Melting point: 165.5-166.5° C.

Example 396

Preparation of (R)-2-nitro-7-{4-[4-(3-trifluoromethylphenoxymethyl)piperidin-1-yl]phenoxymethyl}-6,7-dihydro-5H-imidazo[2,1-b][1,3]oxazine The title compound was prepared in the same manner as in Example 86 using suitable starting materials.
Pink Powder
Melting point: 160.9-161.4° C.

Example 397

Preparation of (R)-2-nitro-7-(4-{4-[3-(4-trifluoromethylphenoxy)propyl]piperidin-1-yl}phenoxymethyl)-6,7-dihydro-5H-imidazo[2,1-b][1,3]oxazine The title compound was prepared in the same manner as in Example 86 using suitable starting materials.
Pale Yellow Powder
Melting point: 185-186° C.

Example 398

Preparation of (R)-2-nitro-7-(4-{4-[2-(4-trifluoromethylbenzyloxy)ethyl]piperidin-1-yl}phenoxymethyl)-6,7-dihydro-5H-imidazo[2,1-b][1,3]oxazine The title compound was prepared in the same manner as in Example 86 using suitable starting materials.
Yellow Solid
Melting point: 154.5-155.2° C.

Example 399

Preparation of (R)-2-nitro-7-(4-{4-[2-(4-trifluoromethoxybenzyloxy)ethyl]piperidin-1-yl}phenoxymethyl)-6,7-dihydro-5H-imidazo[2,1-b][1,3]oxazine The title compound was prepared in the same manner as in Example 86 using suitable starting materials.
Orange Solid
Melting point: 147.5-148° C.

Example 400

Preparation of (R)-2-nitro-7-(4-{4-[3-(4-trifluoromethylphenyl)propyl]piperidin-1-yl}phenoxymethyl)-6,7-dihydro-5H-imidazo[2,1-b][1,3]oxazine The title compound was prepared in the same manner as in Example 1 using suitable starting materials.
Pale Yellow Solid
Melting point: 178-179° C.

Example 401

Preparation of (R)-7-{4-[4-(3-chloro-5-trifluoromethylpyridin-2-yloxy)piperidin-1-yl]phenoxymethyl}-2-nitro-6,7-dihydro-5H-imidazo[2,1-b][1,3]oxazine The title compound was prepared in the same manner as in Example 86 using suitable starting materials.
Pale Yellow Powder
Melting point: 161-162° C.

Example 402

Preparation of 7-methyl-2-nitro-7-{4-[4-(4-trifluoromethoxybenzyl)piperazin-1-yl]phenoxymethyl}-6,7-dihydro-5H-imidazo[2,1-b][1,3]oxazine The title compound was prepared in the same manner as in Example 3 using suitable starting materials.
Yellow Powder
Melting point: 178.8-178.9° C.

Example 403

Preparation of 7-methyl-2-nitro-7-{4-[4-(4-trifluoromethylbenzyl)piperazin-1-yl]phenoxymethyl}-6,7-dihydro-5H-imidazo[2,1-b][1,3]oxazine The title compound was prepared in the same manner as in Example 3 using suitable starting materials.
Yellow Powder
Melting point: 155.7-156.4° C.

Example 404

Preparation of 7-methyl-2-nitro-7-(4-{4-[(E)-3-(4-trifluoromethylphenyl)allyl]piperazin-1-yl}phenoxymethyl)-6,7-dihydro-5H-imidazo[2,1-b][1,3]oxazine The title compound was prepared in the same manner as in Example 3 using suitable starting materials.
Yellow Powder
Melting point: 186.2-186.9° C.

Example 405

Preparation of (R)-2-nitro-7-(4-{4-[3-(5-trifluoromethylpyridin-2-yloxy)propyl]piperidin-1-yl}phenoxymethyl)-6,7-dihydro-5H-imidazo[2,1-b][1,3]oxazine The title compound was prepared in the same manner as in Example 86 using suitable starting materials.
Yellow Powder
Melting point: 175.0-175.8° C.

Example 406

Preparation of (R)-2-nitro-7-{6-{4-[2-(4-trifluoromethoxyphenyl)ethyl]piperidin-1-yl}pyridin-3-yloxymethyl}-6,7-dihydro-5H-imidazo[2,1-b][1,3]oxazine The title compound was prepared in the same manner as in Example 86 using suitable starting materials.
Pale Yellow Flocculent Crystal
Melting point: 194° C.

Example 407

Preparation of (R)-2-nitro-7-{4-[4-(5-trifluoromethylpyridin-2-yloxymethyl)piperidin-1-yl]phenoxymethyl}-6,7-dihydro-5H-imidazo[2,1-b][1,3]oxazine The title compound was prepared in the same manner as in Example 1 using suitable starting materials.
White Powder
Melting point: 199.5-199.9° C.

Example 408

Preparation of (R)-2-nitro-7-{4-[1'-(4-trifluoromethoxybenzyl)-4,4'-bipiperidin-1-yl]phenoxymethyl}-6,7-dihydro-5H-imidazo[2,1-b][1,3]oxazine The title compound was prepared in the same manner as in Example 363 using suitable starting materials.
White Powder
Melting point: 209.8-215.1° C.

Example 409

Preparation of 7-methyl-2-nitro-7-(4-{4-[3-(4-trifluoromethoxyphenyl)propyl]piperidin-1-yl}phenoxymethyl)-6,7-dihydro-5H-imidazo[2,1-b][1,3]oxazine The title compound was prepared in the same manner as in Example 1 using suitable starting materials.
Yellow Powder
Melting point: 154.2-156.2° C.

Example 410

Preparation of (R)-2-nitro-7-{6-[4-(4-trifluoromethoxybenzyl)piperidin-1-yl]pyridin-3-yloxymethyl}-6,7-dihydro-5H-imidazo[2,1-b][1,3]oxazine The title compound was prepared in the same manner as in Example 86 using suitable starting materials.
White Powder
Melting point: 180.7° C.

Example 411

Preparation of 7-methyl-2-nitro-7-(4-{4-[(E)-3-(4-trifluoromethoxyphenyl)allyl]piperazin-1-yl}phenoxymethyl)-6,7-dihydro-5H-imidazo[2,1-b][1,3]oxazine The title compound was prepared in the same manner as in Example 3 using suitable starting materials.
Yellow Powder
Melting point: 158.3-159.2° C.

Example 412

Preparation of (R)-2-nitro-7-(6-{4-[3-(4-trifluoromethylphenyl)propyl]piperidin-1-yl}pyridin-3-yloxymethyl)-6,7-dihydro-5H-imidazo[2,1-b][1,3]oxazine The title compound was prepared in the same manner as in Example 86 using suitable starting materials.
Pale Yellow Powder
Melting point: 171.7° C.

Example 413

Preparation of (R)-2-nitro-7-{4-[4-(4-trifluoromethyl-cyclohexylmethyl)piperazin-1-yl]phenoxymethyl}-6,7-dihydro-5H-imidazo[2,1-b][1,3]oxazine The title compound was prepared in the same manner as in Example 3 using suitable starting materials.
Yellow Powder
Melting point: 212.5-213.2° C.

Example 414

Preparation of (R)-2-nitro-7-{4-[4-(4-trifluoromethyl-cyclohexylmethyl)piperazin-1-yl]phenoxymethyl}-6,7-dihydro-5H-imidazo[2,1-b][1,3]oxazine The title compound was prepared in the same manner as in Example 3 using suitable starting materials.
Yellow Powder
Melting point: 214.4-214.8° C.

Example 415

Preparation of (R)-2-nitro-7-{4-[1'-(4-trifluoromethylbenzyl)-4,4'-bipiperidin-1-yl]phenoxymethyl}-6,7-dihydro-5H-imidazo[2,1-b][1,3]oxazine The title compound was prepared in the same manner as in Example 363 using suitable starting materials.
Pale Yellow Powder
Melting point: 223-225° C.

Example 416

Preparation of (R)-2-nitro-7-(4-{4-[2-(4-trifluoromethylphenyl)ethyl]piperidin-1-yl}phenoxymethyl)-6,7-dihydro-5H-imidazo[2,1-b][1,3]oxazine The title compound was prepared in the same manner as in Example 86 using suitable starting materials.
Pale Yellow Solid
Melting point: 211.3° C.

Example 417

Preparation of (R)-2-nitro-7-(6-{4-[2-(4-trifluoromethylphenyl)ethyl]piperidin-1-yl}pyridin-3-yloxymethyl)-6,7-dihydro-5H-imidazo[2,1-b][1,3]oxazine The title compound was prepared in the same manner as in Example 86 using suitable starting materials.
Pale Yellow Solid
Melting point: 211.2° C.

Example 418

Preparation of N-ethyl-N-[4-((R)-2-nitro-6,7-dihydro-5H-imidazo[2,1-b][1,3]oxazin-7-ylmethoxy)phenyl]-N-[1-(4-trifluoromethoxyphenyl)piperidin-4-yl]amine The title compound was prepared in the same manner as in Example 1 using suitable starting materials.
Pale Yellow Powder
Melting point: 166.4-168.1° C.

Example 419

Preparation of N-methyl-N-[4-((R)-2-nitro-6,7-dihydro-5H-imidazo[2,1-b][1,3]oxazin-7-ylmethoxy)phenyl]-N-[1-(4-trifluoromethoxyphenyl)piperidin-4-yl]amine The title compound was prepared in the same manner as in Example 1 using suitable starting materials.
Orange Powder
Melting point: 182.1-184.2° C.

Example 420

Preparation of 4-[4-((R)-2-nitro-6,7-dihydro-5H-imidazo[2,1-b][1,3]oxazin-7-ylmethoxy)phenyl]piperazine-1-carboxylic acid ethyl ester Triethylamine (0.31 ml) was added to a methylene chloride suspension (6 ml) of (R)-2-nitro-7-(4-piperazin-1-ylphenoxymethyl)-6,7-dihydro-5H-imidazo[2,1-b][1,3]oxazine (0.40 g). Subsequently, chloroethyl formate (0.11 ml) was added thereto dropwise under ice cooling, and the mixture was stirred for 14 hours while it gradually returned to room temperature. A 0.5 N hydrochloric acid aqueous solution was then added to the reaction mixture, followed by extraction with methylene chloride. After washing the organic layer with water and a saturated sodium chloride aqueous solution, the organic layer was dried over anhydrous sodium sulfate and the solvent was distilled off under reduced pressure. The residue thus obtained was purified by silica gel column chromatography (methylene chloride:methanol=90:10) and recrystallized from acetone-water to afford the title compound as a pale yellow powder (0.36 g).
Melting point: 218° C.

Example 421

Preparation of (2-hydroxy-4-trifluoromethylphenyl)-{4-[4-((R)-2-nitro-6,7-dihydro-5H-imidazo[2,1-b][1,3]oxazin-7-ylmethoxy)phenyl]piperazin-1-yl}methanone 1-Hydroxybenzotriazole (0.19 g) and 1-ethyl-3-(3-dimethylaminopropyl)carbodiimide hydrochloride (0.24 g) were added to a DMF solution (5 ml) of (R)-2-nitro-7-(4-piperazin-1-ylphenoxymethyl)-6,7-dihydro-5H-imidazo[2,1-b][1,3]oxazine (0.40 g) and 4-(trifluoromethyl)salicylic acid (0.25 g), and the mixture was stirred at room temperature for 11 hours. Water was added to the reaction mixture. After stirring the mixture for a while, the precipitate was collected by filtration. The resulting crude product was purified by silica gel column chromatography (methylene chloride:methanol=90:10) and recrystallized from ethanol-acetone to afford the title compound as a white powder (0.42 g).
Melting point: 217-220° C.

Example 422

Preparation of (R)-2-nitro-7-(6-{4-[3-(4-trifluoromethoxyphenyl)propyl]piperidin-1-yl}pyridin-3-yloxymethyl)-6,7-dihydro-5H-imidazo[2,1-b][1,3]oxazine The title compound was prepared in the same manner as in Example 86 using suitable starting materials.
Yellow Solid
Melting point: 159.0-159.5° C.

Example 423

Preparation of (R)-2-nitro-7-{4-[4-(2,2,2-trifluoroethyl)piperazin-1-yl]phenoxymethyl}-6,7-dihydro-5H-imidazo[2,1-b][1,3]oxazine The title compound was prepared in the same manner as in Example 1 using suitable starting materials.
Yellow Powder
Melting point: 186.5-187.2° C.

Example 424

Preparation of (R)-2-nitro-7-{4-[4-(4-trifluoromethoxyphenyl)-3,6-dihydro-2H-pyridin-1-yl]phenoxymethyl}-6,7-dihydro-5H-imidazo[2,1-b][1,3]oxazine The title compound was prepared in the same manner as in Example 86 using suitable starting materials.
Yellow Powder
Melting point: 200.5-201.5° C.

Example 425

Preparation of (R)-2-nitro-7-{4-[4-(4-trifluoromethoxybenzyl)-3,6-dihydro-2H-pyridin-1-yl]phenoxymethyl}-6,7-dihydro-5H-imidazo[2,1-b][1,3]oxazine The title compound was prepared in the same manner as in Example 86 using suitable starting materials.
Yellow Solid
Melting point: 164.8-165.2° C.

Example 426

Preparation of (R)-7-[4-(4-methanesulfonylpiperazin-1-yl)phenoxymethyl]-2-nitro-6,7-dihydro-5H-imidazo[2,1-b][1,3]oxazine Triethylamine (0.31 ml) was added to a methylene chloride suspension (6 ml) of (R)-2-nitro-7-(4-piperazin-1-ylphenoxymethyl)-6,7-dihydro-5H-imidazo[2,1-b][1,3]oxazine (0.40 g). Subsequently, methanesulfonyl chloride (0.09 ml) was added thereto dropwise under ice cooling, and the mixture was stirred for 14 hours while it gradually returned to room temperature. A 0.5 N hydrochloric acid aqueous solution was added to the reaction mixture, followed by extraction with methylene chloride. The organic layer was washed with water and a saturated sodium chloride aqueous solution, dried over anhydrous sodium sulfate, and the solvent was then distilled off under reduced pressure. The resulting residue was purified by silica gel column chromatography (methylene chloride:methanol=90:10) and recrystallized from methylene chloride-methanol to afford the title compound as a beige powder (0.15 g).
Melting point: 149-151° C.

Example 427

Preparation of (R)-2-nitro-7-(6-{4-[2-(4-trifluoromethoxyphenoxy)ethyl]piperidin-1-yl}pyridin-3-yloxymethyl)-6,7-dihydro-5H-imidazo[2,1-b][1,3]oxazine The title compound was prepared in the same manner as in Example 86 using suitable starting materials.
Pale Yellow Powder
Melting point: 137.6-140.9° C.

Example 428

Preparation of (R)-2-nitro-7-(4-{4-[4-(5-trifluoromethylpyridin-2-yloxy)benzyl]piperazin-1-yl}phenoxymethyl)-6,7-dihydro-5H-imidazo[2,1-b][1,3]oxazine (R)-2-Nitro-7-(4-piperazin-1-ylphenoxymethyl)-6,7-dihydro-5H-imidazo[2,1-b][1,3]oxazine (0.50 g), 4-(5-trifluoromethylpyridin-2-yloxy)benzaldehyde (0.41 g), N-methylpyrrolidone (10 ml), and sodium triacetoxyborohydride (0.44 g) were mixed and stirred at room temperature for 16 hours. The reaction mixture was added to a 1 N sodium hydroxide aqueous solution. The precipitated crystal was collected by filtration. The crude crystal was purified by silica gel column chromatography (methylene chloride:ethyl acetate=8:2→methylene chloride:ethyl acetate=2:8) and recrystallized from acetone-ether to afford the title compound as a pale yellow powder (0.55 g).
Melting point: 229-230° C.

Example 429

Preparation of (R)-2-nitro-7-{6-[4-(4-trifluoromethoxyphenoxymethyl)piperidin-1-yl]pyridin-3-yloxymethyl}-6,7-dihydro-5H-imidazo[2,1-b][1,3]oxazine The title compound was prepared in the same manner as in Example 86 using suitable starting materials.
Pale Yellow Powder
Melting point: 182.9-183.3° C.

Example 430

Preparation of (R)-2-nitro-7-{4-[4-(4-trifluoromethoxyphenyl)piperidin-1-ylmethyl]phenoxymethyl}-6,7-dihydro-5H-imidazo[2,1-b][1,3]oxazine The title compound was prepared in the same manner as in Example 428 using suitable starting materials.
Pale Brown Solid
Melting point: 165-167° C.

Example 431

Preparation of (R)-2-nitro-7-{4-[4-(4-trifluoromethoxybenzyl)piperidin-1-ylmethyl]phenoxymethyl}-6,7-dihydro-5H-imidazo[2,1-b][1,3]oxazine The title compound was prepared in the same manner as in Example 428 using suitable starting materials.
Pale Brown Solid
Melting point: 159.5-160.5° C.

Example 432

Preparation of (R)-2-nitro-7-{4-[1-(4-trifluoromethylbenzyl)-1,2,3,6-tetrahydropyridin-4-yl]phenoxymethyl}-6,7-dihydro-5H-imidazo[2,1-b][1,3]oxazine hydrochloride Sodium triacetoxyborohydride (0.631 g) was added to a mixture of (R)-2-nitro-7-[4-(1,2,3,6-tetrahydro-pyridin-4-yl)phenoxymethyl]-6,7-dihydro-5H-imidazo[2,1-b][1,3]oxazine trifluoroacetate (1.0 g), 4-(trifluoromethyl)benzaldehyde (0.41 ml) and N-methylpyrrolidone (10 ml), and the mixture was stirred at room temperature for 9 hours. A sodium hydrogen carbonate aqueous solution was added to the reaction mixture and stirred for 10 minutes. The precipitate was then collected by filtration. The residue thus obtained was purified by basic silica gel column chromatography (methylene chloride). The resulting product was dissolved in methylene chloride (30 ml), a 1 N hydrochloric acid ethanol solution (1.32 ml) was added thereto and then stirred. Thereafter, the solvent was distilled off under reduced pressure, ethyl acetate was added to the residue, and the mixture was stirred at room temperature. The precipitate was collected by filtration, and the solid thus obtained was recrystallized using ethanol-water to afford the title compound as a slightly yellow powder (0.52 g).
Melting point: 210-213° C.

Example 433

Preparation of (R)-7-(4-{4-[3-fluoro-4-(4-trifluoromethoxybenzyloxy)benzyl]piperazin-1-yl}phenoxymethyl)-2-nitro-6,7-dihydro-5H-imidazo[2,1-b][1,3]oxazine The title compound was prepared in the same manner as in Example 363 using suitable starting materials.
Pale Brown Solid
Melting point: 150-151° C.

Example 434

Preparation of (R)-7-(4-{4-[2-fluoro-4-(4-trifluoromethoxybenzyloxy)benzyl]piperazin-1-yl}phenoxymethyl)-2-nitro-6,7-dihydro-5H-imidazo[2,1-b][1,3]oxazine The title compound was prepared in the same manner as in Example 363 using suitable starting materials.
Pale Brown Solid
  Melting point: 157-158° C.

Example 435

Preparation of (R)-7-(4-{4-[3-methoxy-4-(4-trifluoromethoxybenzyloxy)benzyl]piperazin-1-yl}phenoxymethyl)-2-nitro-6,7-dihydro-5H-imidazo[2,1-b][1,3]oxazine The title compound was prepared in the same manner as in Example 363 using suitable starting materials.
Colorless Solid
  Melting point: 149.5-150° C.

Example 436

Preparation of (R)-7-{4-[4-((E)-3,7-dimethyl-octa-2,6-dienyl)piperazin-1-yl]phenoxymethyl}-2-nitro-6,7-dihydro-5H-imidazo[2,1-b][1,3]oxazine The title compound was prepared in the same manner as in Example 363 using suitable starting materials.
Pale Brown Solid
  Melting point: 142.5-144° C.

Example 437

Preparation of (R)-7-(4-{4-[5-(4-chlorophenyl)furan-2-ylmethyl]piperazin-1-yl}phenoxymethyl)-2-nitro-6,7-dihydro-5H-imidazo[2,1-b][1,3]oxazine The title compound was prepared in the same manner as in Example 363 using suitable starting materials.
Yellow Solid
  Melting point: 222-223.5° C.

Example 438

Preparation of (R)-7-[4-(4-adamantan-2-ylpiperazin-1-yl)phenoxymethyl]-2-nitro-6,7-dihydro-5H-imidazo[2,1-b][1,3]oxazine The title compound was prepared in the same manner as in Example 363 using suitable starting materials.
Colorless Solid
  Melting point: 245.5-246.5° C.

Example 439

Preparation of 2-{4-[4-((R)-2-nitro-6,7-dihydro-5H-imidazo[2,1-b][1,3]oxazin-7-ylmethoxy)phenyl]piperazin-1-ylmethyl}-5-(4-trifluoromethylbenzyloxy)phenol hydrochloride The title compound was prepared in the same manner as in Example 432 using suitable starting materials.
Pale Yellow Powder
  Melting point: 192-194° C.

Example 440

Preparation of (R)-7-(4-{4-[2-methoxy-4-(4-trifluoromethylbenzyloxy)benzyl]piperazin-1-yl}phenoxymethyl)-2-nitro-6,7-dihydro-5H-imidazo[2,1-b][1,3]oxazine hydrochloride The title compound was prepared in the same manner as in Example 432 using suitable starting materials.
Pale Yellow Powder
  Melting point: 214-217° C.

Example 441

Preparation of (R)-2-nitro-7-(4-{4-[5-(4-trifluoromethylphenyl)thiophen-2-ylmethyl]piperazin-1-yl}phenoxymethyl)-6,7-dihydro-5H-imidazo[2,1-b][1,3]oxazine The title compound was prepared in the same manner as in Example 363 using suitable starting materials.
Pale Brown Solid
  Melting point: 225-226° C.

Example 442

Preparation of (R)-2-nitro-7-(4-{4-[5-(4-trifluoromethoxyphenyl)thiophen-2-ylmethyl]piperazin-1-yl}phenoxymethyl)-6,7-dihydro-5H-imidazo[2,1-b][1,3]oxazine The title compound was prepared in the same manner as in Example 363 using suitable starting materials.
Pale Brown Solid
  Melting point: 222-224° C.

Example 443

Preparation of (R)-2-nitro-7-(4-{4-[5-(4-trifluoromethylphenyl)furan-2-ylmethyl]piperazin-1-yl}phenoxymethyl)-6,7-dihydro-5H-imidazo[2,1-b][1,3]oxazine The title compound was prepared in the same manner as in Example 363 using suitable starting materials.
Pale Yellow Solid
  Melting point: 235-237° C.

Example 444

Preparation of (R)-2-nitro-7-(4-{4-[5-(4-trifluoromethoxyphenyl)furan-2-ylmethyl]piperazin-1-yl}phenoxymethyl)-6,7-dihydro-5H-imidazo[2,1-b][1,3]oxazine The title compound was prepared in the same manner as in Example 363 using suitable starting materials.
Pale Yellow Solid
  Melting point: 148.5-149.5° C.

Example 445

Preparation of (R)-2-nitro-7-{4-[4-(5-trifluoromethylbenzofuran-2-ylmethyl)piperidin-1-yl]phenoxymethyl}-6,7-dihydro-5H-imidazo[2,1-b][1,3]oxazine The title compound was prepared in the same manner as in Example 86 using suitable starting materials.
Pale Yellow Powder
Melting point: 159-161° C.

Example 446

Preparation of (R)-2-nitro-7-{4-[4-(4-trifluoromethylsulfanylphenoxy)piperidin-1-yl]phenoxymethyl}-6,7-dihydro-5H-imidazo[2,1-b][1,3]oxazine The title compound was prepared in the same manner as in Example 86 using suitable starting materials.
Yellow Powder
Melting point: 162.6-163.9° C.

Example 447

Preparation of (R)-2-nitro-7-(4-{1-[4-(4-trifluoromethylbenzyloxy)benzyl]-1,2,3,6-tetrahydropyridin-4-yl}phenoxymethyl)-6,7-dihydro-5H-imidazo[2,1-b][1,3]oxazine hydrochloride Sodium triacetoxyborohydride (0.63 g) was added to a mixture of (R)-2-nitro-7-[4-(1,2,3,6-tetrahydropyridin-4-yl)phenoxymethyl]-6,7-dihydro-5H-imidazo[2,1-b][1,3]oxazine trifluoroacetate (1.0 g), 4-(4-trifluoromethylbenzyloxy)benzaldehyde (0.72 g) and N-methylpyrrolidone (10 ml), and the mixture was stirred at room temperature for 11 hours. A sodium hydrogen carbonate aqueous solution was added to the reaction mixture and stirred for 10 minutes. The precipitate was collected by filtration. The residue thus obtained was purified by basic silica gel column chromatography (methylene chloride). The resulting product was dissolved in methylene chloride (30 ml), a 4 N hydrochloric acid ethyl acetate solution (0.49 ml) was added thereto, and the mixture was stirred for a while. The solvent was distilled off under reduced pressure, and ethyl acetate was added to the residue. The mixture was stirred for 20 minutes and then crystal was collected by filtration. The solid obtained was recrystallized from ethanol-water to afford the title compound as a yellow powder (0.58 g).
Melting point: 212-214° C.

Example 448

Preparation of (R)-2-nitro-7-(4-{4-[4-(4-trifluoromethylbenzylsulfanyl)benzyl]piperazin-1-yl}phenoxymethyl)-6,7-dihydro-5H-imidazo[2,1-b][1,3]oxazine hydrochloride The title compound was prepared in the same manner as in Example 447 using suitable starting materials.
Slightly Yellow Powder
Melting point: 181-184° C.

Example 449

Preparation of N-methyl-N-{1-[4-((R)-2-nitro-6,7-dihydro-5H-imidazo[2,1-b][1,3]oxazin-7-ylmethoxy)phenyl]piperidin-4-yl}-N-(4-trifluoromethoxybenzyl)amine The title compound was prepared in the same manner as in Example 180 using suitable starting materials.
Colorless Solid
Melting point: 173-174° C.

Example 450

Preparation of N-methyl-N-(2-{1-[4-((R)-2-nitro-6,7-dihydro-5H-imidazo[2,1-b][1,3]oxazin-7-ylmethoxy)phenyl]piperidin-4-yl}-ethyl)-N-(4-trifluoromethoxyphenyl)amine The title compound was prepared in the same manner as in Example 1 using suitable starting materials.
Yellow Solid
Melting point: 166.5-167° C.

Example 451

Preparation of N-methyl-N-{1-[4-((R)-2-nitro-6,7-dihydro-5H-imidazo[2,1-b][1,3]oxazin-7-ylmethoxy)phenyl]piperidin-4-ylmethyl}-N-(4-trifluoromethoxybenzyl)amine The title compound was prepared in the same manner as in Example 1 using suitable starting materials.
Yellow Solid
Melting point: 181.5-182.5° C.

Example 452

Preparation of (R)-2-nitro-7-{4-[4-(4-trifluoromethylsulfanylbenzyl)piperidin-1-yl]phenoxymethyl}-6,7-dihydro-5H-imidazo[2,1-b][1,3]oxazine The title compound was prepared in the same manner as in Example 1 using suitable starting materials.
Yellow Powder
Melting point: 191.4-192.6° C.

Example 453

Preparation of (R)-2-nitro-7-(4-{4-[4-(4-trifluoromethylphenylmethanesulfonyl)benzyl]piperazin-1-yl}phenoxymethyl)-6,7-dihydro-5H-imidazo[2,1-b][1,3]oxazine hydrochloride The title compound was prepared in the same manner as in Example 447 using suitable starting materials.
Slightly Yellow Powder
Melting point: 222-225° C.

Example 454

Preparation of (R)-2-nitro-7-(4-{4-[4-(4-trifluoromethylphenylmethanesulfinyl)benzyl]piperazin-1-yl}phenoxymethyl)-6,7-dihydro-5H-imidazo[2,1-b][1,3]oxazine hydrochloride The title compound was prepared in the same manner as in Example 447 using suitable starting materials.
Beige Powder
Melting point: 205-208° C.

Example 455

Preparation of (R)-2-nitro-7-{4-[4-(5-trifluoromethylbenzofuran-2-ylmethoxy)piperidin-1-yl]phenoxymethyl}-6,7-dihydro-5H-imidazo[2,1-b][1,3]oxazine The title compound was prepared in the same manner as in Example 445 using suitable starting materials.
Pale Yellow Powder
Melting point: 156-158° C.

Example 456

Preparation of (R)-2-nitro-7-{4-[4-(4-trifluoromethoxyphenylsulfanyl)piperidin-1-yl]phenoxymethyl}-6,7-dihydro-5H-imidazo[2,1-b][1,3]oxazine The title compound was prepared in the same manner as in Example 445 using suitable starting materials.
White Powder
Melting point: 161-162° C.

Example 457

Preparation of (R)-2-nitro-7-(4-{4-[2-(4-trifluoromethoxyphenylsulfanyl)ethyl]piperidin-1-yl}phenoxymethyl)-6,7-dihydro-5H-imidazo[2,1-b][1,3]oxazine The title compound was prepared in the same manner as in Example 445 using suitable starting materials.
White Powder
Melting point: 166.7-167.3° C.

Example 458

Preparation of (R)-2-nitro-7-(4-{4-[4-(4-trifluoromethylbenzyloxy)benzyl]-3,6-dihydro-2H-pyridin-1-yl}phenoxymethyl)-6,7-dihydro-5H-imidazo[2,1-b][1,3]oxazine The title compound was prepared in the same manner as in Example 445 using suitable starting materials.
Yellow Powder
Melting point: 183-184° C.

Example 459

Preparation of 1'-[4-((R)-2-nitro-6,7-dihydro-5H-imidazo[2,1-b][1,3]oxazin-7-ylmethoxy)phenyl]-[1,4']piperidinyl-4-ol 4-(tert-Butyldimethylsilanyloxy)-1'-[4-((R)-2-nitro-6,7-dihydro-5H-imidazo[2,1-b][1,3]oxazin-7-ylmethoxy)phenyl][1,4']bipiperidinyl (190 mg) was dissolved in tetrahydrofuran (5 ml). While being stirred at room temperature, 1 M tetra butyl ammonium fluoride (1.11 ml) was added thereto, followed by stirring at 50° C. for 5 hours. The reaction mixture was concentrated under reduced pressure. The resulting residue was purified by silica gel column chromatography (methylene chloride:methanol=100:0→methylene chloride:methanol=80:20) and recrystallized from methanol-isopropyl ether to afford the title compound as a yellow solid (40 mg).
Melting point: 234.5-235° C.

Example 460

Preparation of 2-methoxy-4-((E)-3-{4-[4-((R)-2-nitro-6,7-dihydro-5H-imidazo[2,1-b][1,3]oxazin-7-ylmethoxy)phenyl]piperazin-1-yl}propenyl)phenol The title compound was prepared in the same manner as in Example 428 using suitable starting materials.
Pale Brown Solid
Melting point: 109-111° C.

Example 461

Preparation of 1-{1-[4-((R)-2-nitro-6,7-dihydro-5H-imidazo[2,1-b][1,3]oxazin-7-ylmethoxy)phenyl]piperidin-4-ylmethyl}piperidin-4-ol The title compound was prepared in the same manner as in Example 459 using suitable starting materials.
Colorless Solid
Melting point: 189-190.5° C.

Example 462

Preparation of 1-(4-chlorophenoxy)-3-{4-[4-NR)-2-nitro-6,7-dihydro-5H-imidazo[2,1-b][1,3]oxazin-7-ylmethoxy)phenyl]piperazin-1-yl}propan-2-ol (R)-2-Nitro-7-(4-piperazin-1-ylphenoxymethyl)-6,7-dihydro-5H-imidazo[2,1-b][1,3]oxazine (250 mg), 2-(4-chlorophenoxymethyl)oxirane (154 mg) and N-methylpyrrolidone (7 ml) were mixed and stirred at 100° C. for 21 hours. The mixture was cooled to room temperature and water (23 ml) was added thereto, followed by stirring for 5 minutes. The precipitated crystal was collected by filtration and dried at 60° C. The residue thus obtained was purified by silica gel column chromatography (methylene chloride:methanol=100:0→methylene chloride:methanol=97:3) and recrystallized from 1,2-dichloroethane-methanol-ethyl acetate to afford the title compound as a colorless solid (204 mg).
Melting point: 203-205° C.

Example 463

Preparation of 1-{4-[4-((R)-2-nitro-6,7-dihydro-5H-imidazo[2,1-b][1,3]oxazin-7-ylmethoxy)phenyl]piperazin-1-yl}-3-(4-trifluoromethoxyphenoxy)propan-2-ol The title compound was prepared in the same manner as in Example 462 using suitable starting materials.
Yellow Solid
Melting point: 184.5-185° C.

Example 464

Preparation of (R)-7-{4-[4-(3,4-dichlorobenzyl)piperidin-1-yl]phenoxymethyl}-2-nitro-6,7-dihydro-5H-imidazo[2,1-b][1,3]oxazine The title compound was prepared in the same manner as in Example 445 using suitable starting materials.
Pale Yellow Powder
Melting point: 190-192° C.

Example 465

Preparation of (R)-7-(4-{4-[4-((E)-3,7-dimethylocta-2,6-dienyloxy)benzyl]piperazin-1-yl}phenoxymethyl)-2-nitro-6,7-dihydro-5H-imidazo[2,1-b][1,3]oxazine The title compound was prepared in the same manner as in Example 428 using suitable starting materials.
Yellow Solid
Melting point: 145-146.5° C.

Example 466

Preparation of (R)-7-[4-(4-[(E)-3-[4-((E)-3,7-dimethylocta-2,6-dienyloxy)phenyl]allyl]piperazin-1-yl)phenoxymethyl]-2-nitro-6,7-dihydro-5H-imidazo[2,1-b][1,3]oxazine The title compound was prepared in the same manner as in Example 428 using suitable starting materials.
Yellow Solid
Melting point: 154-155° C.

Example 467

Preparation of 1'-[4-((R)-2-nitro-6,7-dihydro-5H-imidazo[2,1-b][1,3]oxazin-7-ylmethoxy)benzyl]-[1,4']bipiperidinyl-4-ol The title compound was prepared in the same manner as in Example 428 using suitable starting materials.
Colorless Solid
Melting point: 164-165° C.

Example 468

Preparation of 1-{1-[4-((R)-2-nitro-6,7-dihydro-5H-imidazo[2,1-b][1,3]oxazin-7-ylmethoxy)benzyl]piperidin-4-ylmethyl}piperidin-4-ol The title compound was prepared in the same manner as in Example 428 using suitable starting materials.
Colorless Solid
Melting point: 174-175° C.

Example 469

Preparation of (R)-7-{4-[4-(3,4-dichlorophenoxy)piperidin-1-yl]phenoxymethyl}-2-nitro-6,7-dihydro-5H-imidazo[2,1-b][1,3]oxazine The title compound was prepared in the same manner as in Example 445 using suitable starting materials.
Pale Yellow Powder
Melting point: 180-181° C.

Example 470

Preparation of 1-[4-((R)-2-nitro-6,7-dihydro-5H-imidazo[2,1-b][1,3]oxazin-7-ylmethoxy)phenyl]-4-(4-trifluoromethylphenyl)piperidin-4-ol A mixture of toluene-4-sulfonic acid (R)-4-(2-chloro-4-nitroimidazol-1-yl)-2-hydroxybutyl ester (1.16 g), 1-(4-hydroxyphenyl)-4-(4-trifluoromethylphenyl)piperidin-4-ol (1.0 g), tripotassium phosphate (2.52 g) in ethanol (10 ml) was stirred at 60° C. for 15 hours under an argon atmosphere. The reaction mixture was added to an ammonium chloride aqueous solution, and the mixture was stirred for a while. The precipitated crude crystal was collected by filtration and dried at 60° C. The crude product thus obtained was purified by silica gel column chromatography (methylene chloride:ethyl acetate=1:1) and recrystallized from acetone-water to afford the title compound as a beige powder (0.63 g).
Melting point: 201-202° C.

Example 471

Preparation of (R)-7-{4-[4-methoxy-4-(4-trifluoromethylphenyl)piperidin-1-yl]phenoxymethyl}-2-nitro-6,7-dihydro-5H-imidazo[2,1-b][1,3]oxazine The title compound was prepared in the same manner as in Example 470 using suitable starting materials.
Slightly Yellow Powder
Melting point: 168-169° C.

Example 472

Preparation of (R)-7-{4-[4-methoxy-4-(4-trifluoromethoxyphenyl)piperidin-1-yl]phenoxymethyl}-2-nitro-6,7-dihydro-5H-imidazo[2,1-b][1,3]oxazine The title compound was prepared in the same manner as in Example 470 using suitable starting materials.
Pale Yellow Powder
Melting point: 160-161° C.

Example 473

Preparation of 1-[4-((R)-2-nitro-6,7-dihydro-5H-imidazo[2,1-b][1,3]oxazin-7-ylmethoxy)phenyl]-4-(4-trifluoromethoxyphenyl)piperidin-4-ol The title compound was prepared in the same manner as in Example 470 using suitable starting materials.
Beige Powder
Melting point: 204-206° C.

Example 474

Preparation of (R)-2-nitro-7-(4-{4-[4-(4-trifluoromethoxyphenoxy)phenoxy]piperidin-1-yl}phenoxymethyl)-6,7-dihydro-5H-imidazo[2,1-b][1,3]oxazine The title compound was prepared in the same manner as in Example 470 using suitable starting materials.
Pale Brown Powder
Melting point: 140-142° C.

Example 475

Preparation of (S)-2-nitro-7-{4-[4-(4-trifluoromethoxybenzyl)piperidin-1-yl]phenoxymethyl}-6,7-dihydro-5H-imidazo[2,1-b][1,3]oxazine The title compound was prepared in the same manner as in Example 470 using suitable starting materials.
Pale Yellow Powder
Melting point: 171-172° C.

Example 476

Preparation of (R)-2-nitro-7-{4-[1-(4-trifluoromethoxybenzyl)piperidin-4-ylmethoxy]phenoxymethyl}-6,7-dihydro-5H-imidazo[2,1-b][1,3]oxazine The title compound was prepared in the same manner as in Example 428 using suitable starting materials.
Pale Brown Solid
Melting point: 149.5-150° C.

Example 477

Preparation of (R)-2-nitro-7-(4-{2-[1-(4-trifluoromethoxybenzyl)piperidin-4-yl]-ethoxy}phenoxymethyl)-6,7-dihydro-5H-imidazo[2,1-b][1,3]oxazine The title compound was prepared in the same manner as in Example 428 using suitable starting materials.
Pale Brown Solid
Melting point: 132-133° C.

Example 478

Preparation of (R)-2-nitro-7-(4-{(E)-3-[4-(4-trifluoromethoxybenzyl)piperazin-1-yl]propenyl}phenoxymethyl)-6,7-dihydro-5H-imidazo[2,1-b][1,3]oxazine The title compound was prepared in the same manner as in Example 428 using suitable starting materials.
Pale Brown Solid
Melting point: 163-164° C.

Example 479

Preparation of (R)-7-(4-{4-[4-(furan-2-ylmethoxy)benzyl]piperazin-1-yl}phenoxymethyl)-2-nitro-6,7-dihydro-5H-imidazo[2,1-b][1,3]oxazine The title compound was prepared in the same manner as in Example 428 using suitable starting materials.
Colorless Solid
Melting point: 190-192° C.

Example 480

Preparation of (R)-2-nitro-7-(4-{4-[4-(pyridin-2-ylmethoxy)benzyl]piperazin-1-yl}phenoxymethyl)-6,7-dihydro-5H-imidazo[2,1-b][1,3]oxazine The title compound was prepared in the same manner as in Example 428 using suitable starting materials.
Colorless Solid
Melting point: 213-214° C.

Example 481

Preparation of (R)-2-nitro-7-(4-{4-[4-(thiophen-2-ylmethoxy)benzyl]piperazin-1-yl}phenoxymethyl)-6,7-dihydro-5H-imidazo[2,1-b][1,3]oxazine The title compound was prepared in the same manner as in Example 428 using suitable starting materials.
Colorless Solid
Melting point: 208-209.5° C.

Example 482

Preparation of (R)-2-nitro-7-[4-(4-{1-[4-(4-trifluoromethylbenzyloxy)phenyl]-ethyl}piperazin-1-yl)phenoxymethyl}-6,7-dihydro-5H-imidazo[2,1-b][1,3]oxazine (R)-2-Nitro-7-(4-piperazin-1-ylphenoxymethyl)-6,7-dihydro-5H-imidazo[2,1-b][1,3]oxazine (0.56 g) was added to an N-methylpyrrolidone solution (5 ml) of 1-(1-chloroethyl)-4-(4-trifluoromethylbenzyloxy)benzene (0.54 g). Subsequently, diisopropylethylamine (0.54 ml) was added thereto, and the mixture was stirred at room temperature for 12 hours. Thereafter, the mixture was heated to 60° C. and stirred for 7 hours. Water was added to the reaction mixture and the precipitated solid was collected by filtration. The solid thus obtained was purified by basic silica gel column chromatography (methylene chloride) and recrystallized from acetone-water to afford the title compound as a slightly yellow powder (0.15 g).
Melting point: 190-191° C.

Example 483

Preparation of (R)-2-nitro-7-(4-{4-[4-(pyridin-4-ylmethoxy)benzyl]piperazin-1-yl}phenoxymethyl)-6,7-dihydro-5H-imidazo[2,1-b][1,3]oxazine The title compound was prepared in the same manner as in Example 428 using suitable starting materials.
Colorless Solid
Melting point: 186-187° C.

Example 484

Preparation of (R)-7-(4-{4-[4-(3,5-dimethyl-isoxazol-4-ylmethoxy)benzyl]piperazin-1-yl}phenoxymethyl)-2-nitro-6,7-dihydro-5H-imidazo[2,1-b][1,3]oxazine The title compound was prepared in the same manner as in Example 428 using suitable starting materials.
Colorless Solid
Melting point: 122-123.5° C.

Example 485

Preparation of (R)-2-nitro-7-(4-{4-[4-(6-trifluoromethylpyridin-3-ylmethoxy)benzyl]piperazin-1-yl}phenoxymethyl)-6,7-dihydro-5H-imidazo[2,1-b][1,3]oxazine The title compound was prepared in the same manner as in Example 428 using suitable starting materials.
Colorless Solid
Melting point: 191-192° C.

Example 486

Preparation of (R)-2-nitro-7-(4-{4-[4-(pyrazin-2-ylmethoxy)benzyl]piperazin-1-yl}phenoxymethyl)-6,7-dihydro-5H-imidazo[2,1-b][1,3]oxazine The title compound was prepared in the same manner as in Example 428 using suitable starting materials.
Yellow Solid
Melting point: 233-233.5° C.

Example 487

Preparation of (R)-7-(4-{4-[4-(3-methyl-[1,2,4]oxadiazol-5-ylmethoxy)benzyl]piperazin-1-yl}phenoxymethyl)-2-nitro-6,7-dihydro-5H-imidazo[2,1-b][1,3]oxazine The title compound was prepared in the same manner as in Example 428 using suitable starting materials.
Colorless Solid
Melting point: 194-195° C.

Example 488

Preparation of (R)-7-(4-{4-[4-(2-methyl-thiazol-4-ylmethoxy)benzyl]piperazin-1-yl}phenoxymethyl)-2-nitro-6,7-dihydro-5H-imidazo[2,1-b][1,3]oxazine The title compound was prepared in the same manner as in Example 428 using suitable starting materials.
Colorless Solid
Melting point: 186.5-187° C.

Example 489

Preparation of (R)-2-nitro-7-(4-{4-[4-(pyridin-3-ylmethoxy)benzyl]piperazin-1-yl}phenoxymethyl)-6,7-dihydro-5H-imidazo[2,1-b][1,3]oxazine The title compound was prepared in the same manner as in Example 428 using suitable starting materials.
Colorless Solid
Melting point: 212.5-213° C.

Example 490

Preparation of (R)-7-[4-(4-{1-methyl-1-[4-(4-trifluoromethylbenzyloxy)phenyl]ethyl}piperazin-1-yl)phenoxymethyl]-2-nitro-6,7-dihydro-5H-imidazo[2,1-b][1,3]oxazine The title compound was prepared in the same manner as in Example 470 using suitable starting materials.
Slightly Yellow Powder
Melting point: 186-187° C.

Example 491

Preparation of (S)-2-nitro-7-(4-{4-[4-(4-trifluoromethylphenoxy)benzyl]piperazin-1-yl}phenoxymethyl)-6,7-dihydro-5H-imidazo[2,1-b][1,3]oxazine 4-[4-((S)-2-Nitro-6,7-dihydro-5H-imidazo[2,1-b][1,3]oxazin-7-ylmethoxy)phenyl]piperazine-1-carboxylic acid tert-butyl ester (300 mg) was suspended in methylene chloride (2 ml). Trifluoroacetic acid (2 ml) was added to the suspension, and the mixture was stirred at room temperature for 1 hour. The reaction mixture was concentrated under reduced pressure. Methylene chloride (2 ml) and triethylamine (0.83 ml) were added to the residue and stirred at room temperature for 10 minutes. The reaction mixture was concentrated under reduced pressure and then dissolved in DMF (2 ml). Potassium carbonate (123 mg) was added thereto and 1-(bromomethyl)-4-(4-trifluoromethylphenoxy)benzene (197 mg) was further added under ice cooling, and the mixture was stirred at room temperature for 4 hours. Water was added to the reaction mixture, and the precipitated solid was collected by filtration. The crude product thus obtained was purified by silica gel column chromatography (methylene chloride:ethyl acetate=1:0→methylene chloride:ethyl acetate=2:3→methylene chloride:methanol=10:1) and recrystallized from acetone-water to afford the title compound as a pale yellow solid (197 mg).
Melting point: 182.2-185.4° C.

Example 492

Preparation of (S)-2-nitro-7-(4-{4-[4-(4-trifluoromethylphenoxy)benzyl]piperidin-1-yl}phenoxymethyl)-6,7-dihydro-5H-imidazo[2,1-b][1,3]oxazine The title compound was prepared in the same manner as in Example 470 using suitable starting materials.
Yellow Solid
Melting point: 198.0-199.3° C.

Example 493

Preparation of 4-[4-(2-nitro-6,7-dihydro-5H-imidazo[2,1-b][1,3]oxazin-7-ylmethoxy)benzyl]piperidine-1-carboxylic acid tert-butyl ester The title compound was prepared in the same manner as in Example 1 using suitable starting materials.
White Powder
1H NMR (CDCl3) δ 1.06-1.17 (m, 2H), 1.46 (s, 9H), 1.55-1.66 (m, 3H), 2.32-2.42 (m, 1H), 2.46-2.52 (m, 3H), 2.54-2.71 (m, 2H), 3.97-4.24 (m, 5H), 4.28-4.33 (m, 1H), 4.72-4.78 (m, 1H), 6.83 (d, J=8.5 Hz, 2H), 7.06 (d, J=8.5 Hz, 2H), 7.46 (s, 1H).

Example 494

Preparation of 4-{2-[4-(2-nitro-6,7-dihydro-5H-imidazo[2,1-b][1,3]oxazin-7-ylmethoxy)phenyl]ethyl}piperidine-1-carboxylic acid tert-butyl ester The title compound was prepared in the same manner as in Example 1 using suitable starting materials.
White Powder
1H NMR (CDCl3) δ 1.05-1.34 (m, 4H), 1.47 (s, 9H), 1.52-1.60 (m, 3H), 2.29-2.37 (m, 1H), 2.44-2.55 (m, 3H), 2.42-2.65 (m, 2H), 3.95-4.20 (m, 5H), 4.25-4.30 (m, 1H), 4.72-4.79 (m, 1H), 6.81 (d, J=8.7 Hz, 2H), 7.05 (d, J=8.7 Hz, 2H), 7.45 (s, 1H).

Example 495

Preparation of 4-[6-((R)-2-nitro-6,7-dihydro-5H-imidazo[2,1-b][1,3]oxazin-7-ylmethoxy)quinolin-2-yl]piperazine-1-carboxylic acid tert-butyl ester The title compound was prepared in the same manner as in Example 132 using suitable starting materials.
Orange Powder
1H NMR (CDCl3) δ 2.02 (s, 9H), 2.37-2.40 (m, 1H), 2.47-2.50 (m, 1H), 3.66 (br, 4H), 3.68 (br, 4H), 4.12-4.15 (m, 1H), 4.18-4.21 (m, 1H), 4.24-4.27 (m, 1H), 4.34-4.37 (m, 1H), 4.79 (br, 1H), 6.95-6.98 (m, 2H), 7.18-7.20 (m, 1H), 7.43 (s, 1H), 7.64 (d, J=9.1 Hz, 1H), 7.82 (d, J=9.1 Hz, 1H).

Example 496

Preparation of 4-[6-((R)-2-nitro-6,7-dihydro-5H-imidazo[2,1-b][1,3]oxazin-7-ylmethoxy)benzothiazol-2-yl]piperazine-1-carboxylic acid tert-butyl ester The title compound was prepared in the same manner as in Example 132 using suitable starting materials.
White Powder
1H NMR (CDCl3) δ 1.49 (s, 9H), 2.38-2.40 (m, 1H), 2.48-2.51 (m, 1H), 3.58 (br, 8H), 4.11-4.17 (m, 1H), 4.20-4.24 (m, 2H), 4.32-4.35 (m, 1H), 4.75-4.77 (m, 1H), 6.90-6.92 (m, 1H), 7.18 (d, J=2.5 Hz, 1H), 7.45-7.48 (m, 2H).

Example 497

Preparation of (R)-7-[4-(4,4-dimethoxypiperidin-1-yl)phenoxymethyl]-2-nitro-6,7-dihydro-5H-imidazo[2,1-b][1,3]oxazine The title compound was prepared in the same manner as in Example 1 using suitable starting materials.
Yellow Solid
1H NMR (CDCl3) δ 1.90 (t, 4H), 2.17-2.48 (m, 2H), 3.12 (t, J=5.9 Hz, 4H), 3.23 (s, 6H), 4.05-4.18 (m, 3H), 4.18-4.32 (dd, J=10 Hz, 4.2 Hz, 1H), 4.70-4.76 (m, 1H), 6.80-6.95 (m, 4H), 7.45 (s, 1H).

Example 498

Preparation of 1-[4-((R)-2-nitro-6,7-dihydro-5H-imidazo[2,1-b][1,3]oxazin-7-ylmethoxy)phenyl]piperidin-4-one (R)-7-[4-(4,4-Dimethoxypiperidin-1-yl)phenoxymethyl]-2-nitro-6,7-dihydro-5H-imidazo[2,1-b][1,3]oxazine (5.16 g), acetone (100 ml) and water (17 ml) were mixed. A 6 N hydrochloric acid aqueous solution (41 ml) was added thereto, followed by stirring at room temperature overnight. The reaction mixture was concentrated under reduced pressure. The remaining water layer was ice-cooled and neutralized by adding a 20% sodium carbonate aqueous solution. After being stirred at the same temperature for 10 minutes, the precipitated crystal was collected by filtration. The crystal thus obtained was dried at 60° C. to afford the title compound as a yellow solid (4.57 g).
1H NMR (CDCl3) δ 2.20 (m, 6H), 3.48 (t, J=5.9 Hz, 4H), 4.05-4.32 (m, 4H), 4.70-4.80 (m, 1H), 6.87 (d, J=9.2 Hz, 2H), 6.96 (d, J=9.1 Hz, 2H), 7.45 (s, 1H).

Example 499

Preparation of {4-[4-((R)-2-nitro-6,7-dihydro-5H-imidazo[2,1-b][1,3]oxazin-7-ylmethoxy)phenyl]piperazin-1-yl}carbamic acid tert-butyl ester The title compound was prepared in the same manner as in Example 1 using suitable starting materials.
Yellow Powder
1H NMR (CDCl3) δ 1.47 (s, 9H), 2.33-2.47 (m, 2H), 2.93-2.97 (m, 4H), 3.18-3.22 (m, 4H), 4.10-4.25 (m, 3H), 4.25-4.35 (dd, J=10 Hz, 4.3 Hz, 1H), 4.65-4.80 (m, 1H), 5.46 (br s, 1H), 6.78-6.92 (m, 4H), 7.45 (s, 1H).

Example 500

Preparation of 4-[4-((R)-2-nitro-6,7-dihydro-5H-imidazo[2,1-b][1,3]oxazin-7-ylmethoxy)phenoxy]piperidine-1-carboxylic acid tert-butyl ester The title compound was prepared in the same manner as in Example 1 using suitable starting materials.
White Powder
1H NMR (CDCl3) δ 1.46 (s, 9H), 1.65-1.77 (m, 2H), 1.86-1.93 (m, 2H), 2.35-2.54 (m, 2H), 3.29-3.41 (m, 2H), 3.68-3.80 (m, 2H), 4.10-4.38 (m, 5H), 4.74-4.80 (m, 1H), 6.81-6.90 (m, 4H), 7.46 (s, 1H).

Example 501

Preparation of 4-[4-((S)-2-nitro-6,7-dihydro-5H-imidazo[2,1-b][1,3]oxazin-7-ylmethoxy)phenoxy]piperidine-1-carboxylic acid tert-butyl ester The title compound was prepared in the same manner as in Example 1 using suitable starting materials.
White Powder
1H NMR (CDCl3) δ 1.47 (s, 9H), 1.64-1.77 (m, 2H), 1.83-1.95 (m, 2H), 2.32-2.52 (m, 2H), 3.25-3.37 (m, 2H), 3.65-3.78 (m, 2H), 4.12-4.38 (m, 5H), 4.71-4.78 (m, 1H), 6.80-6.88 (m, 4H), 7.45 (s, 1H).

Example 502

Preparation of 4-[5-((S)-2-nitro-6,7-dihydro-5H-imidazo[2,1-b][1,3]oxazin-7-ylmethoxy)benzooxazol-2-yl]piperazine-1-carboxylic acid tert-butyl ester The title compound was prepared in the same manner as in Example 69 using suitable starting materials.
Yellow Powder
1H NMR (CDCl3) δ 1.49 (s, 9H), 2.38-2.41 (m, 1H), 2.48-2.52 (m, 1H), 3.55-3.57 (m, 4H), 3.65-3.66 (m, 4H), 4.10-4.16 (m, 1H), 4.19-4.22 (m, 2H), 4.30-4.33 (m, 1H), 4.75-4.77 (m, 1H), 6.59-6.61 (m, 1H), 6.91-6.92 (d, J=2.5 Hz, 1H), 7.15 (d, J=8.7 Hz, 1H), 7.46 (s, 1H).

Example 503

Preparation of 4-[5-((R)-2-nitro-6,7-dihydro-5H-imidazo[2,1-b][1,3]oxazin-7-ylmethoxy)benzooxazol-2-yl]piperazine-1-carboxylic acid tert-butyl ester The title compound was prepared in the same manner as in Example 69 using suitable starting materials.
Yellow Powder
1H NMR (CDCl3) δ 1.49 (s, 9H), 2.38-2.41 (m, 1H), 2.48-2.49 (m, 1H), 3.55-3.57 (m, 4H), 3.65-3.67 (m, 4H), 4.10-4.16 (m, 1H), 4.20-4.23 (m, 2H), 4.30-4.33 (m, 1H), 4.75-4.77 (m, 1H), 6.59-6.61 (m, 1H), 6.91-6.92 (d, J=2.5 Hz, 1H), 7.15 (d, J=8.7 Hz, 1H), 7.46 (s, 1H).

Example 504

Preparation of (S)-7-[4-(4,4-dimethoxypiperidin-1-yl)phenoxymethyl]-2-nitro-6,7-dihydro-5H-imidazo[2,1-b][1,3]oxazine The title compound was prepared in the same manner as in Example 69 using suitable starting materials.
Pale Yellow Powder
1H NMR (CDCl3) δ 1.89-1.91 (m, 4H), 2.34-2.38 (m, 1H), 2.46-2.49 (m, 1H), 3.10-3.13 (m, 4H), 3.23 (s, 6H), 4.10-4.22 (m, 3H), 4.26-4.29 (m, 1H), 4.71-4.74 (m, 1H), 6.82-6.84 (m, 2H), 6.89-6.92 (m, 2H), 7.45 (s, 1H).

Example 505

Preparation of 1-[4-((S)-2-nitro-6,7-dihydro-5H-imidazo[2,1-b][1,3]oxazin-7-ylmethoxy)phenyl]piperidin-4-one The title compound was prepared in the same manner as in Example 498 using suitable starting materials.
Pale Yellow Powder
1H NMR (DMSO-d6) δ 2.42 (m, 1H), 2.43 (m, 1H), 2.50-2.51 (m, 4H), 3.37-3.46 (m, 5H), 4.10-4.11 (m, 1H), 4.17-4.25 (m, 2H), 4.86-4.88 (m, 1H), 6.90-6.92 (m, 2H), 7.00-7.02 (m, 2H), 8.09 (s, 1H).

Example 506

Preparation of 5-((S)-2-nitro-6,7-dihydro-5H-imidazo[2,1-b][1,3]oxazin-7-ylmethoxy)-1,3-dihydroisoindole-2-carboxylic acid tert-butyl ester The title compound was prepared in the same manner as in Example 69 using suitable starting materials.
Pale Yellow Powder
1H NMR (CDCl3) δ 1.52 (s, 9H), 2.37-2.41 (m, 1H), 2.48-2.50 (m, 1H), 4.11-4.17 (m, 1H), 4.20-4.24 (m, 2H), 4.30-4.33 (m, 1H), 4.59-4.66 (m, 4H), 4.75-4.77 (m, 1H), 6.77-6.84 (m, 2H), 7.13-7.19 (m, 1H), 7.46 (s, 1H).

Example 507

Preparation of 5-((R)-2-nitro-6,7-dihydro-5H-imidazo[2,1-b][1,3]oxazin-7-ylmethoxy)-1,3-dihydroisoindole-2-carboxylic acid tert-butyl ester The title compound was prepared in the same manner as in Example 69 using suitable starting materials.
Yellow Powder
1H NMR (CDCl3) δ 1.52 (s, 9H), 2.37-2.42 (m, 1H), 2.48-2.50 (m, 1H), 4.11-4.17 (m, 1H), 4.19-4.24 (m, 2H), 4.30-4.34 (m, 1H), 4.59-4.66 (m, 4H), 4.74-4.78 (m, 1H), 6.77-6.84 (m, 2H), 7.13-7.19 (m, 1H), 7.46 (s, 1H).

Example 508

Preparation of 7-((S)-2-nitro-6,7-dihydro-5H-imidazo[2,1-b][1,3]oxazin-7-ylmethoxy)-3,4-dihydro-1H-isoquinoline-2-carboxylic acid tert-butyl ester The title compound was prepared in the same manner as in Example 69 using suitable starting materials.
Pale Yellow Powder
1H NMR (CDCl3) δ 1.49 (s, 9H), 2.36-2.39 (m, 1H), 2.46-2.49 (m, 1H), 2.77 (br, 2H), 3.63 (br, 2H), 4.10-4.23 (m, 3H), 4.28-4.31 (m, 1H), 4.54 (s, 2H), 4.74-4.75 (m, 1H), 6.65 (m, 1H), 6.73-6.75 (m, 1H), 7.05-7.07 (m, 1H), 7.46 (s, 1H).

Example 509

Preparation of 7-((R)-2-nitro-6,7-dihydro-5H-imidazo[2,1-b][1,3]oxazin-7-ylmethoxy)-3,4-dihydro-1H-isoquinoline-2-carboxylic acid tert-butyl ester The title compound was prepared in the same manner as in Example 69 using suitable starting materials.
Yellow Powder
1H NMR (CDCl3) δ 1.49 (s, 9H), 2.36-2.39 (m, 1H), 2.46-2.49 (m, 1H), 2.77 (br, 2H), 3.62 (br, 2H), 4.10-4.23 (m, 3H), 4.28-4.31 (m, 1H), 4.53 (s, 2H), 4.73-4.76 (m, 1H), 6.65 (d, J=2.3 Hz, 1H), 6.73-6.75 (m, 1H), 7.05-7.07 (m, 1H), 7.46 (s, 1H).

Example 510

Preparation of 7-((R)-2-nitro-6,7-dihydro-5H-imidazo[2,1-b][1,3]oxazin-7-ylmethoxy)-1,3,4,5-tetrahydrobenzo[c]azepine-2-carboxylic acid tert-butyl ester The title compound was prepared in the same manner as in Example 132 using suitable starting materials.
White Powder
1H NMR (CDCl3) δ 1.39 (s, 9H), 1.76-1.77 (m, 2H), 2.37 (m, 1H), 2.47 (m, 1H), 2.89 (m, 2H), 3.64-3.68 (m, 2H), 4.11-4.22 (m, 3H), 4.30-4.37 (m, 3H), 4.74 (m, 1H), 6.64-6.71 (m, 2H), 7.10-7.11 (m, 1H), 7.45 (s, 1H).

Example 511

Preparation of 6-((S)-2-nitro-6,7-dihydro-5H-imidazo[2,1-b][1,3]oxazin-7-ylmethoxy)-3,4-dihydro-1H-isoquinoline-2-carboxylic acid tert-butyl ester The title compound was prepared in the same manner as in Example 132 using suitable starting materials.
White Powder
1H NMR (CDCl3) δ 1.49 (s, 9H), 2.36-2.39 (m, 1H), 2.46-2.49 (m, 1H), 2.79-2.81 (m, 2H), 3.62 (m, 2H), 4.10-4.22 (m, 3H), 4.29-4.32 (m, 1H), 4.51 (s, 2H), 4.73-4.75 (m, 1H), 6.68 (d, J=2.4 Hz, 1H), 6.74-6.76 (m, 1H), 7.02-7.05 (m, 1H), 7.45 (s, 1H).

Example 512

Preparation of 6-((R)-2-nitro-6,7-dihydro-5H-imidazo[2,1-b][1,3]oxazin-7-ylmethoxy)-3,4-dihydro-1H-isoquinoline-2-carboxylic acid tert-butyl ester The title compound was prepared in the same manner as in Example 69 using suitable starting materials.
Pale Yellow Powder
1H NMR (CDCl3) δ 1.49 (s, 9H), 2.36-2.39 (m, 1H), 2.46-2.49 (m, 1H), 2.79-2.81 (m, 2H), 3.62 (m, 2H), 4.10-4.22 (m, 3H), 4.29-4.32 (m, 1H), 4.51 (s, 2H), 4.73-4.75 (m, 1H), 6.68 (d, J=2.4 Hz, 1H), 6.74-6.76 (m, 1H), 7.02-7.05 (m, 1H), 7.45 (s, 1H).

Example 513

Preparation of 7-((S)-2-nitro-6,7-dihydro-5H-imidazo[2,1-b][1,3]oxazin-7-ylmethoxy)-1,3,4,5-tetrahydrobenzo[c]azepine-2-carboxylic acid tert-butyl ester The title compound was prepared in the same manner as in Example 132 using suitable starting materials.
Yellow Powder
1H NMR (CDCl3) δ 1.39 (s, 9H), 1.76-1.77 (m, 2H), 2.37 (m, 1H), 2.47 (m, 1H), 2.89 (m, 2H), 3.64-3.68 (m, 2H), 4.11-4.22 (m, 3H), 4.30-4.37 (m, 3H), 4.74 (m, 1H), 6.64-6.71 (m, 2H), 7.10-7.11 (m, 1H), 7.45 (s, 1H).

Example 514

Preparation of (2R,5S)-2,5-dimethyl-4-[4-((S)-2-nitro-6,7-dihydro-5H-imidazo[2,1-b][1,3]oxazin-7-ylmethoxy)phenyl]piperazine-1-carboxylic acid tert-butyl ester The title compound was prepared in the same manner as in Example 132 using suitable starting materials.
Yellow Powder
1H NMR (CDCl3) δ 0.96 (d, J=6.5 Hz, 3H), 1.26 (d, J=6.8 Hz, 3H), 1.48 (s, 9H), 2.34-2.42 (m, 1H), 2.42-2.53 (m, 1H), 2.94 (m, 1H), 3.22-3.25 (m, 1H), 3.41-3.45 (m, 1H), 3.77-3.85 (m, 2H), 4.11-4.25 (m, 3H), 4.26-4.29 (m, 1H), 4.43 (br, 1H), 4.73 (m, 1H), 6.79-6.84 (m, 4H), 7.44 (s, 1H).

Example 515

Preparation of (2R,5S)-2,5-dimethyl-4-[4-((R)-2-nitro-6,7-dihydro-5H-imidazo[2,1-b][1,3]oxazin-7-ylmethoxy)phenyl]piperazine-1-carboxylic acid tert-butyl ester The title compound was prepared in the same manner as in Example 132 using suitable starting materials.
Yellow Powder
1H NMR (CDCl3) δ 0.96 (d, J=6.5 Hz, 3H), 1.26 (d, J=6.8 Hz, 3H), 1.48 (s, 9H), 2.34-2.42 (m, 1H), 2.42-2.53 (m, 1H), 2.94 (m, 1H), 3.22-3.25 (m, 1H), 3.41-3.45 (m, 1H), 3.77-3.85 (m, 2H), 4.11-4.25 (m, 3H), 4.26-4.29 (m, 1H), 4.43 (br, 1H), 4.73 (m, 1H), 6.79-6.84 (m, 4H), 7.44 (s, 1H).

Example 516

Preparation of 4-[5-((R)-2-nitro-6,7-dihydro-5H-imidazo[2,1-b][1,3]oxazin-7-ylmethoxy)pyridin-2-yl]piperazine-1-carboxylic acid tert-butyl ester The title compound was prepared in the same manner as in Example 1 using suitable starting materials.
Pale Brown Solid
1H NMR (CDCl3) δ 1.48 (s, 9H), 2.42-2.44 (m, 2H), 3.39-3.43 (m, 4H), 3.51-3.57 (m, 4H), 4.12-4.27 (m, 4H), 4.65-4.78 (m, 1H), 6.64 (d, J=9.0 Hz, 1H), 7.19 (dd, J=10.0 Hz, 3.3 Hz, 1H), 7.45 (s, 1H), 7.94 (d, J=3.0 Hz, 1H).

Example 517

Preparation of 4-[5-((S)-2-nitro-6,7-dihydro-5H-imidazo[2,1-b][1,3]oxazin-7-ylmethoxy)pyridin-2-yl]piperazine-1-carboxylic acid tert-butyl ester The title compound was prepared in the same manner as in Example 1 using suitable starting materials.
Pale Brown Solid
1H NMR (CDCl3) δ 1.48 (s, 9H), 2.28-2.50 (m, 2H), 3.36-3.47 (m, 4H), 3.47-3.58 (m, 4H), 4.12-4.27 (m, 4H), 4.65-4.78 (m, 1H), 6.64 (d, J=9.0 Hz, 1H), 7.19 (dd, J=10.0 Hz, 3.3 Hz, 1H), 7.45 (s, 1H), 7.94 (d, J=3.0 Hz, 1H).

Example 518

Preparation of (R)-7-[4-((2S,5R)-2,5-dimethyl-piperazin-1-yl)phenoxymethyl]-2-nitro-6,7-dihydro-5H-imidazo[2,1-b][1,3]oxazine trifluoroacetate Trifluoroacetic acid (4 ml) was added to a dichloromethane solution (4 ml) of (2R,5S)-2,5-dimethyl-4-[4-((R)-2-nitro-6,7-dihydro-5H-imidazo[2,1-b][1,3]oxazin-7-ylmethoxy)phenyl]piperazine-1-carboxylic acid tert-butyl ester (1.31 g), and the mixture was stirred overnight. The reaction mixture was concentrated under reduced pressure to afford the title compound as a brown amorphous compound (1.35 g).
1H NMR (DMSO-d6) δ 0.84 (d, J=10.2 Hz, 3H), 1.21 (d, J=10.6 Hz, 3H), 2.15-2.40 (m, 2H), 2.71-2.85 (m, 2H), 3.08-3.26 (m, 2H), 3.36-3.40 (m, 2H), 4.11-4.33 (m, 4H), 4.88-4.91 (m, 1H), 6.96-6.99 (d, J=14.8 Hz, 2H), 7.08-7.11 (d, J=14.8 Hz, 2H), 8.10 (s, 1H), 8.89 (br, 1H), 9.21 (br, 1H).

Example 519

Preparation of 5-[4-((S)-2-nitro-6,7-dihydro-5H-imidazo[2,1-b][1,3]oxazin-7-ylmethoxy)phenyl]-2,5-diazabicyclo[2.2.1]heptane-2-carboxylic acid tert-butyl ester The title compound was prepared in the same manner as in Example 69 using suitable starting materials.
Powder
1H NMR (CDCl3) δ 1.40-1.44 (br, 9H), 1.83-2.08 (m, 2H), 2.32-2.48 (m, 2H), 3.01-3.22 (m, 1H), 3.32-3.65 (m, 3H), 4.07-4.36 (m, 5H), 4.31-4.46 (m, 1H), 4.60 (br, 1H), 6.47-6.50 (m, 2H), 6.82-6.85 (m, 2H), 7.44 (s, 1H).

Example 520

Preparation of 4-[4'-((R)-2-nitro-6,7-dihydro-5H-imidazo[2,1-b][1,3]oxazin-7-ylmethoxy)biphenyl-4-yl]piperazine-1-carboxylic acid tert-butyl ester The title compound was prepared in the same manner as in Example 1 using suitable starting materials.
Pale Yellow Solid
1H NMR (DMSO-d6) δ 1.43 (s, 9H), 2.13-2.42 (m, 2H), 3.1-3.15 (t, J=4.9 Hz, 4H), 3.40-3.55 (t, J=5.4 Hz, 4H), 4.04-4.40 (m, 4H), 4.88-4.96 (m, 1H), 7.01 (d, J=8.4 Hz, 2H), 7.04 (J=8.5 Hz, 2H), 7.50 (d, J=8.8 Hz, 2H), 7.55 (d, J=8.8 Hz, 2H), 8.11 (s, 1H).

Example 521

Preparation of 4-[4'-((S)-2-nitro-6,7-dihydro-5H-imidazo[2,1-b][1,3]oxazin-7-ylmethoxy)biphenyl-4-yl]piperazine-1-carboxylic acid tert-butyl ester The title compound was prepared in the same manner as in Example 1 using suitable starting materials.
Pale Yellow Solid
1H NMR (DMSO-d6) δ 1.43 (s, 9H), 2.13-2.42 (m, 2H), 3.1-3.15 (t, J=4.9 Hz, 4H), 3.40-3.55 (t, J=5.4 Hz, 4H), 4.04-

4.40 (m, 4H), 4.88-4.96 (m, 1H), 7.01 (d, J=8.4 Hz, 2H), 7.04 (J=8.5 Hz, 2H), 7.50 (d, J=8.8 Hz, 2H), 7.55 (d, J=8.8 Hz, 2H), 8.11 (s, 1H).

Example 522

Preparation of (S)-7-[4-(2,5-diazabicyclo[2.2.1]hept-2-yl)phenoxymethyl]-2-nitro-6,7-dihydro-5H-imidazo[2,1-b][1,3]oxazine trifluoroacetate The title compound was prepared in the same manner as in Example 518 using suitable starting materials.
Brown Amorphous
1H NMR (DMSO-d6) δ 1.87-1.90 (m, 1H), 2.11-2.29 (m, 3H), 3.13-3.18 (m, 3H), 3.57-3.60 (m, 1H), 4.09-4.21 (m, 4H), 4.41-4.53 (m, 2H), 4.80-4.91 (m, 1H), 6.61-6.64 (d, J=15.0 Hz, 2H), 6.90-6.93 (d, J=15.0 Hz, 2H), 8.10 (s, 1H), 8.52 (br, 1H), 8.96 (br, 1H).

Example 523

Preparation of 5-[4-((R)-2-nitro-6,7-dihydro-5H-imidazo[2,1-b][1,3]oxazin-7-ylmethoxy)phenyl]-2,5-diazabicyclo[2.2.1]heptane-2-carboxylic acid tert-butyl ester The title compound was prepared in the same manner as in Example 132 using suitable starting materials.
Pale Yellow Powder
1H NMR (CDCl3) δ 1.40-1.44 (br, 9H), 1.83-2.06 (m, 2H), 2.33-2.48 (m, 2H), 3.02-3.22 (m, 1H), 3.32-3.52 (m, 2H), 3.54-3.60 (m, 1H), 4.08-4.31 (m, 5H), 4.46-4.61 (m, 1H), 4.70-4.73 (m, 1H), 6.48-6.50 (m, 2H), 6.82-6.85 (m, 2H), 7.44 (s, 1H).

Example 524

Preparation of (R)-7-[4-(2,5-diazabicyclo[2.2.1]hept-2-yl)phenoxymethyl]-2-nitro-6,7-dihydro-5H-imidazo[2,1-b][1,3]oxazine The title compound was prepared in the same manner as in Example 518 using suitable starting materials.
Brown Amorphous
1H NMR (DMSO-d6) δ 1.64-2.40 (m, 4H), 2.83-4.40 (m, 11H), 4.84 (m, 1H), 6.51-6.53 (d, J=14.8 Hz, 2H), 6.84-6.87 (d, J=14.9 Hz, 2H), 8.09 (s, 1H).

Example 525

Preparation of 4-[4-((R)-2-nitro-6,7-dihydro-5H-imidazo[2,1-b][1,3]oxazin-7-ylmethoxy)phenyl]piperidine-1-carboxylic acid tert-butyl ester The title compound was prepared in the same manner as in Example 1 using suitable starting materials.
Reddish Brown Solid
1H NMR (CDCl3) δ 1.48 (s, 9H), 1.51-1.64 (m, 3H), 1.78 (d, J=12.6 Hz, 2H), 2.32-2.42 (m, 1H), 2.44-2.52 (m, 1H), 2.55-2.63 (m, 1H), 2.79 (br s, 2H), 4.10-4.35 (m, 5H), 4.70-4.79 (m, 1H), 6.86 (d, J=8.7 Hz, 2H), 7.13 (d, J=8.6 Hz, 2H), 7.45 (s, 1H).

Example 526

Preparation of (R)-7-[4-(4,4-diethoxypiperidin-1-yl)phenoxymethyl]-2-nitro-6,7-dihydro-5H-imidazo[2,1-b][1,3]oxazine The title compound was prepared in the same manner as in Example 86 using suitable starting materials.
Yellow Powder
1H NMR (CDCl3) δ 1.20 (t, J=7.1 Hz, 6H), 1.89-1.95 (m, 4H), 2.31-2.41 (m, 1H), 2.45-2.52 (m, 1H), 3.08-3.17 (m, 4H), 3.51 (q, J=7.1 Hz, 4H), 4.07-4.24 (m, 3H), 4.28 (dd, J=10.1 Hz, 4.2 Hz, 1H), 4.71-4.76 (m, 1H), 6.81-6.85 (m, 2H), 6.88-6.93 (m, 2H), 7.44 (s, 1H).

Example 527

Preparation of (R)-2-nitro-7-(4-piperazin-1-ylphenoxymethyl)-6,7-dihydro-5H-imidazo[2,1-b][1,3]oxazine A 4 N hydrochloric acid 1,4-dioxane solution (22 ml) was gradually added to a methylene chloride (22 ml) suspension of 4-[4-((R)-2-nitro-6,7-dihydro-5H-imidazo[2,1-b][1,3]oxazin-7-ylmethoxy)phenyl]piperazine-1-carboxylic acid tert-butyl ester (4.51 g), and the mixture was stirred at room temperature for 2 hours. The mixture was diluted with ethyl acetate and the precipitate was collected by filtration. The solid thus obtained was subjected to triturate with ethanol, collected by filtration and then dried. Hydrochloride of the title product was dissolved in water and neutralized using a 5 N sodium hydroxide aqueous solution under ice cooling, followed by stirring. The precipitate was collected by filtration and dried at 60° C. to afford the title compound as a yellow powder (3.0 g).
1H NMR (CDCl3) δ 2.31-2.42 (m, 1H), 2.44-2.53 (m, 1H), 3.01-3.08 (m, 8H), 4.08-4.23 (m, 3H), 4.29 (dd, J=10.2 Hz, 4.2 Hz, 1H), 4.69-4.75 (m, 1H), 6.83-6.87 (m, 2H), 6.87-6.91 (m, 2H), 7.45 (s, 1H).

Example 528

Preparation of (R)-2-nitro-7-(4-piperazin-1-ylphenoxymethyl)-6,7-dihydro-5H-imidazo[2,1-b][1,3]oxazine trifluoroacetate The title compound was prepared in the same manner as in Example 518 using suitable starting materials.
Pale Brown Powder
1H NMR (DMSO-d6) δ 2.13-2.24 (m, 1H), 2.26-2.34 (m, 1H), 3.16-3.29 (m, 8H), 4.10 (dt, J=5.1 Hz, 12.4 Hz, 1H), 4.14-4.22 (m, 2H), 4.25 (dd, J=11.1 Hz, 3.3 Hz, 1H), 4.84-4.90 (m, 1H), 6.91-6.95 (m, 2H), 6.95-6.99 (m, 2H), 8.10 (s, 1H), 8.77 (brs, 2H).

Example 529

Preparation of 1'-[4-((R)-2-nitro-6,7-dihydro-5H-imidazo[2,1-b][1,3]oxazin-7-ylmethoxy)phenyl]-[4,4']bipiperidinyl-1-carboxylic acid tert-butyl ester The title compound was prepared in the same manner as in Example 86 using suitable starting materials.

Pale Yellow Powder

1H NMR (CDCl3) δ 1.10-1.33 (m, 4H), 1.35-1.45 (m, 2H), 1.46 (s, 9H), 1.65-1.75 (m, 2H), 1.77-1.85 (m, 2H), 2.25-2.48 (m, 2H), 2.49-2.77 (m, 4H), 3.51-3.59 (m, 2H), 4.05-4.23 (m, 5H), 4.24-4.29 (m, 1H), 4.71-4.77 (m, 1H), 6.81-6.85 (m, 2H), 6.88-6.92 (m, 2H), 7.44 (s, 1H).

Example 530

Preparation of 4-[4-((R)-2-nitro-6,7-dihydro-5H-imidazo[2,1-b][1,3]oxazin-7-ylmethoxy)phenyl]-3,6-dihydro-2H-pyridine-1-carboxylic acid tert-butyl ester The title compound was prepared in the same manner as in Example 86 using suitable starting materials.
White Powder 1H NMR (CDCl3) δ 1.49 (s, 9H), 2.34-2.44 (m, 1H), 2.44-2.53 (m, 3H), 3.61-3.67 (m, 2H), 4.03-4.09 (m, 2H), 4.09-4.18 (m, 1H), 4.18-4.26 (m, 2H), 4.33 (dd, J=10.2 Hz, 4.2 Hz, 1H), 4.72-4.80 (m, 1H), 5.91-6.02 (m, 1H), 6.85-6.92 (m, 2H), 7.32 (d, J=8.8 Hz, 2H), 7.46 (s, 1H).

Example 531

Preparation of (R)-2-nitro-7-[4-(1,2,3,6-tetrahydro-pyridin-4-yl)phenoxymethyl]-6,7-dihydro-5H-imidazo[2,1-b][1,3]oxazine trifluoroacetate The title compound was prepared in the same manner as in Example 518 using suitable starting materials.
Pale Green Powder 1H NMR (DMSO-d6) δ 2.14-2.26 (m, 1H), 2.28-2.38 (m, 1H), 2.61-2.69 (m, 2H), 3.27-3.39 (m, 2H), 3.71-3.78 (m, 2H), 4.10 (dt, J=5.2 Hz, 12.4 Hz, 1H), 4.15-4.22 (m, 1H), 4.28 (dd, J=11.1 Hz, 5.8 Hz, 1H), 4.34 (dd, J=11.1 Hz, 3.2 Hz, 1H), 4.88-4.95 (m, 1H), 6.09-6.13 (m, 1H), 7.01 (d, J=8.9 Hz, 2H), 7.45 (d, J=8.9 Hz, 2H), 8.11 (s, 1H), 8.80 (brs, 2H).

Example 532

Preparation of 4-(tert-butyldimethylsilanyloxy)-1'-[4-((R)-2-nitro-6,7-dihydro-5H-imidazo[2,1-b][1,3]oxazin-7-ylmethoxy)phenyl]-[1,4']piperidinyl The title compound was prepared in the same manner as in Example 1 using suitable starting materials.
Yellow Powder 1H NMR (CDCl3) δ 0.04 (s, 6H), 0.89 (s, 9H), 1.53-1.96 (m, 7H), 2.31-2.53 (m, 6H), 2.64 (t, J=10.6 Hz, 2H), 2.82 (br s, 2H), 3.59 (d, J=12.1 Hz, 2H), 3.72 (br s, 1H), 4.05-4.22 (m, 3H), 4.22-4.30 (dd, J=10.0 Hz, 4.3 Hz, 1H), 4.68-4.77 (m, 1H), 6.82 (d, J=9.1 Hz, 2H), 6.89 (d, J=9.1 Hz, 2H), 7.45 (s, 1H).

Example 533

Preparation of (R)-7-(4-{4-[4-(tert-butyldimethylsilanyloxy)piperidin-1-ylmethyl]piperidin-1-yl}phenoxymethyl)-2-nitro-6,7-dihydro-5H-imidazo[2,1-b][1,3]oxazine The title compound was prepared in the same manner as in Example 470 using suitable starting materials.
Reddish Yellow Powder 1H NMR (CDCl3) δ 0.05 (s, 6H), 0.89 (s, 9H), 1.25-1.38 (m, 2H), 1.50-1.65 (m, 3H), 1.73 (br s, 2H), 1.85 (d, J=12.4 Hz, 2H), 2.05-2.25 (m, 4H), 2.28-2.40 (m, 1H), 2.40-2.50 (m, 1H), 2.50-2.70 (m, 4H), 3.52 (d, J=12.0 Hz, 2H), 3.63-3.72 (m, 1H), 4.04-4.21 (m, 3H), 4.21-4.30 (dd, J=10.3 Hz, 4.3 Hz, 1H), 4.65-4.75 (m, 1H), 6.76-6.85 (m, 2H), 6.85-6.94 (m, 2H), 7.44 (s, 1H).

Example 534

Preparation of 4-[4-((R)-2-nitro-6,7-dihydro-5H-imidazo[2,1-b][1,3]oxazin-7-ylmethoxy)phenoxymethyl]piperidine-1-carboxylic acid tert-butyl ester The title compound was prepared in the same manner as in Example 470 using suitable starting materials.
Yellow Solid 1H NMR (CDCl3) δ 1.18-1.30 (m, 2H), 1.46 (s, 9H), 1.81 (d, J=13.1 Hz, 2H), 1.93 (br s, 1H), 2.33-2.44 (m, 1H), 2.44-2.53 (m, 1H), 2.74 (br s, 2H), 3.75 (d, J=6.4 Hz, 2H), 4.06-4.30 (m, 5H), 4.68-4.76 (m, 1H), 6.78-6.87 (m, 4H), 7.45 (s, 1H).

Example 535

Preparation of 4-{2-[4-((R)-2-nitro-6,7-dihydro-5H-imidazo[2,1-b][1,3]oxazin-7-ylmethoxy)phenoxy]ethyl}piperidine-1-carboxylic acid tert-butyl ester The title compound was prepared in the same manner as in Example 470 using suitable starting materials.
Yellow Solid 1H NMR (CDCl3) δ 1.10-1.21 (m, 2H), 1.46 (s, 9H), 1.64-1.75 (m, 6H), 2.30-2.41 (m, 1H), 2.41-2.53 (m, 1H), 2.70 (br s, 2H), 3.96 (t, J=5.9 Hz, 2H), 4.01-4.24 (m, 4H), 4.24-4.31 (dd, J=10.2 Hz, 4.2 Hz, 1H), 4.68-4.76 (m, 1H), 6.76-6.85 (m, 4H), 7.45 (s, 1H).

Example 536

Preparation of (R)-2-nitro-7-[4-(piperidin-4-ylmethoxy)phenoxymethyl]-6,7-dihydro-5H-imidazo[2,1-b][1,3]oxazine The title compound was prepared in the same manner as in Example 518 using suitable starting materials.
Pale Brown Solid 1H NMR (CDCl3) δ 1.23-1.34 (m, 2H), 1.76-1.97 (m, 5H), 2.31-2.45 (m, 1H), 2.45-2.53 (m, 1H), 2.60-2.75 (m, 2H), 3.14 (d, J=12.1 Hz, 2H), 3.74 (d, J=6.3 Hz, 2H), 4.04-4.32 (m, 3H), 4.68-4.78 (m, 1H), 6.78-6.88 (m, 4H), 7.45 (s, 1H).

Example 537

Preparation of (R)-2-nitro-7-[4-(2-piperidin-4-yl-ethoxy)phenoxymethyl]-6,7-dihydro-5H-imidazo[2,1-b][1,3]oxazine The title compound was prepared in the same manner as in Example 518 using suitable starting materials.
Yellow Solid 1H NMR (CDCl3) δ 1.14-1.30 (m, 2H), 1.61-1.83 (m, 5H), 2.05-2.53 (m, 3H), 2.60-2.70 (m, 2H), 3.10 (d, J=12.1 Hz, 2H), 3.95 (t, J=6.2 Hz, 2H), 4.02-4.31 (m, 4H), 4.70-4.78 (m, 1H), 6.83 (s, 4H), 7.45 (s, 1H).

Example 538

Preparation of 4-{(E)-3-[4-((R)-2-nitro-6,7-dihydro-5H-imidazo[2,1-b][1,3]oxazin-7-ylmethoxy)phenyl]allyl}piperazine-1-carboxylic acid tert-butyl ester The title compound was prepared in the same manner as in Example 470 using suitable starting materials.
Yellow Solid
1H NMR (CDCl3) δ 1.46 (s, 9H), 2.28-2.52 (m, 6H), 3.15 (d, J=6.7 Hz, 2H), 3.46 (br s, 4H), 4.07-4.18 (m, 1H), 4.18-4.27 (m, 2H), 4.30-4.38 (dd, J=10.2 Hz, 4.2 Hz, 1H), 4.70-4.82 (m, 1H), 6.10-6.20 (m, 1H), 6.46 (d, J=15.8 Hz, 1H), 6.86 (d, J=8.6 Hz, 2H), 7.32 (d, J=8.6 Hz, 2H), 7.46 (s, 1H).

Example 539

Preparation of (R)-2-nitro-7-[4-((E)-3-piperazin-1-yl-propenyl)phenoxymethyl]-6,7-dihydro-5H-imidazo[2,1-b][1,3]oxazine trifluoroacetate The title compound was prepared in the same manner as in Example 518 using suitable starting materials.
Yellow Powder
1H NMR (CDCl3) δ 2.33 (m, 2H), 2.60 (s, 1H), 3.28-3.56 (m, 4H), 3.56-3.78 (m, 4H), 4.06-4.42 (m, 4H), 4.78-4.88 (m, 2H), 6.05-6.18 (m, 1H), 6.66 (d, J=15.6 Hz, 1H), 6.89 (d, J=8.7 Hz, 2H), 7.35 (d, J=8.6 Hz, 2H), 7.62 (s, 1H).

Examples 540 to 772

The following products were prepared in the same manner as in Examples above using suitable starting materials.

TABLE 1

| Example No. | $R^A$ | $R^B$ | $R^C$ | $R^D$ | $R^E$ | MS (M + 1) |
|---|---|---|---|---|---|---|
| Example 540 | —H | —H | —H | —H | —H | 450 |
| Example 541 | —H | —H | —C₆H₅ | —H | —H | 526 |
| Example 542 | —H | —H | —OCH₃ | —H | —H | 480 |
| Example 543 | —H | —H | —H | —OCH₃ | —H | 480 |
| Example 544 | —H | —OCH₃ | —OCH₃ | —OCH₃ | —H | 540 |
| Example 545 | —H | —H | —OH | —H | —H | 466 |
| Example 546 | —H | —H | —CH₃ | —H | —H | 464 |
| Example 547 | —H | —H | —CH(CH₃)₂ | —H | —H | 492 |
| Example 548 | —H | —H | —C(CH₃)₃ | —H | —H | 506 |
| Example 549 | —H | —H | —NO₂ | —H | —H | 495 |
| Example 550 | —H | —H | —CN | —H | —H | 475 |
| Example 551 | —H | —H | —NHCOCH₃ | —H | —H | 507 |
| Example 552 | —H | —H | —O(CH₂)₃N(CH₃)₂ | —H | —H | 551 |
| Example 553 | —H | —H | —H | —H | —Cl | 484 |
| Example 554 | —H | —H | —H | —Cl | —H | 484 |
| Example 555 | —H | —Cl | —H | —H | —H | 484 |
| Example 556 | —H | —H | —H | —H | —CF₃ | 518 |
| Example 557 | —H | —H | —H | —CF₃ | —H | 518 |
| Example 558 | —H | —H | —CH₃ | —CH₃ | —H | 478 |
| Example 559 | —CH₃ | —H | —CH₃ | —CH₃ | —H | 492 |
| Example 560 | —H | —Cl | —H | —Cl | —Cl | 554 |
| Example 561 | —H | —H | —H | —H | —OCF₃ | 534 |
| Example 562 | —H | —H | —CF₃ | —H | —H | 518 |
| Example 563 | —H | —H | —OCH₃ | —OCH₃ | —H | 510 |
| Example 564 | —H | —H | —F | —H | —H | 468 |
| Example 565 | —H | —H | —OC₆H₅ | —H | —H | 542 |
| Example 566 | —H | —H | —OCH₂C₆H₅ | —H | —H | 556 |
| Example 567 | —H | —H | —H | —OCF₃ | —H | 534 |
| Example 568 | —H | —H | —Cl | —Cl | —H | 518 |
| Example 569 | —H | —H | —O(CH₂)₇CH₃ | —H | —H | 578 |
| Example 570 | —H | —H | —CO₂CH₃ | —H | —H | 508 |
| Example 571 | —H | —Cl | —H | —Cl | —H | 518 |
| Example 572 | —H | —H | —N(CH₃)₂ | —H | —H | 493 |

TABLE 2

| | | | | | | |
|---|---|---|---|---|---|---|
| Example 573 | —H | —H | —OCH₃ | —F | —H | 498 |
| Example 574 | —H | —H | —OCH₃ | —CH₃ | —H | 494 |
| Example 575 | —H | —H | —SCH₃ | —H | —H | 496 |
| Example 576 | —H | —H | —OCOCH₃ | —H | —H | 508 |

TABLE 2-continued

| Example No. | | | | | | MS (M+1) |
|---|---|---|---|---|---|---|
| Example 577 | —H | —H | —O(CH$_2$)$_3$CH$_3$ | —H | —H | 506 |
| Example 578 | —H | —H | —SO$_2$CH$_3$ | —H | —H | 528 |
| Example 579 | —H | —H | —Cl | —CF$_3$ | —H | 552 |
| Example 580 | —H | —H | —H | —SCF$_3$ | —H | 550 |
| Example 581 | —H | —H | —Cl | —F | —H | 502 |
| Example 582 | —H | —H | —CH$_2$CH(CH$_3$)$_2$ | —H | —H | 506 |
| Example 583 | —H | —H | —N(C$_6$H$_5$)$_2$ | —H | —H | 617 |
| Example 584 | —F | —F | —F | —F | —F | 540 |
| Example 585 | —H | —H | —OCH$_2$C$_6$H$_5$ | —OCH$_2$C$_6$H$_5$ | —H | 662 |
| Example 586 | —H | —H | —OCH$_2$CH=CH$_2$ | —H | —H | 506 |
| Example 587 | —H | —H | —OCHF$_2$ | —H | —H | 516 |
| Example 588 | —H | —H | —OCH(CH$_3$)$_2$ | —H | —H | 508 |
| Example 589 | —H | —H | —H | —H | —NHSO$_2$CH$_3$ | 543 |
| Example 590 | —H | —H | —N(C$_4$H$_9$-n)$_2$ | —H | —H | 577 |
| Example 591 | —H | —H | —OCH$_2$C$_6$H$_5$ | —Cl | —H | 590 |
| Example 592 | —H | —H | —OC(CH$_3$)$_3$ | —H | —H | 522 |

TABLE 3

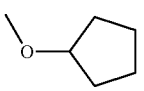

| Example No. | R$^A$ | R$^B$ | R$^C$ | R$^D$ | R$^E$ | MS (M+1) |
|---|---|---|---|---|---|---|
| Example 593 | —H | —H | —OCH$_3$ | 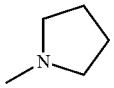 | —H | 564 |
| Example 594 | —H | —H | 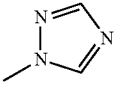 | —H | —H | 519 |
| Example 595 | —H | —H | 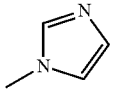 | —H | —H | 517 |
| Example 596 | —H | —H | 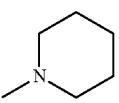 | —H | —H | 516 |
| Example 597 | —H | —H |  | —H | —H | 533 |

TABLE 4

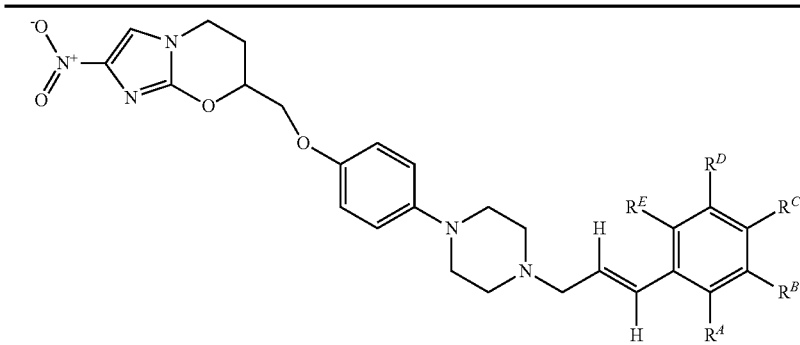

| Example No. | $R^A$ | $R^B$ | $R^C$ | $R^D$ | $R^E$ | MS (M + 1) |
|---|---|---|---|---|---|---|
| Example 598 | —H | —H | —H | —H | —H | 476 |
| Example 599 | —H | —H | —OCH$_3$ | —H | —H | 506 |
| Example 600 | —H | —H | —CF$_3$ | —H | —H | 544 |
| Example 601 | —H | —H | —Cl | —Cl | —H | 544 |
| Example 602 | —H | —H | —Cl | —H | —H | 510 |
| Example 603 | —H | —H | —H | —Cl | —H | 510 |
| Example 604 | —H | —H | —CN | —H | —H | 501 |
| Example 605 | —H | —H | —H | —Cl | —Cl | 544 |
| Example 606 | —H | —H | —OCOCH$_3$ | —OCH$_3$ | —H | 564 |
| Example 607 | —H | —H | —NO$_2$ | —H | —H | 521 |
| Example 608 | —H | —H | —N(C$_2$H$_5$)$_2$ | —H | —H | 547 |
| Example 609 | —H | —H | —N(CH$_3$)$_2$ | —H | —H | 519 |
| Example 610 | —H | —H | —H | —H | —OH | 494 |
| Example 611 | —H | —OCH$_3$ | —OH | —OCH$_3$ | —H | 552 |
| Example 612 | —H | —H | —OH | —OCH$_3$ | —H | 522 |
| Example 613 | —H | —H | —C$_2$H$_5$ | —H | —H | 504 |
| Example 614 | —H | —H | —(CH$_2$)$_5$CH$_3$ | —H | —H | 560 |
| Example 615 | —H | —H | —OCH$_2$C$_6$H$_5$ | —H | —H | 582 |
| Example 616 | —H | —H | —OC$_6$H$_5$ | —H | —H | 568 |
| Example 617 | —H | —H | —CH(CH$_3$)$_2$ | —H | —H | 518 |
| Example 618 | —H | —H | —O(CH$_2$)$_5$CH$_3$ | —H | —H | 576 |
| Example 619 | —H | —H | —OCF$_3$ | —H | —H | 560 |

TABLE 5

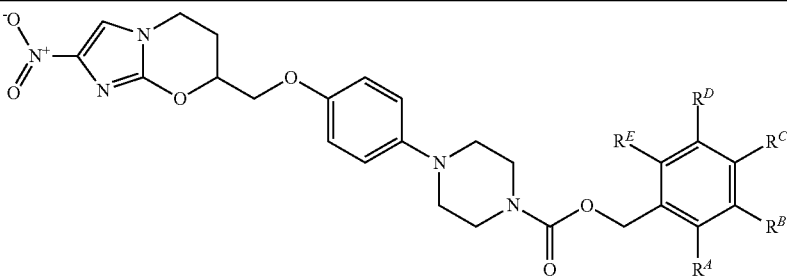

| Example No. | $R^A$ | $R^B$ | $R^C$ | $R^D$ | $R^E$ | MS (M + 1) |
|---|---|---|---|---|---|---|
| Example 620 | —H | —H | —OCH$_3$ | —H | —H | 524 |
| Example 621 | —H | —H | —CH$_3$ | —H | —H | 508 |
| Example 622 | —H | —H | —H | —H | —Cl | 528 |
| Example 623 | —H | —H | —Cl | —H | —H | 528 |
| Example 624 | —H | —H | —CH(CH$_3$)$_2$ | —H | —H | 536 |
| Example 625 | —H | —H | —CO$_2$CH$_3$ | —H | —H | 552 |
| Example 626 | —H | —H | —H | —H | —H | 494 |
| Example 627 | —H | —H | —SCH$_3$ | —H | —H | 540 |
| Example 628 | —H | —H | —OCH$_3$ | —OCH$_3$ | —H | 554 |
| Example 629 | —H | —H | —NO$_2$ | —H | —H | 539 |
| Example 630 | —H | —H | —H | —CF$_3$ | —H | 562 |
| Example 631 | —H | —H | —H | —Cl | —H | 528 |
| Example 632 | —H | —H | —O(CH$_2$)$_3$CH$_3$ | —H | —H | 566 |
| Example 633 | —H | —OCH$_3$ | —OCH$_3$ | —OCH$_3$ | —H | 584 |
| Example 634 | —H | —H | —CH$_3$ | —CH$_3$ | —H | 522 |
| Example 635 | —H | —H | —H | —H | —NHCOCH$_3$ | 551 |
| Example 636 | —H | —H | —CF$_3$ | —H | —H | 562 |
| Example 637 | —H | —H | —Cl | —Cl | —H | 562 |

TABLE 5-continued

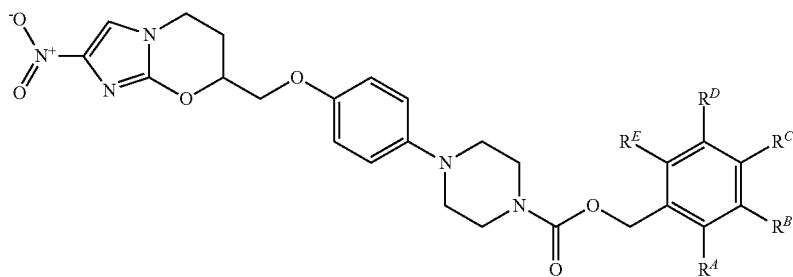

| Example No. | R$^A$ | R$^B$ | R$^C$ | R$^D$ | R$^E$ | MS (M + 1) |
|---|---|---|---|---|---|---|
| Example 638 | —H | —H | —F | —H | —H | 512 |
| Example 639 | —H | —H | —OCF$_3$ | —H | —H | 578 |
| Example 640 | —H | —H | —CH$_2$C$_6$H$_5$ | —H | —H | 600 |
| Example 641 | —H | —H | —C(CH$_3$)$_3$ | —H | —H | 550 |
| Example 642 | —H | —H | —OC$_2$H$_5$ | —H | —H | 538 |

TABLE 6

| Example 643 | —H | —H | —SCF$_3$ | —H | —H | 594 |
| Example 644 | —H | —CF$_3$ | —H | —CF$_3$ | —H | 630 |
| Example 645 | —H | —H | —H | —OCF$_3$ | —H | 578 |
| Example 646 | —H | —H | —H | —H | —OCF$_3$ | 578 |
| Example 647 | —F | —F | —F | —F | —F | 584 |
| Example 648 | —H | —Cl | —H | —Cl | —H | 562 |
| Example 649 | —H | —H | —C$_2$H$_5$ | —H | —H | 522 |
| Example 650 | —H | —H | —C$_6$H$_5$ | —H | —H | 570 |
| Example 651 | —H | —H | —H | —H | —CF$_3$ | 562 |

TABLE 6-continued

| Example 652 | —H | —H | ![imidazole] | —H | —H | |
| Example 653 | —H | —H | ![pyrrole] | —H | —H | 559 |

TABLE 7

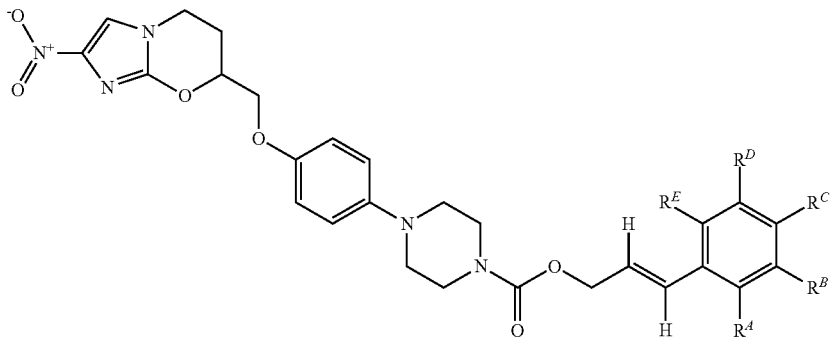

| Example No. | R$^A$ | R$^B$ | R$^C$ | R$^D$ | R$^E$ | MS (M + 1) |
|---|---|---|---|---|---|---|
| Example 654 | —H | —H | —Cl | —Cl | —H | 588 |
| Example 655 | —H | —H | —Cl | —H | —H | 554 |
| Example 656 | —H | —H | —CF$_3$ | —H | —H | 588 |
| Example 657 | —H | —H | —H | —CF$_3$ | —H | 588 |
| Example 658 | —H | —H | —OCF$_3$ | —H | —H | 604 |
| Example 659 | —H | —H | —F | —H | —H | 538 |

TABLE 8

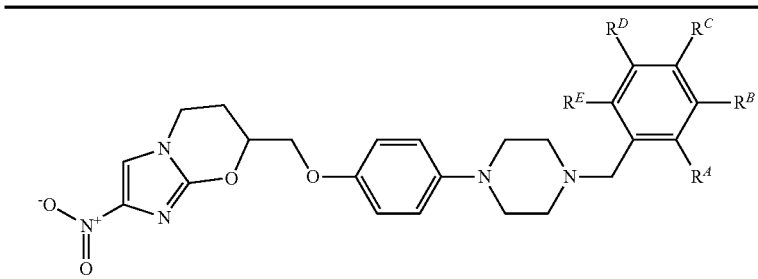

| Example No. | $R^A$ | $R^B$ | $R^C$ | $R^D$ | $R^E$ | MS (M + 1) |
|---|---|---|---|---|---|---|
| Example 660 | —H | —H | —OCF$_3$ | —H | —H | 534 |
| Example 661 | —H | —H | —H | —OC$_6$H$_5$ | —H | 542 |
| Example 662 | —H | —H | —Cl | —H | —Cl | 518 |
| Example 663 | —H | —H | —H | —H | —OCH$_2$C$_6$H$_5$ | 556 |
| Example 664 | —H | —H | —CH=CHC$_6$H$_5$ (trans) | —H | —H | 552 |
| Example 665 | —H | —H | —OCH$_2$CH$_3$ | —H | —H | 508 |
| Example 666 | —H | —H | —Cl | —H | —F | 502 |
| Example 667 | —H | —H | —H | —OCH$_2$C$_6$H$_5$ | —H | 556 |
| Example 668 | —H | —H | —SC$_2$H$_5$ | —H | —H | 510 |

TABLE 9

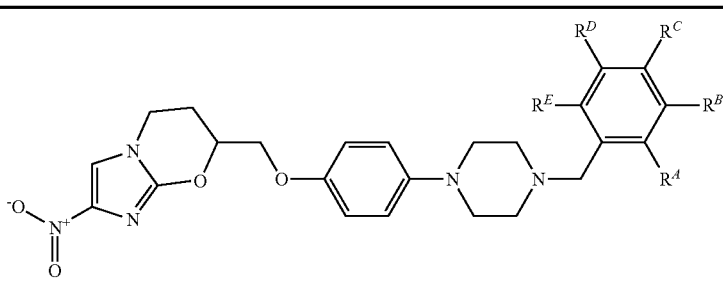

| Example No. | $R^A$ | $R^B$ | $R^C$ | $R^D$ | $R^E$ | MS (M + 1) |
|---|---|---|---|---|---|---|
| Example 669 | —H | —H |  | —H | —H | 595 |
| Example 670 | —H | —H | —H | 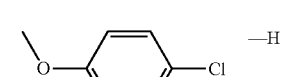 | —H | 576 |
| Example 671 | —H | —H | —H | 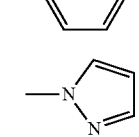 | —H | 516 |
| Example 672 | —H | —H | 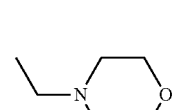 | —H | —H | 549 |
| Example 673 | —H | —H | 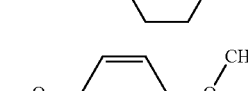 | —H | —H | 572 |
| Example 674 | —H | —H | 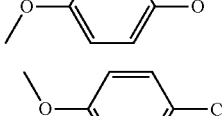 | —H | —H | 576 |
| Example 675 | —H | —H | —H | 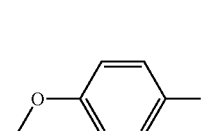 | —H | 560 |

TABLE 9-continued

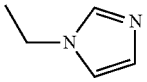

| Example No. | R^A | R^B | R^C | R^D | R^E | MS (M + 1) |
|---|---|---|---|---|---|---|
| Example 676 | —H | —H | 1-ethyl-imidazol-2-yl | —H | —H | 530 |

TABLE 10

| Example No. | R^A | R^B | R^C | R^D | R^E | MS (M + 1) |
|---|---|---|---|---|---|---|
| Example 677 | —H | —H | —F | —H | —H | 544 |
| Example 678 | —H | —H | —CF₃ | —H | —H | 594 |
| Example 679 | —H | —H | —OCF₃ | —H | —H | 610 |
| Example 680 | —H | —H | —OCH₃ | —H | —H | 556 |
| Example 681 | —H | —H | —Cl | —H | —H | 560 |
| Example 682 | —H | —H | —Cl | —Cl | —H | 594 |
| Example 683 | —H | —H | —Cl | —CH₃ | —H | 574 |
| Example 684 | —H | —H | —SCH₃ | —H | —H | 572 |
| Example 685 | —H | —H | —OCH₂C₆H₅ | —H | —H | 632 |
| Example 686 | —H | —H | —F | —CF₃ | —H | 612 |

TABLE 11

| Example No. | R^F | MS (M + 1) |
|---|---|---|
| Example 687 | —CH₂CH═CH₂ | 458 |
| Example 688 | -3-Pyridyl | 495 |
| Example 689 | -2-Pyridyl | 495 |
| Example 690 | —CH₂C₆H₅ | 508 |
| Example 691 | —CH₂CH₂C₆H₅ | 522 |
| Example 692 | —CCC₆H₅ | 518 |
| Example 693 | -4-Pyridyl | 495 |

TABLE 12
| Example No. | R$^F$ | MS (M + 1) |
|---|---|---|
| Example 694 | 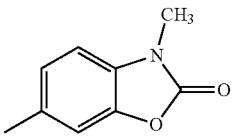 | 542 |
| Example 695 | 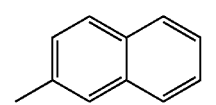 | 565 |
| Example 696 | 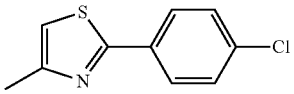 | 544 |
| Example 697 | 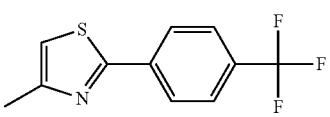 | 611 |
| Example 698 | 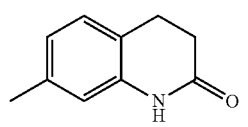 | 645 |
| Example 699 | 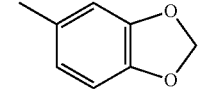 | 563 |
| Example 700 | | 538 |
TABLE 13
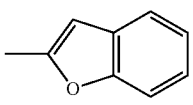
| Example No. | R$^G$ | MS (M + 1) |
|---|---|---|
| Example 701 | | 490 |
TABLE 13-continued
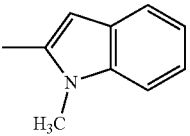
| Example No. | R$^G$ | MS (M + 1) |
|---|---|---|
| Example 702 | | 503 |

TABLE 13-continued
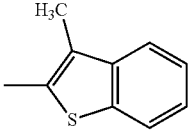
| Example No. | $R^G$ | MS (M + 1) |
|---|---|---|
| Example 703 | 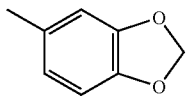 | 520 |
| Example 704 | 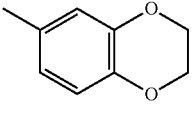 | 494 |
| Example 705 | 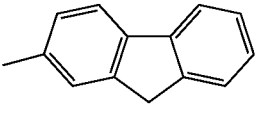 | 508 |
| Example 706 | 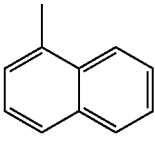 | 538 |
| Example 707 | 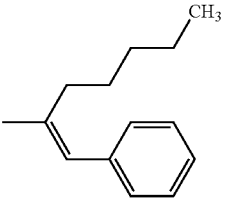 | 500 |
| Example 708 | 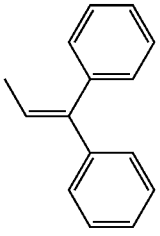 | 546 |
| Example 709 | 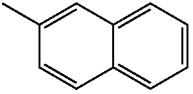 | 552 |
TABLE 14
| Example 710 | 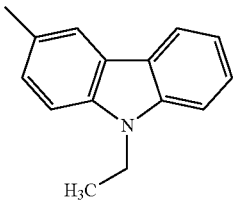 | 500 |
|---|---|---|
| Example 711 | 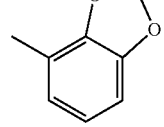 | 567 |
| Example 712 | 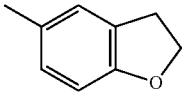 | 494 |
| Example 713 | 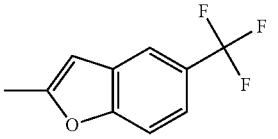 | 492 |
| Example 714 | 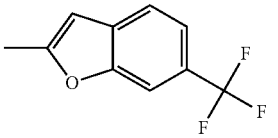 | 558 |
| Example 715 | 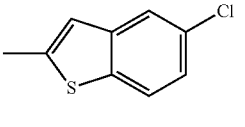 | 558 |
| Example 716 | 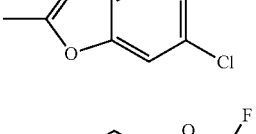 | 540 |
| Example 717 | 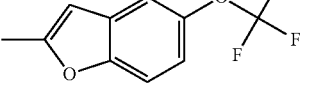 | 524 |
| Example 718 | 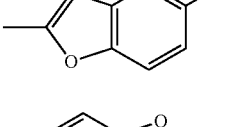 | 574 |
| Example 719 | 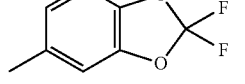 | 524 |
| Example 720 | | 530 |

TABLE 15
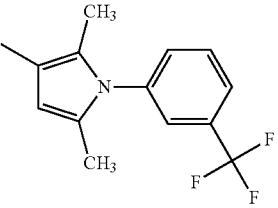 [SMILES: Cc1cc(C)n(-c2cccc(C(F)(F)F)c2)c1C]
| Example No. | $R^G$ | MS (M + 1) |
|---|---|---|
| Example 721 | 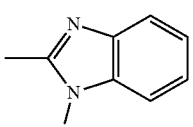 | 501 |
| Example 722 | 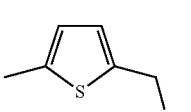 | 516 |
| Example 723 | 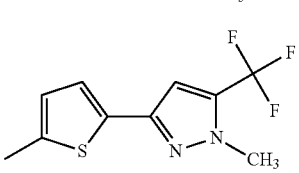 | 550 |
| Example 724 | 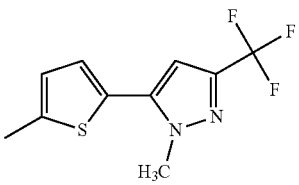 | 631 |
| Example 725 | 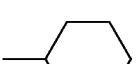 | 490 |
| Example 726 | 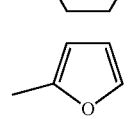 | 533 |
| Example 727 | 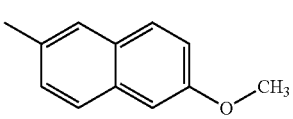 | 567 |
| Example 728 | 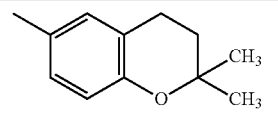 | 563 |
| Example 729 | 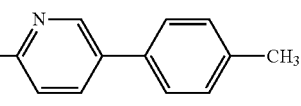 | 549 |
| Example 730 | 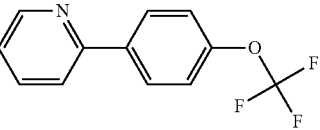 | 466 |
TABLE 16
| Example 731 | | 538 |
| Example 732 | | 490 |
| Example 733 | | 611 |
| Example 734 | | 504 |
| Example 735 | | 484 |
| Example 736 | | 604 |
| Example 737 | | 604 |
| Example 738 | | 456 |
| Example 739 | | 440 |
| Example 740 | | 530 |
TABLE 17
| Example 741 | | 534 |
| Example 742 | | 541 |
| Example 743 | | 611 |

TABLE 17-continued
| | | |
|---|---|---|
| Example 744 | 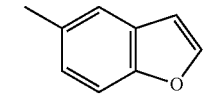 | 490 |
| Example 745 | 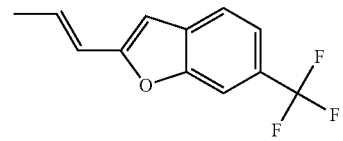 | 584 |
| Example 746 | 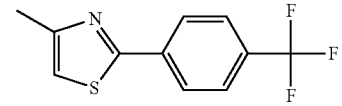 | 601 |
| Example 747 | 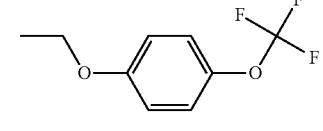 | 564 |
| Example 748 | 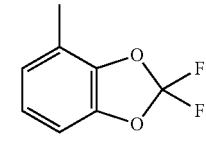 | 530 |
| Example 749 | 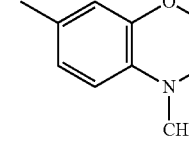 | 521 |
| Example 750 | 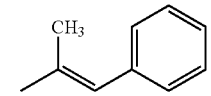 | 490 |
TABLE 18
| | | |
|---|---|---|
| Example 751 | 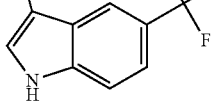 | 557 |
| Example 752 | 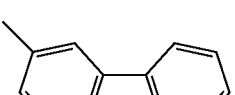 | 539 |
| Example 753 | 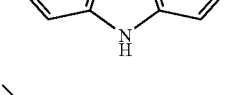 | 593 |
TABLE 18-continued
| | | |
|---|---|---|
| Example 754 | 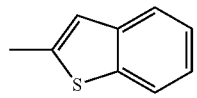 | 501 |
| Example 755 | 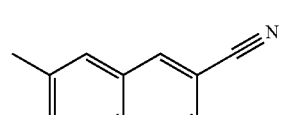 | 523 |
| Example 756 | 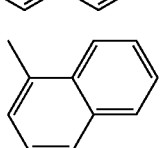 | 612 |
| Example 757 | 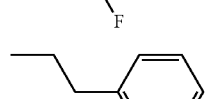 | 628 |
| Example 758 | | 578 |
| Example 759 | | 464 |
| Example 760 | | 506 |
TABLE 19
| | | |
|---|---|---|
| Example 761 | | 506 |
| Example 762 | | 525 |
| Example 763 | | 518 |
| Example 764 | | 478 |

TABLE 19-continued

| Example No. | Structure | MS |
|---|---|---|
| Example 765 | 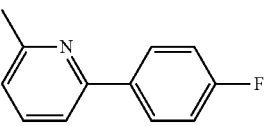 | 545 |
| Example 766 | 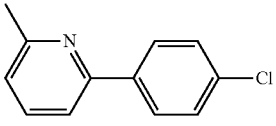 | 561 |
| Example 767 | 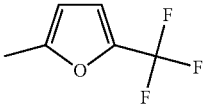 | 508 |
| Example 768 | 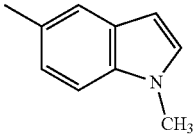 | 503 |
| Example 769 | 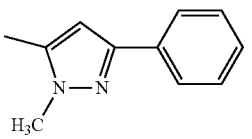 | 530 |
| Example 770 | 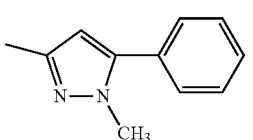 | 530 |

TABLE 20

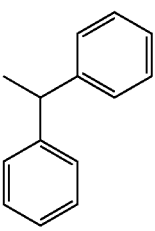

| Example No. | $R^H$ | MS (M + 1) |
|---|---|---|
| Example 771 | 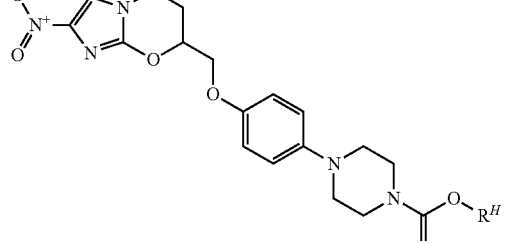 | 570 |
| Example 772 | 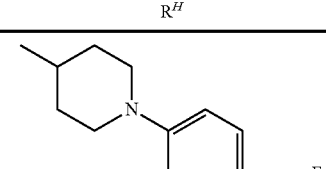 | 631 |

Test Example 1

Antimicrobial Assay (Agar Plate Dilution Method)

The minimum inhibitory concentration of the 2,3-dihydro-6-nitro-imidazo[2,1-b]oxazole compound obtained in Example 228 against *Mycobacterium tuberculosis* (*M. tuberculosis* H37Rv) was determined using a 7H11 medium (manufactured by BBL). The above strain had been cultured on a 7H9 medium (manufactured by BBL) and stored by freezing at −80° C. The number of viable cells had been counted. A bacterial suspension with a final viable cell count of approximately $10^6$ CFU/ml was prepared by using the bacterial stock mentioned above. Approximately 5 µl of the thus prepared bacterial suspension was inoculated onto the 7H11 agar medium containing the test compound and then cultured at 37° C. for 14 days. Thereafter, the culture was subjected to a test to determine the minimum inhibitory concentration. The minimum inhibitory concentration of the compound against *M. tuberculosis* H37Rv was ≤0.0004 µg/ml.

Test Example 2

Antimicrobial Assay (Agar Plate Dilution Method)

The minimal inhibitory concentrations against *Mycobacterium tuberculosis* (*M. tuberculosis* kurono) of the compounds listed in the table below were determined using a 7H11 medium (manufactured by BBL). *M. tuberculosis* kurono strain had been cultured on a 7H9 medium (manufactured by BBL) and stored by freezing at −80° C. The number of viable cells had been counted. A bacterial suspension with a final viable cell count of approximately $10^6$ CFU/ml was prepared by using a bacterial stock mentioned above. Approximately 5 µl of the thus prepared bacterial suspension was inoculated onto the 7H11 agar medium containing the test compounds and then cultured at 37° C. for 14 days. Thereafter, the culture was subjected to a test to determine the minimum inhibitory concentration.

The results are shown in the table below.

TABLE 21

| Compound Tested | Minimum Inhibitory Concentration (µg/ml) |
|---|---|
| Compound of Example 1 | 0.024 |
| Compound of Example 3 | 0.05 |
| Compound of Example 53 | 0.1 |
| Compound of Example 56 | 0.012 |
| Compound of Example 64 | ≤0.006 |
| Compound of Example 79 | 0.012 |
| Compound of Example 90 | 0.012 |
| Compound of Example 143 | 0.1 |
| Compound of Example 147 | 0.05 |
| Compound of Example 153 | 0.024 |
| Compound of Example 182 | ≤0.0015 |
| Compound of Example 198 | ≤0.0015 |
| Compound of Example 206 | ≤0.0015 |
| Compound of Example 228 | 0.0008 |
| Compound of Example 254 | 0.0008 |
| Compound of Example 282 | 0.006 |
| Compound of Example 290 | 0.0008 |
| Compound of Example 299 | 0.0008 |
| Compound of Example 304 | 0.012 |
| Compound of Example 335 | 0.0015 |
| Compound of Example 364 | 0.024 |
| Compound of Example 372 | 0.006 |
| Compound of Example 379 | 0.1 |
| Compound of Example 380 | 0.012 |
| Compound of Example 382 | 0.012 |
| Compound of Example 383 | 0.003 |
| Compound of Example 395 | 0.003 |
| Compound of Example 400 | ≤0.0004 |
| Compound of Example 411 | 0.006 |
| Compound of Example 414 | 0.006 |
| Compound of Example 415 | 0.0015 |
| Compound of Example 446 | 0.003 |
| Compound of Example 471 | 0.012 |
| Compound of Example 490 | 0.0008 |

The invention claimed is:

1. A compound represented by Formula (1):

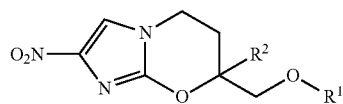

(1)

or a salt thereof,
wherein $R^1$ is a group represented by Formula (2):

-A-L1-B-L2-C-D    (2)

wherein A represents a divalent group selected from (A1) to (A12):
(A1) tetrahydroisoquinolinediyl,
(A2) tetrahydroquinolinediyl,
(A3) tetrahydrobenzoazepinediyl,
(A4) benzoxazolediyl,
(A5) benzothiazolediyl,
(A6) indolediyl,
(A7) isoindolinediyl,
(A8) naphthalenediyl,
(A9) quinolinediyl,
(A10) phenylene,
(A11) biphenyldiyl, and
(A12) pyridinediyl,
these groups (A1) to (A12) being optionally substituted on the ring(s) with at least one group selected from the group consisting of halogen and lower alkyl;

L1 represents a single bond, lower alkylene, —N(lower alkyl)-, —O—, —O-lower alkylene, —O-lower alkylene-O—, lower alkylene-O—, lower alkylene-O-lower alkylene, or lower alkenylene;
B represents a divalent group selected from (B1) to (B11):
(B1) tetrahydropyridinediyl,
(B2) diazepinediyl,
(B3) diazabicycloheptanediyl,
(B4) tetrahydrotriazolopyrazinediyl,
(B5) tetrahydroimidazopyrazinediyl,
(B6) azabicyclooctanediyl,
(B7) oxazolediyl,
(B8) piperazinediyl,
(B9) piperidinediyl,
(B10) thiazolediyl, and
(B11) phenylene,
these groups (B1) to (B11) being optionally substituted on the ring(s) with at least one group selected from the group consisting of lower alkyl, halo-lower alkyl, alkenyl, lower alkoxy, halo-lower alkoxy, lower alkoxycarbonyl, lower alkenyloxycarbonyl, hydroxy, lower alkylsulfonyl, and halo-lower alkylsulfonyl;
wherein, when A is (A10) or (A12), B is selected from (B1) to (B10);
L2 represents a single bond, —CO—, —COO—, —COO-lower alkynylene, —COO-lower alkylene (this lower alkylene is optionally substituted with phenyl), —COO-lower alkenylene, —N(lower alkyl)-, —N(lower alkyl)-lower alkylene, —NH—, —NH-lower alkylene, —O—, —O-lower alkylene, —S—, lower alkylene (this lower alkylene is optionally substituted with optionally protected hydroxy), lower alkylene (this lower alkylene is optionally substituted with optionally protected hydroxy)-O—, lower alkylene-N-(lower alkyl)-, lower alkylene-N(lower alkyl)-lower alkylene, lower alkylene-O-lower alkylene, lower alkylene-S—, or lower alkenylene (this lower alkenylene is optionally substituted with lower alkyl or phenyl);
C represents a divalent group or a single bond selected from (C1) to (C28):
(C1) tetrahydroquinolinediyl,
(C2) dihydrobenzodioxindiyl,
(C3) dihydrobenzoxazolediyl,
(C4) dihydrobenzofurandiyl,
(C5) dihydrobenzoxazinediyl,
(C6) adamantanediyl,
(C7) benzothiophenediyl,
(C8) benzodioxolediyl,
(C9) benzimidazolediyl,
(C10) benzofurandiyl,
(C11) carbazolediyl,
(C12) chromandiyl,
(C13) cyclohexanediyl,
(C14) fluorenediyl,
(C15) furandiyl,
(C16) imidazopyridinediyl,
(C17) imidazolediyl,
(C18) indolediyl,
(C19) naphthalenediyl,
(C20) piperidinediyl,
(C21) pyrazolediyl,
(C22) pyridinediyl,
(C23) pyrrolediyl,
(C24) quinolinediyl,
(C25) thiazolediyl, (C26) thiophenediyl,
(C27) phenylene, and
(C28) single bond,
these groups (C1) to (C27) being optionally substituted on the ring(s) with at least one group selected from the group consisting of alkoxy, halo-lower alkoxy, alkyl, haloalkyl, halogen, hydroxy, lower alkoxycarbonyl, oxo, lower alkanoylamino, lower alkanoyloxy, nitro, lower alkylthio, halo-lower alkylthio, cyclo-lower-alkyl, cyclo-lower alkoxy, cyano, lower alkoxycarbonylamino, nitro, amino, (mono- or di-lower alkyl)amino, lower alkylsulfonyl, lower alkylsulfonylamino, alkenyloxy, and (mono- or di-lower alkyl)amino lower alkoxy;

D represents a group or an atom selected from (D1) to (D35):
(D1) oxadiazolyl-lower alkoxy,
(D2) triazolyl,
(D3) isoxazolyl-lower alkoxy,
(D4) imidazolyl,
(D5) imidazolyl-lower alkyl,
(D6) thiazolyl-lower alkoxy,
(D7) thienyl,
(D8) thienyl-lower alkoxy,
(D9) furyl-lower alkoxy,
(D10) tetrahydropyranyl,
(D11) pyrazinyl-lower alkoxy,
(D12) piperazinylphenyl,
(D13) pyrazolyl,
(D14) pyridyl,
(D15) pyridyloxy,
(D16) pyridyl-lower alkoxy,
(D17) pyrrolidinyl,
(D18) pyrrolyl,
(D19) phenyl,
(D20) (mono- or di-phenyl)amino,
(D21) phenyl-lower alkyl,
(D22) phenyl-lower alkenyl,
(D23) (phenyl-lower alkyl)(lower alkyl)amino,
(D24) (phenyl-lower alkyl)amino,
(D25) phenyl-lower alkylsulfonyl,
(D26) phenyl-lower alkylsulfinyl,
(D27) phenyl-lower alkylthio,
(D28) phenyl-lower alkenyloxy,
(D29) phenyl-lower alkoxy,
(D30) phenyl-lower alkoxyphenyl,
(D31) phenoxy,
(D32) phenoxy-lower alkyl,
(D33) phenoxypiperidyl,
(D34) morpholinyl-lower alkyl, and
(D35) hydrogen,
these groups (D1) to (D34) being optionally substituted on the ring(s) with at least one group selected from the group consisting of lower alkyl, halo-lower alkyl, lower alkylthio, lower alkoxy, halo-lower alkoxy, and halogen, and $R^2$ represents hydrogen or lower alkyl.

2. The compound according to claim 1, or a salt thereof, wherein
C is selected from groups (C1) to (C27).

3. The compound according to claim 2, or a salt thereof, wherein, in Formula (2), A is
(A1) tetrahydroisoquinolinediyl,
(A2) tetrahydroquinolinediyl,
(A9) quinolinediyl,
(A10) phenylene,
(A11) biphenyldiyl, or
(A12) pyridinediyl,
these groups (A1), (A2), and (A9) to (A12) being optionally substituted on the ring(s) with at least one group selected from the group consisting of halogen and lower alkyl.

4. The compound according to claim 2, or a salt thereof, wherein, in Formula (2), A is
(A1) tetrahydroisoquinolinediyl,
(A2) tetrahydroquinolinediyl,
(A9) quinolinediyl,
(A10) phenylene,
(A11) biphenyldiyl, or
(A12) pyridinediyl,
these groups (A1), (A2), and (A9) to (A12) being optionally substituted on the ring(s) with one or two halogen atoms;

L1 is a single bond, lower alkylene, —O—, —O-lower alkylene, or lower alkylene-O—;

B is
(B7) oxazolediyl,
(B8) piperazinediyl,
(B9) piperidinediyl,
(B10) thiazolediyl, or
(B11) phenylene,
these groups (B7) to (B11) being optionally substituted on the ring with at least one or two groups selected from the group consisting of lower alkyl, halo-lower alkyl, halo-lower alkoxy, hydroxy, and halo-lower alkylsulfonyl;

L2 is a single bond, —N(lower alkyl)-, —O—, —O-lower alkylene, lower alkylene, lower alkylene-O—, or lower alkenylene;

C is
(C13) cyclohexanediyl,
(C20) piperidinediyl,
(C27) phenylene, or
(C28) single bond,
these groups (C13), (C20), and (C27) being optionally substituted on the ring with one or two groups selected from the group consisting of halo-lower alkoxy, halo-lower alkyl, hydroxy, and halo-lower alkylthio;

D is
(D21) phenyl-lower alkyl,
(D24) (phenyl-lower alkyl)amino,
(D29) phenyl-lower alkoxy,
(D31) phenoxy, or
(D35) hydrogen,
these groups (D21), (D24), (D29), and (D31) being optionally substituted on the ring with one or two groups selected from the group consisting of halo-lower alkyl and halo-lower alkoxy,
with the proviso that when A is (A10) or (A12), C is (C13), (C20), or (C27).

5. The compound according to claim 2, or a salt thereof, which is represented by Formula (1-1):

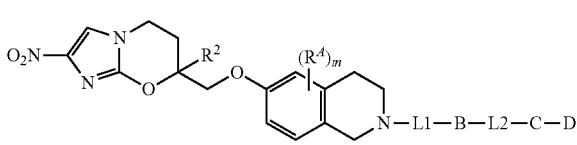

(1-1)

wherein $R^4$ is halogen or lower alkyl, m is 0, 1, or 2, wherein when m is 2, each $R^4$ is the same or different, and $R^2$, L1, B, L2, C, and D are the same as defined above;

Formula (1-2):

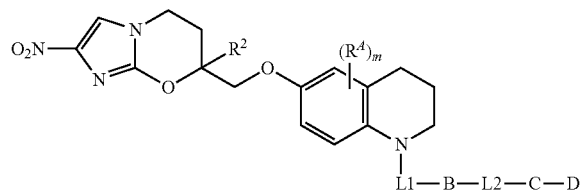

wherein $R^A$, m, $R^2$, L1, B, L2, C, and D are the same as defined above;

Formula (1-3):

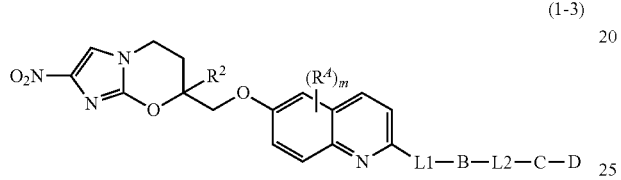

wherein $R^A$, m, $R^2$, L1, B, L2, C, and D are the same as defined above;

Formula (1-4):

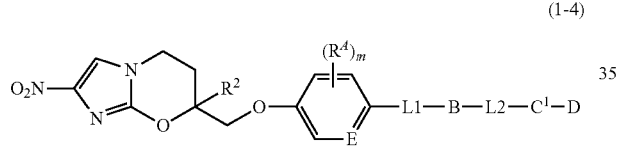

wherein E is N or CH; $C^1$ is a divalent group selected from groups (C1) to (C27) above (the substituents on the ring(s) of these groups are the same as defined above); and $R^A$, m, $R^2$, L1, B, L2, and D are the same as defined above; or Formula (1-5):

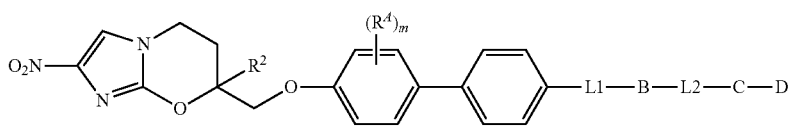

wherein $R^A$, m, $R^2$, L1, B, L2, C, and D are the same as defined above.

6. The compound of claim 1, which is selected from the group consisting of the following compounds, or a salt thereof:

2-nitro-7-{4-[4-(4-trifluoromethoxyphenoxy)piperidin-1-yl]phenoxymethyl}-6,7-dihydro-5H-imidazo[2,1-b][1,3]oxazine;

2-nitro-7-{4-[4-(4-trifluoromethoxybenzyl)piperazin-1-yl]phenoxymethyl}-6,7-dihydro-5H-imidazo[2,1-b][1,3]oxazine;

2-nitro-7-{4-[2-(4-trifluoromethoxyphenoxymethyl)oxazol-4-yl]phenoxymethyl}-6,7-dihydro-5H-imidazo[2,1-b][1,3]oxazine;

2-nitro-7-{4-[2-(4-trifluoromethoxyphenyl)thiazol-4-yl]phenoxymethyl}-6,7-dihydro-5H-imidazo[2,1-b][1,3]oxazine;

2-nitro-7-[4-(4-{3-[4-(4-trifluoromethoxyphenoxy)phenyl]propyl}piperazin-1-yl)phenoxymethyl]-6,7-dihydro-5H-imidazo[2,1-b][1,3]oxazine;

2-nitro-7-(6-{4-[2-(4-trifluoromethoxyphenoxy)ethyl]piperidin-1-yl}pyridin-3-yloxymethyl)-6,7-dihydro-5H-imidazo[2,1-b][1,3]oxazine;

N-methyl-N-{1-[4-((R)-2-nitro-6,7-dihydro-5H-imidazo[2,1-b][1,3]oxazin-7-ylmethoxy)phenyl]piperidin-4-yl}-N-(4-trifluoromethoxyphenyl)amine;

6-(2-nitro-6,7-dihydro-5H-imidazo[2,1-b][1,3]oxazin-7-ylmethoxy)-1-[3-(4-trifluoromethoxyphenoxy)propyl]-1,2,3,4-tetrahydroquinoline;

7-{3-fluoro-4-[4-(4-trifluoromethoxyphenoxy)piperidin-1-yl]phenoxymethyl}-2-nitro-6,7-dihydro-5H-imidazo[2,1-b][1,3]oxazine;

6-((R)-2-nitro-6,7-dihydro-5H-imidazo[2,1-b][1,3]oxazin-7-ylmethoxy)-2-(4-trifluoromethoxybenzyloxy)quinoline (R)-2-nitro-7-(4-{4-[4-(4-trifluoromethylbenzyloxy)benzyl]piperazin-1-yl}phenoxymethyl)-6,7-dihydro-5H-imidazo[2,1-b][1,3]oxazine;

(R)-2-nitro-7-(4-{4-[4-(4-trifluoromethoxybenzyloxy)phenyl]piperazin-1-yl}phenoxymethyl)-6,7-dihydro-5H-imidazo[2,1-b][1,3]oxazine, (R)-2-nitro-7-(4-{1-[4-(4-trifluoromethoxybenzyloxy)benzyl]piperidin-4-yloxy}phenoxymethyl)-6,7-dihydro-5H-imidazo[2,1-b][1,3]oxazine;

(R)-2-nitro-7-(4-{4-[4-(4-trifluoromethoxyphenoxy)benzyl]piperidin-1-yl}phenoxymethyl)-6,7-dihydro-5H-imidazo[2,1-b][1,3]oxazine;

(S)-2-nitro-7-(4-{4-[4-(4-trifluoromethylbenzyloxy)benzyl]piperidin-1-yl}phenoxymethyl)-6,7-dihydro-5H-imidazo[2,1-b][1,3]oxazine;

(S)-2-nitro-7-{4'-[4-(4-trifluoromethoxyphenoxy)piperidin-1-ylmethyl]biphenyl-4-yloxymethyl}-6,7-dihydro-5H-imidazo[2,1-b][1,3]oxazine;

N-(4-{4-[4-((S)-2-nitro-6,7-dihydro-5H-imidazo[2,1-b][1,3]oxazin-7-ylmethoxy)phenyl]piperazin-1-ylmethyl}phenyl)-N-(4-trifluoromethylbenzyl)amine;

(R)-7-(4-{(R)-3-methyl-4-[4-(4-trifluoromethylbenzyloxy)benzyl]piperazin-1-yl}phenoxymethyl)-2-nitro-6,7-dihydro-5H-imidazo[2,1-b][1,3]oxazine;

6-((R)-2-nitro-6,7-dihydro-5H-imidazo[2,1-b][1,3]oxazin-7-ylmethoxy)-2-[4-(4-trifluoromethylbenzyloxy)benzyl]-1,2,3,4-tetrahydroisoquinoline;

(R)-7-(4-{(R)-2-methyl-4-[4-(4-trifluoromethoxyphenoxy)benzyl]piperazin-1-yl}phenoxymethyl)-2-nitro-6,7-dihydro-5H-imidazo[2,1-b][1,3]oxazine;

2-nitro-7-{4-[1-(4-trifluoromethoxybenzyl)piperidin-4-yl]phenoxymethyl}-6,7-dihydro-5H-imidazo[2,1-b][1,3]oxazine;

(R)-2-nitro-7-(4-{4-[(E)-3-(4-trifluoromethylphenyl)allyl]piperazin-1-yl}phenoxymethyl)-6,7-dihydro-5H-imidazo[2,1-b][1,3]oxazine;

1-[4'-((R)-2-nitro-6,7-dihydro-5H-imidazo[2,1-b][1,3]oxazin-7-ylmethoxy)biphenyl-4-yl]-4-trifluoromethylpiperidin-4-ol;

(R)-2-nitro-7-{4-[4-(nonafluorobutane-1-sulfonyl)piperazin-1-yl]phenoxymethyl}-6,7-dihydro-5H-imidazo[2,1-b][1,3]oxazine;

7-methyl-2-nitro-7-(4-{4-[2-(4-trifluoromethoxyphenyl)ethyl]piperidin-1-yl}phenoxymethyl)-6,7-dihydro-5H-imidazo[2,1-b][1,3]oxazine;

(R)-2-nitro-7-{4-[4-(4-trifluoromethoxybenzyl)piperidin-1-yl]phenoxymethyl}-6,7-dihydro-5H-imidazo[2,1-b][1,3]oxazine;

(R)-2-nitro-7-(4-{4-[3-(3-trifluoromethylphenoxy)propyl]piperidin-1-yl}phenoxymethyl)-6,7-dihydro-5H-imidazo[2,1-b][1,3]oxazine;

(R)-2-nitro-7-(4-{4-[3-(4-trifluoromethylphenyl)propyl]piperidin-1-yl}phenoxymethyl)-6,7-dihydro-5H-imidazo[2,1-b][1,3]oxazine;

7-methyl-2-nitro-7-(4-{4-[(E)-3-(4-trifluoromethoxyphenyl)allyl]piperazin-1-yl}phenoxymethyl)-6,7-dihydro-5H-imidazo[2,1-b][1,3]oxazine;

(R)-2-nitro-7-{4-[4-(4-trifluoromethyl-cyclohexylmethyl)piperazin-1-yl]phenoxymethyl}-6,7-dihydro-5H-imidazo[2,1-b][1,3]oxazine;

(R)-2-nitro-7-{4-[1'-(4-trifluoromethylbenzyl)-4,4'-bipiperidin-1-yl]phenoxymethyl}-6,7-dihydro-5H-imidazo[2,1-b][1,3]oxazine;

(R)-2-nitro-7-{4-[4-(4-trifluoromethylsulfanylphenoxy)piperidin-1-yl]phenoxymethyl}-6,7-dihydro-5H-imidazo[2,1-b][1,3]oxazine;

(R)-7-{4-[4-methoxy-4-(4-trifluoromethylphenyl)piperidin-1-yl]phenoxymethyl}-2-nitro-6,7-dihydro-5H-imidazo[2,1-b][1,3]oxazine; and (R)-7-[4-(4-{1-methyl-1-[4-(4-trifluoromethylbenzyloxy)phenyl]ethyl}piperazin-1-yl)phenoxymethyl]-2-nitro-6,7-dihydro-5H-imidazo[2,1-b][1,3]oxazine.

7. A pharmaceutical composition comprising a compound of claim 1, or a salt thereof, and a pharmaceutically acceptable carrier.

8. A therapeutic agent for treating tuberculosis, comprising a compound of claim 1, or a salt thereof, and a pharmaceutically acceptable carrier.

9. A method for treating tuberculosis, comprising administering an effective amount of a compound of claim 1, or a salt thereof, to a patient.

* * * * *